United States Patent
Baum et al.

(10) Patent No.: US 9,445,594 B2
(45) Date of Patent: Sep. 20, 2016

(54) MOLECULES HAVING CERTAIN PESTICIDAL UTILITIES, INTERMEDIATES, COMPOSITIONS, AND PROCESSES, RELATED THERETO

(71) Applicant: Dow AgroSciences LLC, Indianapolis, IN (US)

(72) Inventors: Erich W. Baum, Greenwood, IN (US); Lindsey G. Fischer, Indianapolis, IN (US); Gary D. Crouse, Noblesville, IN (US); Thomas C. Sparks, Greenfield, IN (US); Natalie C. Giampietro, Carmel, IN (US); William H. Dent, III, Indianapolis, IN (US); Noormohamed M. Niyaz, Indianapolis, IN (US); Jeff Petkus, Indianapolis, IN (US); David A. Demeter, Fishers, IN (US); William Thomas Lambert, Westfield, IN (US); CaSandra L. McLeod, Indianapolis, IN (US); Emily Marie Rigsbee, Bloomington, IN (US); James M. Renga, Spokane, WA (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/806,058

(22) Filed: Jul. 22, 2015

(65) Prior Publication Data
US 2016/0021883 A1 Jan. 28, 2016

Related U.S. Application Data

(60) Provisional application No. 62/028,090, filed on Jul. 23, 2014.

(51) Int. Cl.
| | | |
|---|---|---|
| *A01N 43/653* | (2006.01) |
| *A01N 43/82* | (2006.01) |
| *A01N 43/84* | (2006.01) |
| *C07D 249/08* | (2006.01) |
| *C07D 401/12* | (2006.01) |
| *C07D 403/12* | (2006.01) |
| *C07D 405/12* | (2006.01) |
| *C07D 413/12* | (2006.01) |

(52) U.S. Cl.
CPC ............ *A01N 43/653* (2013.01); *A01N 43/82* (2013.01); *A01N 43/84* (2013.01); *C07D 249/08* (2013.01); *C07D 401/12* (2013.01); *C07D 403/12* (2013.01); *C07D 405/12* (2013.01); *C07D 413/12* (2013.01)

(58) Field of Classification Search
CPC .... A01N 43/653; A01N 43/82; A01N 43/84; C07D 249/08; C07D 401/12; C07D 403/12; C07D 405/12; C07D 413/12
See application file for complete search history.

(56) References Cited

U.S. PATENT DOCUMENTS

| | | | | |
|---|---|---|---|---|
| 8,748,340 B2* | 6/2014 | Crouse | ............... | A61K 31/4196 504/100 |
| 9,107,410 B2* | 8/2015 | Crouse | ............... | A61K 31/4196 |
| 2014/0274688 A1* | 9/2014 | Fischer | ................. | A01N 47/42 504/100 |

* cited by examiner

*Primary Examiner* — Jane C Oswecki
(74) *Attorney, Agent, or Firm* — Yung H. Lee

(57) ABSTRACT

This disclosure relates to the field of molecules having pesticidal utility against pests in Phyla Nematoda, Arthropoda, and/or Mollusca, processes to produce such molecules and intermediates used in such processes, compositions containing such molecules, and processes of using such molecules against such pests. These molecules may be used, for example, as nematicides, acaricides, insecticides, miticides, and/or molluscicides. This document discloses molecules having the following formula ("Formula One").

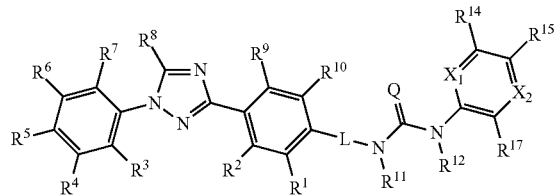

39 Claims, No Drawings

MOLECULES HAVING CERTAIN PESTICIDAL UTILITIES, INTERMEDIATES, COMPOSITIONS, AND PROCESSES, RELATED THERETO

CROSS REFERENCE TO RELATED APPLICATIONS

This application claims the benefit of, and priority from, U.S. Provisional Patent Application Ser. No. 62/028,090 filed 23 Jul. 2014, the entire disclosure of which is hereby expressly incorporated by reference.

FIELD OF THE DISCLOSURE

This disclosure relates to the field of molecules having pesticidal utility against pests in Phyla Arthropoda, Mollusca, and/or Nematoda, processes to produce such molecules, intermediates used in such processes, compositions containing such molecules, and processes of using such molecules and compositions against such pests. These molecules and compositions may be used, for example, as acaricides, insecticides, miticides, molluscicides, and/or nematicides.

BACKGROUND OF THE DISCLOSURE

"Many of the most dangerous human diseases are transmitted by insect vectors" (Rivero, A., Vezilier, J., Weill, M., Read, A., Gandon, S., Insect Control of Vector-Borne Diseases: When is Insect Resistance a Problem? Public Library of Science Pathogens, Vol. 6, No. 8, p. 1-9, 2010). "Historically, malaria, dengue, yellow fever, plague, filariasis, louse-borne typhus, trypanomiasis, leishmaniasis, and other vector borne diseases were responsible for more human disease and death in the $17^{th}$ through the early $20^{th}$ centuries than all other causes combined" (Gubler, D., Resurgent Vector-Borne Diseases as a Global Health Problem, *Emerging Infectious Diseases*, Vol. 4, No. 3, p. 442-450, 1998). Vector-borne diseases are responsible for about 17% of the global parasitic and infectious diseases. Malaria alone causes over 800,000 deaths a year, 85% of which occur in children under 5 years of age. Each year there are about 50 to about 100 million cases of dengue fever. A further 250,000 to 500,000 cases of dengue hemorrhagic fever occur each year (Matthews, G., *Integrated Vector Management: Controlling Vectors of Malaria and Other Insect Vector Borne Diseases*, Ch. 1, p. 1-2011). Vector control plays a critical role in the prevention and control of infectious diseases. However, insecticide resistance, including resistance to multiple insecticides, has arisen in all insect species that are major vectors of human diseases (Rivero et al). Recently, more than 550 pest arthropod species have developed resistance to at least one pesticide (Whalon, M., Mota-Sanchez, D., Hollingworth, R., Analysis of Global Pesticide Resistance in Arthropods, *Global Pesticide Resistance in Arthropods*, Ch. 1, p. 5-33, 2008).

Each year insects, plant pathogens, and weeds, destroy more than 40% of all potential food production. This loss occurs despite the application of pesticides and the use of a wide array of non-chemical controls, such as, crop rotations and biological controls. If just some of this food could be saved, it could be used to feed the more than three billion people in the world who are malnourished (Pimental, D., Pest Control in World Agriculture, *Agricultural Sciences*—Vol. II, 2009).

Plant parasitic nematodes are among the most widespread pests, and are frequently one of the most insidious and costly. It has been estimated that losses attributable to nematodes are from about 9% in developed countries to about 15% in undeveloped countries. However, in the United States of America a survey of 35 States on various crops indicated nematode-derived losses of up to 25% (Nicol, J., Turner S.; Coyne, L.; den Nijs, L., Hocksland, L., Tahna-Maafi, Z., Current Nematode Threats to World Agriculture, *Genomic and Molecular Genetics of Plant—Nematode Interactions*, p. 21-43, 2011).

It is noted that gastropods (slugs and snails) are pests of less economic importance than other arthropods or nematodes, but in certain areas they may reduce yields substantially, severely affecting the quality of harvested products, as well as, transmitting human, animal, and plant diseases. While only a few dozen species of gastropods are serious regional pests, a handful of species are important pests on a world-wide scale. In particular, gastropods affect a wide variety of agricultural and horticultural crops, such as, arable, pastoral, and fiber crops; vegetables; bush and tree fruits; herbs; and ornamentals (Speiser, B., Molluscicides, *Encyclopedia of Pest Management*, Ch. 219, p. 506-508, 2002).

Termites cause damage to all types of private and public structures, as well as, to agricultural and forestry resources. In 2005, it was estimated that termites cause over US$50 billion in damage world-wide each year (Korb, J., Termites, *Current Biology*, Vol. 17, No. 23, 2007).

Consequently, for many reasons, including those mentioned above, there is an on-going need for the costly (estimated to be about US$256 million per pesticide in 2010), time-consuming (on average about 10 years per pesticide), and difficult, discovery and development of new pesticides (The Cost of New Agrochemical Product Discovery, Development & Registration, and Research & Development predictions for the Future, Crop Life America, 2010).

DEFINITIONS

The examples given in the definitions are generally non-exhaustive and must not be construed as limiting the molecules disclosed in this document. It is understood that a substituent should comply with chemical bonding rules and steric compatibility constraints in relation to the particular molecule to which it is attached.

"Alkenyl" means an acyclic, unsaturated (at least one carbon-carbon double bond), branched or unbranched, substituent consisting of carbon and hydrogen, for example, vinyl, allyl, butenyl, pentenyl, and hexenyl.

"Alkenyloxy" means an alkenyl further consisting of a carbon-oxygen single bond, for example, allyloxy, butenyloxy, pentenyloxy, hexenyloxy.

"Alkoxy" means an alkyl further consisting of a carbon-oxygen single bond, for example, methoxy, ethoxy, propoxy, isopropoxy, butoxy, isobutoxy, and tert-butoxy.

"Alkyl" means an acyclic, saturated, branched or unbranched, substituent consisting of carbon and hydrogen, for example, methyl, ethyl, propyl, isopropyl, butyl, and tert-butyl.

"Alkynyl" means an acyclic, unsaturated (at least one carbon-carbon triple bond), branched or unbranched, substituent consisting of carbon and hydrogen, for example, ethynyl, propargyl, butynyl, and pentynyl.

"Alkynyloxy" means an alkynyl further consisting of a carbon-oxygen single bond, for example, pentynyloxy, hexynyloxy, heptynyloxy, and octynyloxy.

"Aryl" means a cyclic, aromatic substituent consisting of hydrogen and carbon, for example, phenyl, naphthyl, and biphenyl.

"Cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl, tetrahydronaphthyl, hexahydronaphthyl, and octahydronaphthyl.

"Cycloalkenyloxy" means a cycloalkenyl further consisting of a carbon-oxygen single bond, for example, cyclobutenyloxy, cyclopentenyloxy, norbornenyloxy, and bicyclo[2.2.2]octenyloxy.

"Cycloalkyl" means a monocyclic or polycyclic, saturated substituent consisting of carbon and hydrogen, for example, cyclopropyl, cyclobutyl, cyclopentyl, norbornyl, bicyclo[2.2.2]octyl, and decahydronaphthyl.

"Cycloalkoxy" means a cycloalkyl further consisting of a carbon-oxygen single bond, for example, cyclopropyloxy, cyclobutyloxy, cyclopentyloxy, norbornyloxy, and bicyclo[2.2.2]octyloxy.

"Halo" means fluoro, chloro, bromo, and iodo.

"Haloalkoxy" means an alkoxy further consisting of, from one to the maximum possible number of identical or different, halos, for example, fluoromethoxy, trifluoromethoxy, 2,2-difluoropropoxy, chloromethoxy, trichloromethoxy, 1,1,2,2-tetrafluoroethoxy, and pentafluoroethoxy.

"Haloalkyl" means an alkyl further consisting of, from one to the maximum possible number of, identical or different, halos, for example, fluoromethyl, trifluoromethyl, 2,2-difluoropropyl, chloromethyl, trichloromethyl, and 1,1,2,2-tetrafluoroethyl.

"Heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen. Examples of aromatic heterocyclyl substituents include, but are not limited to, benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl. Examples of fully saturated heterocyclyl substituents include, but are not limited to, piperazinyl, piperidinyl, morpholinyl, pyrrolidinyl, tetrahydrofuranyl, and tetrahydropyranyl. Examples of partially unsaturated heterocyclyl substituents include, but are not limited to, 1,2,3,4-tetrahydro-quinolinyl, 4,5-dihydro-oxazolyl, 4,5-dihydro-1H-pyrazolyl, 4,5-dihydro-isoxazolyl, and 2,3-dihydro-[1,3,4]-oxadiazolyl. Additional examples include the following:

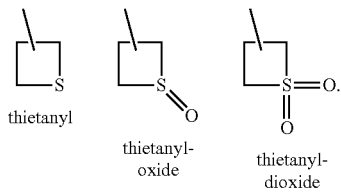

DETAILED DESCRIPTION OF THE DISCLOSURE

This document discloses molecules having the following formula ("Formula One")

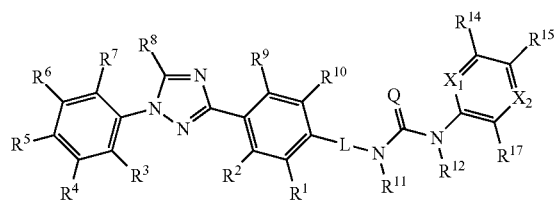

Formula One wherein:

(A) $R^1$, $R^2$, $R^3$, $R^4$, $R^5$, $R^6$, $R^7$, $R^9$, and $R^{10}$ are each independently selected from the group consisting of the group consisting of H, F, Cl, Br, I, CN, $NO_2$, OH, $(C_1-C_4)$alkyl, $(C_2-C_4)$alkenyl, $(C_1-C_4)$haloalkyl, $(C_1-C_4)$alkoxy, $(C_1-C_4)$haloalkoxy, and $(C_3-C_6)$cycloalkyl, wherein each alkyl, alkenyl, haloalkyl, alkoxy, haloalkoxy, cycloalkyl, are optionally substituted with one or more substituents independently selected from the group consisting of the group consisting of H, F, Cl, Br, I, CN, $NO_2$, OH, $(C_1-C_4)$alkyl, $(C_2-C_4)$alkenyl, $(C_1-C_4)$haloalkyl, $(C_1-C_4)$alkoxy, $(C_1-C_4)$haloalkoxy, and $(C_3-C_6)$cycloalkyl;

(B) $R^8$ is H;

(C) L is selected from the group consisting of the group consisting of (1) a bond connecting nitrogen to carbon in the ring, and (2) a $(C_1)$alkyl or a $(C_3-C_4)$alkyl wherein said alkyl is optionally substituted with one or more substituents independently selected from the group consisting of the group consisting of F, Cl, CN, OH, and oxo;

(D) $R^{11}$ and $R^{12}$ are each independently selected from the group consisting of the group consisting of H, $(C_1-C_4)$alkyl, $(C_2-C_4)$alkenyl, $(C_2-C_4)$alkenyloxy, $(C_2-C_4)$alkynyl, $(C_2-C_4)$alkynyloxy, $(C_1-C_4)$haloalkyl, $(C_1-C_4)$alkoxy, $(C_1-C_4)$haloalkoxy, $(C_3-C_6)$cycloalkyl, $(C_3-C_6)$cycloalkoxy, $(C_3-C_6)$cycloalkenyl, $(C_3-C_6)$cycloalkenyloxy, $((C_1-C_4)$alkyl)$((C_3-C_6)$cycloalkyl), $C(O)((C_1-C_4)$alkyl), $((C_1-C_4)$alkyl)$C(O)((C_1-C_4)$alkyl), $((C_1-C_4)$alkyl)$C(O)O((C_1-C_4)$alkyl), and $C(S)NH_2$, wherein each alkyl, alkenyl, alkenyloxy, alkynyl, alkynyloxy, haloalkyl, alkoxy, haloalkoxy, cycloalkyl, cycloalkoxy, cycloalkenyl, and cycloalkenyloxy, are optionally substituted with one or more substituents independently selected from the group consisting of the group consisting of H, F, Cl, Br, I, CN, $NO_2$, OH, and oxo;

(E) $X_1$ is selected from the group consisting of the group consisting of N and $CR^{13}$, wherein $R^{13}$ is selected from the group consisting of the group consisting of H, F, Cl, Br, I, CN, $NO_2$, OH, $(C_1-C_4)$alkyl, $(C_2-C_4)$alkenyl, $(C_2-C_4)$alkenyloxy, $(C_2-C_4)$alkynyl, $(C_2-C_4)$alkynyloxy, $(C_1-C_4)$haloalkyl, $(C_1-C_4)$alkoxy, $(C_1-C_4)$haloalkoxy, $(C_3-C_6)$cycloalkyl, $(C_3-C_6)$cycloalkoxy, $(C_3-C_6)$cycloalkenyl, and $(C_3-C_6)$cycloalkenyloxy, wherein each alkyl, alkenyl, alkenyloxy, alkynyl, alkynyloxy, haloalkyl, alkoxy, haloalkoxy, cycloalkyl, cycloalkoxy, cycloalkenyl, or cycloalkenyloxy, are optionally substituted with one or more substituents independently selected from the group consisting of H, F, Cl, Br, I, CN, $NO_2$, OH, and oxo;

(F) $X_2$ is selected from the group consisting of the group consisting of N and $CR^{16}$, wherein $R^{16}$ is selected from the group consisting of the group consisting of (H), H, F, Cl, Br, I, CN, $NO_2$, OH, $(C_1-C_4)$alkyl, $(C_2-C_4)$alkenyl, $(C_2-C_4)$alkenyloxy, $(C_2-C_4)$alkynyl, $(C_2-C_4)$alkynyloxy, $(C_1-C_4)$haloalkyl, $(C_1-C_4)$alkoxy, $(C_1-C_4)$haloalkoxy, $(C_3-C_6)$cycloalkyl, $(C_3-C_6)$cycloalkoxy, $(C_3-C_6)$cycloalkenyl, phenyl, and $(C_3-C_6)$cycloalkenyloxy, wherein each alkyl, alkenyl, alkenyloxy, alkynyl, alkynyloxy, haloalkyl, alkoxy, haloalkoxy, cycloalkyl, cycloalkoxy, cycloalkenyl, phenyl, and cycloalkenyloxy, are optionally substituted with one or more substituents independently selected from the group consisting of the group consisting of H, F, Cl, Br, I, CN, $NO_2$, OH, and oxo;

(G) $R^{14}$ and $R^{15}$ are each independently selected from the group consisting of the group consisting of (H), H, F, Cl, Br, I, CN, $NO_2$, OH, $(C_1\text{-}C_4)$alkyl, $(C_1\text{-}C_4)$haloalkyl, $(C_1\text{-}C_4)$alkoxy, $(C_1\text{-}C_4)$haloalkoxy, $C(O)O((C_1\text{-}C_4)$alkyl), $S((C_1\text{-}C_4)$alkyl), $N((C_1\text{-}C_4)$alkyl)$_2$, and phenyl, wherein each alkyl, alkenyl, haloalkyl, alkoxy, haloalkoxy, and phenyl, are optionally substituted with one or more substituents independently selected from the group consisting of the group consisting of H, F, Cl, Br, I, CN, $NO_2$, OH, and oxo;

(H) $R^{15}$ and $R^{16}$ may together be a 4-membered saturated or unsaturated, hydrocarbyl link, wherein said hydrocarbyl link may optionally be substituted with one or more substituents independently selected from the group consisting of the group consisting of H, F, Cl, Br, I, CN $NO_2$, OH, $(C_1\text{-}C_4)$alkyl, $(C_1\text{-}C_4)$haloalkyl, and $(C_1\text{-}C_4)$alkoxy;

(I) $R^{17}$ is selected from the group consisting of the group consisting of H, F, Cl, Br, I, CN, $NO_2$, OH, $(C_1\text{-}C_8)$alkyl, $(C_2\text{-}C_8)$alkenyl, $(C_2\text{-}C_4)$alkynyl, $(C_3\text{-}C_6)$cycloalkyl, $(C_1\text{-}C_4)$alkoxy, $(C_1\text{-}C_4)$haloalkyl, $(C_1\text{-}C_4)$haloalkoxy, $(C_1\text{-}C_8)$alkylphenyl, phenyl, and heterocyclyl, wherein each alkyl, alkenyl, alkynyl, cycloalkyl, alkoxy, haloalkyl, haloalkoxy, phenyl, and heterocyclyl, are optionally substituted with one or more substituents independently selected from the group consisting of the group consisting of H, F, Cl, Br, I, CN, $NO_2$, OH, $(C_1\text{-}C_8)$alkyl, $(C_3\text{-}C_6)$cycloalkyl, and $S((C_1\text{-}C_4)$alkyl); and (J) Q is selected from the group consisting of the group consisting of O and S.

In another embodiment $R^1$, $R^2$, $R^3$, $R^4$, $R^6$, $R^7$, $R^8$, $R^9$, and $R^{10}$ are H. This embodiment may be used in combination with the other embodiments of $R^5$, $R^{11}$, $R^{12}$, $R^{13}$, $R^{14}$, $R^{15}$, $R^{16}$, $R^{17}$, $X_1$, $X_2$, L, and Q.

In another embodiment $R^5$ is $CF_3$, $OCF_3$, or $OCF_2CF_3$. This embodiment may be used in combination with the other embodiments of $R^1$, $R^2$, $R^3$, $R^4$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $X_1$, $X_2$, L, and Q.

In another embodiment L is a bond. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $X_1$, $X_2$, and Q.

In another embodiment L is —$CH_2$—, —$CH_2CH_2CH_2$—, or —$CH_2CH_2CH_2CH_2$—. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $X_1$, $X_2$, and Q.

In another embodiment $R^{11}$ is H or $C(O)CH_3$. This embodiment may be used in combination with the other embodiments of $R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, $X_1$, $X_2$, L, and Q.

In another embodiment $R^{12}$ is H or $C(S)NH_2$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $R^{16}$, $R^{17}$, $X_1$, $X_2$, L, and Q.

In another embodiment $X_1$ is N. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $X_2$, L, and Q.

In another embodiment $X_1$ is $CR^{13}$, wherein $R^{13}$ is H, Cl, $CH_3$, $CH(CH_3)_2$, $OCH_3$, or $CF_3$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $R^{14}$, $R^{15}$, $R^{16}$, $R^{17}$, $X_2$, L, and Q.

In another embodiment $R^{14}$ is H, Cl, $CH_3$, $OCH_2CH_3$, or phenyl. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{13}$, $R^{15}$, $R^{16}$, $R^{17}$, $X_1$, $X_2$, L, and Q.

In another embodiment $R^{15}$ is H, F, Cl, CN, $CH_3$, $OCH_3$, $OCH_2CH_3$, $SCH_3$, $N(CH_3)_2$, or $C(O)OCH_2CH_3$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $R^{16}$, $R^{17}$, $X_1$, $X_2$, L, and Q.

In another embodiment $R^{16}$ is H, Cl, $CH_3$, $CH(CH_3)_2$, or $OCH_3$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $R^{17}$, $X_1$, $X_2$, L, and Q.

In another embodiment $R^{16}$ is phenyl that is substituted with $CH_3$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $R^{16}$, $X_1$, $X_2$, L, and Q.

In another embodiment $R^{15}$ and $R^{16}$ together are —CH=CH—CH=CH—. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{17}$, $X_1$, $X_2$, L, and Q.

In another embodiment $R^{17}$ is H, Cl, $CH_3$, $CH_2CH_3$, $CH_2CH_2CH_3$, $CH(CH_3)_2$, $C(CH_3)_3$, $CH(CH_3)CH_2$ $CH(CH_3)_2$, $CF_3$, —C≡CH, —$C(CH_3)$=$CH_2$, $OCH_3$, $OCH_2CH_3$, $OCF_3$, or $CH_2$phenyl. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $R^{16}$, $X_1$, $X_2$, L, and Q.

In another embodiment $R^{17}$ is cyclopropyl that is substituted with cyclopropyl. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $R^{16}$, $X_1$, $X_2$, L, and Q.

In another embodiment $R^{17}$ is phenyl that is substituted with one or more substituents selected from the group consisting of the group consisting of F, $CH_3$, $CH_2CH_3$, $CH(CH_3)_2$, cyclopropyl, and $SCH_3$. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $R^{16}$, $X_1$, $X_2$, L, and Q.

In another embodiment $R^{17}$ is 1-pyrazolyl, 2-furyl, 3-pyridyl, 1-morpholinyl, 2-(1,3,4-oxadiazolyl), 3-(1,2,4-oxadiazolyl), or 2-(1,3,4-triazolyl) that is substituted with one or more substituents selected from the group consisting of the group consisting of $CH(CH_3)_2$ and cyclopropyl. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $R^{16}$, $X_1$, $X_2$, L, and Q.

In another embodiment Q is O. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $X_1$, $X_2$, and L.

In another embodiment Q is S. This embodiment may be used in combination with the other embodiments of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $X_1$, $X_2$, and L.

In another embodiment:

(A) $R^1$, $R^2$, $R^3$, $R^4$, $R^5$, $R^6$, $R^7$, $R^9$, and $R^{10}$ are each independently selected from the group consisting of the group consisting of H, $(C_1\text{-}C_4)$haloalkyl, and $(C_1\text{-}C_4)$haloalkoxy;

(B) $R^8$ is H;

(C) L is a bond, $(C_1)$alkyl, or $(C_3\text{-}C_4)$alkyl;

(D) $R^{11}$ and $R^{12}$ are each independently selected from the group consisting of the group consisting of H, $C(O)((C_1\text{-}C_4)$alkyl), and $C(S)NH_2$;

(E) $X_1$ is selected from the group consisting of the group consisting of N and $CR^{13}$, wherein $R^{13}$ is selected from the group consisting of the group consisting of H, F, Cl, Br, I, $(C_1\text{-}C_4)$alkyl, $(C_1\text{-}C_4)$haloalkyl, and $(C_1\text{-}C_4)$alkoxy;

(F) $X_2$ is selected from the group consisting of the group consisting of N and $CR^{16}$,
  wherein $R^{16}$ is selected from the group consisting of the group consisting of (H), H, F, Cl, Br, I, $(C_1-C_4)$alkyl, $(C_1-C_4)$alkoxy, and phenyl;
(G) $R^{14}$ and $R^{15}$ are each independently selected from the group consisting of the group consisting of (H), H, F, Cl, Br, I, CN, $(C_1-C_4)$alkyl, $(C_1-C_4)$alkoxy, $C(O)O((C_1-C_4)$alkyl), $S((C_1-C_4)$alkyl), and $N((C_1-C_4)$alkyl$)_2$;
(H) $R^{15}$ and $R^{16}$ may together be a 4-membered saturated or unsaturated, hydrocarbyl link;
(I) $R^{17}$ is selected from the group consisting of the group consisting of H, F, Cl, Br, I, $(C_1-C_8)$alkyl, $(C_2-C_8)$alkenyl, $(C_2-C_4)$alkynyl, $(C_3-C_6)$cycloalkyl, $(C_1-C_4)$alkoxy, $(C_1-C_4)$haloalkyl, $(C_1-C_4)$haloalkoxy, $(C_1-C_8)$alkylphenyl, phenyl, and heterocyclyl,
  wherein each alkyl, alkenyl, alkynyl, cycloalkyl, alkoxy, haloalkyl, haloalkoxy, phenyl and heterocyclyl, are optionally substituted with one or more substituents independently selected from the group consisting of the group consisting of H, F, Cl, Br, I, $(C_1-C_8)$alkyl, $(C_3-C_6)$cycloalkyl, and $S((C_1-C_4)$alkyl); and
(J) Q is selected from the group consisting of the group consisting of O and S.

In another embodiment:
(A) $R^1$, $R^2$, $R^3$, $R^4$, $R^5$, $R^6$, $R^7$, $R^9$, and $R^{10}$ are each independently selected from the group consisting of the group consisting of H, $(C_1-C_4)$haloalkyl, and $(C_1-C_4)$haloalkoxyy;
(B) $R^8$ is H;
(C) L is a bond, $(C_1)$alkyl, or $(C_3-C_4)$alkyl;
(D) $R^{11}$ and $R^{12}$ are each independently selected from the group consisting of the group consisting of H, $C(O)((C_1-C_4)$alkyl), and $C(S)NH_2$;
(E) $X_1$ is selected from the group consisting of the group consisting of N and $CR^{13}$,
  wherein $R^{13}$ is selected from the group consisting of the group consisting of H and $(C_1-C_4)$alkyl;
(F) $X_2$ is selected from the group consisting of the group consisting of N and $CR^{16}$,
  wherein $R^{16}$ is selected from the group consisting of the group consisting of (H), H, F, Cl, Br, I, $(C_1-C_4)$alkyl, and $(C_1-C_4)$alkoxy;
(G) $R^{14}$ and $R^{15}$ are each independently selected from the group consisting of the group consisting of (H), H, F, Cl, Br, I, $(C_1-C_4)$alkyl, $(C_1-C_4)$alkoxy, and $N((C_1-C_4)$alkyl$)_2$;
(H) $R^{15}$ and $R^{16}$ may together be a 4-membered saturated or unsaturated, hydrocarbyl link;
(I) $R^{17}$ is selected from the group consisting of the group consisting of H, F, Cl, Br, I, $(C_1-C_8)$alkyl, $(C_2-C_8)$alkenyl, $(C_2-C_4)$alkynyl, $(C_3-C_6)$cycloalkyl, $(C_1-C_4)$alkoxy, $(C_1-C_4)$haloalkyl, $(C_1-C_4)$haloalkoxy, $(C_1-C_8)$alkylphenyl, phenyl, and heterocyclyl,
  wherein each alkyl, alkenyl, alkynyl, cycloalkyl, alkoxy, haloalkyl, haloalkoxy, phenyl and heterocyclyl, are optionally substituted with one or more substituents independently selected from the group consisting of the group consisting of H, F, Cl, Br, I, $(C_1-C_8)$alkyl, $(C_3-C_6)$cycloalkyl, and $S((C_1-C_4)$alkyl); and
(J) Q is selected from the group consisting of the group consisting of O and S.

In another embodiment:
(A) $R^1$, $R^2$, $R^3$, $R^4$, $R^5$, $R^6$, $R^7$, $R^9$, and $R^{10}$ are each independently selected from the group consisting of the group consisting of H, $(C_1-C_4)$haloalkyl, or $(C_1-C_4)$haloalkoxy;
(B) $R^8$ is H;
(C) L is a bond, $(C_1)$alkyl, or $(C_3-C_4)$alkyl;
(D) $R^{11}$ and $R^{12}$ are each independently selected from the group consisting of the group consisting of H and $C(S)NH_2$;
(E) $X_1$ is selected from the group consisting of the group consisting of N and $CR^{13}$,
  wherein $R^{13}$ is selected from the group consisting of the group consisting of H and $(C_1-C_4)$alkyl;
(F) $X_2$ is selected from the group consisting of the group consisting of N and $CR^{16}$,
  wherein $R^{16}$ is selected from the group consisting of the group consisting of (H), H, F, Cl, Br, I, and $(C_1-C_4)$alkoxy;
(G) $R^{14}$ and $R^{15}$ are each independently selected from the group consisting of the group consisting of (H), H, F, Cl, Br, I, $(C_1-C_4)$alkyl, and $(C_1-C_4)$alkoxy;
(H) $R^{15}$ and $R^{16}$ may together be a 4-membered saturated or unsaturated, hydrocarbyl link;
(I) $R^{17}$ is selected from the group consisting of the group consisting of H, F, Cl, Br, I, $(C_1-C_8)$alkyl, $(C_2-C_8)$alkenyl, $(C_2-C_4)$alkynyl, $(C_3-C_6)$cycloalkyl, $(C_1-C_4)$alkoxy, $(C_1-C_4)$haloalkyl, $(C_1-C_4)$haloalkoxy, $(C_1-C_8)$alkylphenyl, phenyl, and heterocyclyl,
  wherein each alkyl, alkenyl, alkynyl, cycloalkyl, alkoxy, haloalkyl, haloalkoxy, phenyl and heterocyclyl, are optionally substituted with one or more substituents independently selected from the group consisting of the group consisting of H, F, Cl, Br, I, $(C_1-C_8)$alkyl, $(C_3-C_6)$cycloalkyl, and $S((C_1-C_4)$alkyl); and
(J) Q is selected from the group consisting of the group consisting of O and S.

In another embodiment:
(A) $R^1$, $R^2$, $R^3$, $R^4$, $R^5$, $R^6$, $R^7$, $R^9$, and $R^{10}$ are each independently selected from the group consisting of the group consisting of H and $(C_1-C_4)$haloalkoxy;
(B) $R^8$ is H;
(C) L is a bond, $(C_1)$alkyl, or $(C_3-C_4)$alkyl;
(D) $R^{11}$ and $R^{12}$ are each independently selected from the group consisting of the group consisting of H and $C(S)NH_2$;
(E) $X_1$ is selected from the group consisting of the group consisting of N and $CR^{13}$,
  wherein $R^{13}$ is H;
(F) $X_2$ is $CR^{16}$,
  wherein $R^{16}$ is selected from the group consisting of the group consisting of (H), H, F, Cl, Br, I, and $(C_1-C_4)$ alkoxy;
(G) $R^{14}$ and $R^{15}$ are each independently selected from the group consisting of the group consisting of (H), H, F, Cl, Br, I, $(C_1-C_4)$alkyl, and $(C_1-C_4)$alkoxy;
(H) $R^{15}$ and $R^{16}$ may together be a 4-membered saturated or unsaturated, hydrocarbyl link;
(I) $R^{17}$ is selected from the group consisting of the group consisting of H, $(C_1-C_8)$ alkyl, $(C_3-C_6)$cycloalkyl, phenyl, and heterocyclyl;
  wherein each alkyl, alkenyl, alkynyl, cycloalkyl, alkoxy, haloalkyl, haloalkoxy, phenyl and heterocyclyl, are optionally substituted with one or more substituents independently selected from the group consisting of the group consisting of H, $(C_1-C_8)$ alkyl, and $(C_3-C_6)$cycloalkyl; and
(J) Q is selected from the group consisting of the group consisting of O and S.

Preparation of Ureas and Thioureas

Ureas disclosed herein may be prepared from the corresponding isocyanates 1-2, wherein $R^1$, $R^2$, $R^3$, $R^4$, $R^5$, $R^6$, $R^7$, $R^8$, $R^9$, $R^{10}$, and L are as previously disclosed. Usually, isocyanates 1-2 are not isolated, but may be instead generated in situ from a suitable precursor and used directly in the preparation of a urea. Suitable precursors are amines 1-1, wherein $R^1$, $R^2$, $R^3$, $R^4$, $R^5$, $R^6$, $R^7$, $R^8$, $R^9$, $R^{10}$, and L are as previously disclosed, may be converted into an isocyanate by using one of several common reagents such as phosgene, diphosgene, triphosgene, or carbonyldiimidazole (Scheme 1, step 1a), in a mixed solvent system such as dichloromethane and water or diethyl ether and water, in the presence of a base such as sodium bicarbonate or triethylamine, at temperatures from about −10° C. to about 50° C.

Scheme 1

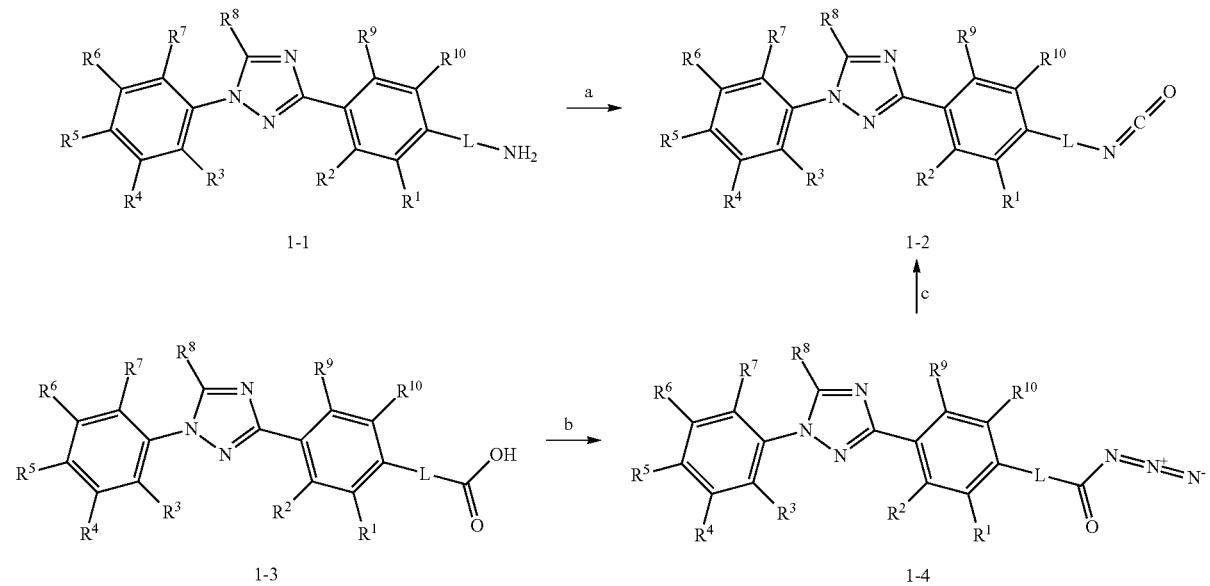

Alternatively, isocyanates 1-2 may be generated via a Curtius rearrangement of acyl azides 1-4, wherein $R^1$, $R^2$, $R^3$, $R^4$, $R^5$, $R^6$, $R^7$, $R^8$, $R^9$, $R^{10}$, and L are as previously disclosed, which, in turn, may be prepared from corresponding carboxylic acids 1-3, wherein $R^1$, $R^2$, $R^3$, $R^4$, $R^5$, $R^6$, $R^7$, $R^8$, $R^9$, $R^{10}$, and L are as previously disclosed. Formation of acyl azides 1-4 (step 1b) may occur either by treatment of the carboxylic acid with ethyl chloroformate and sodium azide in the presence of an amine base such as triethylamine, or with diphenylphosphoryl azide in the presence of an amine base such as triethylamine. Acyl azides 1-4 may then undergo a Curtius rearrangement, leading to corresponding isocyanates 1-2. Depending on the nature of the particular acyl azide, this rearrangement may occur spontaneously at about room temperature (about 22° C.), or it may require heating from about 40° C. to about 100° C. in a suitable solvent, such as toluene, or acetonitrile, or an ethereal solvent such as dioxane or tetrahydrofuran. Arylacetic acids azides are known. Due to their reactivity, however they are not often isolated as pure materials. Accordingly, acyl azides are not always fully characterized, but may simply be heated directly without characterization, to generate isocyanates 1-2.

Scheme 2

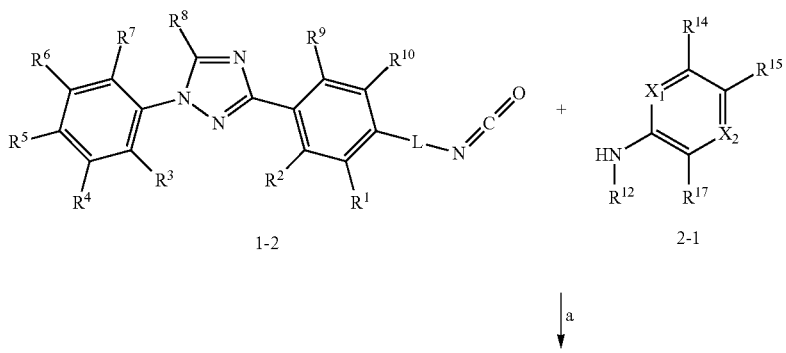

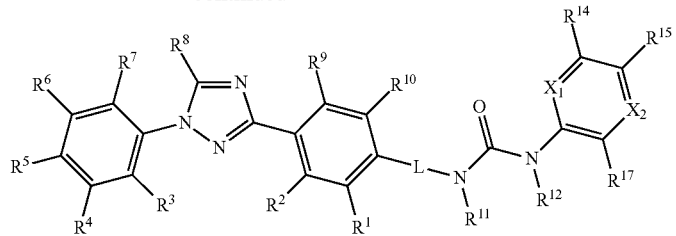

2-2

↓ b

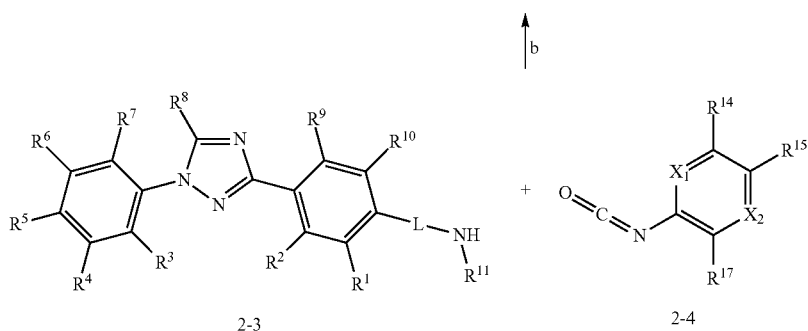

2-3    2-4

Isocyanates 1-2 may be treated directly with aryl amines 2-1, wherein $X_1$, $X_2$, $R^{12}$, $R^{13}$, $R^{14}$, $R^{15}$, $R^{16}$, and $R^{17}$ are as previously disclosed, either in the absence of base or in the presence of about 0.1 equivalents to about 2 equivalents of an inorganic base such as cesium carbonate or sodium hydride, or in the presence of an amine base such as triethylamine or diisopropylethylamine, or in the presence of an organometallic base such as n-butyllithium, resulting in the formation of ureas 2-2, wherein $R^{11}$ is H and $R^1$, $R^2$, $R^3$, $R^4$, $R^5$, $R^6$, $R^7$, $R^8$, $R^{10}$, $R^{12}$, $R^{13}$, $R^{14}$, $R^{15}$, $R^{16}$, $R^{17}$, L, $X_1$, and $X_2$ are as previously disclosed (Scheme 2, step 2a). The reaction may be performed at temperatures from about 0° C. to about 100° C., preferably from about 20° C. to about 80° C., in an aprotic solvent or solvent mixture chosen from acetonitrile, acetone, toluene, tetrahydrofuran, 1,2-dichloroethane, or dichloromethane. Alternatively, amines 2-3, wherein $R^1$, $R^2$, $R^3$, $R^4$, $R^5$, $R^6$, $R^7$, $R^8$, $R^9$, $R^{10}$, $R^{11}$ and L are as previously disclosed, may be treated with isocyanates 2-4, wherein $X_1$, $X_2$, $R^{13}$, $R^{14}$, $R^{15}$, $R^{16}$, and $R^{17}$ are as previously disclosed, under similar conditions to provide ureas 2-2, wherein $R^{12}$ is H and $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $R^{16}$, $R^{17}$, L, $X_1$, and $X_2$ are as previously disclosed (step 2b).

Alternatively, ureas 2-2 may be prepared by first preparing O-aryl carbamates of amines 2-3 using phenyl chloroformate or para-nitrophenyl chloroformates, followed by treatment with aryl amines 2-1 using conditions described above.

Thioureas 3-2, wherein $R^{11}$ is H and $R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, L, $X_1$, and $X_2$ are as previously disclosed, may be prepared from the corresponding aryl amines 2-1 by treatment with aryl isothiocyanates 3-1, wherein $R^1$, $R^2$, $R^3$, $R^4$, $R^5$, $R^6$, $R^7$, $R^8$, $R^9$, $R^{10}$, and L are as previously disclosed (Scheme 3) (WO 2011/017513), under a variety of conditions. For example, heating the two intermediates in tetrahydrofuran or isopropyl alcohol or dichloromethane or other suitable solvents, either without base or in the presence of an inorganic base such as cesium carbonate or potassium carbonate, or in the presence of an amine base such as triethylamine, at a temperature of from about 20° C. to about 65° C. for about 1 hour to about 24 hours, may result in the formation of the thioureas 3-2, wherein $R^{12}$ is H and $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $R^{16}$, $R^{17}$, L, $X_1$, and $X_2$ are as previously disclosed (step 3a). Alternatively, amines 2-3 may be combined with aryl isothiocyanates 3-3, wherein $X_1$, $X_2$, $R^{13}$, $R^{14}$, $R^{15}$, $R^{16}$, and $R^{17}$ are as previously disclosed, under conditions similar to those described above, to produce a thiourea (step 3b).

Alternatively, thioureas 3-2 may be prepared by first preparing O-aryl thiocarbamates of amines 2-3 using phenyl chlorothionoformate, treatment with aryl amines 2-1 using conditions described above.

Scheme 3

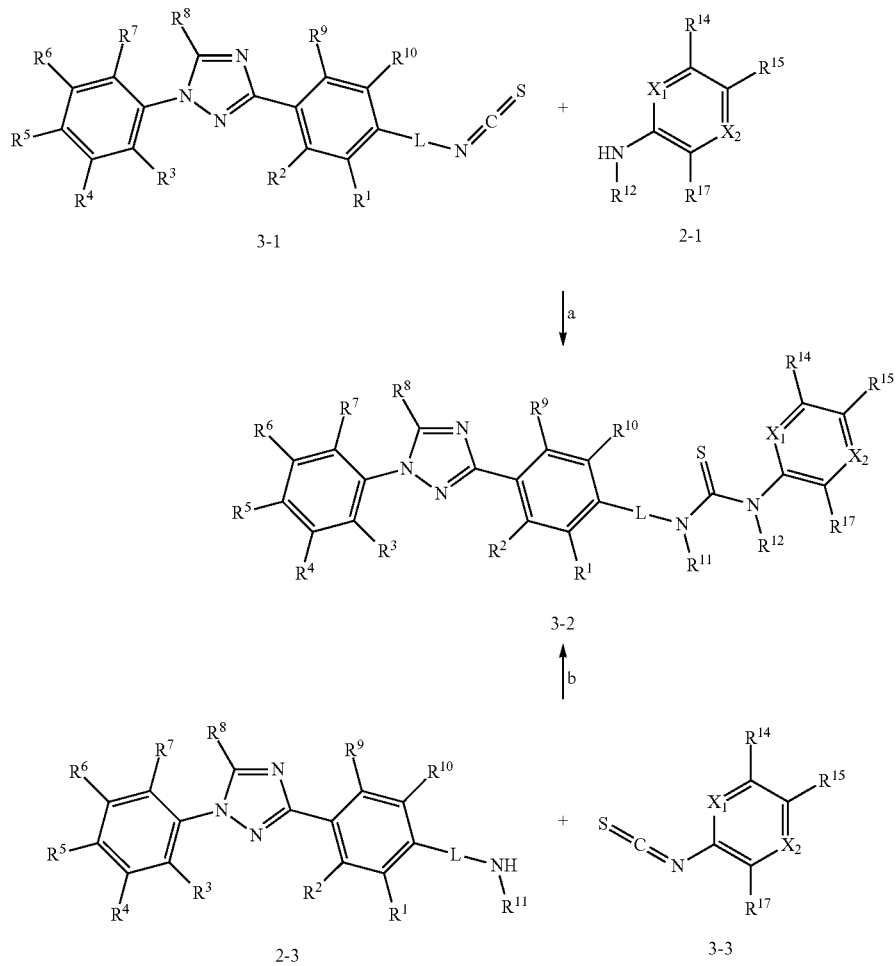

Preparation of Triaryl-Intermediates

Molecules of Formula One may be prepared by making triaryl intermediates and then linking them to appropriate intermediates to form desired compounds. A wide variety of triaryl intermediates may be used to prepare molecules of Formula One, provided that such triaryl intermediates contain a suitable functional group to which desired functional groups may be attached, functional groups such as amino, isocyanate, carboxyl, or halogen (preferably bromo or iodo). These triaryl intermediates can be prepared by methods previously described in the chemical literature, including WO 2009/102736, the entire disclosure of which is hereby incorporated by reference.

Triaryl acids 1-3, wherein L is a bond, used as precursors in the preparation of the molecules of Formula One may be prepared according to procedures described in US 2012/0202688. Some of the procedures described above require use of halo-triaryl intermediates 4-4, wherein $R^1$, $R^2$, $R^3$, $R^4$, $R^5$, $R^6$, $R^7$, $R^8$, $R^9$, and $R^{10}$ are as previously disclosed. Triazoles 4-2, wherein $R^1$, $R^2$, $R^8$, $R^9$, and $R^{10}$ are as previously disclosed. (Scheme 4, step 4a) may be prepared in two steps from benzamides 4-1, wherein $R^1$, $R^2$, $R^8$, $R^9$, and $R^{10}$ are as previously disclosed, under reported conditions (WO 2009/102736). Triazoles 4-2 may then be coupled to aryl halides 4-3, wherein $R^3$, $R^4$, $R^5$, $R^6$, and $R^7$ are as previously disclosed, such as 4-trifluoromethoxyphenyl iodobenzene, in the presence of cesium carbonate or potassium phosphate, in a polar aprotic solvent such as N,N-dimethylformamide. This reaction may be catalyzed by a copper salt such as copper(I) iodide in the presence of a chelator such as 8-hydroxyquinoline, both present in about 0.05 equivalents to about 0.25 equivalents, at a temperature ranging between about 80° C. and about 140° C., to form halo-triaryl intermediates 4-4 (step 4b).

Scheme 4

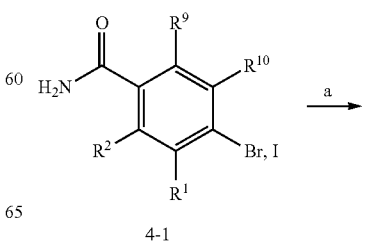

4-1

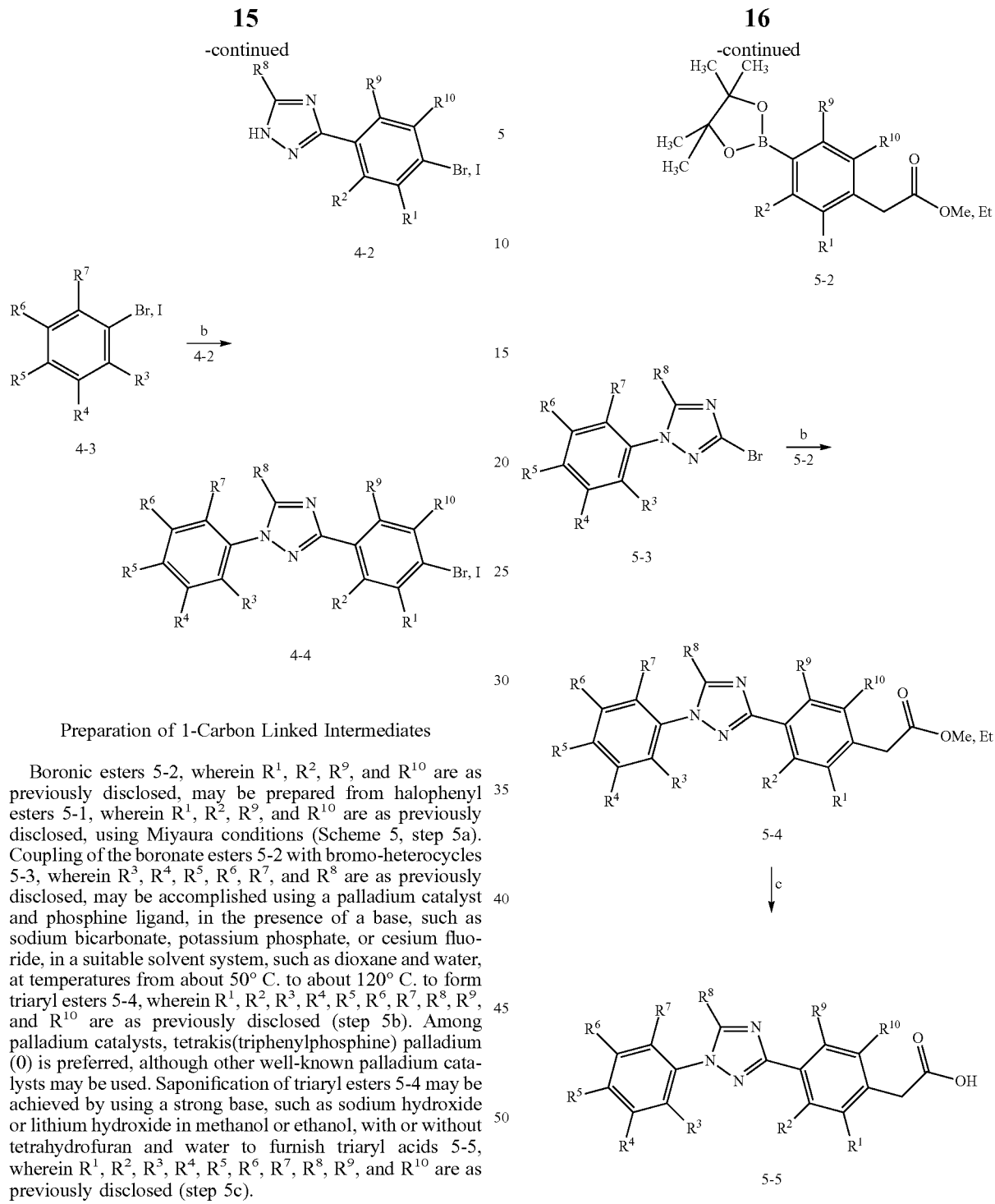

Preparation of 1-Carbon Linked Intermediates

Boronic esters 5-2, wherein $R^1$, $R^2$, $R^9$, and $R^{10}$ are as previously disclosed, may be prepared from halophenyl esters 5-1, wherein $R^1$, $R^2$, $R^9$, and $R^{10}$ are as previously disclosed, using Miyaura conditions (Scheme 5, step 5a). Coupling of the boronate esters 5-2 with bromo-heterocycles 5-3, wherein $R^3$, $R^4$, $R^5$, $R^6$, $R^7$, and $R^8$ are as previously disclosed, may be accomplished using a palladium catalyst and phosphine ligand, in the presence of a base, such as sodium bicarbonate, potassium phosphate, or cesium fluoride, in a suitable solvent system, such as dioxane and water, at temperatures from about 50° C. to about 120° C. to form triaryl esters 5-4, wherein $R^1$, $R^2$, $R^3$, $R^4$, $R^5$, $R^6$, $R^7$, $R^8$, $R^9$, and $R^{10}$ are as previously disclosed (step 5b). Among palladium catalysts, tetrakis(triphenylphosphine) palladium (0) is preferred, although other well-known palladium catalysts may be used. Saponification of triaryl esters 5-4 may be achieved by using a strong base, such as sodium hydroxide or lithium hydroxide in methanol or ethanol, with or without tetrahydrofuran and water to furnish triaryl acids 5-5, wherein $R^1$, $R^2$, $R^3$, $R^4$, $R^5$, $R^6$, $R^7$, $R^8$, $R^9$, and $R^{10}$ are as previously disclosed (step 5c).

Scheme 5

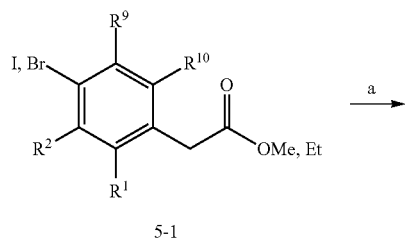

Halobenzyl amines 6-1, wherein $R^1$, $R^2$, $R^9$, and $R^{10}$ are as previously disclosed, may be protected using benzyl chloroformate in the presence of a base, such as triethylamine in an aprotic solvent, such as dichloromethane at about −10° C. to about 10° C. to provide N-carboxybenzyl (Cbz) protected benzyl amines 6-2, wherein $R^1$, $R^2$, $R^9$, and $R^{10}$ are as previously disclosed (Scheme 6, step 6a). Alternatively, other N-protecting groups such as tert-butoxycarbonyl (BOC) or 9-fluorenylmethylcarbonyl (Fmoc) may be employed. N-Cbz protected boronic esters 6-3, wherein $R^1$, $R^2$, $R^9$, and $R^{10}$ are as previously disclosed, may be prepared using Miyaura conditions (step 6b).

Scheme 6

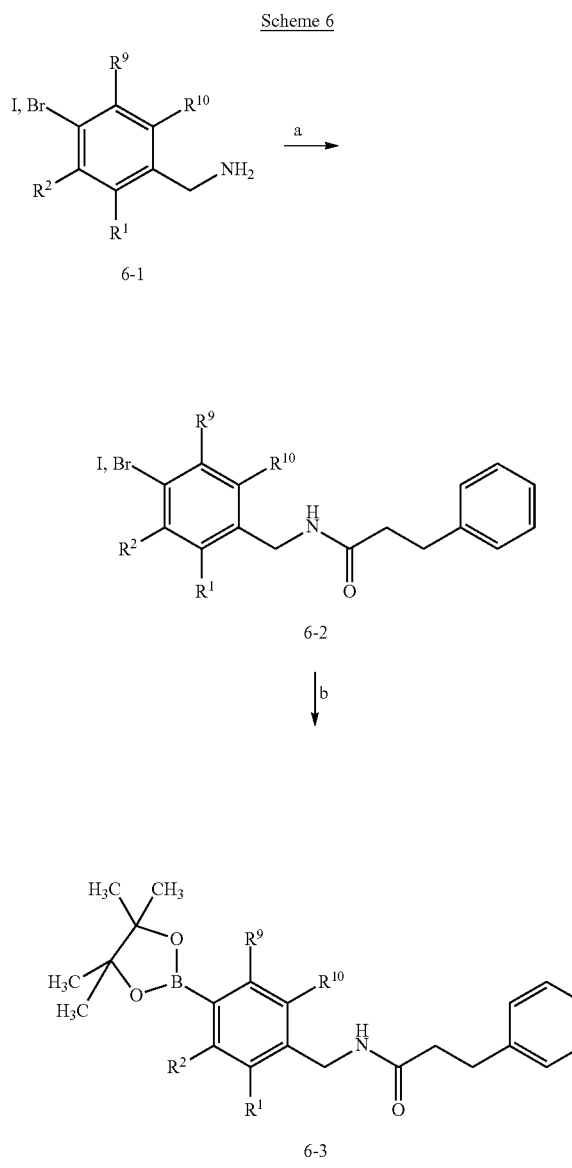

Scheme 7

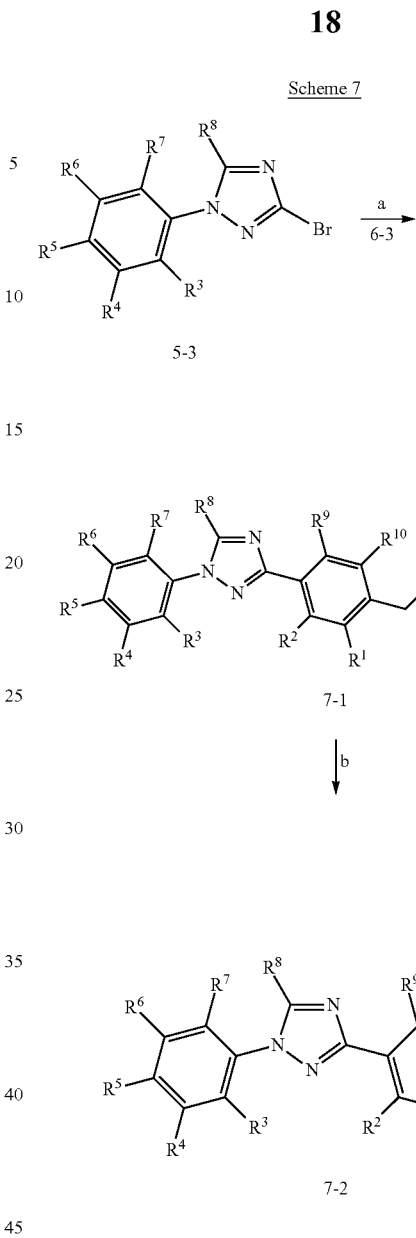

Coupling of the boronate esters 6-3 with a bromo-heterocycles 5-3 may be accomplished using a palladium catalyst and phosphine ligand, in the presence of a base, such as sodium bicarbonate, potassium phosphate, or cesium fluoride, in a suitable solvent system, such as dioxane and water, at temperatures from about 50° C. to about 120° C. to form N-protected aminoalkylphenyl intermediates 7-1, wherein $R^1$, $R^2$, $R^3$, $R^4$, $R^5$, $R^6$, $R^7$, $R^8$, $R^9$, and $R^{10}$ are as previously disclosed (Scheme 7, step 7a). Deprotection of the Cbz group may be accomplished under acidic conditions with a strong acid, such as hydrogen bromide, followed by free basing with a base, such as sodium bicarbonate or sodium hydroxide, to furnish the triaryl amines 7-2, wherein $R^1$, $R^2$, $R^3$, $R^4$, $R^5$, $R^6$, $R^7$, $R^8$, $R^9$, and $R^{10}$ are as previously disclosed (step 7b).

Alternatively, triaryl amines 7-2 may also be prepared as described in Scheme 8. Reduction of triaryl aldehydes 8-1, wherein $R^1$, $R^2$, $R^3$, $R^4$, $R^5$, $R^6$, $R^7$, $R^8$, $R^9$, and $R^{10}$ are as previously disclosed (WO 2009/102736) following procedures outlined in WO 2012/027521 and PCT US 2011/049037 may provide triaryl alcohols 8-2, wherein $R^1$, $R^2$, $R^3$, $R^4$, $R^5$, $R^6$, $R^7$, $R^8$, $R^9$, and $R^{10}$ are as previously disclosed (step 8a). Conversion to the corresponding triaryl azides 8-3, wherein $R^1$, $R^2$, $R^3$, $R^4$, $R^5$, $R^6$, $R^7$, $R^8$, $R^9$, and $R^{10}$ are as previously disclosed may be accomplished by treatment of triaryl alcohols 8-2 with diphenylphosphoryl azide and a base such as 1,8-diazabicyclo[5.4.0]undec-7-ene (step 8b). Reduction of the azide group may be accomplished by treatment with a metal reductant such as palladium on carbon in the presence of hydrogen to furnish triaryl amines 7-2 (step 8c).

Scheme 8

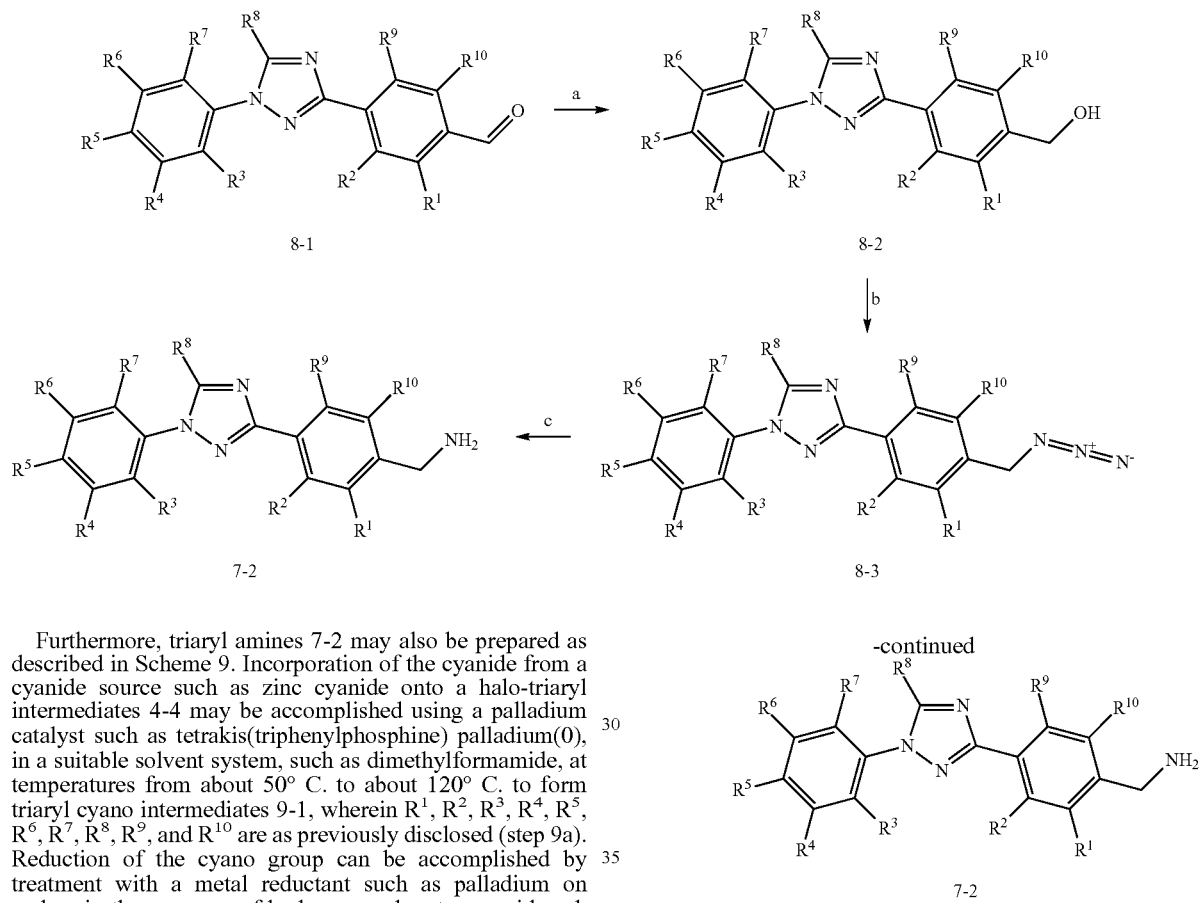

Furthermore, triaryl amines 7-2 may also be prepared as described in Scheme 9. Incorporation of the cyanide from a cyanide source such as zinc cyanide onto a halo-triaryl intermediates 4-4 may be accomplished using a palladium catalyst such as tetrakis(triphenylphosphine) palladium(0), in a suitable solvent system, such as dimethylformamide, at temperatures from about 50° C. to about 120° C. to form triaryl cyano intermediates 9-1, wherein $R^1$, $R^2$, $R^3$, $R^4$, $R^5$, $R^6$, $R^7$, $R^8$, $R^9$, and $R^{10}$ are as previously disclosed (step 9a). Reduction of the cyano group can be accomplished by treatment with a metal reductant such as palladium on carbon in the presence of hydrogen and a strong acid such as hydrogen chloride, followed by free basing of the resultant hydrochloride salt with a base such as sodium bicarbonate or sodium hydroxide, to furnish the triaryl amines 7-2 (step 9b).

Scheme 9

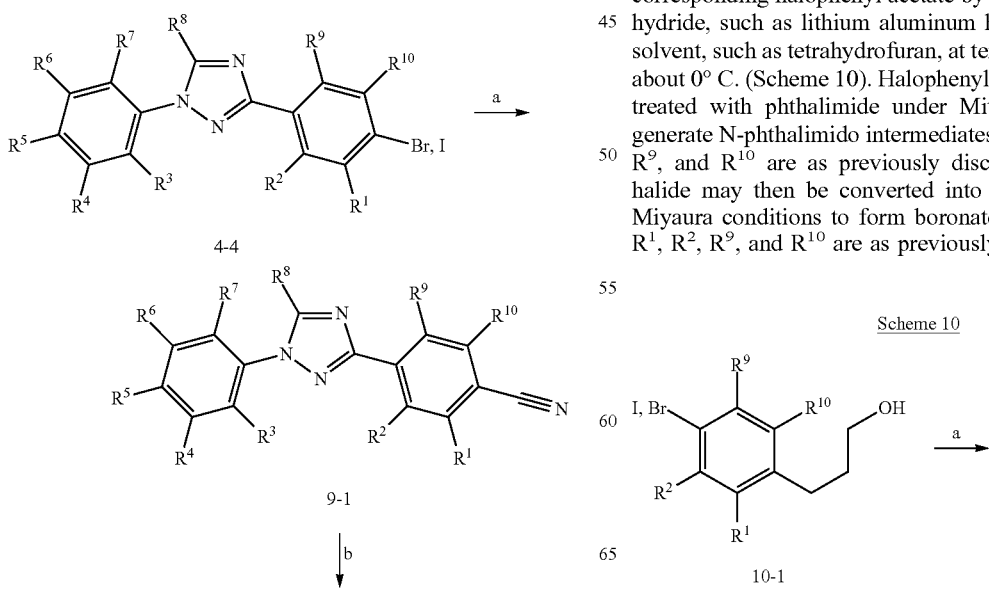

Preparation of 3-Carbon Linked Intermediates

Halophenyl carbinols 10-1, wherein $R^1$, $R^2$, $R^9$, and $R^{10}$ are as previously disclosed, may be prepared from the corresponding halophenyl acetate by reduction with a metal hydride, such as lithium aluminum hydride, in an ethereal solvent, such as tetrahydrofuran, at temperatures at or below about 0° C. (Scheme 10). Halophenyl carbinols 10-1 may be treated with phthalimide under Mitsunobu conditions to generate N-phthalimido intermediates 10-2, wherein $R^1$, $R^2$, $R^9$, and $R^{10}$ are as previously disclosed (step 10a). The halide may then be converted into a boronic ester using Miyaura conditions to form boronate esters 10-3, wherein $R^1$, $R^2$, $R^9$, and $R^{10}$ are as previously disclosed (step 10b).

Scheme 10

21
-continued

22
-continued

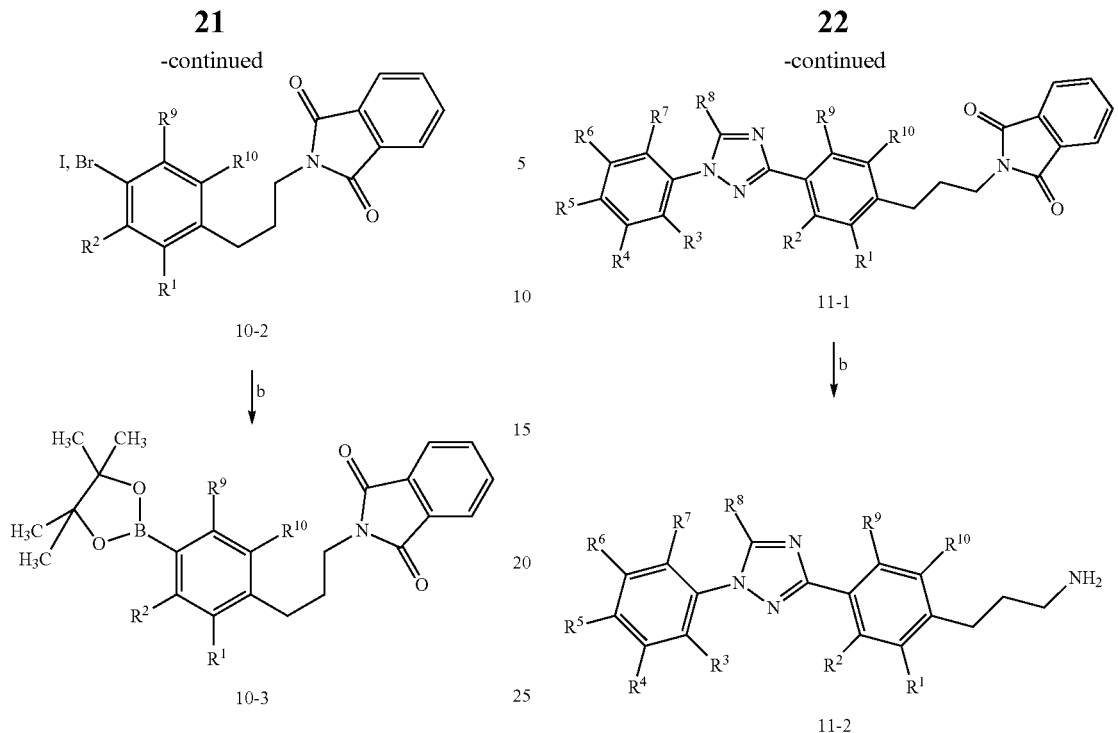

Coupling of the boronate esters 10-3 with a bromo-heterocycles 5-3 may be accomplished using a palladium catalyst, such tetrakis(triphenylphosphine) palladium(0), in the presence of a base, such as sodium bicarbonate, in a suitable solvent system, such as dioxane and water, at temperatures from about 50° C. to about 120° C. to provide N-phthalimido intermediates 11-1, wherein $R^1$, $R^2$, $R^3$, $R^4$, $R^5$, $R^6$, $R^7$, $R^8$, $R^9$, and $R^{10}$ are as previously disclosed (Scheme 11, step 11a). Deprotection of phthalimide using hydrazine and methanol may furnish triaryl amines 11-2, wherein $R^1$, $R^2$, $R^3$, $R^4$, $R^5$, $R^6$, $R^7$, $R^8$, $R^9$, and $R^{10}$ are as previously disclosed (step 11b).

Scheme 11

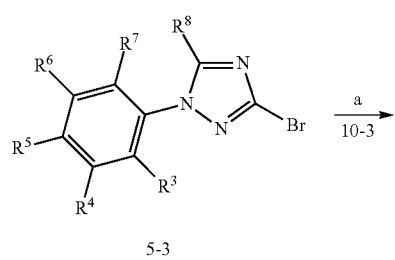

5-3

Alternatively, halo-triaryl intermediates 4-4 may be coupled with a terminal alkynyl alcohol 12-1 in the presence of a palladium catalyst such as bistriphenylphosphine dichloropalladium, copper(I) iodide, and a base such as triethylamine, at temperatures from about 50° C. to about 120° C., to generate the corresponding triaryl-alkynyl carbinols 12-2, wherein $R^1$, $R^2$, $R^3$, $R^4$, $R^5$, $R^6$, $R^7$, $R^8$, $R^9$, and $R^{10}$ are as previously disclosed (Scheme 12, step 12a). Triaryl-alkynyl carbinols 12-2 may be reduced using a transition metal catalyst, such as palladium under an atmosphere of hydrogen to triaryl-alkyl carbinols 12-3, wherein $R^1$, $R^2$, $R^3$, $R^4$, $R^5$, $R^6$, $R^7$, $R^8$, $R^9$, and $R^{10}$ are as previously disclosed (step 12b). The resultant triaryl-alkyl carbinols 12-3, wherein $R^1$, $R^2$, $R^3$, $R^4$, $R^5$, $R^6$, $R^7$, $R^8$, $R^9$, and $R^{10}$ are as previously disclosed, may then be treated with phthalimide under Mitsunobu conditions to generate N-phthalimido intermediates 9-1 (step 12c) which may be converted to triaryl amines 9-2 using hydrazine and methanol (step 12d).

Scheme 12

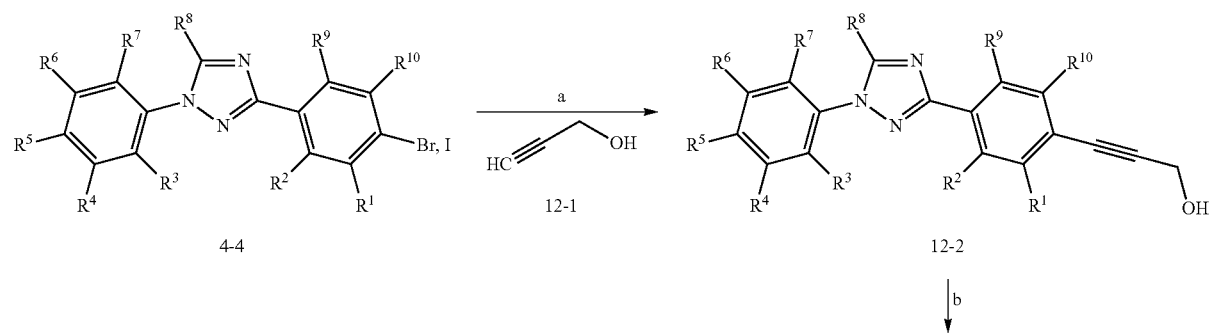

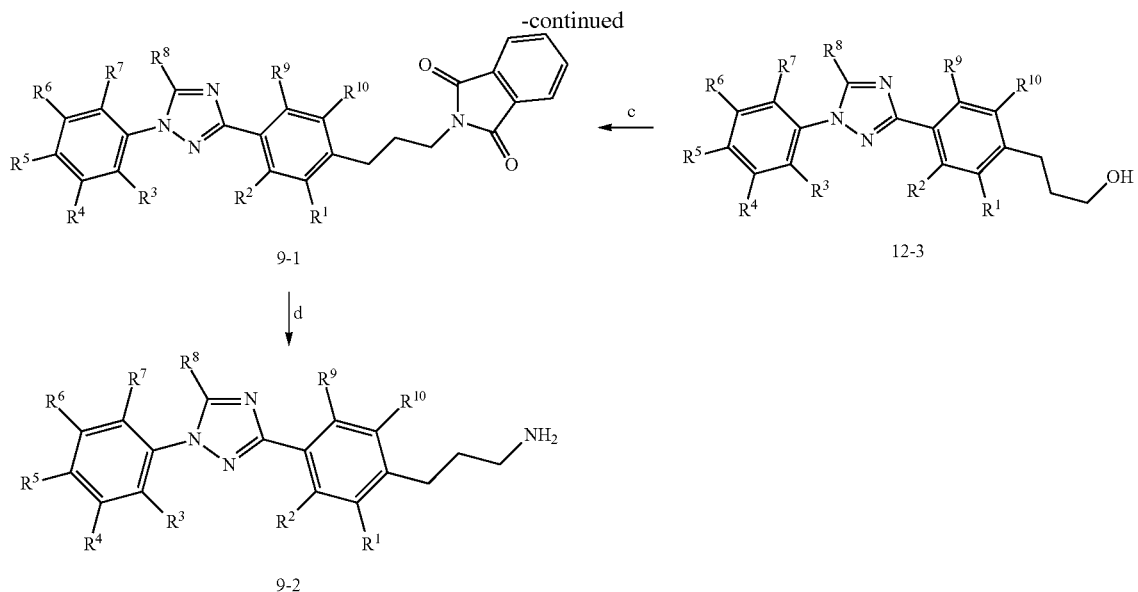

Preparation of 4-Carbon Linked Intermediates

Alternatively, halo-triaryl intermediates 4-4 may be coupled with a terminal alkynyl alcohol 13-1 in the presence of a palladium catalyst such as bistriphenylphosphine dichloropalladium, copper(I) iodide, and a base such as triethylamine, at temperatures from about 50° C. to about 120° C., to generate the corresponding triaryl-alkynyl carbinols 13-2, wherein $R^1$, $R^2$, $R^3$, $R^4$, $R^5$, $R^6$, $R^7$, $R^8$, $R^9$, and $R^{10}$ are as previously disclosed (Scheme 13, step 13a). Triaryl-alkynyl carbinols 13-2 may be reduced using a transition metal catalyst, such as palladium under an atmosphere of hydrogen to triaryl-alkyl carbinols 13-3, wherein $R^1$, $R^2$, $R^3$, $R^4$, $R^5$, $R^6$, $R^7$, $R^8$, $R^9$, and $R^{10}$ are as previously disclosed (step 13b). The resultant triaryl-alkyl carbinols 13-3 may then be treated with phthalimide under Mitsunobu conditions to generate N-phthalimido intermediates 13-4, wherein $R^1$, $R^2$, $R^3$, $R^4$, $R^5$, $R^6$, $R^7$, $R^8$, $R^9$, and $R^{10}$ are as previously disclosed (step 13c), which may be converted to triaryl amines 13-5, wherein $R^1$, $R^2$, $R^3$, $R^4$, $R^5$, $R^6$, $R^7$, $R^6$, $R^9$, and $R^{10}$ are as previously disclosed, using hydrazine and methanol (step 13d).

Scheme 13

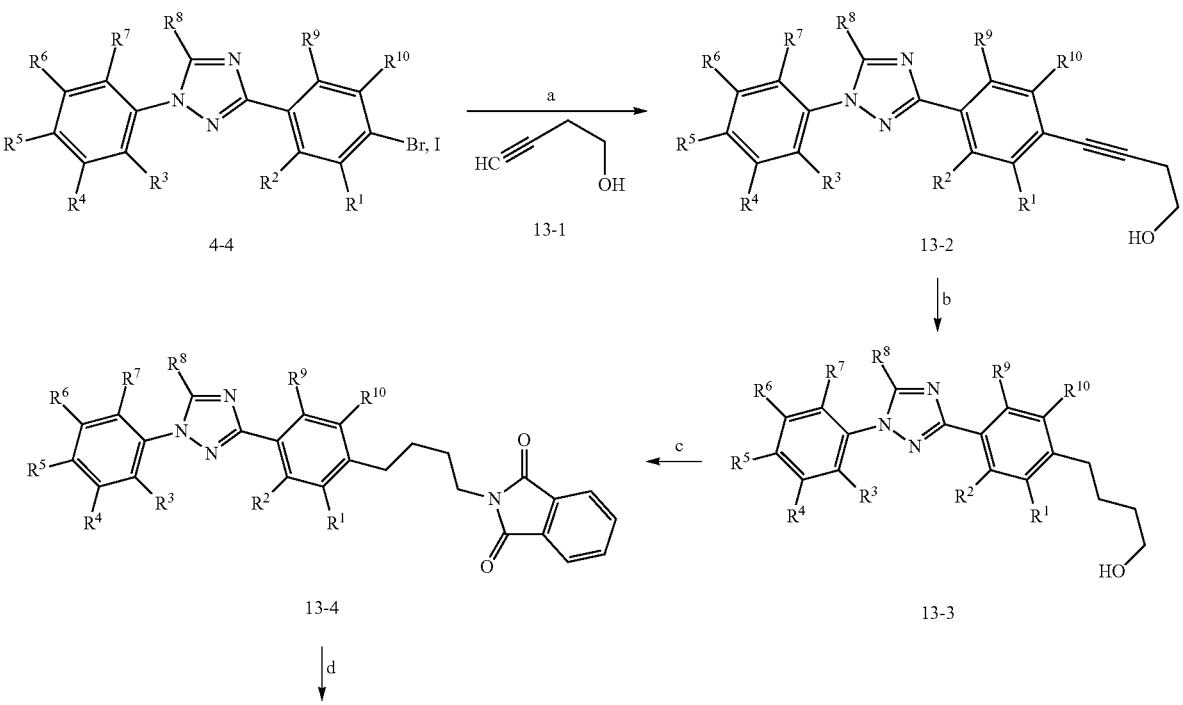

-continued

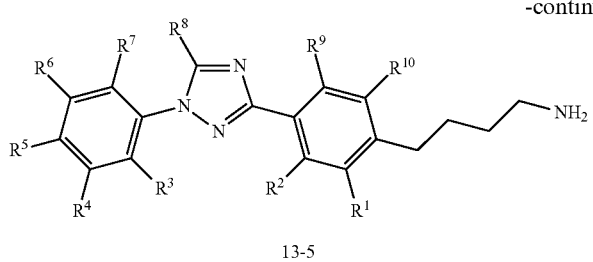

13-5

EXAMPLES

These examples are for illustration purposes and are not to be construed as limiting the disclosure to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Examples using "room temperature" were conducted in climate controlled laboratories with temperatures ranging from about 20° C. to about 24° C. Molecules are given their known names, named according to naming programs within ISIS Draw, ChemDraw or ACD Name Pro. If such programs are unable to name a molecule, the molecule is named using conventional naming rules. $^1$H NMR spectral data are in ppm ($\delta$) and were recorded at 300, 400 or 600 MHz; $^{13}$C NMR spectral data are in ppm ($\delta$) and were recorded at 75, 100 or 150 MHz, and $^{19}$F NMR spectral data are in ppm ($\delta$) and were recorded at 376 MHz, unless otherwise stated.

Example 1

Preparation of 3-bromo-1-(4-(trifluoromethyl)phenyl)-1H-1,2,4-triazole (C1)

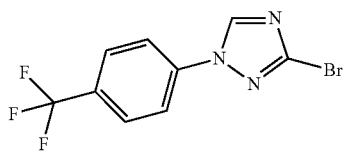 [SMILES: FC(F)(F)c1ccc(-n2cnc(Br)n2)cc1]

3-Bromo-1-(4-isopropoxyphenyl)-1H-1,2,4-triazole (7.15 g, 48.3 mmol), copper(I) iodide (1.25 g, 6.56 mmol), cesium carbonate (18.9 g, 58.0 mmol), and 1-iodo-4-(trifluoromethyl)benzene (8.29 g, 30.5 mmol) were added to dimethylsulfoxide (50 mL) and the solution was degassed with nitrogen for 10 minutes. The solution was heated at 100° C. for 20 hours. After cooling to room temperature, the reaction mixture was diluted with ethyl acetate and filtered through Celite®. The resulting filter cake was rinsed with additional ethyl acetate (100 mL). Saturated aqueous ammonium chloride was added to the filtrate which was then stirred for 30 minutes. The layers were separated and the aqueous layer was extracted with ethyl acetate (2×50 mL). The combined organic extracts were dried over anhydrous magnesium sulfate and concentrated onto Celite®. Purification by silica gel chromatography using 0-100% ethyl acetate/hexanes as eluent provided the title compound as a white solid (5.64 g, 64%): mp 87-89° C.; $^1$H NMR (400 MHz, CDCl$_3$) $\delta$ 8.53 (s, 1H), 7.85-7.77 (m, 4H); ESIMS m/z 292.0 ([M+H]$^+$).

Example 2

Preparation of 4-(1-(4-(trifluoromethyl)phenyl)-1H-1,2,4-triazol-3-yl)aniline (C2)

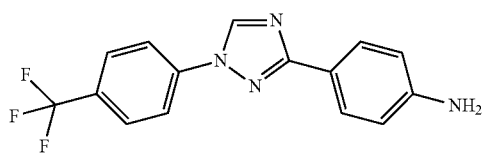 [SMILES: Nc1ccc(-c2ncn(-c3ccc(C(F)(F)F)cc3)n2)cc1]

To 3-bromo-1-(4-(trifluoromethyl)phenyl)-1H-1,2,4-triazole (5.64 g, 18.35 mmol) was added 4-(4,4,5,5-tetramethyl-1,3,2-dioxaborolan-2-yl)aniline (7.42 g, 33.9 mmol), tetrakis(triphenylphosphine) palladium(0) (3.30 g, 2.86 mmol), and potassium carbonate (7.82 g, 56.6 mmol) in 1,2-dimethoxyethane (75 mL) and water (18 mL). The mixture was degassed with nitrogen for 10 minutes. The reaction mixture was heated at 120° C. for 20 h. The reaction was cooled to room temperature and diluted with ethyl acetate (100 mL). The resultant salts were filtered and the filtrated layers were separated. The aqueous layer was separated with ethyl acetate (2×25 mL). The combined organic layers were dried over anhydrous magnesium sulfate and concentrated onto Celite®. Purification by silica gel chromatography using 0-100% ethyl acetate/hexanes as eluent provided the title compound as a yellow solid (4.16 g, 68%): $^1$H NMR (400 MHz, CDCl$_3$) $\delta$ 8.60 (s, 1H), 8.03-7.97 (m, 2H), 7.88 (d, J=8.4 Hz, 2H), 7.77 (d, J=8.5 Hz, 2H), 6.79-6.74 (m, 2H), 3.88 (s, 2H); $^{13}$C NMR (101 MHz, CDCl3) $\delta$ 163.94, 148.07, 139.68, 129.67, 129.34, 128.04, 127.07, 127.04, 127.00, 126.96, 125.05, 120.50, 119.35, 114.87; $^{19}$F NMR (376 MHz, CDCl3) $\delta$ −62.43; ESIMS m/z 305.1 ([M+H]$^+$).

Example 3

Preparation of 1-(2-isopropylphenyl)-3-(4-(1-(4-(trifluoromethyl)phenyl)-1H-1,2,4-triazol-3-yl)phenyl)thiourea (F53)

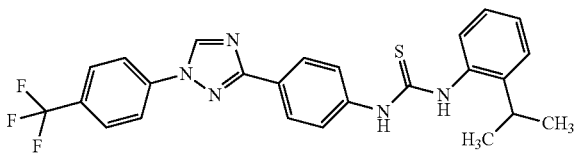 [SMILES: CC(C)c1ccccc1NC(=S)Nc1ccc(-c2ncn(-c3ccc(C(F)(F)F)cc3)n2)cc1]

To 4-(1-(4-(trifluoromethyl)phenyl)-1H-1,2,4-triazol-3-yl)aniline (0.496 g, 1.63 mmol) in a 25 mL vial equipped with a stir bar, Vigreux column, and nitrogen inlet was added tetrahydrofuran (4.08 mL) followed by 1-isopropyl-2-isothiocyanatobenzene (0.826 ml, 4.89 mmol). The reaction was heated to 65° C. overnight. The reaction was cooled to room temperature. The reaction mixture was diluted with dichloromethane and washed with water. The aqueous layer was extracted with dichloromethane (2×). The organic layers were poured through a phase separator and concentrated. Purification by flash column chromatography using 0-20% ethyl acetate/B, where B=1:1 dichloromethane/hexanes as eluent provided a white solid. The solid was dried at 55° C. at about 25 in. Hg providing the title compound as a white solid (0.361 g, 46%).

Example 4

Preparation of 1-(2-propylphenyl)-3-(4-(1-(4-(trifluoromethoxy)phenyl)-1H-1,2,4-triazol-3-yl)phenyl)urea (F37)

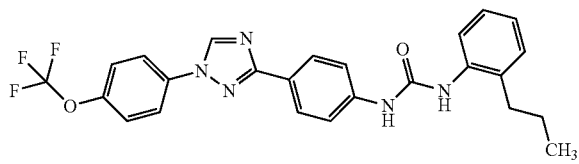 [SMILES: CCCc1ccccc1NC(=O)Nc1ccc(-c2ncn(-c3ccc(OC(F)(F)F)cc3)n2)cc1]

To 4-(1-(4-(trifluoromethoxy)phenyl)-1H-1,2,4-triazol-3-yl)benzoyl azide (Crouse, G. D., et al. PCT Int. Appl., 2013, WO 2013009791 A1 20130117) (0.150 g, 0.401 mmol) in a 25 mL vial equipped with a stir bar and Vigreux column was added 1,2-dichloroethane (2.67 mL). The reaction was heated to reflux until disappearance of azide was observed by liquid chromatography/mass spectrometry (LC/MS). The reaction was cooled and 2-propylaniline (0.0560 mL, 0.401 mmol) was added. The reaction was heated to reflux overnight. The reaction was cooled. The solid was collected, washed with hexanes, and dried at 50° C. at about 25 in. Hg providing the title compound as a white solid (0.148 g, 77%).

The following compounds were prepared according to the procedures disclosed in Example 4:

1-(2-Ethynylphenyl)-3-(4-(1-(4-(trifluoromethoxy)phenyl)-1H-1,2,4-triazol-3-yl)phenyl)urea (F5)

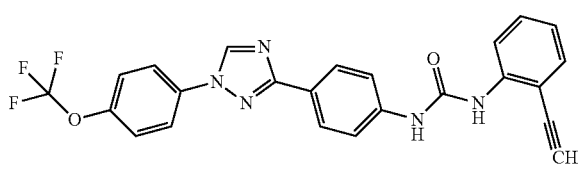 [SMILES: C#Cc1ccccc1NC(=O)Nc1ccc(-c2ncn(-c3ccc(OC(F)(F)F)cc3)n2)cc1]

Isolated as a white solid (0.122 g, 66%).

1-(2-(Tert-butyl)phenyl)-3-(4-(1-(4-(trifluoromethoxy)phenyl)-1H-1,2,4-triazol-3-yl)phenyl)urea (F38)

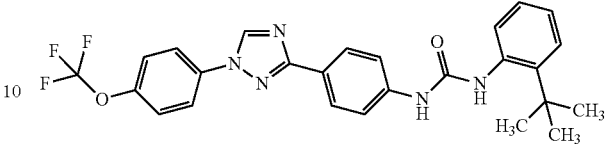

Isolated as a white solid (0.116 g, 58%).

Example 5

Preparation of 1-(2-(4-methylpentan-2-yl)phenyl)-3-(4-(1-(4-(trifluoromethoxy)phenyl)-1H-1,2,4-triazol-3-yl)phenyl)urea (F18)

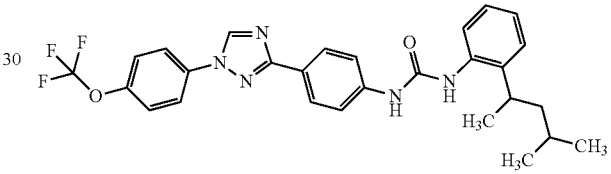

To 4-(1-(4-(trifluoromethoxy)phenyl)-1H-1,2,4-triazol-3-yl)benzoyl azide (0.150 g, 0.401 mmol) in a 25 mL vial equipped with a stir bar and Vigreux column was added 1,2-dichloroethane (2.7 mL). The reaction was heated to reflux until disappearance of azide was observed by LC/MS. The reaction was cooled and 2-(4-methylpentan-2-yl)aniline (DE 10229595) (0.071 g, 0.401 mmol) was added. The reaction was heated to reflux overnight. The reaction was cooled and adsorbed onto Celite®. Purification by flash column chromatography provided the title compound as a white solid (0.151 g, 72%).

The following compounds were prepared according to the procedures disclosed in Example 5:

1-(2-Ethylphenyl)-3-(4-(1-(4-(trifluoromethoxy)phenyl)-1H-1,2,4-triazol-3-yl)phenyl)urea (F46)

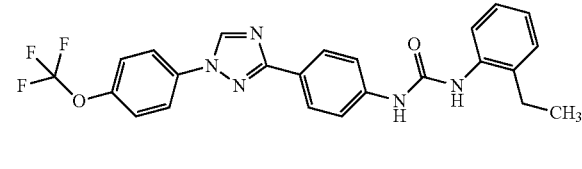 [SMILES: CCc1ccccc1NC(=O)Nc1ccc(-c2ncn(-c3ccc(OC(F)(F)F)cc3)n2)cc1]

Isolated as a white solid (0.155 g, 83%).

1-(2-([1,1'-Bi(cyclopropan)]-2-yl)phenyl)-3-(4-(1-(4-(trifluoromethoxy)phenyl)-1H-1,2,4-triazol-3-yl)phenyl)urea (F49)

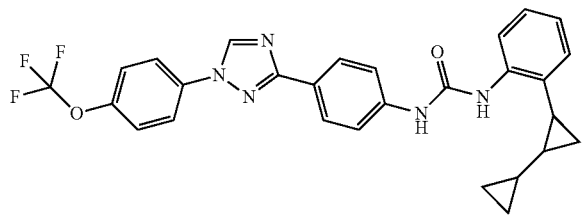 [SMILES: O=C(Nc1ccc(-c2ncn(-c3ccc(OC(F)(F)F)cc3)n2)cc1)Nc1ccccc1C1CC1C1CC1]

Isolated as a white solid (0.101 g, 49%) using 2-([1,1'-bi(cyclopropane)]-2-yl)aniline (WO 2006/061226).

Example 6

Preparation of 1-(4-(1-(4-(trifluoromethoxy)phenyl)-1H-1,2,4-triazol-3-yl)phenyl)-3-(2-(trifluoromethyl)phenyl)urea (F64)

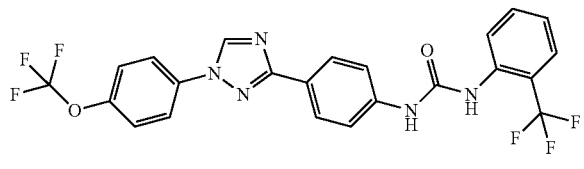 [SMILES: O=C(Nc1ccc(-c2ncn(-c3ccc(OC(F)(F)F)cc3)n2)cc1)Nc1ccccc1C(F)(F)F]

To 4-(1-(4-(trifluoromethoxy)phenyl)-1H-1,2,4-triazol-3-yl)benzoyl azide (0.150 g, 0.401 mmol) in a 25 mL vial equipped with a stir bar and Vigreux column was added 1,2-dichloroethane (2.7 mL). The reaction was heated to reflux until disappearance of azide was observed by LC/MS. The reaction was cooled and 2-(trifluoromethyl) aniline.HCl (0.062 ml, 0.401 mmol) was added. The reaction was heated to reflux overnight. The reaction was cooled. The solid was filtered, washed with dichloromethane and hexanes, and dried providing the title compound as a white solid (0.158 g, 78%).

The following compounds were prepared according to the procedures disclosed in Example 6:

1-(2-(Prop-1-en-2-yl)phenyl)-3-(4-(1-(4-(trifluoromethoxy)phenyl)-1H-1,2,4-triazol-3-yl)phenyl)urea (F61)

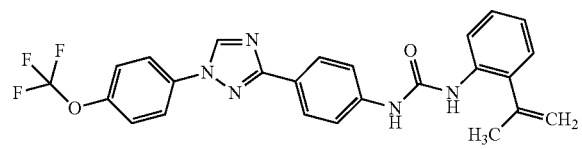 [SMILES: C=C(C)c1ccccc1NC(=O)Nc1ccc(-c2ncn(-c3ccc(OC(F)(F)F)cc3)n2)cc1]

Isolated as a white solid (0.055 g, 29%).

1-(2-(Trifluoromethoxy)phenyl)-3-(4-(1-(4-(trifluoromethoxy)phenyl)-1H-1,2,4-triazol-3-yl)phenyl)urea (F26)

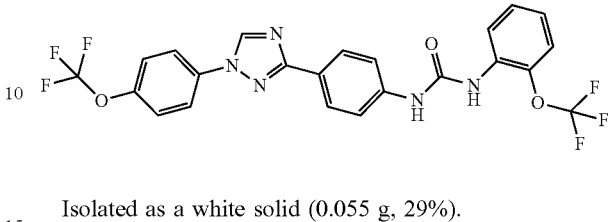

Isolated as a white solid (0.055 g, 29%).

1-(2-Morpholinophenyl)-3-(4-(1-(4-(trifluoromethoxy)phenyl)-1H-1,2,4-triazol-3-yl)phenyl)urea (F69)

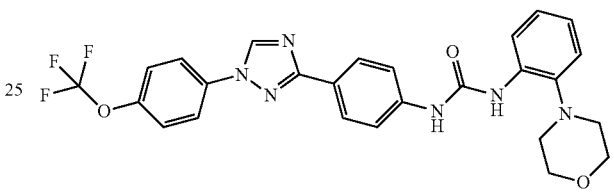

Isolated as a white solid (0.136 g, 65%).

1-(3',4',5'-Trifluoro-[1,1'-biphenyl]-2-yl)-3-(4-(1-(4-(trifluoromethoxy)phenyl)-1H-1,2,4-triazol-3-yl)phenyl)urea (F9)

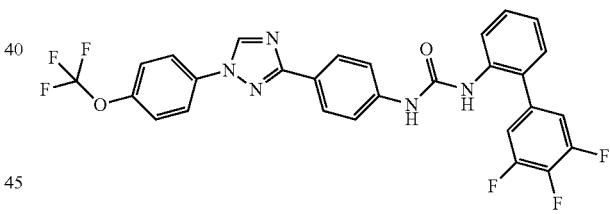

Isolated as a white solid (0.149 g, 65%).

Example 7

Preparation of 1-([1,1'-biphenyl]-2-yl)-3-(4-(1-(4-(perfluoroethoxy)phenyl)-1H-1,2,4-triazol-3-yl)phenyl)urea (F68)

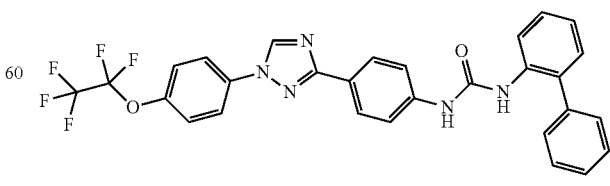

To 4-(1-(4-(perfluoroethoxy)phenyl)-1H-1,2,4-triazol-3-yl)benzoyl azide (WO 2009/102736) (0.150 g, 0.354 mmol)

in a 25 mL vial equipped with a stir bar and Vigreux column was added 1,2-dichloroethane (2.4 mL). The reaction was heated to 85° C. until disappearance of azide was observed by LC/MS. The reaction was cooled and [1,1'-biphenyl]-2-amine (0.060 g, 0.354 mmol) was added. The reaction was heated to 70° C. overnight. The reaction was cooled and concentrated. Purification by flash column chromatography provided the title compound as a white solid (0.178 g, 89%).

The following compounds were prepared according to the procedures disclosed in Example 7:

1-(2-Isopropylphenyl)-3-(4-(1-(4-(perfluoroethoxy)phenyl)-1H-1,2,4-triazol-3-yl)phenyl)urea (F54)

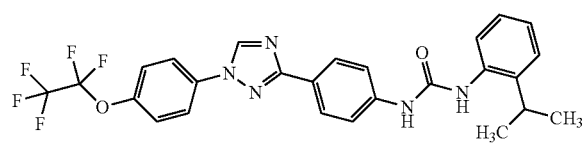 [SMILES: CC(C)c1ccccc1NC(=O)Nc1ccc(-c2ncn(-c3ccc(OC(F)(F)C(F)(F)F)cc3)n2)cc1]

Isolated as a white solid (0.067 g, 36%).

1-(2-Cyclopropylphenyl)-3-(4-(1-(4-(perfluoroethoxy)phenyl)-1H-1,2,4-triazol-3-yl)phenyl)urea (F15)

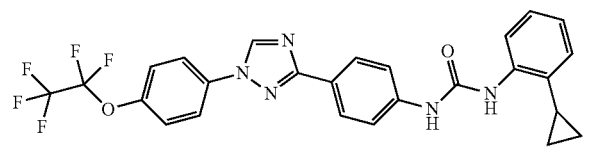 [SMILES: O=C(Nc1ccc(-c2ncn(-c3ccc(OC(F)(F)C(F)(F)F)cc3)n2)cc1)Nc1ccccc1C1CC1]

Isolated as a white solid (0.065 g, 35%).

1-(2-Isopropylphenyl)-3-(4-(1-(4-(trifluoromethoxy)phenyl)-1H-1,2,4-triazol-3-yl)phenyl)urea (F33)

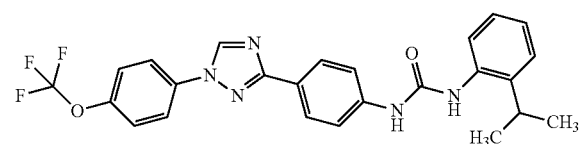

Isolated as a white solid (0.166 g, 86%).

1-(4-(1-(4-(Perfluoroethoxy)phenyl)-1H-1,2,4-triazol-3-yl)phenyl)-3-(2-(trifluoromethoxy)phenyl)urea (F1)

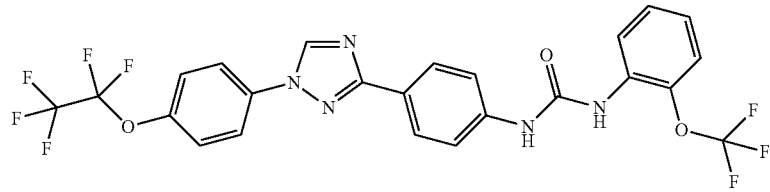 [SMILES: O=C(Nc1ccc(-c2ncn(-c3ccc(OC(F)(F)C(F)(F)F)cc3)n2)cc1)Nc1ccccc1OC(F)(F)F]

Isolated as a white solid (0.163 g, 80%).

1-(2-Isopropyl-5-methylphenyl)-3-(4-(1-(4-(perfluoroethoxy)phenyl)-1H-1,2,4-triazol-3-yl)phenyl)urea (F57)

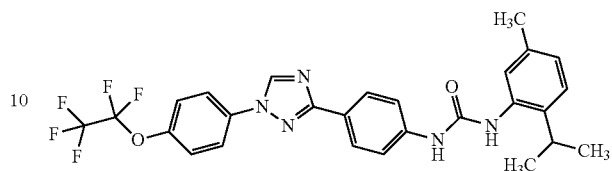

Isolated as a white solid (0.099 g, 51%).

Example 8

Preparation of 1-(3-ethoxyphenyl)-3-(4-(1-(4-(trifluoromethoxy)phenyl)-1H-1,2,4-triazol-3-yl)phenyl)urea (F39)

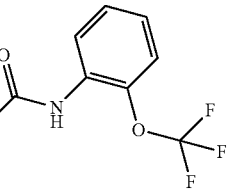

To 4-(1-(4-(trifluoromethoxy)phenyl)-1H-1,2,4-triazol-3-yl)benzoyl azide (0.150 g, 0.401 mmol) in a 25 mL vial equipped with a stir bar and Vigreux column was added 1,2-dichloroethane (2.7 ml). The reaction was heated to reflux until disappearance of azide was observed by LC/MS. The reaction was cooled and triethylamine (0.061 mL, 0.441 mmol) and 3-ethoxyaniline.HCl (0.070 g, 0.401 mmol) were added. The reaction was heated to reflux overnight. The reaction was cooled. The solid was filtered, washed with dichloromethane and hexanes, and dried providing the title compound as a white solid (0.118 g, 61%).

Example 9

Preparation of 2-(3-(4-bromophenyl)propyl)isoindoline-1,3-dione (C3)

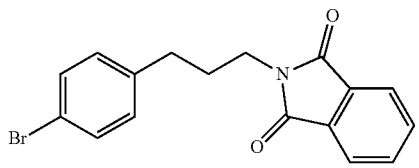 [SMILES: O=C1c2ccccc2C(=O)N1CCCc1ccc(Br)cc1]

To 3-(4-bromophenyl)propan-1-ol (4.70 g, 21.9 mmol), isoindoline-1,3-dione (3.54 g, 24.04 mmol) and triphenylphosphine (6.88 g, 26.2 mmol) in a 500 mL round-bottomed flask equipped with a stir bar, nitrogen, and addition funnel cooled in an ice water bath was added diisopropyl azodicarboxylate (5.10 mL, 26.2 mmol). The reaction was allowed to warm to room temperature over the weekend. The reaction mixture was adsorbed onto Celite®. Purification by flash column chromatography using 5-20% ethyl acetate/hexanes as eluent provided a solid which was dried overnight at 50° C. at about 25 in. Hg providing the title compound as a white solid (6.51 g, 87%): mp 88-90° C.; $^1$H NMR (400 MHz, CDCl$_3$) δ 7.86-7.79 (m, 2H), 7.71 (dd, J=5.5, 3.0 Hz, 2H), 7.38-7.32 (m, 2H), 7.11-7.04 (m, 2H), 3.73 (t, J=7.1 Hz, 2H), 2.68-2.59 (m, 2H), 2.07-1.96 (m, 2H); ESIMS m/z 346 ([M+2]$^+$).

Example 10

Preparation of 2-(3-(4-(4,4,5,5-tetramethyl-1,3,2-dioxaborolan-2-yl)phenyl)propyl)isoindoline-1,3-dione (C4)

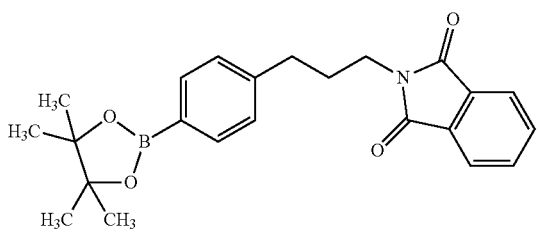 [SMILES: CC1(C)OB(c2ccc(CCCN3C(=O)c4ccccc4C3=O)cc2)OC1(C)C]

To 2-(3-(4-bromophenyl)propyl)isoindoline-1,3-dione (6.46 g, 18.8 mmol), 4,4,4',4',5,5,5',5'-octamethyl-2,2'-bi(1,3,2-dioxaborolane) (7.15 g, 28.2 mmol), [1,1'-bis(diphenylphosphino)ferrocene]dichloropalladium(II) (0.831 g, 1.13 mmol), and 1,1'-bis(diphenylphosphino)ferrocene (0.624 g, 1.13 mmol) in a 200 mL round-bottomed flask equipped with a stir bar and nitrogen was added potassium acetate (5.53 g, 56.3 mmol) followed by dioxane (56.9 mL). The reaction mixture was evacuated and purged with nitrogen. The reaction was heated to 80° C. overnight. The reaction was determined to be complete by LC/MS. The reaction was cooled. The reaction was diluted with ethyl acetate and washed with water. The aqueous layer was extracted with ethyl acetate. The combined organic layers were washed with brine, dried over sodium sulfate, filtered, and concentrated. Purification by flash column chromatography using 5-20% ethyl acetate/hexanes as eluent provided the title compound as a yellow oil (7.41 g, 101% yield): $^1$H NMR (400 MHz, CDCl$_3$) δ 7.82 (dd, J=5.4, 3.0 Hz, 2H), 7.72-7.67 (m, 4H), 7.23-7.17 (m, 2H), 3.74 (t, J=7.2 Hz, 2H), 2.75-2.65 (m, 2H), 2.08-1.97 (m, 2H), 1.33 (s, 12H); $^{13}$C NMR (101 MHz, CDCl$_3$) δ 168.38, 144.40, 134.93, 133.84, 132.09, 127.73, 123.17, 83.62, 60.40, 37.81, 33.42, 29.71, 24.85; ESIMS m/z 392 ([M+H]$^+$).

Example 11

Preparation of 2-(3-(4-(1-(4-(trifluoromethoxy)phenyl)-1H-1,2,4-triazol-3-yl)phenyl)propyl)isoindoline-1,3-dione (C5)

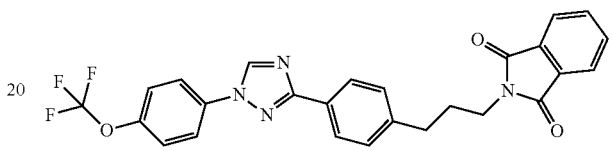

3-Bromo-1-(4-(trifluoromethoxy)phenyl)-1H-1,2,4-triazole (0.50 g, 1.6 mmol), 2-(3-(4-(4,4,5,5-tetramethyl-1,3,2-dioxaborolan-2-yl)phenyl)propyl)isoindoline-1,3-dione (0.64 g, 1.6 mmol), sodium bicarbonate (0.27 g, 3.3 mmol), and tetrakis(triphenylphosphine) palladium(0) (0.19 g, 0.16 mmol) in dioxane (12 mL) and water (4.1 mL) was capped in a 10-20 mL vial and heated on a Biotage Initiator® microwave reactor for 30 minutes at 140° C., with external IR-sensor temperature monitoring from the side of the vessel. The mixture was diluted with ethyl acetate and washed with water. The aqueous layer was extracted with ethyl acetate. The combined organic layers were washed with brine, dried over sodium sulfate, filtered, and concentrated. Purification by flash column chromatography using 0-30% ethyl acetate/B, where B=1:1 dichloromethane/hexanes provided a solid which was dried under house vacuum overnight providing the title compound as a white solid (0.42 g, 53% yield): mp 145-148° C.; $^1$H NMR (400 MHz, CDCl$_3$) δ 8.54 (d, J=0.8 Hz, 1H), 8.08 (d, J=8.1 Hz, 2H), 7.84 (ddd, J=5.5, 3.0, 0.8 Hz, 2H), 7.82-7.77 (m, 2H), 7.69 (ddd, J=5.5, 3.0, 0.8 Hz, 2H), 7.38 (dt, J=9.0, 1.0 Hz, 2H), 7.31 (d, J=8.0 Hz, 2H), 3.78 (t, J=7.2 Hz, 2H), 2.79-2.71 (m, 2H), 2.08 (p, J=7.5 Hz, 2H); $^{19}$F NMR (376 MHz, CDCl$_3$) δ −58.03; ESIMS m/z 493 ([M+H]$^+$).

Example 12

Preparation of 3-(4-(1-(4-(trifluoromethoxy)phenyl)-1H-1,2,4-triazol-3-yl)phenyl)propan-1-amine (C6)

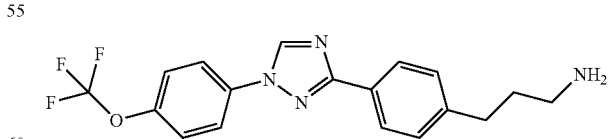

To 2-(3-(4-(1-(4-(trifluoromethoxy)phenyl)-1H-1,2,4-triazol-3-yl)phenyl) propyl)isoindoline-1,3-dione (0.373 g, 0.758 mmol) in a 25 mL vial equipped with a stir bar, Vigreux column, and nitrogen was added methanol (7.6 mL) followed by hydrazine monohydrate (0.110 mL, 2.27 mmol). The reaction was heated to 50° C. The reaction mixture was cooled to room temperature and diluted with dichloromethane. The layers were separated and the aqueous layer was extracted with dichloromethane (2×). The organic layers were washed with sodium hydroxide (1 N, 4×), poured through a phase separator and concentrated. The off-white solid was dried over the weekend at 50° C. at about 25 in. Hg providing the title compound as an off-white solid (0.262 g, 95%): $^1$H NMR (400 MHz, DMSO-$d_6$) δ 9.38 (s, 1H), 8.10-8.04 (m, 2H), 8.04-7.98 (m, 2H), 7.66-7.59 (m, 2H), 7.35 (d, J=8.1 Hz, 2H), 2.69-2.63 (m, 2H), 2.56 (t, J=6.9 Hz, 2H), 1.74-1.59 (m, 2H), NH$_2$ not observed; $^{19}$F NMR (376 MHz, DMSO-$d_6$) δ −56.96; ESIMS m/z 363 ([M+H]$^+$).

Example 13

Preparation of 4-methyl-2-nitro-1-(prop-1-en-2-yl)benzene (C7)

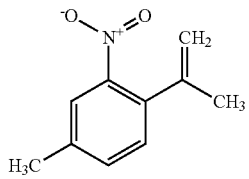

1-Chloro-4-methyl-2-nitrobenzene (0.771 mL, 5.83 mmol), 4,4,5,5-tetramethyl-2-(prop-1-en-2-yl)-1,3,2-dioxaborolane (1.32 mL, 6.99 mmol), bis(triphenyl phosphine)palladium(II) chloride (0.327 g, 0.466 mmol), sodium carbonate (0.741 g, 6.99 mmol) in water (2.9 mL) and dioxane (11.4 mL) was capped in two separate 10-20 mL vials and heated on a Biotage Initiator® microwave reactor for 30 minutes at 140° C., with external IR-sensor temperature monitoring from the side of the vessel. The contents of the two vials were combined and diluted with ethyl acetate and washed with water. The aqueous layer was extracted with ethyl acetate (2×). The combined organic layers were dried over magnesium sulfate, filtered, and concentrated. Purification by flash column chromatography using 1-5% ethyl acetate/hexanes provided the title compound as a yellow oil (0.986 g, 95%): IR (thin film) 3084 (w), 2976 (m), 2919 (w), 1641 (w), 1560 (w), 1526 (vs), 1349 (s) cm$^{-1}$; $^1$H NMR (400 MHz, CDCl$_3$) δ 7.68-7.65 (m, 1H), 7.37-7.32 (m, 1H), 7.21 (d, J=7.9 Hz, 1H), 5.15 (p, J=1.5 Hz, 1H), 4.91 (p, J=1.0 Hz, 1H), 2.42 (s, 3H), 2.06 (t, J=1.2 Hz, 3H); $^{13}$C NMR (101 MHz, CDCl$_3$) δ 148.06, 142.71, 138.30, 136.15, 133.38, 130.32, 124.29, 115.17, 23.32, 20.81.

Example 14

Preparation of 2-isopropyl-5-methylaniline (C8)

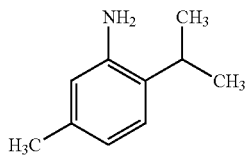

To 4-methyl-2-nitro-1-(prop-1-en-2-yl)benzene (0.986 g, 5.56 mmol) in a 100 mL round-bottomed flask equipped with a stir bar was added ethyl acetate (55.6 mL) and palladium on carbon (1.18 g, 0.556 mmol). The reaction was evacuated and backfilled with hydrogen (balloon). The reaction was stirred under an atmosphere of hydrogen overnight. The reaction mixture was filtered through a pad of Celite® and concentrated providing the title compound as a clear and colorless oil (0.788 g, 95%): IR (thin film) 3464 (m), 3372 (m), 3011 (m), 2959 (s), 2869 (m), 1621 (m), 1575 (m), 1509 (m) cm$^{-1}$; $^1$H NMR (400 MHz, CDCl$_3$) δ 7.03 (d, J=7.8 Hz, 1H), 6.61 (dd, J=7.8, 1.7 Hz, 1H), 6.54-6.50 (m, 1H), 3.59 (bs, 2H), 2.87 (hept, J=6.8 Hz, 1H), 2.24 (s, 3H), 1.24 (d, J=6.8 Hz, 6H); $^{13}$C NMR (101 MHz, CDCl$_3$) δ 143.14, 136.16, 129.82, 125.33, 119.79, 116.55, 99.97, 27.36, 22.41, 20.96.

Example 15

Preparation of 1-isopropyl-2-isothiocyanato-4-methylbenzene (C9)

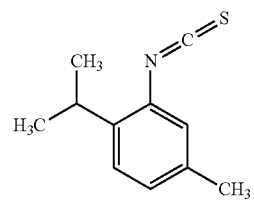

To 2-isopropyl-5-methylaniline (1.0 g, 6.7 mmol) in a 25 mL vial equipped with a stir bar, Vigreux column, and nitrogen was added carbon disulfide (3.0 mL, 50 mmol). The reaction was heated to 40° C. and cooled immediately. To this solution was added triethylamine (0.93 mL, 6.7 mmol). The reaction was heated to 50° C. for 90 minutes and cooled to room temperature overnight. The reaction mixture was transferred to a 100 mL round-bottomed flask and concentrated. The residue was taken up in acetonitrile (33.5 mL) and treated with N,N'-diisopropylcarbodiimide (1.04 mL, 6.70 mmol). The reaction was stopped after a few h and concentrated. Purification by flash column chromatography using 2.5-5% ethyl acetate/hexanes as eluent provided a mixture of products. Re-purification by reversed phase column chromatography using 5-100% acetonitrile/water as eluent provided the title compound (65% in dichloromethane, 0.62 g, 31%), which was used without further purification: IR (thin film) 2963 (m), 2924 (m), 2869 (w), 2089 (vs), 1611 (w), 1501 (m) cm$^{-1}$; $^1$H NMR (300 MHz, CDCl$_3$) δ 7.16 (d, J=8.6 Hz, 1H), 7.09-7.03 (m, 2H), 3.19 (h, J=6.8 Hz, 1H), 2.30 (s, 3H), 1.24 (d, J=6.9 Hz, 6H); $^{13}$C NMR (101 MHz, CDCl$_3$) δ 141.50, 136.70, 134.59, 128.84, 128.58, 127.12, 126.05, 29.20, 22.83, 20.62.

Example 16

Preparation of 1-(2-isopropyl-5-methylphenyl)-3-(3-(4-(1-(4-(trifluoromethoxy)phenyl)-1H-1,2,4-triazol-3-yl)phenyl)propyl)thiourea (F29)

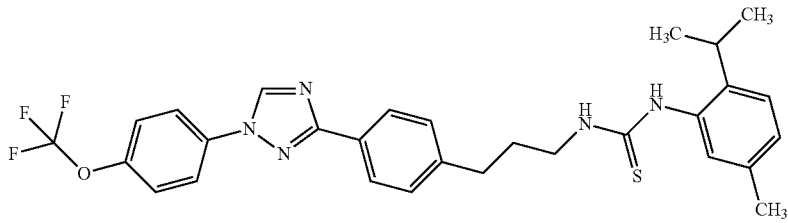

To 3-(4-(1-(4-(trifluoromethoxy)phenyl)-1H-1,2,4-triazol-3-yl)phenyl)propan-1-amine (0.160 g, 0.442 mmol) in a 25 mL vial equipped with a stir bar was added 1-isopropyl-2-isothiocyanato-4-methylbenzene (65% in dichloromethane, 0.156 g, 0.530 mmol) in dichloromethane (6.31 ml) followed by triethylamine (0.062 ml, 0.442 mmol). The reaction was stirred overnight at room temperature. The reaction mixture was diluted with ethyl acetate and adsorbed onto Celite®. Purification by flash column chromatography using 2.5-40% ethyl acetate/B, where B=1:1 dichloromethane/hexanes as eluent provided a white solid. The solid was dried overnight at 50° C. at about 25 in. Hg providing the title compound as a white solid (0.172 g, 70%).

Example 17

Preparation of N-(4-(1-(4-(trifluoromethoxy)phenyl)-1H-1,2,4-triazol-3-yl)phenyl)acetamide (C10)

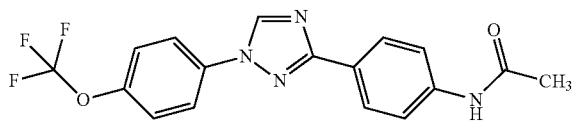 [SMILES: CC(=O)Nc1ccc(-c2ncn(-c3ccc(OC(F)(F)F)cc3)n2)cc1]

To a stirred solution containing 4-(1-(4-(trifluoromethoxy)phenyl)-1H-1,2,4-triazol-3-yl)aniline (WO 2009/102736) (0.272 g, 0.849 mmol) and pyridine (0.137 mL, 1.90 mmol) dissolved in dichloromethane (2.1 mL) at 0° C. was added acetyl chloride (0.079 mL, 1.10 mmol) dropwise. The reaction was warmed to room temperature and stirred for 1 hour. The solution was diluted with dichloromethane (20 mL) and washed successively with hydrogen chloride (1 N, 1×15 mL), saturated aqueous sodium bicarbonate (1×15 mL) and saturated sodium chloride solution (15 mL). The organic layer was dried over magnesium sulfate, filtered, and concentrated to afford the title compound (0.291 g, 95%): mp 169-171° C.; $^1$H NMR (400 MHz, CDCl$_3$) δ 8.55 (s, 1H), 8.15 (d, J=8.7 Hz, 2H), 7.80 (d, J=9.1 Hz, 2H), 7.63 (d, J=8.6 Hz, 2H), 7.39 (d, J=9.0 Hz, 2H), 7.28 (s, 1H), 2.22 (s, 3H). ESIMS m/z 362 ([M+H]$^+$).

Example 18

Preparation of N-(m-tolylcarbamothioyl)-N-(4-(1-(4-(trifluoromethoxy)phenyl)-1H-1,2,4-triazol-3-yl)phenyl)acetamide (F67)

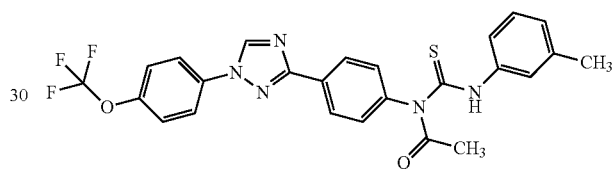

To N-(4-(1-(4-(trifluoromethoxy)phenyl)-1H-1,2,4-triazol-3-yl)phenyl)acetamide in tetrahydrofuran (1.1 mL) cooled to −78° C. was added n-butyllithium (2.5 M, 0.13 mL). The reaction was stirred for 1 hour. 1-Isothiocyanato-3-methylbenzene was added and the solution was slowly warmed to 0° C. over 1 hour. The mixture was quenched with aqueous ammonium chloride and extracted with ethyl acetate. The organic layer was dried over magnesium sulfate, filtered, and concentrated. The residue was purified via radial chromatography using a 97:3 chloroform/methanol mixture as eluent providing the title compound as a tan solid (0.062 g, 55%).

Example 19

Preparation of N-(2-methylphenyl)-N-(4-{1-[4-(trifluoromethoxy)phenyl]-1H-1,2,4-triazol-3-yl}phenyl)dicarbonimidothioic diamide (F19)

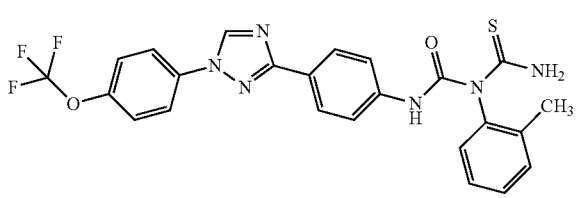 [SMILES: Cc1ccccc1N(C(=O)Nc1ccc(-c2ncn(-c3ccc(OC(F)(F)F)cc3)n2)cc1)C(N)=S]

4-(1-(4-(Trifluoromethoxy)phenyl)-1H-1,2,4-triazol-3-yl)benzoyl azide (0.255 g, 0.680 mmol) was dissolved in anhydrous toluene (4 mL) and heated at 110° C. for 2 hours. The reaction was cooled to room temperature and 1-(o-tolyl)

thiourea (0.113 g, 0.680 mmol) was added. The reaction was stirred at room temperature for 2 hours, then diluted with water and extracted with ethyl acetate (2×). The combined organic layers were dried over sodium sulfate, filtered, and concentrated. The residue was loaded onto a Celite® cartridge with methanol, and the cartridge was dried in a vacuum oven overnight. Purification by flash column chromatography using 2.5-40% ethyl acetate/B, where B=1:1 dichloromethane/hexanes as eluent provided a white solid. Purification by reverse-phase flash chromatography using 0-100% acetonitrile/water as eluent followed by normal phase flash chromatography using 0-30% ethyl acetate/dichloromethane as eluent provided the title compound as a white solid (0.0265 g, 8%).

The following compounds were prepared according to the procedures disclosed in Example 19:

N-[2-(Propan-2-yl)phenyl]-N-(4-{1-[4-(trifluoromethoxy)phenyl]-1H-1,2,4-triazol-3-yl}phenyl)dicarbonimidothioic diamide (F6)

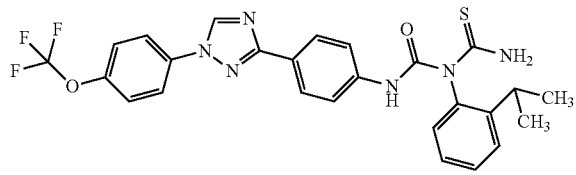 [SMILES: CC(C)c1ccccc1N(C(=O)Nc1ccc(-c2ncn(-c3ccc(OC(F)(F)F)cc3)n2)cc1)C(N)=S]

Isolated as a white solid (0.161 g, 52%).

N-(2-Ethylphenyl)-N-(4-{1-[4-(trifluoromethoxy)phenyl]-1H-1,2,4-triazol-3-yl}phenyl)dicarbonimidothioic diamide (F52)

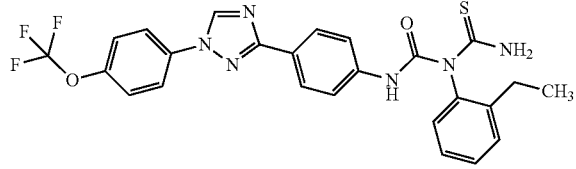 [SMILES: CCc1ccccc1N(C(=O)Nc1ccc(-c2ncn(-c3ccc(OC(F)(F)F)cc3)n2)cc1)C(N)=S]

Isolated as a white solid (0.050 g, 20%).

Example 20

Preparation of 1-(2-(1H-pyrrol-1-yl)phenyl)-3-(4-(1-(4-(trifluoromethoxy)phenyl)-1H-1,2,4-triazol-3-yl)phenyl)urea (F13)

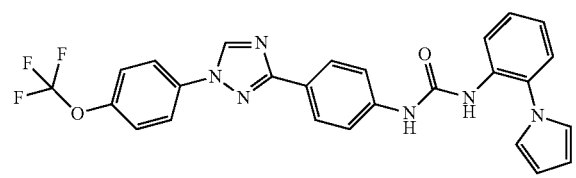 [SMILES: O=C(Nc1ccc(-c2ncn(-c3ccc(OC(F)(F)F)cc3)n2)cc1)Nc1ccccc1-n1cccc1]

4-(1-(4-(Trifluoromethoxy)phenyl)-1H-1,2,4-triazol-3-yl)benzoyl azide (0.086 g, 0.23 mmol) in isopropanol (1.1 mL) was heated at 80° C. for 2 hours. The reaction was cooled to room temperature and 2-(1H-pyrrol-1-yl)aniline (0.040 g, 0.25 mmol) and cesium carbonate (0.12 g, 0.36 mmol) were added. The reaction was stirred overnight at room temperature. The reaction was diluted with water and extracted with ethyl acetate. The organic layers were dried over sodium sulfate, filtered and concentrated. The residue was loaded onto Celite® cartridge and purified by flash chromatography using 0-100% ethyl acetate/B, where B=1:1 dichloromethane/hexanes as eluent to provide the title compound as a white solid (0.010 g, 9%).

The following compounds were prepared according to the procedures disclosed in Example 20:

1-(2-Benzylphenyl)-3-(4-(1-(4-(trifluoromethoxy)phenyl)-1H-1,2,4-triazol-3-yl)phenyl)urea (F51)

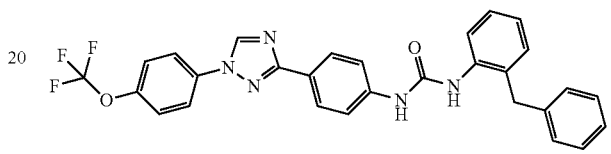

Isolated as a white solid (0.042 mg, 35%).

1-(2-(Furan-2-yl)phenyl)-3-(4-(1-(4-(trifluoromethoxy)phenyl)-1H-1,2,4-triazol-3-yl)phenyl)urea (F21)

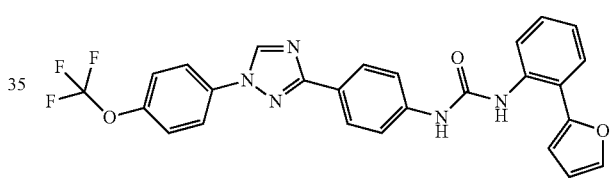

Isolated as an orange solid (0.0475 g, 28%).

1-(2-(4-Isopropyl-4H-1,2,4-triazol-3-yl)phenyl)-3-(4-(1-(4-(trifluoromethoxy)phenyl)-1H-1,2,4-triazol-3-yl)phenyl)urea (F55)

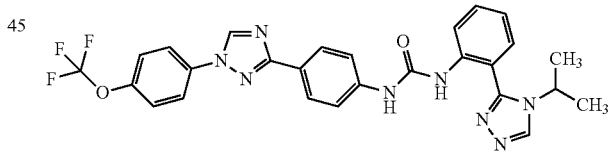

Isolated as a white solid (0.0515 g, 31%).

Example 21

Preparation of 1-(2-(4-isopropyl-4H-1,2,4-triazol-3-yl)phenyl)-3-(4-(1-(4-(trifluoromethoxy)phenyl)-1H-1,2,4-triazol-3-yl)phenyl)thiourea (F48)

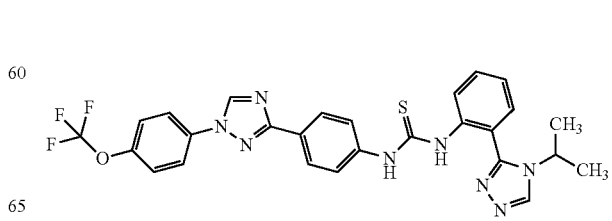

3-(4-Isothiocyanatophenyl)-1-(4-(trifluoromethoxy)phenyl)-1H-1,2,4-triazole (WO 2011/017513) (0.088 g, 0.24 mmol), 2-(4-isopropyl-4H-1,2,4-triazol-3-yl)aniline (0.080 g, 0.40 mmol), and cesium carbonate (0.16 g, 0.50 mmol) in isopropyl alcohol (1.2 mL) was stirred at room temperature overnight. The reaction was diluted with water and extracted with ethyl acetate. The organic layers were dried over sodium sulfate, filtered and concentrated. The residue was loaded onto Celite® cartridge and purified by flash chromatography using 0-100% ethyl acetate/B, where B=1:1 dichloromethane/hexanes as eluent to provide the title compound as a yellow solid (0.028 g, 20%).

The following compounds were prepared according to the procedures disclosed in Example 21:

1-(2-Benzylphenyl)-3-(4-(1-(4-(trifluoromethoxy)phenyl)-1H-1,2,4-triazol-3-yl)phenyl)thiourea (F58)

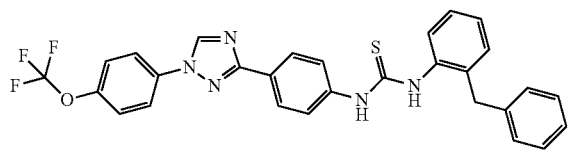

Isolated as a white solid (0.172 mg, 46%).

1-(2-(Furan-2-yl)phenyl)-3-(4-(1-(4-(trifluoromethoxy)phenyl)-1H-1,2,4-triazol-3-yl)phenyl)thiourea (F30)

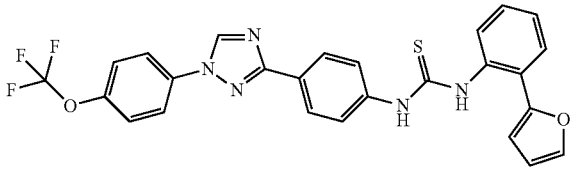 [SMILES: FC(F)(F)Oc1ccc(-n2cnc(-c3ccc(NC(=S)Nc4ccccc4-c4ccco4)cc3)n2)cc1]

Isolated as an off-white solid (0.175 g, 81%).

1-(2-(1,3,4-Oxadiazol-2-yl)phenyl)-3-(4-(1-(4-(trifluoromethoxy)phenyl)-1H-1,2,4-triazol-3-yl)phenyl)thiourea (F44)

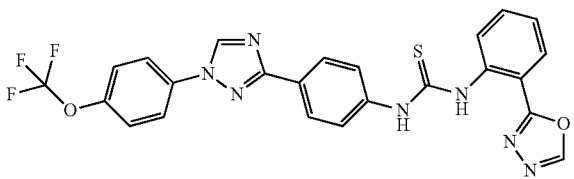 [SMILES: FC(F)(F)Oc1ccc(-n2cnc(-c3ccc(NC(=S)Nc4ccccc4-c4nnco4)cc3)n2)cc1]

Isolated as a white solid (0.225 g, 32%).

1-(2-(5-Cyclopropyl-1,2,4-oxadiazol-3-yl)phenyl)-3-(4-(1-(4-(trifluoromethoxy)phenyl)-1H-1,2,4-triazol-3-yl)phenyl)thiourea (F23)

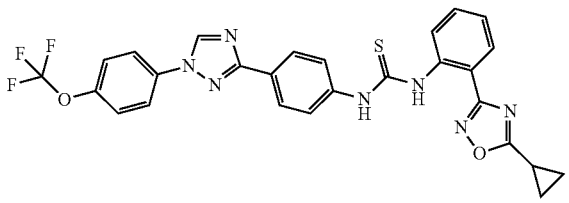 [SMILES: FC(F)(F)Oc1ccc(-n2cnc(-c3ccc(NC(=S)Nc4ccccc4-c4noc(C5CC5)n4)cc3)n2)cc1]

Isolated as a pale yellow solid (0.055 g, 14%).

1-(2-(1H-Pyrrol-1-yl)phenyl)-3-(4-(1-(4-(trifluoromethoxy)phenyl)-1H-1,2,4-triazol-3-yl)phenyl)thiourea (F74)

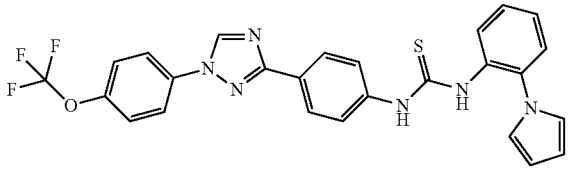 [SMILES: FC(F)(F)Oc1ccc(-n2cnc(-c3ccc(NC(=S)Nc4ccccc4-n4cccc4)cc3)n2)cc1]

Isolated as a white solid (0.012 g, 3%).

1-(2-(2,5-Dimethyl-1H-pyrrol-1-yl)phenyl)-3-(4-(1-(4-(trifluoromethoxy)phenyl)-1H-1,2,4-triazol-3-yl)phenyl)thiourea (F75)

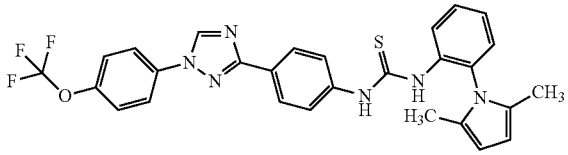 [SMILES: Cc1ccc(C)n1-c1ccccc1NC(=S)Nc1ccc(-c2ncn(-c3ccc(OC(F)(F)F)cc3)n2)cc1]

Isolated as an off-white solid (0.120 g, 32%).

Example 22

Preparation of O-phenyl(4-(1-(4-(trifluoromethoxy)phenyl)-1H-1,2,4-triazol-3-yl)phenyl)carbamothioate (C11)

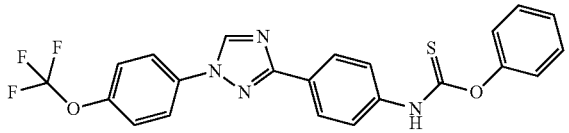 [SMILES: FC(F)(F)Oc1ccc(-n2cnc(-c3ccc(NC(=S)Oc4ccccc4)cc3)n2)cc1]

To a 250 mL three-necked round bottomed flask fitted with a magnetic stirrer, 4-(1-(4-(trifluoromethoxy)phenyl)-1H-1,2,4-triazol-3-yl)aniline (Brown, A.; et al. PCT Int. Appl., 2011, WO 2011017504 A1, 5.00 g, 14.4 mmol) (5.00 g, 15.6 mmol) in toluene (50 mL) was added pyridine (1.47 mL, 15.6 mmol) and O-phenyl chlorothionoformate (2.60 g, 15.6 mmol), stirred under nitrogen for 2 hours. The resulting reaction mixture was cooled to room temperature. The precipitated solid was filtered and washed with hydrogen chloride (0.5 M) to yield the title compound as an off white solid (6.00 g, 84%): mp 177-182° C.; $^1$H NMR (400 MHz, DMSO-d$_6$) δ 11.89 (d, J=99.6 Hz, 1H), 9.41 (s, 1H), 8.12 (s, 4H), 7.97 (s, 1H), 7.63 (d, J=5.8 Hz, 3H), 7.46 (t, J=7.4 Hz, 2H), 7.32 (s, 1H), 7.21 (d, J=8.0 Hz, 2H); ESIMS m/z 458 ([M+H]$^+$).

Example 23

Preparation of 1-(2-cyclopropylphenyl)-3-(4-(1-(4-(trifluoromethoxy)phenyl)-1H-1,2,4-triazol-3-yl)phenyl)urea (F40)

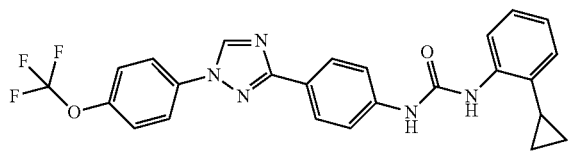 [SMILES: O=C(Nc1ccc(-c2ncn(-c3ccc(OC(F)(F)F)cc3)n2)cc1)Nc1ccccc1C1CC1]

To a round bottomed flask was added 4-(1-(4-(trifluoromethoxy)phenyl)-1H-1,2,4-triazol-3-yl)benzoyl azide (0.200 g, 0.534 mmol). The flask was evacuated and back-filled with nitrogen, and then toluene (5.3 mL) was added. The reaction mixture was heated to 100° C. for 1 hour. The reaction was then cooled to room temperature, and 2-cyclopropylaniline (0.0712 g, 0.534 mmol) was added. The reaction mixture was stirred for an additional 1 hour. Water and ethyl acetate were added. The organics were separated and concentrated onto silica gel. Purification via flash chromatography using ethyl acetate/hexanes as eluent provided the title compound as a white solid (0.113 g, 44%).

Example 24

Preparation of 1-(2'-isopropyl-[1,1'-biphenyl]-2-yl)-3-(4-(1-(4-(trifluoromethoxy)phenyl)-1H-1,2,4-triazol-3-yl)phenyl)thiourea (F28)

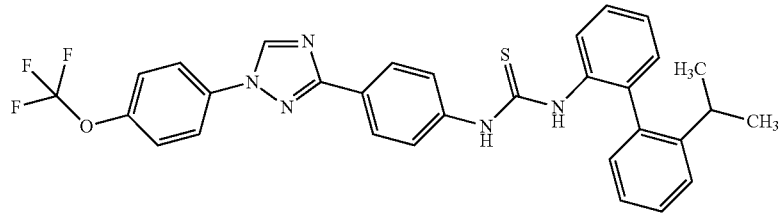 [SMILES: CC(C)c1ccccc1-c1ccccc1NC(=S)Nc1ccc(-c2ncn(-c3ccc(OC(F)(F)F)cc3)n2)cc1]

To a 50 mL three-necked round bottomed flask equipped with condenser and nitrogen inlet was charged with 2'-isopropyl-[1,1'-biphenyl]-2-amine (0.090 g, 0.55 mmol), potassium carbonate (0.090 g, 0.65 mmol) and O-phenyl(4-(1-(4-(trifluoromethoxy)phenyl)-1H-1,2,4-triazol-3-yl)phenyl)carbamothioate (Intermediate C11; 0.25 mg, 0.55 mmol) in dry dichloromethane (10 mL). The reaction mixture was stirred at 50° C. for 2 hours. The reaction mixture was cooled to room temperature, filtered through Celite®, filtrate was concentrated under reduced pressure. The residue was diluted with dichloromethane (50 mL) and washed with water (50 mL) and brine (50 mL). The organic layer was dried over sodium sulfate and filtered. The filtrate was concentrated under reduced pressure to yield the crude product as a brown solid. Purification by flash column chromatography using hexanes as eluent provided the title compound as an off white solid (0.070 g, 22%).

The following compounds were prepared according to the procedure disclosed in Example 24:

1-(2'-Ethyl-[1,1'-biphenyl]-2-yl)-3-(4-(1-(4-(trifluoromethoxy)phenyl)-1H-1,2,4-triazol-3-yl)phenyl)thiourea (F4)

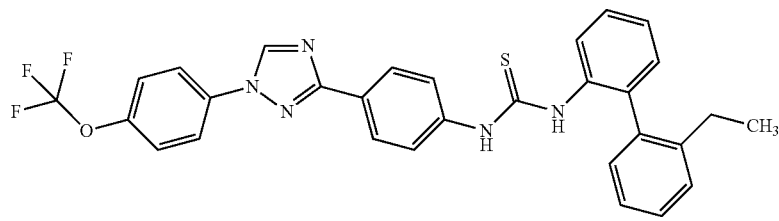

Isolated as an off-white solid (0.075 g, 25%).

1-(2'-(Methylthio)-[1,1'-biphenyl]-2-yl)-3-(4-(1-(4-(trifluoromethoxy)phenyl)-1H-1,2,4-triazol-3-yl)phenyl)thiourea (F42)

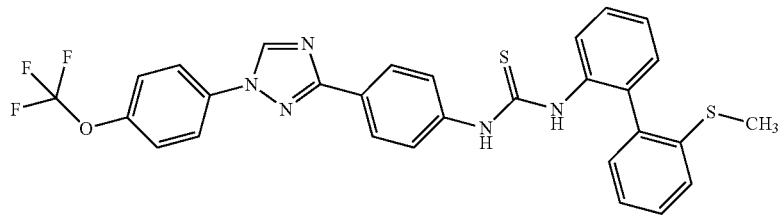 [SMILES: CSc1ccccc1-c1ccccc1NC(=S)Nc1ccc(-c2ncn(-c3ccc(OC(F)(F)F)cc3)n2)cc1]

Isolated as an off-white solid (0.080 g, 25%).

1-([1,1'-Biphenyl]-2-yl)-3-(4-(1-(4-(trifluoromethoxy)phenyl)-1H-1,2,4-triazol-3-yl)phenyl)thiourea (F47)

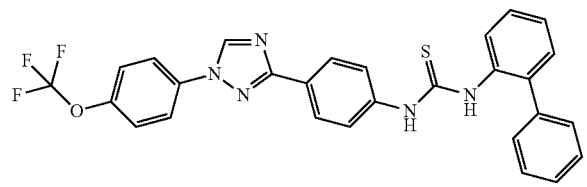

Isolated as an off-white solid (0.095 g, 32%).

1-(3-Phenylpyridin-2-yl)-3-(4-(1-(4-(trifluoromethoxy)phenyl)-1H-1,2,4-triazol-3-yl)phenyl)thiourea (F50)

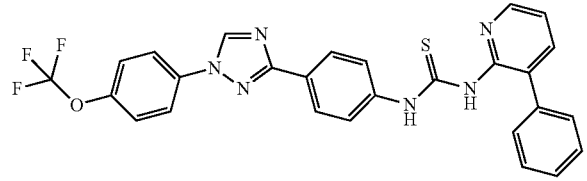 [SMILES: FC(F)(F)Oc1ccc(-n2cnc(-c3ccc(NC(=S)Nc4ncccc4-c4ccccc4)cc3)n2)cc1]

Isolated as a pale yellow solid (0.035 g, 12%).

1-(3-(o-Tolyl)pyridin-2-yl)-3-(4-(1-(4-(trifluoromethoxy)phenyl)-1H-1,2,4-triazol-3-yl)phenyl)thiourea (F11)

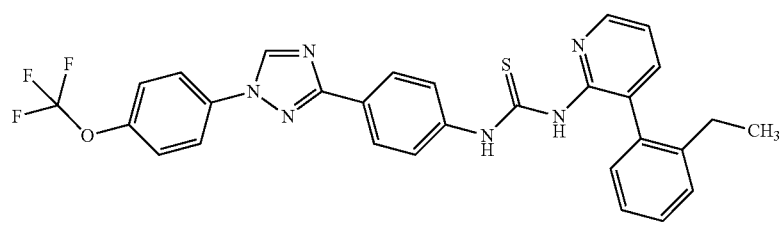

Isolated as a brown solid (0.025 g, 9%).

1-(3-(2-Ethylphenyl)pyridin-2-yl)-3-(4-(1-(4-(trifluoromethoxy)phenyl)-1H-1,2,4-triazol-3-yl)phenyl)thiourea (F20)

Isolated as a brown solid (0.090 g, 30%).

1-(3-(2-(Methylthio)phenyl)pyridin-2-yl)-3-(4-(1-(4-(trifluoromethoxy)phenyl)-1H-1,2,4-triazol-3-yl)phenyl)thiourea (F22)

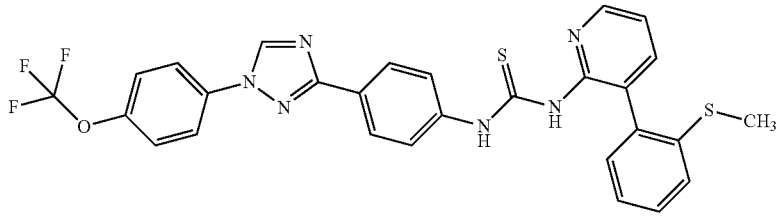

Isolated as an off white solid (0.040 g, 13%).

1-([3,3'-Bipyridin]-2-yl)-3-(4-(1-(4-(trifluoromethoxy)phenyl)-1H-1,2,4-triazol-3-yl)phenyl)thiourea (F56)

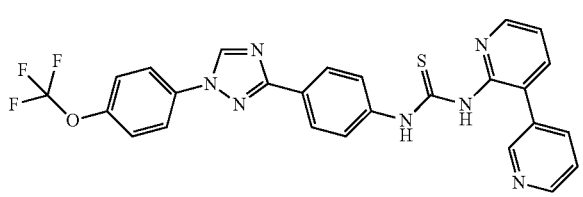

Isolated as an off white solid (0.086 g, 30%).

Example 25

Preparation of 1-([1,1'-biphenyl]-2-yl)-3-(4-(1-(4-(trifluoromethoxy)phenyl)-1H-1,2,4-triazol-3-yl)phenyl)urea (F31)

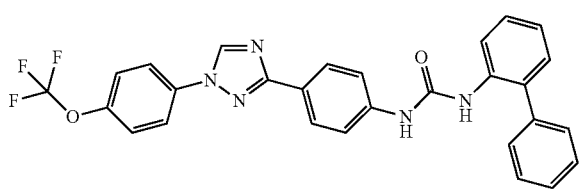

To a three-necked round bottomed flask equipped with condenser and nitrogen inlet was charged with oxalyl chloride (0.378 g, 2.98 mmol). Tetrahydrofuran (25 mL) was added and the reaction was cooled to 0° C. 4-(1-(4-(Trifluoromethoxy)phenyl)-1H-1,2,4-triazol-3-yl)aniline (0.800 g, 2.50 mmol) and triethylamine (1.74 mL, 12.5 mmol) were added at 0° C. After 30 minutes, [1,1'-biphenyl]-2-amine (0.508 g, 3.00 mmol) dissolved in tetrahydrofuran (25 mL) was added to the reaction mixture. The resulting reaction mixture was slowly warmed to room temperature. Upon completion, the reaction mixture was quenched with water (50 mL) and extracted with ethyl acetate (150 mL×2). The organic phase was washed with brine (50 mL). The combined organic layers were dried over sodium sulfate and were then concentrated under reduced pressure. Purification by flash column chromatography using 0-30% ethyl acetate/hexanes provided the title compound as an off white solid (0.560 g, 87%).

The following compounds were prepared according to the procedure disclosed in Example 25:

1-(3-(2-(Methylthio)phenyl)pyridin-2-yl)-3-(4-(1-(4-(trifluoromethoxy)phenyl)-1H-1,2,4-triazol-3-yl)phenyl)urea (F59)

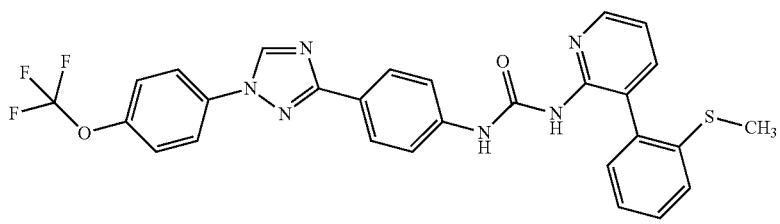

Isolated as an off white solid (0.009 g, 1%).

1-([3,3'-Bipyridin]-2-yl)-3-(4-(1-(4-(trifluoromethoxy)phenyl)-1H-1,2,4-triazol-3-yl)phenyl)urea (F66)

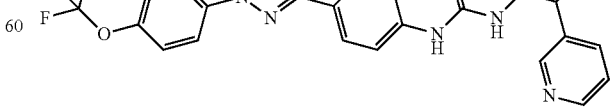

Isolated as an off white solid (0.100 g, 16%).

1-(2'-Isopropyl-[1,1'-biphenyl]-2-yl)-3-(4-(1-(4-(trifluoromethoxy)phenyl)-1H-1,2,4-triazol-3-yl)phenyl)urea (F63)

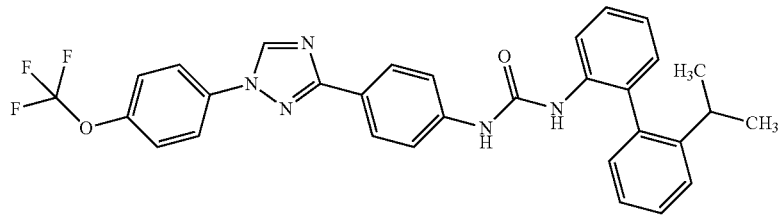 [SMILES: CC(C)c1ccccc1-c1ccccc1NC(=O)Nc1ccc(-c2ncn(-c3ccc(OC(F)(F)F)cc3)n2)cc1]

Isolated as a yellow solid (0.470 g, 68%).

1-(2'-Ethyl-[1,1'-biphenyl]-2-yl)-3-(4-(1-(4-(trifluoromethoxy)phenyl)-1H-1,2,4-triazol-3-yl)phenyl)urea (F35)

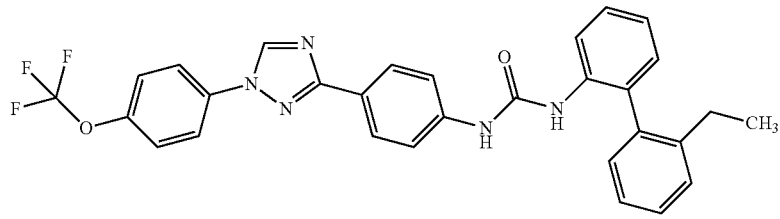 [SMILES: CCc1ccccc1-c1ccccc1NC(=O)Nc1ccc(-c2ncn(-c3ccc(OC(F)(F)F)cc3)n2)cc1]

Isolated as an off white solid (0.050 g, 7%).

1-(2'-(Methylthio)-[1,1'-biphenyl]-2-yl)-3-(4-(1-(4-(trifluoromethoxy)phenyl)-1H-1,2,4-triazol-3-yl)phenyl)urea (F60)

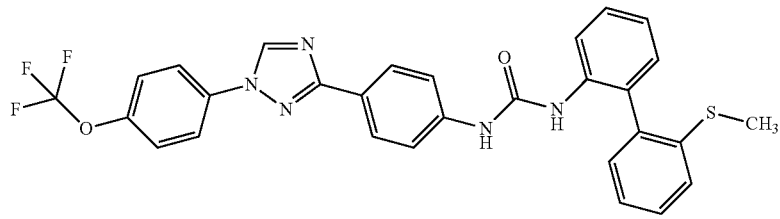

Isolated as an off white solid (0.300 g, 42%).

1-(2-(Pyridin-3-yl)phenyl)-3-(4-(1-(4-(trifluoromethoxy)phenyl)-1H-1,2,4-triazol-3-yl)phenyl)urea (F62)

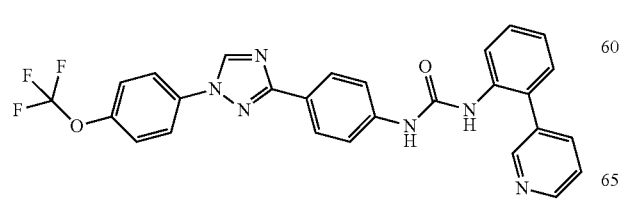

Isolated as a yellow solid (0.153 g, 23%).

1-(3-Phenylpyridin-2-yl)-3-(4-(1-(4-(trifluoromethoxy)phenyl)-1H-1,2,4-triazol-3-yl)phenyl)urea (F32)

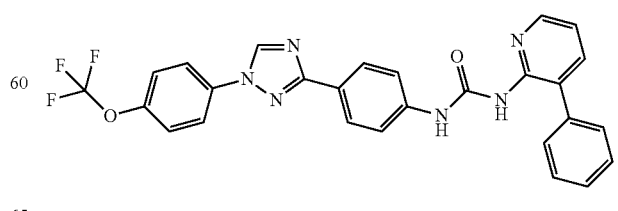

Isolated as an off white solid (0.010 g, 1%).

1-(3-(o-Tolyl)pyridin-2-yl)-3-(4-(1-(4-(trifluoromethoxy)phenyl)-1H-1,2,4-triazol-3-yl)phenyl) urea (F24)

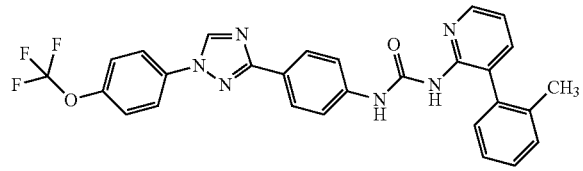

Isolated as an off white solid (0.010 g, 1%).

1-(3-(2-Ethylphenyl)pyridin-2-yl)-3-(4-(1-(4-(trifluoromethoxy)phenyl)-1H-1,2,4-triazol-3-yl)phenyl) urea (F16)

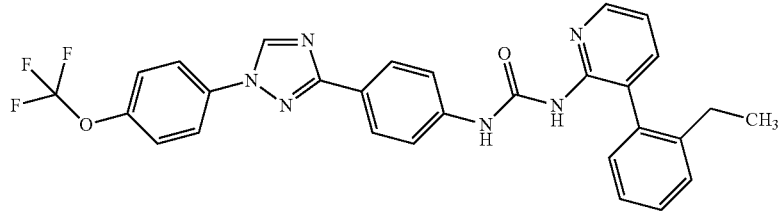 [SMILES: CCc1ccccc1-c1cccnc1NC(=O)Nc1ccc(-c2ncn(-c3ccc(OC(F)(F)F)cc3)n2)cc1]

Isolated as an off white solid (0.050 g, 7%).

Example 26

Preparation of 1-(4-ethoxyphenyl)-3-(4-(1-(4-(trifluoromethoxy)phenyl)-1H-1,2,4-triazol-3-yl)phenyl) urea (F2)

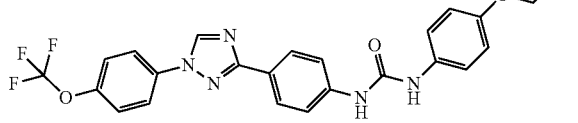

4-(1-(4-(Trifluoromethoxy)phenyl)-1H-1,2,4-triazol-3-yl)benzoyl azide (0.124 g, 0.332 mmol) was suspended in dry toluene (1 mL). The off-white slurry was heated to 100° C. for 1 hour and then cooled to room temperature. 4-ethoxyaniline (0.0680 g, 0.496 mmol) was added dropwise and stirring was continued at room temperature for 18 h. The resulting precipitate was collected by vacuum filtration, washed with ethyl acetate, and dried in vacuo to provide the title compound as an off-white solid (0.107 g, 69%): mp 243-245° C.; $^1$H NMR (300 MHz, DMSO-$d_6$) δ 9.36 (s, 1H), 8.84 (s, 1H), 8.54 (s, 1H), 8.06 (d, J=9.1 Hz, 2H), 8.01 (d, J=8.8 Hz, 2H), 7.65-7.55 (m, 4H), 7.36 (d, J=9.0 Hz, 2H), 6.86 (d, J=9.0 Hz, 2H), 3.98 (q, J=7.0 Hz, 2H), 1.31 (t, J=7.0 Hz, 3H); ESIMS m/z 484 ([M+H]$^+$).

The following compounds were prepared according to the procedure disclosed in Example 26:

1-(6-Methoxypyridin-3-yl)-3-(4-(1-(4-(trifluoromethoxy)phenyl)-1H-1,2,4-triazol-3-yl)phenyl) urea (F10)

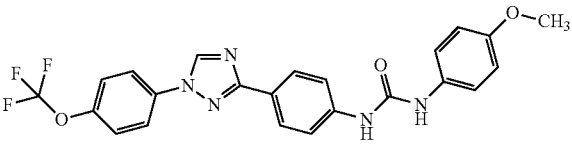 [SMILES: COc1ccc(NC(=O)Nc2ccc(-c3ncn(-c4ccc(OC(F)(F)F)cc4)n3)cc2)cc1]

Isolated as a lavender solid (0.090 g, 58%).

1-(6-Chloro-2-methylpyridin-3-yl)-3-(4-(1-(4-(trifluoromethoxy)phenyl)-1H-1,2,4-triazol-3-yl)phenyl) urea (F36)

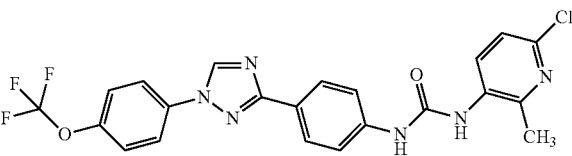 [SMILES: Cc1nc(Cl)ccc1NC(=O)Nc1ccc(-c2ncn(-c3ccc(OC(F)(F)F)cc3)n2)cc1]

Isolated as a tan solid (0.225 g, 57%).

1-(6-Ethoxypyridin-3-yl)-3-(4-(1-(4-(trifluoromethoxy)phenyl)-1H-1,2,4-triazol-3-yl)phenyl) urea (F8)

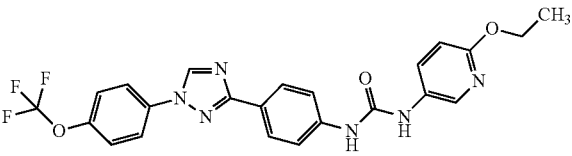 [SMILES: CCOc1ccc(NC(=O)Nc2ccc(-c3ncn(-c4ccc(OC(F)(F)F)cc4)n3)cc2)cn1]

Isolated as an off-white solid (0.0298 g, 23%).

Ethyl 6-methyl-5-(3-(4-(1-(4-(trifluoromethoxy)phenyl)-1H-1,2,4-triazol-3-yl)phenyl)ureido)picolinate (F41)

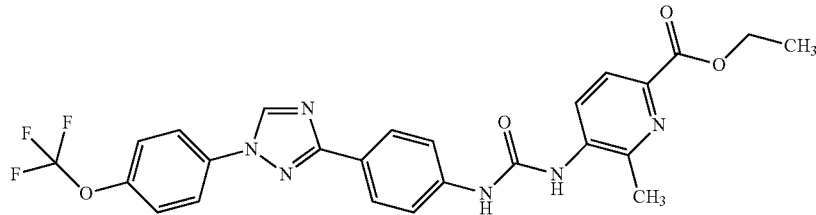 [SMILES: CCOC(=O)c1ccc(NC(=O)Nc2ccc(-c3ncn(-c4ccc(OC(F)(F)F)cc4)n3)cc2)c(C)n1]

Isolated as a light pink solid (0.0666 g, 57%).

Example 27

Preparation of 1-(4-fluorophenyl)-3-(4-(1-(4-(trifluoromethoxy)phenyl)-1H-1,2,4-triazol-3-yl)phenyl)urea (F17)

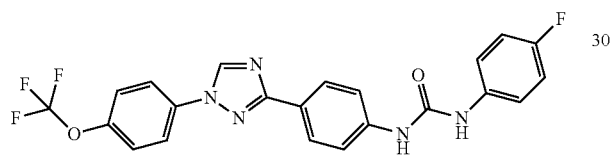

To 4-(1-(4-(trifluoromethoxy)phenyl)-1H-1,2,4-triazol-3-yl)aniline (0.200 g, 0.624 mmol) and 1-fluoro-4-isocyanatobenzene (0.257 g, 1.87 mmol) in a 25 mL round-bottomed flask was added tetrahydrofuran (10 mL). The solution was heated to 65° C. for 2 hours before the solvent was removed under reduced pressure. Purification by flash column chromatography provided the title compound (0.140 g, 49%).

Example 28

Preparation of benzyl 4-bromobenzylcarbamate (C12)

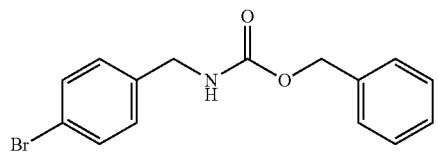

In a 500 mL flask, (4-bromophenyl)methanaminium chloride (10.0 g, 44.9 mmol) and sodium hydroxide (4.00 g, 100 mmol) were dissolved in tetrahydrofuran (80 mL) and water (80 mL). The flask was placed in an ice water bath and benzyl carbonochloridate (7.06 mL, 49.4 mmol) was added dropwise. The reaction was allowed to stir for 3 h. The reaction was then poured into brine solution and extracted with ethyl acetate (3×150 mL). The combined organic layers were dried over magnesium sulfate, filtered, and concentrated to give the title compound as a white solid (14.1 g, 97%): $^1$H NMR (400 MHz, DMSO-$d_6$) δ 7.88 (t, J=6.1 Hz, 1H), 7.58-7.46 (m, 2H), 7.46-7.27 (m, 5H), 7.23 (d, J=8.2 Hz, 2H), 5.06 (s, 2H), 4.19 (d, J=6.2 Hz, 2H); $^{13}$C NMR (101 MHz, DMSO-$d_6$) δ 156.34, 139.19, 137.05, 131.10, 129.22, 128.32, 127.78, 127.73, 119.79, 65.44, 43.22; ESIMS m/z 320 ([M+H]$^+$).

Example 29

Preparation of benzyl 4-(4,4,5,5-tetramethyl-1,3,2-dioxaborolan-2-yl)benzylcarbamate (C13)

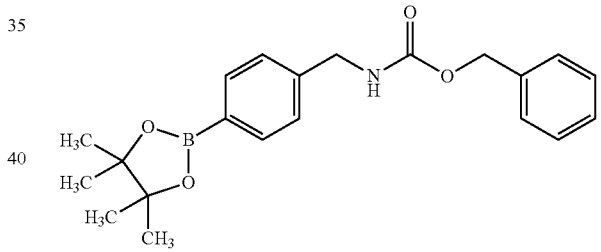

In a 500 mL flask, benzyl 4-bromobenzylcarbamate (14.1 g, 44.0 mmol), 4,4,4',4',5,5,5',5'-octamethyl-2,2'-bi(1,3,2-dioxaborolane) (12.3 g, 48.4 mmol), and potassium acetate (8.64 g, 88.0 mmol) were charged as solids and suspended in dioxane (200 mL). The suspension was sparged with nitrogen gas for 10 minutes, then [1,1'-bis(diphenylphosphino)ferrocene]dichloropalladium(II) (1.61 g, 2.20 mmol) was added. The reaction was evacuated with vacuum and purged with nitrogen gas (2×). The reaction was then warmed to an internal temperature of 70° C. and stirred for 18 hours. The reaction was cooled to room temperature, poured into brine and extracted with ethyl acetate (3×250 mL). The combined organics were dried over magnesium sulfate, filtered, and concentrated. The resulting residue was purified by flash chromatography using 0-25% ethyl acetate/hexanes as eluent to afford the title compound as a white solid (13.8 g, 81%): $^1$H NMR (400 MHz, DMSO-$d_6$) δ 7.87 (t, J=6.2 Hz, 1H), 7.70-7.60 (m, 2H), 7.46-7.22 (m, 7H), 5.06 (s, 2H), 4.24 (d, J=6.2 Hz, 2H), 1.29 (s, 12H); $^{13}$C NMR (101 MHz, DMSO-$d_6$) δ 156.35, 143.18, 137.12, 134.45, 128.31, 127.69, 126.38, 83.51, 66.32, 65.37, 64.89, 43.83, 24.62; ESIMS m/z 368 ([M+H]$^+$).

The following compounds were prepared according to the procedures disclosed in Example 29:

Methyl 2-(4-(4,4,5,5-tetramethyl-1,3,2-dioxaborolan-2-yl)phenyl)acetate (C14)

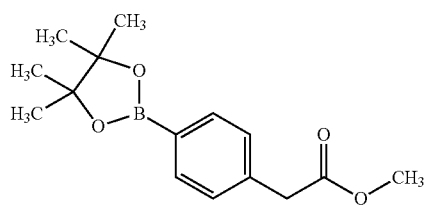

The title compound was prepared as described in Example 29 with methyl 2-(4-bromophenyl)acetate and isolated as a clear liquid (12.6 g, 95%): $^1$H NMR (400 MHz, DMSO-$d_6$) δ 7.73-7.58 (m, 2H), 7.33-7.26 (m, 2H), 3.71 (s, 2H), 3.61 (s, 3H), 1.29 (s, 12H).

Example 30

Preparation of benzyl 4-(1-(4-(trifluoromethoxy)phenyl)-1H-1,2,4-triazol-3-yl)benzylcarbamate (C15)

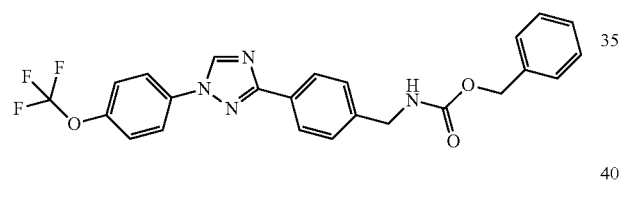

To a 5.0 mL vial, [1,1'-bis(di-tert-butylphosphino)ferrocene]dichloropalladium(II) (0.011 mg, 0.017 mmol), and potassium phosphate (0.14 g, 0.65 mmol) were charged as solids. The vial was sealed with a septum and placed under nitrogen. A solution of 3-bromo-1-(4-(trifluoromethoxy)phenyl)-1H-1,2,4-triazole (WO 2013/009791) (0.10 g, 0.33 mmol) and benzyl 4-(4,4,5,5-tetramethyl-1,3,2-dioxaborolan-2-yl)benzylcarbamate (0.13 g, 0.36 mmol) in dioxane (1.8 mL) was added followed by water (0.45 mL). The reaction mixture was evacuated with vacuum and purged with nitrogen and placed in a pre-heated heating block that at 75° C. for 18 hours. The reaction mixture was then poured into brine solution and extracted with ethyl acetate (3×50 mL). The combined organic layers were dried over magnesium sulfate, filtered, and concentrated. The resulting residue was purified via flash chromatography using 15-80% ethyl acetate/hexanes as eluent to afford the title compound as a white solid (0.13 g, 87%): $^1$H NMR (400 MHz, DMSO-$d_6$) δ 9.40 (s, 1H), 8.16-8.01 (m, 4H), 7.91 (t, J=6.2 Hz, 1H), 7.67-7.58 (m, 2H), 7.48-7.15 (m, 7H), 5.07 (s, 2H), 4.28 (d, J=6.2 Hz, 2H); $^{19}$F NMR (376 MHz, DMSO-$d_6$) δ −56.96; ESIMS m/z 469 ([M+H]$^+$).

Example 31

Preparation of (4-(1-(4-(trifluoromethoxy)phenyl)-1H-1,2,4-triazol-3-yl)phenyl)methanamine (C16)

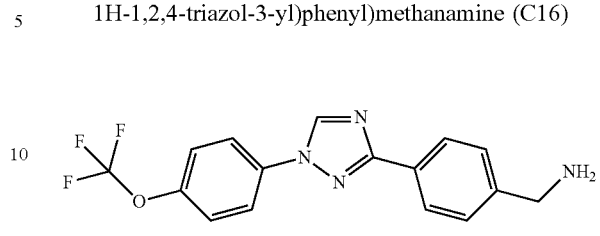

In a 200 mL flask, benzyl 4-(1-(4-(trifluoromethoxy)phenyl)-1H-1,2,4-triazol-3-yl)benzylcarbamate (0.599 g, 1.28 mmol) was suspended in hydrogen bromide in acetic acid (33 wt %, 8.00 mL, 45.7 mmol). The suspension was stirred vigorously at room temperature for 1 hour. To the resulting suspension was added diethyl ether (100 mL), and the reaction mixture was stirred for 30 minutes at room temperature. The resulting precipitate was collected via filtration and treated with sodium hydroxide (1 N) and extracted with ethyl acetate (3×75 mL). The combined organic layers were dried over magnesium sulfate, filtered, and concentrated to give the title compound as a white solid (0.395 g, 92% yield): $^1$H NMR (400 MHz, DMSO-$d_6$) δ 9.45 (s, 1H), 8.25-8.03 (m, 4H), 7.74-7.62 (m, 2H), 7.60-7.48 (m, 2H), 3.85 (s, 2H); $^{19}$F NMR (376 MHz, DMSO-$d_6$) δ −56.97; ESMIS m/z 318 ([M+H]$^+$) (—NH$_2$).

Example 32

Preparation of 1-(2-isopropylphenyl)-3-(4-(1-(4-(trifluoromethoxy)phenyl)-1H-1,2,4-triazol-3-yl)benzyl)thiourea (F45)

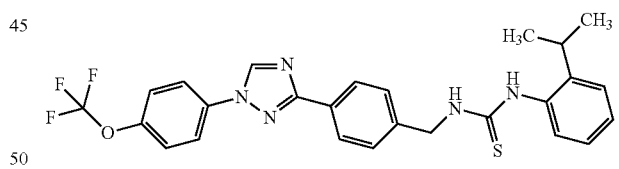

To a solution of (4-(1-(4-(trifluoromethoxy)phenyl)-1H-1,2,4-triazol-3-yl)phenyl)methanamine (0.066 g, 0.20 mmol) in tetrahydrofuran (4.0 mL), 1-isopropyl-2-isothiocyanatobenzene (0.048 g, 0.27 mmol) was added. The reaction mixture was stirred in a pre-heated heating block at 80° C. for 4 hours. The reaction mixture was adsorbed onto Celite® and purified via reverse phase chromatography using 5-100% acetonitrile/water as eluent to afford the title compound as a white solid (0.070 g, 68%): $^1$H NMR (400 MHz, DMSO-$d_6$) δ 9.40 (s, 1H), 9.30 (s, 1H), 8.07 (dd, J=9.4, 7.3 Hz, 4H), 7.81 (s, 1H), 7.68-7.58 (m, 2H), 7.44 (d, J=8.0 Hz, 2H), 7.36 (d, J=7.7 Hz, 1H), 7.29 (t, J=7.5 Hz, 1H), 7.21 (dd, J=13.2, 6.1 Hz, 2H), 4.78 (s, 2H), 3.11 (s, 1H), 1.15 (d, J=6.9 Hz, 6H); $^{19}$F NMR (376 MHz, DMSO-$d_6$) δ −56.96; ESIMS m/z 512 ([M+H]$^+$).

Example 33

Preparation of methyl 2-(4-(1-(4-(trifluoromethoxy)phenyl)-1H-1,2,4-triazol-3-yl)phenyl)acetate (C17)

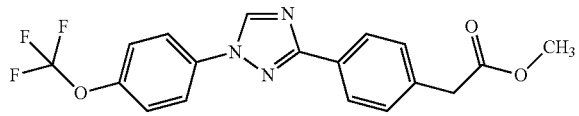 [SMILES: COC(=O)Cc1ccc(-c2ncn(-c3ccc(OC(F)(F)F)cc3)n2)cc1]

In a 200 mL flask, 3-bromo-1-(4-(trifluoromethoxy)phenyl)-1H-1,2,4-triazole (3.45 g, 11.2 mmol), and methyl 2-(4-(4,4,5,5-tetramethyl-1,3,2-dioxaborolan-2-yl)phenyl)acetate (3.71 g, 13.4 mmol) were diluted with dioxane (45 mL) and water (11 mL). This solution was sparged with nitrogen gas for 10 minutes. Then tri-tert-butylphosphonium tetrafluoroborate (0.325 g, 1.12 mmol), diacetoxypalladium (0.126 g, 0.560 mmol) and cesium fluoride (3.40 g, 22.4 mmol) were added as solids. The flask was sealed and evacuated with vacuum and purged with nitrogen gas. The reaction was warmed to an internal temperature of 60° C. and stirred for 18 hours. The reaction was poured into a brine solution and extracted with ethyl acetate (3×50 mL). The combined organics were dried over magnesium sulfate, filtered, and concentrated. The resulting residue was purified by flash chromatography using 0-10% ethyl acetate/hexanes as eluent to afford the title compound as an off white solid (3.45 g, 82%): $^1$H NMR (400 MHz, DMSO-$d_6$) δ 9.41 (s, 1H), 8.11-8.04 (m, 4H), 7.63 (ddt, J=7.9, 2.1, 1.1 Hz, 2H), 7.48-7.36 (m, 2H), 3.77 (s, 2H), 3.64 (s, 3H); $^{19}$F NMR (376 MHz, DMSO-$d_6$) δ −57.02; ESIMS m/z 378 ([M+H]$^+$)

The following compounds were prepared according to the procedures disclosed in Example 33:

Methyl 2-(4-(1-(4-(perfluoroethoxy)phenyl)-1H-1,2,4-triazol-3-yl)phenyl)acetate (C18)

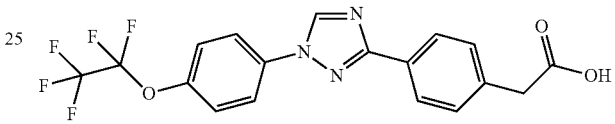

Isolated as a white solid (3.57 g, 59%): $^1$H NMR (400 MHz, DMSO-$d_6$) δ 9.42 (s, 1H), 8.18-8.04 (m, 4H), 7.68-7.58 (m, 2H), 7.48-7.38 (m, 2H), 3.78 (s, 2H), 3.65 (s, 3H); $^{19}$F NMR (376 MHz, DMSO-$d_6$) δ −85.20 (d, J=2.9 Hz), −86.93; ESIMS m/z 428 ([M+H]$^+$).

Example 34

Preparation of 2-(4-(1-(4-(trifluoromethoxy)phenyl)-1H-1,2,4-triazol-3-yl)phenyl)acetic acid (C19)

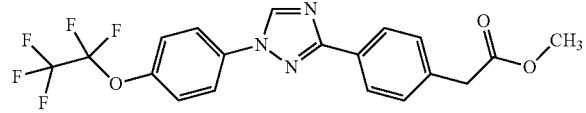 [SMILES: COC(=O)Cc1ccc(-c2ncn(-c3ccc(OC(F)(F)C(F)(F)F)cc3)n2)cc1]

In a 100 mL flask, methyl 2-(4-(1-(4-(trifluoromethoxy)phenyl)-1H-1,2,4-triazol-3-yl)phenyl)acetate (3.45 g, 9.14 mmol) and lithium hydroxide.hydrate (1.15 g, 27.4 mmol) were diluted with tetrahydrofuran (24.4 mL), methanol (24.4 mL), water (12.2 mL). The reaction was stirred at room temperature for 2 hours. The solvent was evaporated and the resulting solid was diluted with water and adjusted to pH 3 with hydrogen chloride (1 N). The resulting precipitate was extracted with ethyl acetate (5×100 mL). The combined organics were dried over magnesium sulfate, filtered, and concentrated to give the title compound as a white solid (3.27 g, 96%): $^1$H NMR (400 MHz, DMSO-$d_6$) δ 12.41 (s, 1H), 9.40 (s, 1H), 8.15-8.03 (m, 4H), 7.63 (dq, J=7.9, 1.0 Hz, 2H), 7.49-7.36 (m, 2H), 3.66 (s, 2H), 3.35 (s, 3H); $^{19}$F NMR (376 MHz, DMSO-$d_6$) δ −56.98; ESIMS m/z 364 ([M+H]$^+$).

The following compounds were prepared according to the procedures disclosed in Example 34:

2-(4-(1-(4-(Perfluoroethoxy)phenyl)-1H-1,2,4-triazol-3-yl)phenyl)acetic acid (C20)

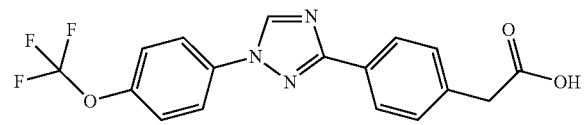 [SMILES: O=C(O)Cc1ccc(-c2ncn(-c3ccc(OC(F)(F)F)cc3)n2)cc1]

Isolated as a white solid (3.40 g, 94%): $^1$H NMR (400 MHz, DMSO-$d_6$) δ 12.41 (s, 1H), 9.41 (s, 1H), 8.15-8.02 (m, 4H), 7.67-7.58 (m, 2H), 7.47-7.37 (m, 2H), 3.66 (s, 2H); $^{19}$F NMR (376 MHz, DMSO-$d_6$) δ −85.20, −86.92; ESIMS m/z 414 ([M+H]$^+$).

Example 35

Preparation of (2-(4-(1-(4-(trifluoromethoxy)phenyl)-1H-1,2,4-triazol-3-yl)phenyl)acetyl azide and 2-(4-(1-(4-(trifluoromethoxy)phenyl)-1H-1,2,4-triazol-3-yl)phenyl)methyl isocyanate (C21)

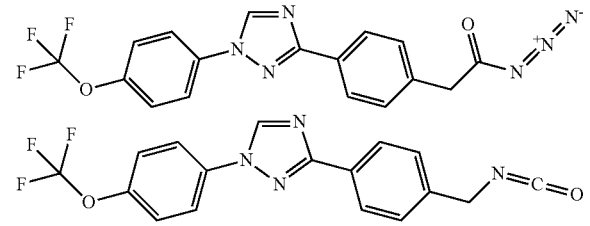

In a 100-mL round bottom flask, equipped with a magnetic stir bar, 2-(4-(1-(4-(trifluoromethoxy)phenyl)-1H-1,2,4-triazol-3-yl)phenyl)acetic acid (2.00 g, 5.51 mmol) was diluted with toluene (37 mL). Then triethylamine (0.767 mL, 5.51 mmol) and diphenyl phosphorazidate (1.19 mL, 5.51 mmol) were added. The reaction was allowed to stir for 2.5 hours at room temperature. The reaction was then poured in to water and extracted with ethyl acetate (3×50 mL). The combined organic layers were dried over anhydrous magnesium sulfate, filtered, and concentrated. The resulting residue was purified via flash column chromatography using 0-10% ethyl acetate/hexanes as eluent to afford the product as an off-white solid (0.800 g, 37%): $^1$H NMR (400 MHz, DMSO-d$_6$) δ 9.41 (d, J=5.9 Hz, 1H), 8.21-7.99 (m, 4H), 7.69-7.57 (m, 2H), 7.57-7.38 (m, 2H), 4.70 (s, 2H); $^{19}$F NMR (376 MHz, DMSO-d$_6$) δ −56.99 (d, J=4.1 Hz); ESIMS m/z 361 ([M+H]$^+$) (methyl carbamate).

The following compounds were prepared according to the procedures disclosed in

Example 35

Physical Properties Indicate that the Isolated Products are Often a Mixture of the Acyl Azide and Rearranged Isocyanate 2-(4-(1-(4-(Perfluoroethoxy)phenyl)-1H-1,2,4-triazol-3-yl)phenyl)acetyl azide and 2-(4-(1-(4-(perfluoroethoxy)phenyl)-1H-1,2,4-triazol-3-yl)phenyl) methyl isocyanate (C22)

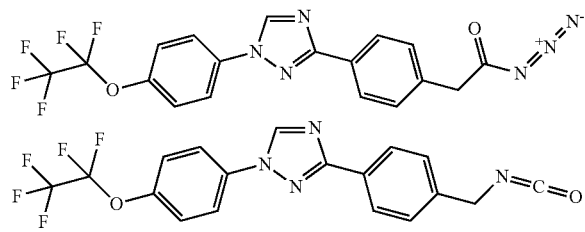

Isolated as a white solid (1.45 g, 46%): $^1$H NMR (400 MHz, DMSO-d$_6$) δ 9.46-9.32 (m, 1H), 8.19-7.97 (m, 4H), 7.68-7.36 (m, 4H), 4.70 (s, 1H), 4.34 (d, J=6.1 Hz, 1H); $^{19}$F NMR (376 MHz, DMSO-d$_6$) δ −85.23 (d, J=9.8 Hz), −86.95 (d, J=8.0 Hz); ESIMS m/z 442 ([M+H]$^+$) (methyl carbamate).

Example 36

Preparation of 1-([1,1'-biphenyl]-2-yl)-3-(4-(1-(4-(trifluoromethoxy)phenyl)-1H-1,2,4-triazol-3-yl)benzyl)urea (F70)

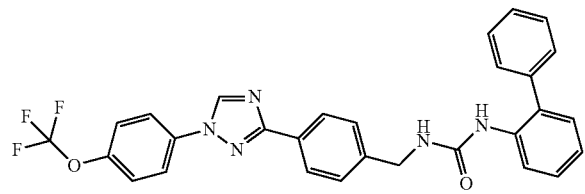 [SMILES: O=C(NCc1ccc(-c2ncn(-c3ccc(OC(F)(F)F)cc3)n2)cc1)Nc1ccccc1-c1ccccc1]

A solution of 2-(4-(1-(4-(trifluoromethoxy)phenyl)-1H-1,2,4-triazol-3-yl)phenyl)acetyl azide (0.100 g, 0.258 mmol) in acetonitrile (1.25 mL) was heated to 80° C. for 2.5 hours. The resulting solution was cooled to room temperature and [1,1'-biphenyl]-2-amine (0.0479 g, 0.283 mmol) and cesium carbonate (0.0920 g, 0.283 mmol) were added as solids. An additional amount of acetonitrile (1.0 mL) was added and the reaction was allowed to stir for 18 hours at room temperature. The reaction mixture was poured into water (20 mL) and extracted with ethyl acetate (3×25 mL). The combined organic layers were dried over magnesium sulfate, filtered, and concentrated. The resulting residue was purified by flash chromatography using 0-80% ethyl acetate/ B, where B=1:1 dichloromethane/hexanes to afford the title compound as a white solid (0.039 g, 28%): $^1$H NMR (400 MHz, DMSO-d6) δ 9.40 (s, 1H), 8.12-8.04 (m, 4H), 7.90 (dd, J=8.2, 1.2 Hz, 1H), 7.63 (dq, J=9.0, 0.9 Hz, 2H), 7.55-7.46 (m, 3H), 7.45-7.36 (m, 5H), 7.33-7.26 (m, 1H), 7.18 (dd, J=7.6, 1.7 Hz, 1H), 7.14-7.06 (m, 2H), 4.32 (d, J=5.8 Hz, 2H); $^{19}$F NMR (376 MHz, DMSO-d6) δ −56.96; ESIMS m/z 530 ([M+H]$^+$).

The following compounds were prepared according to the procedures disclosed in Example 36:

1-(2-Isopropylphenyl)-3-(4-(1-(4-(trifluoromethoxy) phenyl)-1H-1,2,4-triazol-3-yl)benzyl)urea (F65)

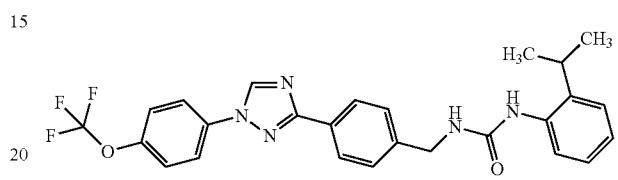

Isolated as a white solid (0.019 g, 15%).

Example 37

Preparation of 1-(2-isopropylphenyl)-3-(4-(1-(4-(perfluoroethoxy)phenyl)-1H-1,2,4-triazol-3-yl)benzyl)urea (F34)

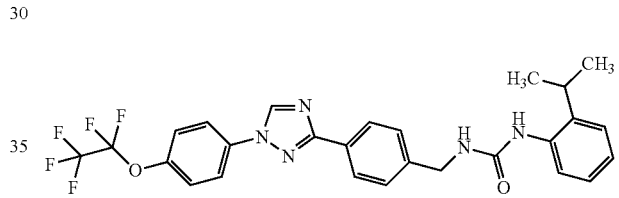

To a 20 mL vial, 2-(4-(1-(4-(perfluoroethoxy)phenyl)-1H-1,2,4-triazol-3-yl)phenyl)acetyl azide (0.100 g, 0.228 mmol) was suspended in acetonitrile (1.5 mL). The suspension was stirred in a pre-heated heating block at 70° C. for 2 hours. The suspension was cooled to room temperature, then 2-isopropylaniline (0.0339 g, 0.251 mmol) and cesium carbonate (0.0890 g, 0.274 mmol) were added. The reaction was allowed to stir for overnight at room temperature. The reaction was filtered through a fritted funnel. The filtrate was concentrated onto Celite® and purified by reverse phase chromatography using 5-100% acetonitrile/water as eluent to provide the title compound as a white solid (0.028 g, 22%).

The following compounds were prepared according to the procedures disclosed in Example 37:

1-([1,1'-Biphenyl]-2-yl)-3-(4-(1-(4-(perfluoroethoxy) phenyl)-1H-1,2,4-triazol-3-yl)benzyl)urea (F73)

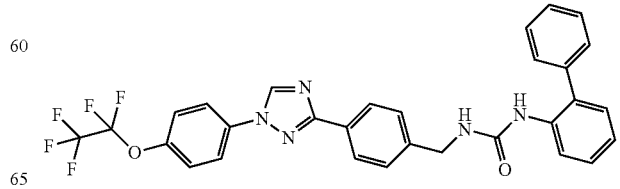

Isolated as a white solid (0.020 g, 15%).

Example 38

Preparation of 1-(4-(1-(4-(trifluoromethoxy)phenyl)-1H-1,2,4-triazol-3-yl)phenyl)-3-(4-(trifluoromethyl)pyridin-3-yl)thiourea (F12)

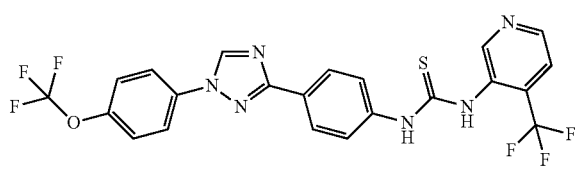 [SMILES: FC(F)(F)Oc1ccc(-n2cnc(-c3ccc(NC(=S)Nc4cnccc4C(F)(F)F)cc3)n2)cc1]

To 4-(trifluoromethyl)pyridin-3-amine (0.091 g, 0.56 mmol) in tetrahydrofuran and under an atmosphere of nitrogen was added sodium hydride (60% in mineral oil, 0.022 g, 0.56 mmol). 3-(4-Isothiocyanatophenyl)-1-(4-(trifluoromethoxy)phenyl)-1H-1,2,4-triazole (WO 2011/017513) (0.10 g, 0.28 mmol) was added and the reaction was allowed to stir for 48 hours. The reaction mixture was concentrated. Purification by silica gel chromatography provided the title compound (0.024 g, 16%).

Example 39

Preparation of 1-(2-isopropylphenyl)-3-(4-(1-(4-(trifluoromethoxy)phenyl)-1H-1,2,4-triazol-3-yl)phenyl)thiourea (F3)

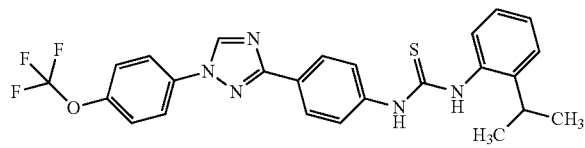 [SMILES: CC(C)c1ccccc1NC(=S)Nc1ccc(-c2ncn(-c3ccc(OC(F)(F)F)cc3)n2)cc1]

To a stirred solution of 4-(1-(4-(trifluoromethoxy)phenyl)-1H-1,2,4-triazol-3-yl)aniline (0.10 g, 0.31 mmol) in tetrahydrofuran (5 mL) was added 1-isopropyl-2-isothiocyanatobenzene (0.10 g, 0.56 mmol). The solution was heated to reflux for 24 hours The solvent was removed under reduced pressure, then triturated with methanol to generate a white solid which was filtered and air-dried to provide the title compound (0.070 g, 45%).

The following compounds were prepared according to the procedures disclosed in Example 39:

1-(4-Cyanophenyl)-3-(4-(1-(4-(trifluoromethoxy)phenyl)-1H-1,2,4-triazol-3-yl)phenyl)thiourea (F7)

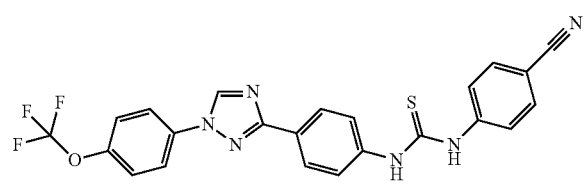 [SMILES: N#Cc1ccc(NC(=S)Nc2ccc(-c3ncn(-c4ccc(OC(F)(F)F)cc4)n3)cc2)cc1]

Isolated as a white solid (0.050 g, 47%).

1-(4-Fluorophenyl)-3-(4-(1-(4-(trifluoromethoxy)phenyl)-1H-1,2,4-triazol-3-yl)phenyl)thiourea (F72)

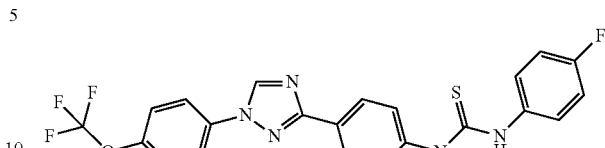

Isolated as a solid (0.200 g, 68%).

1-(Naphthalen-2-yl)-3-(4-(1-(4-(trifluoromethoxy)phenyl)-1H-1,2,4-triazol-3-yl)phenyl)thiourea (F25)

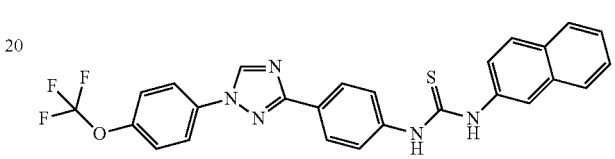

Isolated as a solid (0.050 g, 45%).

1-(4-Methoxyphenyl)-3-(4-(1-(4-(trifluoromethoxy)phenyl)-1H-1,2,4-triazol-3-yl)phenyl)thiourea (F71)

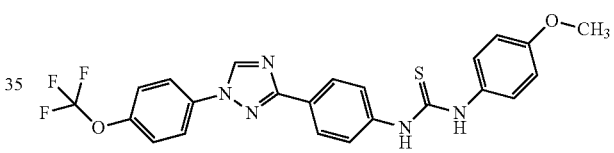

Purification by silica gel chromatography provided the title compound (0.070 g, 47%).

1-(4-Methoxy-2-methylphenyl)-3-(4-(1-(4-(trifluoromethoxy)phenyl)-1H-1,2,4-triazol-3-yl)phenyl)thiourea (F43)

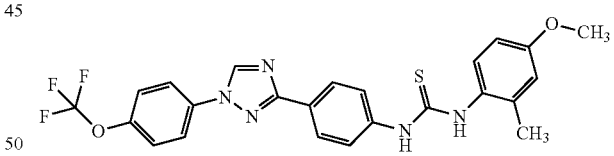

Purification by silica gel chromatography provided the title compound (0.090 g, 58%).

1-(6-(Methylthio)pyridin-3-yl)-3-(4-(1-(4-(trifluoromethoxy)phenyl)-1H-1,2,4-triazol-3-yl)phenyl)thiourea (F27)

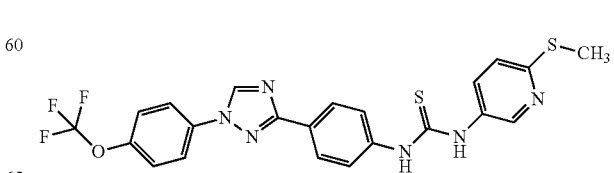

The product was isolated as a solid (0.030 g, 30%).

1-(6-Ethoxypyridin-3-yl)-3-(4-(1-(4-(trifluoromethoxy)phenyl)-1H-1,2,4-triazol-3-yl)phenyl)thiourea (F14)

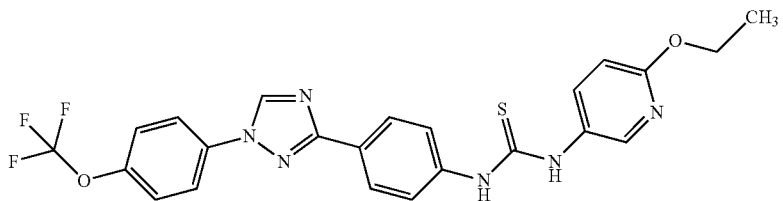 [SMILES: CCOc1ccc(NC(=S)Nc2ccc(-c3ncn(-c4ccc(OC(F)(F)F)cc4)n3)cc2)cn1]

The product was isolated as a solid (0.017 g, 17%).

Example 40

Preparation of 1-(2-isopropylphenyl)-3-(3-(4-(1-(4-(trifluoromethoxy)phenyl)-1H-1,2,4-triazol-3-yl)phenyl)propyl)thiourea (F76)

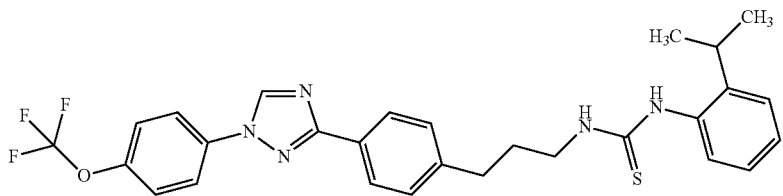

In a 25 mL flask, to a solution of 3-(4-(1-(4-(trifluoromethoxy)phenyl)-1H-1,2,4-triazol-3-yl)phenyl)propan-1-amine (0.160 g, 0.442 mmol) in dichloromethane (2 mL) was added 1-isopropyl-2-isothiocyanatobenzene (0.156 g, 0.530 mmol) in dichloromethane (5 mL) followed by triethylamine (0.062 mL, 0.442 mmol). The reaction mixture was stirred overnight at room temperature. The reaction mixture was diluted with ethyl acetate and adsorbed onto Celite®. Purification by flash column chromatography provided the title compound as a white solid (110 mg, 49%).

The following compounds were prepared according to the procedures disclosed in Example 40:

1-(2-Isopropylphenyl)-3-(4-(4-(1-(4-(trifluoromethoxy)phenyl)-1H-1,2,4-triazol-3-yl)phenyl)butyl)thiourea (F88)

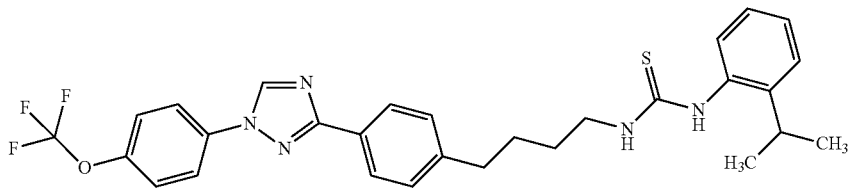

Isolated as a white solid (0.110 g, 50%).

Example 41

Preparation of 1-(o-tolyl)-3-(3-(4-(1-(4-(trifluoromethoxy)phenyl)-1H-1,2,4-triazol-3-yl)phenyl)propyl)urea (F77)

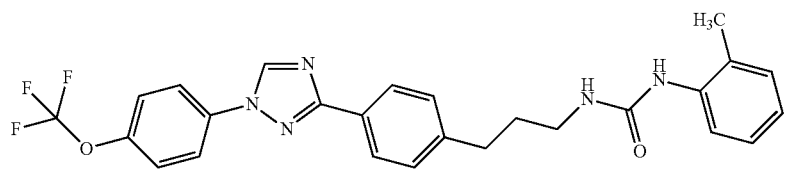

In a 25 mL flask, to a solution of 3-(4-(1-(4-(trifluoromethoxy)phenyl)-1H-1,2,4-triazol-3-yl)phenyl)propan-1-amine (0.160 g, 0.442 mmol) in dichloromethane (2 mL) was added 2-methyl phenylisocyanate (0.06 g, 0.497 mmol) in dichloromethane (5 mL) followed by triethylamine (0.044 g, 0.414 mmol). The reaction mixture was stirred overnight at room temperature. The reaction mixture was diluted with ethyl acetate and adsorbed onto Celite®. Purification by flash column chromatography (reverse phase) 5% acetonitrile/water provided the title compound as a white solid (0.11 g, 53%).

The following compounds were prepared according to the procedures disclosed in Example 41:

1-(2-Isopropylphenyl)-3-(3-(4-(1-(4-(trifluoromethoxy)phenyl)-1H-1,2,4-triazol-3-yl)phenyl)propyl)urea (F78)

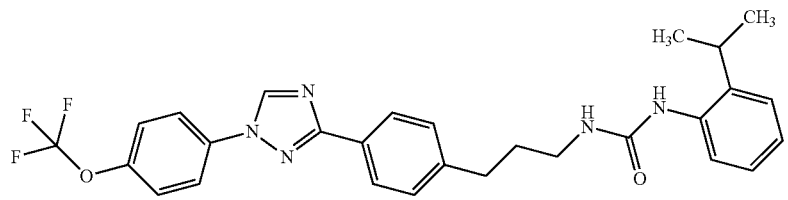

Isolated as an off white solid (0.135 g, 64%).

1-(4-Chlorophenyl)-3-(3-(4-(1-(4-(trifluoromethoxy)phenyl)-1H-1,2,4-triazol-3-yl)phenyl)propyl)urea (F79)

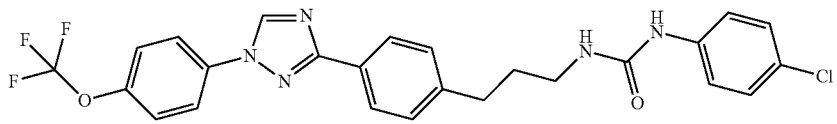 [SMILES: O=C(NCCCc1ccc(-c2ncn(-c3ccc(OC(F)(F)F)cc3)n2)cc1)Nc1ccc(Cl)cc1]

Isolated as a white solid (0.103 g, 47%).

1-(3-Methoxyphenyl)-3-(3-(4-(1-(4-(trifluoromethoxy)phenyl)-1H-1,2,4-triazol-3-yl)phenyl)propyl)urea (F80)

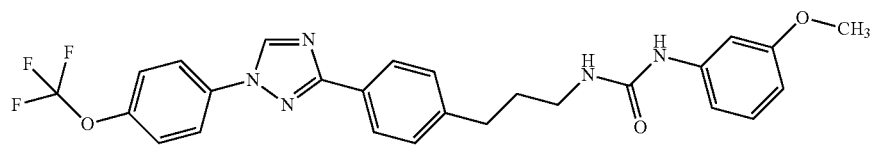 [SMILES: COc1cccc(NC(=O)NCCCc2ccc(-c3ncn(-c4ccc(OC(F)(F)F)cc4)n3)cc2)c1]

Isolated as a white solid (0.101 g, 48%).

1-(2-Methoxyphenyl)-3-(3-(4-(1-(4-(trifluoromethoxy)phenyl)-1H-1,2,4-triazol-3-yl)phenyl)propyl)urea (F81)

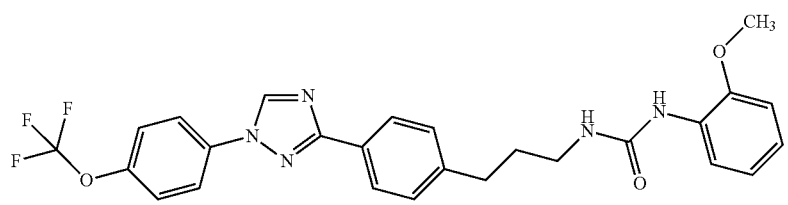 [SMILES: COc1ccccc1NC(=O)NCCCc1ccc(-c2ncn(-c3ccc(OC(F)(F)F)cc3)n2)cc1]

Isolated as a white solid (0.139 g, 61%).

1-(4-Methoxyphenyl)-3-(3-(4-(1-(4-(trifluoromethoxy)phenyl)-1H-1,2,4-triazol-3-yl)phenyl)propyl)urea (F82)

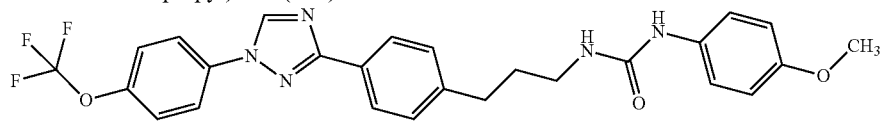

Isolated as a white solid (0.13 g, 61%).

1-(p-Tolyl)-3-(3-(4-(1-(4-(trifluoromethoxy)phenyl)-1H-1,2,4-triazol-3-yl)phenyl)propyl)urea (F83)

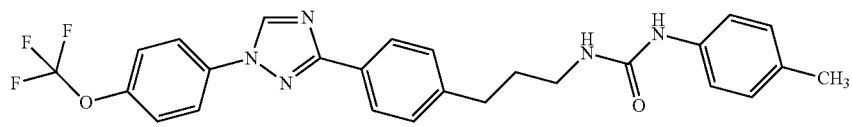 [SMILES: Cc1ccc(NC(=O)NCCCc2ccc(-c3ncn(-c4ccc(OC(F)(F)F)cc4)n3)cc2)cc1]

Isolated as a white solid (0.108 g, 49%).

1-(2-Chlorophenyl)-3-(3-(4-(1-(4-(trifluoromethoxy)phenyl)-1H-1,2,4-triazol-3-yl)phenyl)propyl)urea (F84)

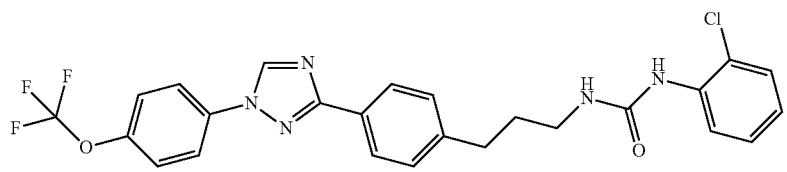

Isolated as a white solid (0.14 g, 61%).

1-(3-Chlorophenyl)-3-(3-(4-(1-(4-(trifluoromethoxy)phenyl)-1H-1,2,4-triazol-3-yl)phenyl)propyl)urea (F85)

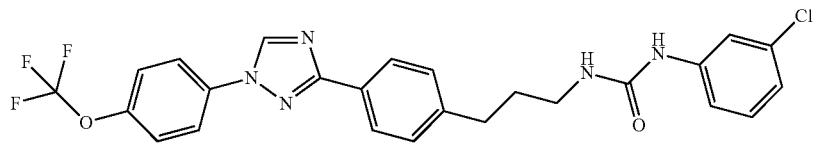 [SMILES: O=C(NCCCc1ccc(-c2ncn(-c3ccc(OC(F)(F)F)cc3)n2)cc1)Nc1cccc(Cl)c1]

Isolated as a white solid (0.14 g, 61%).

1-(2-Ethylphenyl)-3-(3-(4-(1-(4-(trifluoromethoxy)phenyl)-1H-1,2,4-triazol-3-yl)phenyl)propyl)urea (F86)

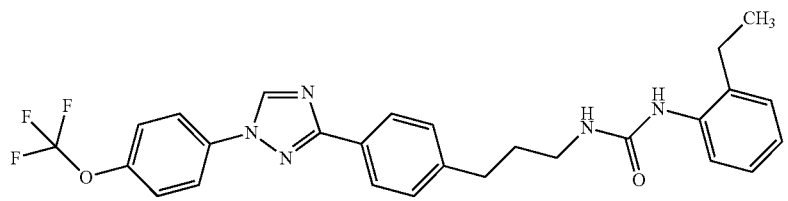 [SMILES: CCc1ccccc1NC(=O)NCCCc1ccc(-c2ncn(-c3ccc(OC(F)(F)F)cc3)n2)cc1]

Isolated as a white solid (0.110 g, 50%).

1-(m-Tolyl)-3-(3-(4-(1-(4-(trifluoromethoxy)phe-
nyl)-1H-1,2,4-triazol-3-yl)phenyl)propyl)urea (F87)

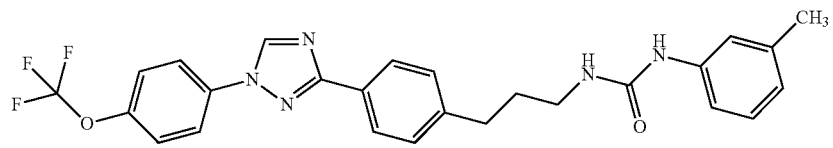 [SMILES: Cc1cccc(NC(=O)NCCCc2ccc(-c3ncn(-c4ccc(OC(F)(F)F)cc4)n3)cc2)c1]

Isolated as a white solid (0.119 g, 55%).

1-(o-Tolyl)-3-(4-(4-(1-(4-(trifluoromethoxy)phenyl)-
1H-1,2,4-triazol-3-yl)phenyl)butyl)urea (F89)

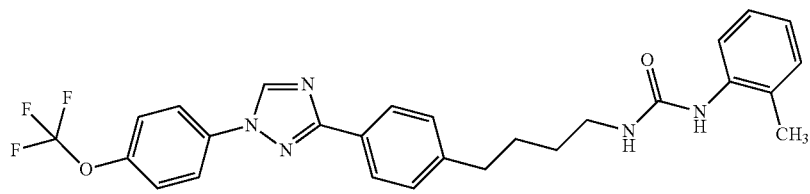

Isolated as a white solid (0.11 g, 50%).

1-(2-Isopropylphenyl)-3-(4-(4-(1-(4-(trifluo-
romethoxy)phenyl)-1H-1,2,4-triazol-3-yl)phenyl)
butyl)urea (F90)

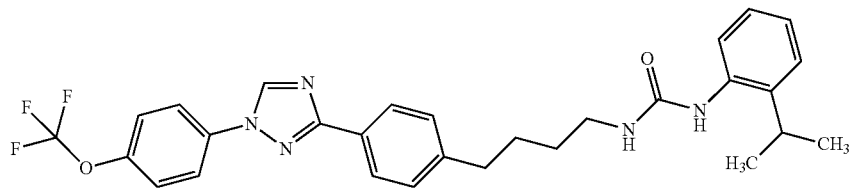

Isolated as a white solid (0.11 g, 54%).

1-(m-Tolyl)-3-(4-(4-(1-(4-(trifluoromethoxy)phe-
nyl)-1H-1,2,4-triazol-3-yl)phenyl)butyl)urea (F91)

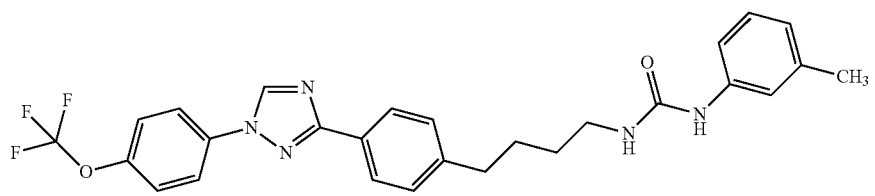 [SMILES: Cc1cccc(NC(=O)NCCCCc2ccc(-c3ncn(-c4ccc(OC(F)(F)F)cc4)n3)cc2)c1]

Isolated as a white solid (0.115 g, 51%).

1-(2-Chlorophenyl)-3-(4-(4-(1-(4-(trifluoromethoxy)
phenyl)-1H-1,2,4-triazol-3-yl)phenyl)butyl)urea
(F92)

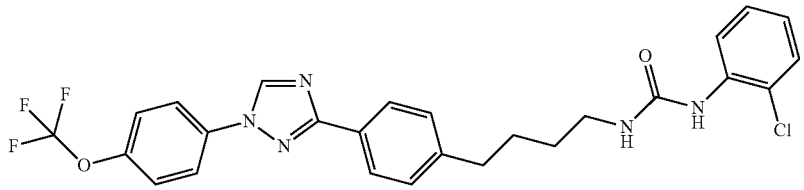 [SMILES: O=C(NCCCCc1ccc(-c2ncn(-c3ccc(OC(F)(F)F)cc3)n2)cc1)Nc1ccccc1Cl]

Isolated as a white solid (0.111 g, 51%).

1-(3-Chlorophenyl)-3-(4-(4-(1-(4-(trifluoromethoxy)
phenyl)-1H-1,2,4-triazol-3-yl)phenyl)butyl)urea
(F93)

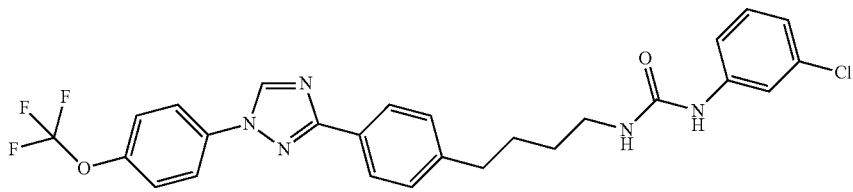 [SMILES: O=C(NCCCCc1ccc(-c2ncn(-c3ccc(OC(F)(F)F)cc3)n2)cc1)Nc1cccc(Cl)c1]

Isolated as a white solid (0.115 g, 54%).

1-(4-Chlorophenyl)-3-(4-(4-(1-(4-(trifluoromethoxy)
phenyl)-1H-1,2,4-triazol-3-yl)phenyl)butyl)urea
(F94)

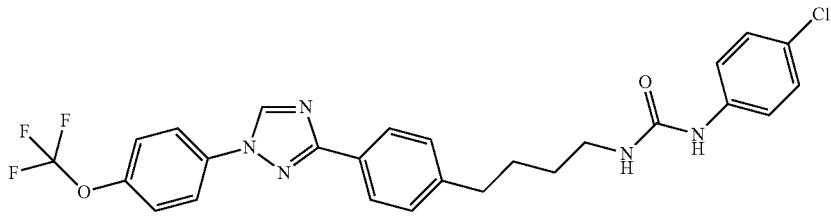 [SMILES: O=C(NCCCCc1ccc(-c2ncn(-c3ccc(OC(F)(F)F)cc3)n2)cc1)Nc1ccc(Cl)cc1]

Isolated as a white solid (0.120 g, 56%).

1-(2-Methoxyphenyl)-3-(4-(4-(1-(4-(trifluoromethoxy)phenyl)-1H-1,2,4-triazol-3-yl)phenyl)
butyl)urea (F95)

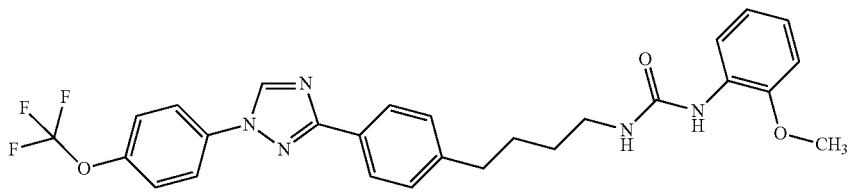 [SMILES: COc1ccccc1NC(=O)NCCCCc1ccc(-c2ncn(-c3ccc(OC(F)(F)F)cc3)n2)cc1]

Isolated as a white solid (0.115 g, 55%).

1-(3-Methoxyphenyl)-3-(4-(4-(1-(4-(trifluoromethoxy)phenyl)-1H-1,2,4-triazol-3-yl)phenyl)butyl)urea (F96)

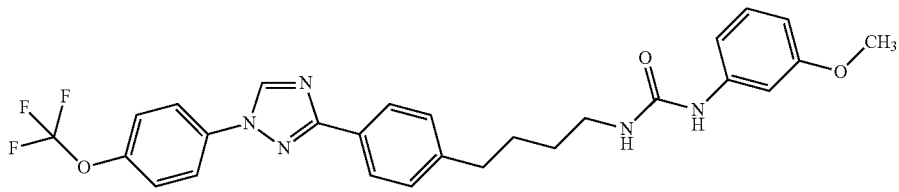 [SMILES: COc1cccc(NC(=O)NCCCCc2ccc(-c3ncn(-c4ccc(OC(F)(F)F)cc4)n3)cc2)c1]

Isolated as a white solid (0.090 g, 43%).

1-(4-Methoxyphenyl)-3-(4-(4-(1-(4-(trifluoromethoxy)phenyl)-1H-1,2,4-triazol-3-yl)phenyl)butyl)urea (F97)

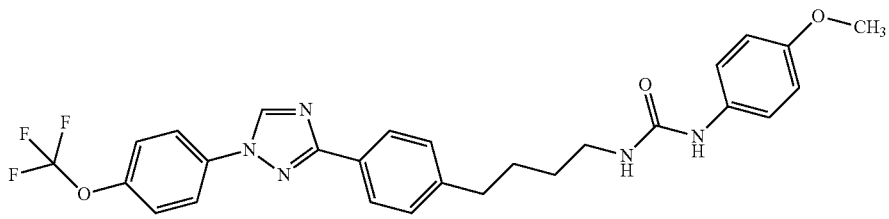 [SMILES: COc1ccc(NC(=O)NCCCCc2ccc(-c3ncn(-c4ccc(OC(F)(F)F)cc4)n3)cc2)cc1]

Isolated as a white solid (0.110 g, 53%).

1-(2-Ethylphenyl)-3-(4-(4-(1-(4-(trifluoromethoxy)phenyl)-1H-1,2,4-triazol-3-yl)phenyl)butyl)urea (F98)

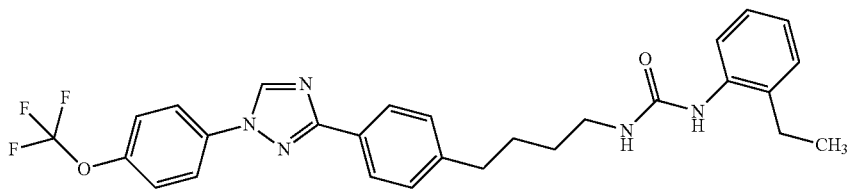

Isolated as a white solid (0.140 g, 67%).

1-(p-Tolyl)-3-(4-(4-(1-(4-(trifluoromethoxy)phenyl)-1H-1,2,4-triazol-3-yl)phenyl)butyl)urea (F99)

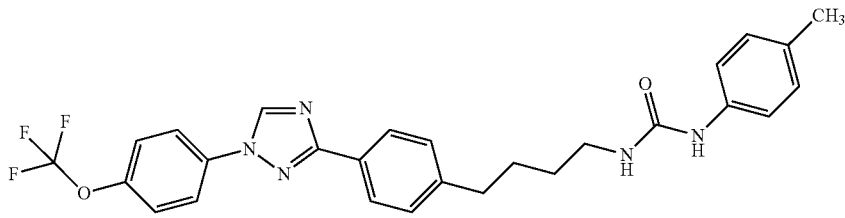 [SMILES: Cc1ccc(NC(=O)NCCCCc2ccc(-c3ncn(-c4ccc(OC(F)(F)F)cc4)n3)cc2)cc1]

Isolated as a white solid (0.122 g, 60%).

Example 42

Preparation of 1-(2-isopropylphenyl)-3-(4-(1-(4-(trifluoromethoxy)phenyl)-1H-1,2,4-triazol-3-yl)benzyl)thiourea (F45)

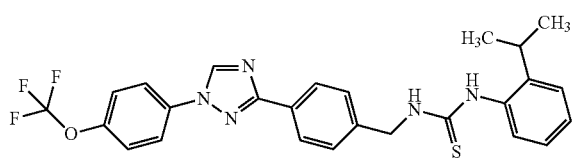 [SMILES: CC(C)c1ccccc1NC(=S)NCc1ccc(-c2ncn(-c3ccc(OC(F)(F)F)cc3)n2)cc1]

In a 100 mL flask, to a solution of (4-(1-(4-(trifluoromethoxy)phenyl)-1H-1,2,4-triazol-3-yl)phenyl) methanamine hydrochloride (0.200 g, 0.598 mmol) in dichloromethane (5 mL) was added triethylamine (0.0720 g, 0.718 mmol) and 1-isopropyl-2-isothiocyanatobenzene (0.106 g, 0.598 mmol) in dichloromethane (5 mL) and the reaction mixture was stirred overnight at room temperature. The reaction mixture was concentrated and the residue purified by flash column chromatography eluting with 10-100% ethyl acetate/B, where B=1:1 dichloromethane/hexanes as eluent to give the title compound as a white solid (0.145 g, 48%).

The following compounds were prepared according to the procedures disclosed in Example 42:

1-(o-Tolyl)-3-(4-(1-(4-(trifluoromethoxy)phenyl)-1H-1,2,4-triazol-3-yl)benzyl)urea (F100)

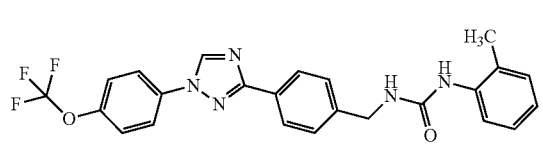 [SMILES: Cc1ccccc1NC(=O)NCc1ccc(-c2ncn(-c3ccc(OC(F)(F)F)cc3)n2)cc1]

Isolated as a white solid (0.095 g, 34%).

1-(2-Ethylphenyl)-3-(4-(1-(4-(trifluoromethoxy)phenyl)-1H-1,2,4-triazol-3-yl)benzyl)urea (F101)

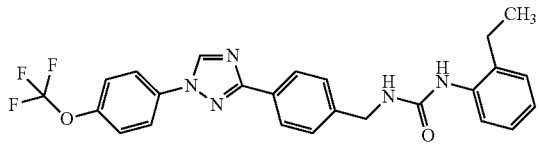 [SMILES: CCc1ccccc1NC(=O)NCc1ccc(-c2ncn(-c3ccc(OC(F)(F)F)cc3)n2)cc1]

Isolated as a white solid (0.080 g, 28%).

1-(p-Tolyl)-3-(4-(1-(4-(trifluoromethoxy)phenyl)-1H-1,2,4-triazol-3-yl)benzyl)urea (F102)

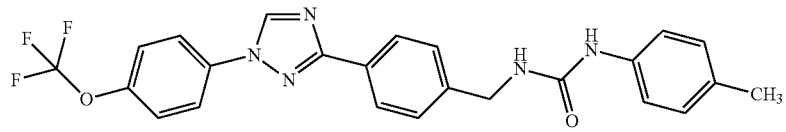 [SMILES: Cc1ccc(NC(=O)NCc2ccc(-c3ncn(-c4ccc(OC(F)(F)F)cc4)n3)cc2)cc1]

Isolated as a white solid (0.060 g, 21%).

1-(3-Chlorophenyl)-3-(4-(1-(4-(trifluoromethoxy)phenyl)-1H-1,2,4-triazol-3-yl)benzyl)urea (F103)

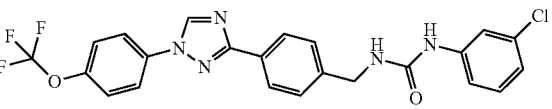

Isolated as a white solid (0.058 g, 20%).

1-(2-Chlorophenyl)-3-(4-(1-(4-(trifluoromethoxy)phenyl)-1H-1,2,4-triazol-3-yl)benzyl)urea (F104)

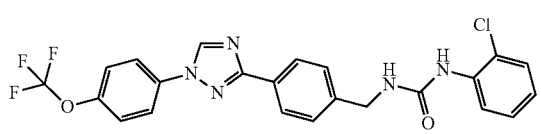 [SMILES: O=C(NCc1ccc(-c2ncn(-c3ccc(OC(F)(F)F)cc3)n2)cc1)Nc1ccccc1Cl]

Isolated as a white solid (0.074 g, 25%).

1-(4-Chlorophenyl)-3-(4-(1-(4-(trifluoromethoxy)phenyl)-1H-1,2,4-triazol-3-yl)benzyl)urea (F105)

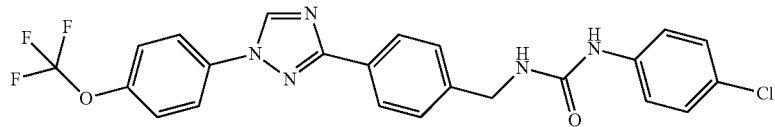 [SMILES: O=C(NCc1ccc(-c2ncn(-c3ccc(OC(F)(F)F)cc3)n2)cc1)Nc1ccc(Cl)cc1]

Isolated as a white solid (0.100 g, 34%).

1-(2-Methoxyphenyl)-3-(4-(1-(4-(trifluoromethoxy)phenyl)-1H-1,2,4-triazol-3-yl)benzyl)urea (F106)

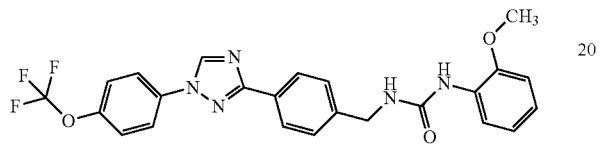

Isolated as a white solid (0.106 g, 37%).

1-(3-Methoxyphenyl)-3-(4-(1-(4-(trifluoromethoxy)phenyl)-1H-1,2,4-triazol-3-yl)benzyl)urea (F107)

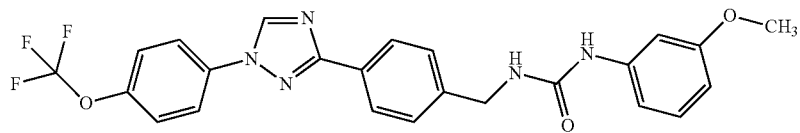 [SMILES: COc1cccc(NC(=O)NCc2ccc(-c3ncn(-c4ccc(OC(F)(F)F)cc4)n3)cc2)c1]

Isolated as a white solid (0.065 g, 23%).

1-(m-Tolyl)-3-(4-(1-(4-(trifluoromethoxy)phenyl)-1H-1,2,4-triazol-3-yl)benzyl)urea (F108)

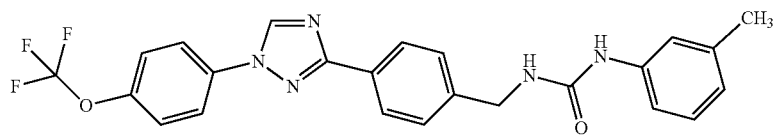 [SMILES: Cc1cccc(NC(=O)NCc2ccc(-c3ncn(-c4ccc(OC(F)(F)F)cc4)n3)cc2)c1]

Isolated as a white solid (0.090 g, 31%).

1-(4-Methoxyphenyl)-3-(4-(1-(4-(trifluoromethoxy)phenyl)-1H-1,2,4-triazol-3-yl)benzyl)urea (F109)

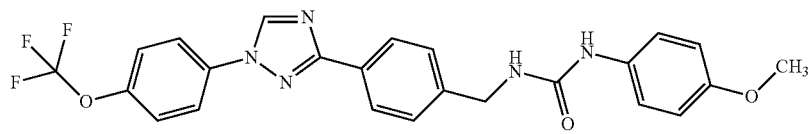 [SMILES: COc1ccc(NC(=O)NCc2ccc(-c3ncn(-c4ccc(OC(F)(F)F)cc4)n3)cc2)cc1]

Isolated as a white solid (0.075 g, 26%).

1-([1,1'-Biphenyl]-2-yl)-3-(3-(4-(1-(4-(trifluoromethoxy)phenyl)-1H-1,2,4-triazol-3-yl)phenyl)propyl)urea (P9)

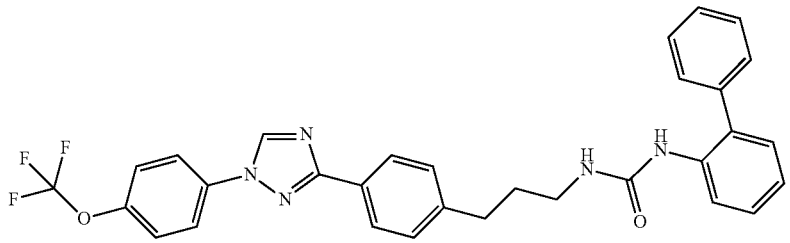 [SMILES: O=C(NCCCc1ccc(-c2ncn(-c3ccc(OC(F)(F)F)cc3)n2)cc1)Nc1ccccc1-c1ccccc1]

Isolated as an off-white solid (0.044 g, 19%).

1-(4-Methoxy-2-methylphenyl)-3-(3-(4-(1-(4-(trifluoromethoxy)phenyl)-1H-1,2,4-triazol-3-yl)phenyl)propyl)urea (P3)

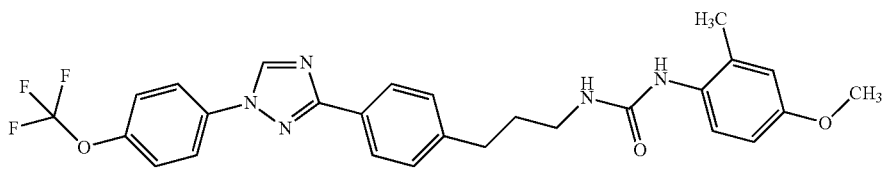 [SMILES: COc1ccc(NC(=O)NCCCc2ccc(-c3ncn(-c4ccc(OC(F)(F)F)cc4)n3)cc2)c(C)c1]

Isolated as an off-white solid (0.094 g, 43%).

Example 43

Preparation of 3-(4-bromophenyl)-1-(4-(trifluoromethoxy)phenyl)-1H-1,2,4-triazole (C23)

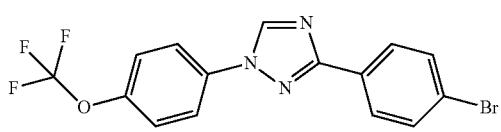

In a 500 mL flask, 3-(4-bromophenyl)-1H-1,2,4-triazole (20.0 g, 89.6 mmol), 1-iodo-4-(trifluoromethoxy)benzene (39.0 g, 135 mmol) were diluted with N,N-dimethylformamide and water (4:1, 100 mL). Then copper(I) iodide (15.3 g, 80.6 mmol), 8-hydroxyquinoline (8.50 g, 58.2 mmol) and cesium carbonate (87.4 g, 269 mmol) were added. The reaction was heated to 150° C. and stirred for 16 hours. The reaction mixture was cooled to room temperature, diluted with ethyl acetate and filtered through Celite®. Brine solution was added to the filtrate and stirred for 15 minutes. The layers were separated and the aqueous layer further extracted with ethyl acetate. The combined organics were dried over magnesium sulfate, filtered, and concentrated. The resulting residue was purified by flash column chromatography using 15% ethyl acetate/petroleum ether as eluent to afford the title compound as a white solid (10.0 g, 29%): mp 100-103° C.; $^1$H NMR (300 MHz, DMSO-d$_6$) δ 9.42 (s, 1H), 8.07 (d, J=9.0 Hz, 2H), 8.05 (d, J=9.0 Hz, 2H), 7.73 (d, J=8.4 Hz, 2H), 7.62 (d, J=8.4 Hz, 2H); ES+ m/z 385 ([M+H]$^+$).

Example 44

Preparation of 3-(4-(1-(4-(trifluoromethoxy)phenyl)-1H-1,2,4-triazol-3-yl)phenyl)prop-2-yn-1-ol (C24)

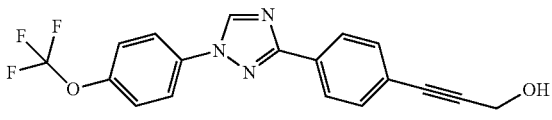 [SMILES: OCC#Cc1ccc(-c2ncn(-c3ccc(OC(F)(F)F)cc3)n2)cc1]

In a 1000 mL flask, 3-(4-bromophenyl)-1-(4-(trifluoromethoxy)phenyl)-1H-1,2,4-triazole (25.0 g, 65.3 mmol) and propargyl alcohol (4.4 g, 78.36 mmol) were diluted with triethylamine (250 mL). Then bis(triphenylphosphine)palladium(II) chloride (0.915 g, 0.0200 mmol), copper(I) iodide (0.320 g, 0.169 mmol) and triphenylphosphine (0.102 g, 0.150 mmol) were added. The reaction was heated to 70° C. and stirred for 16 hours. The reaction mixture was cooled to room temperature, diluted with ethyl acetate and filtered through Celite®. A Brine solution was added to the filtrate and stirred for 15 minutes. The layers were separated and the aqueous layer further extracted with ethyl acetate. The combined organics were dried over magnesium sulfate, filtered, and concentrated. The resulting residue was purified by flash column chromatography using 15% ethyl acetate/petroleum ether as eluent to afford the title compound as yellow solid (8.00 g, 33%): mp 110-113° C.; $^1$H NMR (400 MHz, CDCl$_3$) δ 8.57 (s, 1H), 8.15 (d, J=8.4 Hz, 2H), 7.80 (d, J=9.0 Hz, 2H), 7.54 (d, J=8.4 Hz, 2H), 7.39 (d J=8.4, 2H), 4.53 (d, J=4.8, 2H), 1.80-1.74 (brs, 1H); ES+API m/z 360 ([M+H]$^+$).

The following compounds were prepared according to the procedures disclosed in Example 44:

4-(4-(1-(4-(Trifluoromethoxy)phenyl)-1H-1,2,4-triazol-3-yl)phenyl)but-3-yn-1-ol (C25)

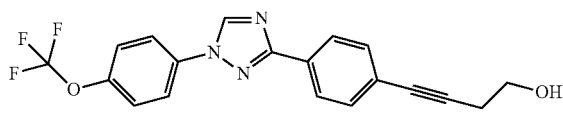 [SMILES: OCCC#Cc1ccc(-c2ncn(-c3ccc(OC(F)(F)F)cc3)n2)cc1]

Isolated as yellow solid (3.6 g, 53%): mp 113-116° C.; $^1$H NMR (300 MHz, DMSO-$d_6$) δ 9.42 (s, 1H), 8.08 (d, J=9.0 Hz, 4H), 7.62 (d, J=8.7 Hz, 2H), 7.53 (d, J=8.4 Hz, 2H), 4.92 (t, J=5.7 Hz, 1H), 3.66-3.56 (m, 2H), 2.59 (t, J=6.6 Hz, 2H); ES+API m/z 374 ([M+H]$^+$).

Example 45

Preparation of 3-(4-(1-(4-(trifluoromethoxy)phenyl)-1H-1,2,4-triazol-3-yl)phenyl)propan-1-ol (C26)

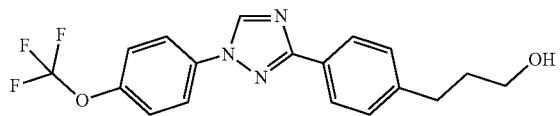 [SMILES: OCCCc1ccc(-c2ncn(-c3ccc(OC(F)(F)F)cc3)n2)cc1]

In a 250 mL flask, to a solution of 3-(4-(1-(4-(trifluoromethoxy)phenyl)-1H-1,2,4-triazol-3-yl)phenyl)propan-1-ol (7.70 g, 21.4 mmol) in methanol (70 mL) was added palladium on carbon (10 wt %, 0.500 g) and the mixture was stirred under hydrogen gas (balloon pressure) overnight. The reaction mixture was filtered over Celite®, washed with methanol and concentrated. Purification by flash column chromatography using 25% ethyl acetate/petroleum ether provided the title compound as a white solid (4 g, 51%): mp 103-106° C.; $^1$H NMR (400 MHz, CDCl$_3$) δ 8.55 (s, 1H), 8.11 (d, J=7.6 Hz, 2H), 7.80 (d, J=8.8 Hz, 2H), 7.38 (d, J=8.4 Hz, 2H), 7.32 (d, J=8.4 Hz, 2H), 3.75-3.68 (m, 2H), 2.81-2.75 (m, 2H), 2.00-1.90 (m, 2H), 1.27 (t, J=5.2 Hz, 1H); ESI+API m/z 364 ([M+H]$^+$).

The following compounds were prepared according to the procedures disclosed in Example 45:

4-(4-(1-(4-(Trifluoromethoxy)phenyl)-1H-1,2,4-triazol-3-yl)phenyl)butan-1-ol (C27)

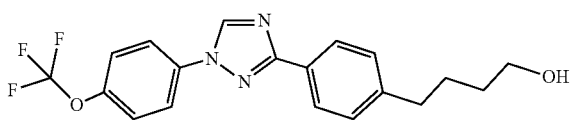 [SMILES: OCCCCc1ccc(-c2ncn(-c3ccc(OC(F)(F)F)cc3)n2)cc1]

Isolated as white solid (2.6 g, 86%): mp 109-112° C.; $^1$H NMR (300 MHz, DMSO-$d_6$) δ 9.37 (s, 1H), 8.08 (d, J=8.7 Hz, 2H), 8.01 (d, J=8.1 Hz, 2H), 7.62 (d, J=9.0 Hz, 2H), 7.34 (d, J=8.1 Hz, 2H), 4.39 (t, J=5.1 Hz, 1H), 3.45-3.38 (m, 2H), 2.64 (t, J=7.6 Hz, 2H), 1.70-1.58 (m, 2H), 1.52-1.40 (m, 2H), 1.25 (s, 2H); ES+API m/z 378 ([M+H]$^+$).

Example 46

Preparation of 2-(3-(4-(1-(4-(trifluoromethoxy)phenyl)-1H-1,2,4-triazol-3-yl)phenyl)propyl)isoindoline-1,3-dione (C5)

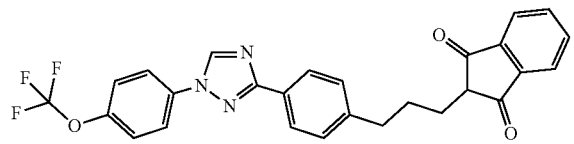 [SMILES: O=C1c2ccccc2C(=O)C1CCCc1ccc(-c2ncn(-c3ccc(OC(F)(F)F)cc3)n2)cc1]

In a 250 mL flask, 3-(4-(1-(4-(trifluoromethoxy)phenyl)-1H-1,2,4-triazol-3-yl)phenyl)propan-1-ol (3.00 g, 8.24 mmol), phthalimide (2.50 g, 17.3 mmol) and triphenylphosphine (5.20 g, 19.8 mmol) were diluted with tetrahydrofuran (30 mL). The reaction mixture was cooled to 0° C. and diisopropylazodicarboxylate (4.00 g, 19.8 mmol) was added. The reaction mixture was stirred at room temperature for 16 hours. The reaction mixture was concentrated and loaded onto silica gel. The resulting slurry was purified by flash column chromatography using 10% ethyl acetate/petroleum ether as eluent to afford the title compound as white solid (2.50 g, 75%); mp 114-118° C.; $^1$H NMR (300 MHz, CDCl$_3$) δ 8.53 (s, 1H), 8.07 (d, J=8.1 Hz, 2H), 7.86-7.76 (m, 4H), 7.72-7.66 (m, 2H), 7.37 (d, J=8.7 Hz, 2H), 7.31 (d, J=7.5 Hz, 2H), 3.77 (t, J=6.9 Hz, 2H), 2.75 (t, J=7.8 Hz, 2H), 2.08 (t, J=6.9 Hz, 2H); ES+API m/z 493 ([M+H]$^+$).

The following compounds were prepared according to the procedures disclosed in Example 46:

2-(4-(4-(1-(4-(Trifluoromethoxy)phenyl)-1H-1,2,4-triazol-3-yl)phenyl)butyl) isoindoline-1,3-dione (C28)

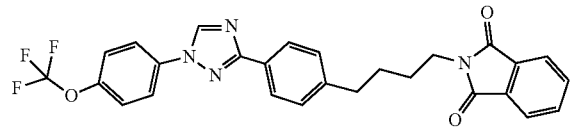 [SMILES: O=C1c2ccccc2C(=O)N1CCCCc1ccc(-c2ncn(-c3ccc(OC(F)(F)F)cc3)n2)cc1]

Isolated as white solid (2.3 g, 65%): $^1$H NMR (300 MHz, CDCl$_3$) δ 8.54 (s, 1H), 8.08 (d, J=8.7 Hz, 2H), 7.90-7.65 (m, 4H), 7.74-7.68 (m, 2H), 7.38 (d, J=8.4 Hz, 2H), 7.28 (d, J=7.8 Hz, 2H), 3.73 (t, J=6.9 Hz, 2H), 2.72 (t, J=7.2 Hz, 2H), 1.80-1.65 (m, 4H), 1.27 (d, J=6.0 Hz, 2H); ES+ m/z 507 ([M+H]$^+$).

Example 47

Preparation of 3-(4-(1-(4-(trifluoromethoxy)phenyl)-1H-1,2,4-triazol-3-yl)phenyl)propan-1-amine (C6)

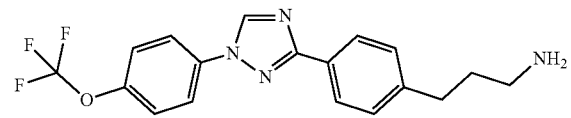 [SMILES: NCCCc1ccc(-c2ncn(-c3ccc(OC(F)(F)F)cc3)n2)cc1]

In a 100 mL flask, 2-(3-(4-(1-(4-(trifluoromethoxy)phenyl)-1H-1,2,4-triazol-3-yl)phenyl)propyl) isoindoline-1,3-dione (2.50 g, 5.08 mmol) was diluted with methanol (25 mL). Hydrazine hydrate (0.740 mL, 15.2 mmol) was added and the reaction mixture was heated to 70° C. and stirred for 3 hours. The reaction mixture was cooled to room temperature, diluted with dichloromethane and washed with sodium hydroxide (1 N). The aqueous layer was further extracted with dichloromethane. The combined organics were dried over magnesium sulfate, filtered, and concentrated. The resulting residue was purified by flash column chromatography using 50% ethyl acetate/petroleum ether as eluent to afford the title compound as white solid (1.60 g, 88%): mp 143-147° C.; $^1$H NMR (400 MHz, DMSO-d$_6$) δ 9.37 (s, 1H), 8.07 (d, J=9.2 Hz, 2H), 8.02 (d, J=8.4 Hz, 2H), 7.62 (d, J=8.4 Hz, 2H), 7.34 (d, J=7.6 Hz, 2H), 2.66 (t, J=7.6 Hz, 2H), 2.56 (t, J=6.8 Hz, 2H), 1.90 (brs, 2H), 1.72-1.62 (m, 2H); ES+ m/z 363 ([M+H]$^+$).

The following compounds were prepared according to the procedures disclosed in Example 47:

4-(4-(1-(4-(Trifluoromethoxy)phenyl)-1H-1,2,4-triazol-3-yl)phenyl)butan-1-amine (C29)

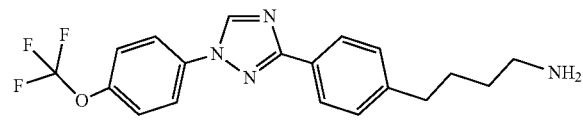 [SMILES: NCCCCc1ccc(-c2ncn(-c3ccc(OC(F)(F)F)cc3)n2)cc1]

Isolated as white solid (1.2 g, 70%): mp 122-125° C.; $^1$H NMR (300 MHz, DMSO-d$_6$) δ 9.37 (s, 1H), 8.07 (d, J=8.7 Hz, 2H), 8.02 (d, J=8.1 Hz, 2H), 7.62 (d, J=8.4 Hz, 2H), 7.34 (d, J=8.1, 2H), 2.63 (t, J=7.2, 2H), 2.60-2.50 (m, 2H), 1.68-1.56 (m, 2H), 1.44-1.32 (m, 2H), 1.18 (d, J=6.3 Hz, 2H); ES+ m/z 377 ([M+H]$^+$).

Example 48

Preparation of 4-(1-(4-(trifluoromethoxy)phenyl)-1H-1,2,4-triazol-3-yl)benzonitrile (C30)

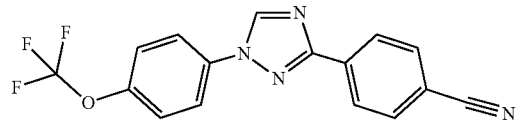 [SMILES: N#Cc1ccc(-c2ncn(-c3ccc(OC(F)(F)F)cc3)n2)cc1]

In a 250 mL flask, 3-(4-bromophenyl)-1-(4-(trifluoromethoxy)phenyl)-1H-1,2,4-triazole (4.00 g, 10.4 mmol) was dissolved in N,N-dimethylformamide (30 mL) under nitrogen atmosphere. Zinc cyanide (1.46 g, 12.4 mmol) and tetrakis(triphenylphosphine) palladium(0) (0.601 g, 0.0500 mmol) were added and the reaction mixture was heated to 110° C. for 16 hours. The reaction mixture was cooled to room temperature, diluted with ethyl acetate and washed with water. The aqueous layer was further extracted with ethyl acetate. The combined organics were washed with water and brine, dried over magnesium sulfate and concentrated. Purification by flash column chromatography eluting with 30% ethyl acetate/hexanes gave the title compound as off-white solid (3.40 g, 94%): mp 172-176° C.; $^1$H NMR (400 MHz, CDCl$_3$): δ 8.60 (s, 1H), 8.31 (d, J=8.8 Hz, 2H), 7.81 (d, J=8.8 Hz, 2H), 7.77 (d, J=8.8 Hz, 2H), 7.41 (d, J=8.8 Hz, 2H); ES+API m/z 331 ([M+H]$^+$).

Example 49

Preparation of (4-(1-(4-(trifluoromethoxy)phenyl)-1H-1,2,4-triazol-3-yl)phenyl) methanamine.hydrochloride (C16A)

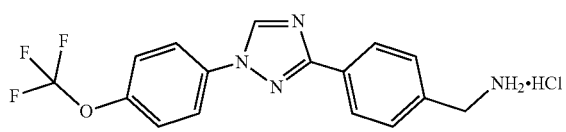

In a 250 mL flask, 4-(1-(4-(trifluoromethoxy)phenyl)-1H-1,2,4-triazol-3-yl)benzonitrile (3.00 g, 9.09 mmol) in ethanol (30 mL) was taken and hydrogen chloride (12 N, 3 mL) was added followed by palladium on carbon (10 wt %, 0.500 g). The reaction mixture was evacuated and purged with hydrogen gas. The reaction mixture was stirred under hydrogen (50 psi) for 24 hours. The reaction mixture was filtered over Celite®, concentrated and the solid obtained triturated with diethyl ether to give the title compound as an off-white solid (2.80 g, 93%): mp 259-263° C.; $^1$H NMR (300 MHz, DMSO-d$_6$) δ 9.43 (s, 1H), 8.37 (bs, 3H), 8.15 (d, J=8.1 Hz, 2H), 8.08 (d, J=9.3 Hz, 2H), 7.63 (d, J=8.1 Hz, 4H), 4.10 (q, J=6.0 Hz, 2H); ES+ m/z 335 ([M+H]$^+$).

Example 50

Preparation of 1-(4-methoxy-2-methylphenyl)-3-(4-(1-(4-(perfluoroethoxy)phenyl)-1H-1,2,4-triazol-3-yl)benzyl)thiourea (F111)

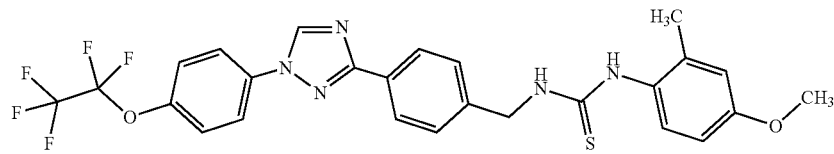 [SMILES: COc1ccc(NC(=S)NCc2ccc(-c3ncn(-c4ccc(OC(F)(F)C(F)(F)F)cc4)n3)cc2)c(C)c1]

To a solution of (4-(1-(4-(perfluoroethoxy)phenyl)-1H-1,2,4-triazol-3-yl)phenyl)methanamine (0.075 mg, 0.20 mmol) in dry tetrahydrofuran (1 mL) was added 1-isothiocyanato-4-methoxy-2-methylbenzene (0.052 mg, 0.29 mmol) and the resulting mixture was stirred at 50° C. for 24 hours. The mixture was concentrated under reduced pressure to give a brown residue, which was purified by flash column chromatography eluting with mixtures of hexanes and ethyl acetate to afford the title compound as a white solid (0.050 g, 46%).

The following compounds were prepared according to the procedures disclosed in Example 50:

Preparation of 1-(4-methoxyphenyl)-3-(4-(1-(4-(perfluoroethoxy)phenyl)-1H-1,2,4-triazol-3-yl)benzyl)thiourea (F110)

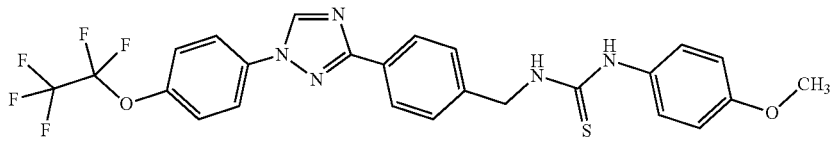 [SMILES: COc1ccc(NC(=S)NCc2ccc(-c3ncn(-c4ccc(OC(F)(F)C(F)(F)F)cc4)n3)cc2)cc1]

Isolated as a white solid (0.054 g, 50%).

1-(4-(Dimethylamino)phenyl)-3-(4-(1-(4-(perfluoroethoxy)phenyl)-1H-1,2,4-triazol-3-yl)benzyl)thiourea (F112)

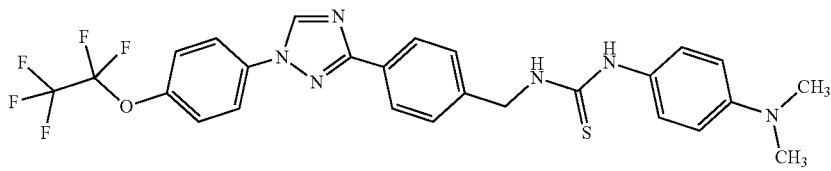 [SMILES: CN(C)c1ccc(NC(=S)NCc2ccc(-c3ncn(-c4ccc(OC(F)(F)C(F)(F)F)cc4)n3)cc2)cc1]

Isolated as a white solid (0.061 g, 56%).

Example 51

Preparation of (4-(1-(4-(perfluoroethoxy)phenyl)-1H-1,2,4-triazol-3-yl)phenyl)methanol (C31)

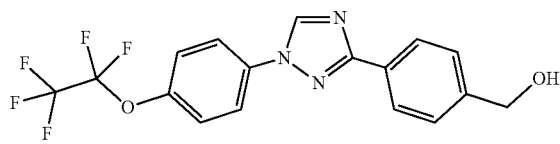 [SMILES: OCc1ccc(-c2ncn(-c3ccc(OC(F)(F)C(F)(F)F)cc3)n2)cc1]

To 4-(1-(4-(perfluoroethoxy)phenyl)-1H-1,2,4-triazol-3-yl)benzaldehyde (WO 2011/017513) (3.00 g, 7.83 mmol) in methanol (40 mL) cooled to 0° C. was added sodium borohydride (0.296 g, 7.83 mmol). The reaction mixture was stirred for 1 hour. The mixture was acidified with aqueous hydrogen chloride (1 N) and diluted with ethyl acetate. The pH was adjusted to 7 by aqueous sodium bicarbonate. The organic phase separated, rinsed with saturated aqueous sodium bicarbonate, brine, dried over magnesium sulfate, filtered, and concentrated to provide the title compound as a solid (3.01 g, 100%): ESIMS m/z 386 ([M+H]$^+$).

Example 52

Preparation of 3-(4-(azidomethyl)phenyl)-1-(4-(perfluoroethoxy)phenyl)-1H-1,2,4-triazole (C32)

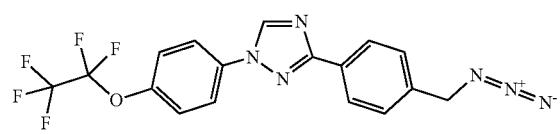 [SMILES: [N-]=[N+]=NCc1ccc(-c2ncn(-c3ccc(OC(F)(F)C(F)(F)F)cc3)n2)cc1]

To (4-(1-(4-(perfluoroethoxy)phenyl)-1H-1,2,4-triazol-3-yl)phenyl)methanol (2.00 g, 5.19 mmol) in tetrahydrofuran (25 mL) was added diphenylphosphoryl azide (1.30 g, 5.71 mmol), followed by dropwise addition of 1,8-diazabicycloundec-7-ene (0.861 mL, 5.71 mmol). The mixture was stirred at room temperature for 6 hours. The mixture was diluted with water and ethyl acetate. The organic phase was separated and rinsed with brine, dried over magnesium sulfate, and concentrated to provide the title compound as a yellow solid (1.85 g, 83%): ESIMS m/z 411 ([M+H]$^+$).

Example 53

Preparation of (4-(1-(4-(perfluoroethoxy)phenyl)-1H-1,2,4-triazol-3-yl)phenyl)methanamine (C33)

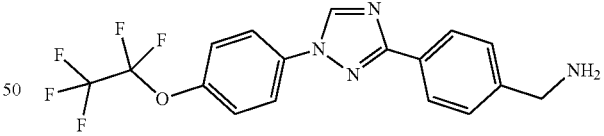

To 3-(4-(azidomethyl)phenyl)-1-(4-(perfluoroethoxy)phenyl)-1H-1,2,4-triazole (0.015 g, 0.037 mmol) in ethyl acetate (10 mL) was added palladium on carbon (10 wt %, 0.010 g, 0.037 mmol). The mixture was stirred under a hydrogen atmosphere (balloon) for 12 hours. The mixture was purged with nitrogen, filtered, and concentrated to provide the title compound as a white solid (0.014 g, 85%): $^1$H NMR (400 MHz, CDCl$_3$) δ 8.56 (s, 1H), 8.12 (d, J=8.2 Hz, 2H), 7.80 (d, J=9.1 Hz, 2H), 7.39 (d, J=9.1 Hz, 4H), 3.87 (s, 2H), 2.42 (s, 2H); $^{19}$F NMR (376 MHz, CDCl$_3$) δ −85.90, −87.86; ESIMS m/z 385 ([M+H]$^+$).

Example 54

Preparation of [1,1'-biphenyl]-3-carbonyl azide (C34)

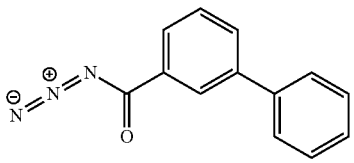 [SMILES: [N-]=[N+]=NC(=O)c1cccc(-c2ccccc2)c1]

To a vial (8 mL) diphenylphosphoryl azide (0.39 mL, 1.8 mmol) and triethylamine (0.25 mL, 1.8 mmol) were added to a stirred solution of biphenyl-3-carboxylic acid (0.30 g, 1.5 mmol) in isopropanol (3 mL). The vial was closed with a lid, and the reaction mixture was stirred for 16 hours at room temperature. The reaction mixture was concentrated, and water (50 mL) was added. The mixture was extracted with ethyl acetate (3×50 mL). The combined extracts were dried over sodium sulfate, filtered, and concentrated to provide the title compound (0.40 g, 100%) was used in the next reaction without characterization or purification.

The following compounds were prepared according to the procedures disclosed in Example 54:

2'-Methyl-[1,1'-biphenyl]-3-carbonyl azide (C35)

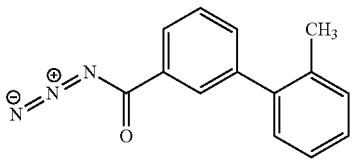 [SMILES: Cc1ccccc1-c1cccc(C(=O)N=[N+]=[N-])c1]

2'-Methyl-[1,1'-biphenyl]-2-carbonyl azide (C36)

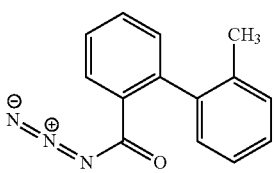 [SMILES: Cc1ccccc1-c1ccccc1C(=O)N=[N+]=[N-]]

3-Isopropylbenzoyl azide (C37)

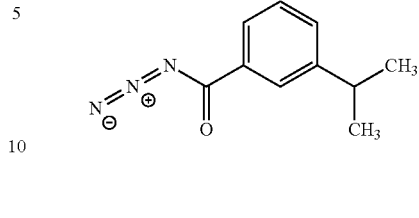

3,5-Dimethylbenzoyl azide (C38)

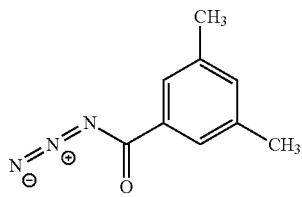

Example 55

Preparation of 1-([1,1'-biphenyl]-3-yl)-3-(3-(4-(1-(4-(trifluoromethoxy)phenyl)-1H-1,2,4-triazol-3-yl)phenyl)propyl)urea (P7)

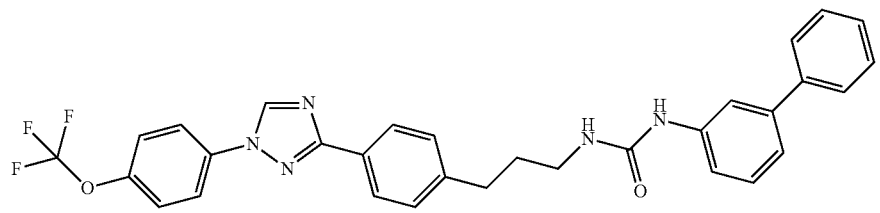 [SMILES: O=C(NCCCc1ccc(-c2ncn(-c3ccc(OC(F)(F)F)cc3)n2)cc1)Nc1cccc(-c2ccccc2)c1]

To a solution of [1,1'-biphenyl]-3-carbonyl azide (0.40 g, 1.8 mmol) was added in 1,2-dichloroethane (5 mL). The reaction mixture was heated at reflux for 3 hours and then cooled to room temperature. 3-(4-(1-(4-(Trifluoromethoxy)phenyl)-1H-1,2,4-triazol-3-yl)phenyl)propan-1-amine (0.50 g, 1.4 mmol) was added to the reaction mixture, which was heated to reflux overnight. The reaction mixture was cooled and concentrated. Purification by high pressure liquid chromatography provided the title compound as an off-white solid (0.11 g, 12%).

The following compounds were prepared according to the procedures disclosed in Example 55:

1-(3-Isopropylphenyl)-3-(3-(4-(1-(4-(trifluoromethoxy)phenyl)-1H-1,2,4-triazol-3-yl)phenyl)propyl)urea (P2)

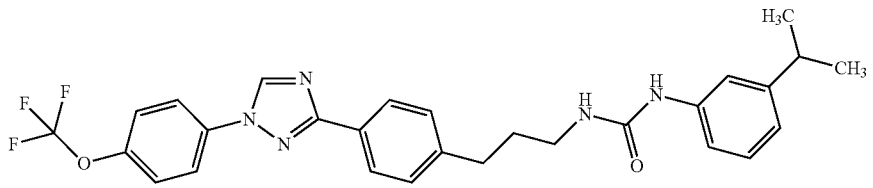 [SMILES: CC(C)c1cccc(NC(=O)NCCCc2ccc(-c3ncn(-c4ccc(OC(F)(F)F)cc4)n3)cc2)c1]

Isolated as an off-white solid (0.227 g, 18%).

1-(3,5-Dimethylphenyl)-3-(3-(4-(1-(4-(trifluoromethoxy)phenyl)-1H-1,2,4-triazol-3-yl)phenyl)propyl)urea (P1)

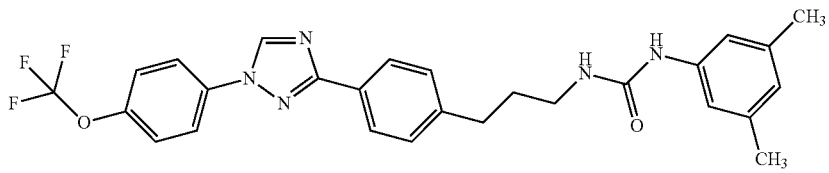 [SMILES: Cc1cc(C)cc(NC(=O)NCCCc2ccc(-c3ncn(-c4ccc(OC(F)(F)F)cc4)n3)cc2)c1]

Isolated as an off-white solid (0.062 g, 5%).

1-(2'-Methyl-[1,1'-biphenyl]-2-yl)-3-(3-(4-(1-(4-(trifluoromethoxy)phenyl)-1H-1,2,4-triazol-3-yl)phenyl)propyl)urea (FA1)

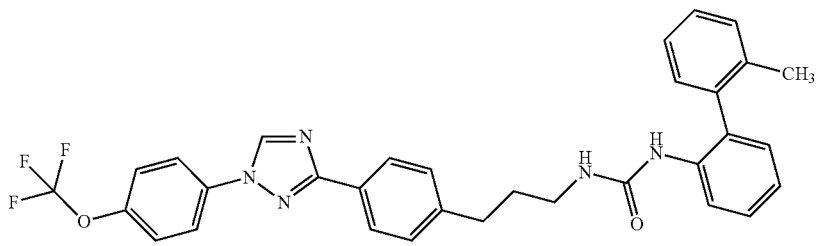 [SMILES: Cc1ccccc1-c1ccccc1NC(=O)NCCCc1ccc(-c2ncn(-c3ccc(OC(F)(F)F)cc3)n2)cc1]

Isolated as an off-white solid (0.135 g, 12%).

1-(2'-Methyl-[1,1'-biphenyl]-3-yl)-3-(3-(4-(1-(4-(trifluoromethoxy)phenyl)-1H-1,2,4-triazol-3-yl)phenyl)propyl)urea (FA2)

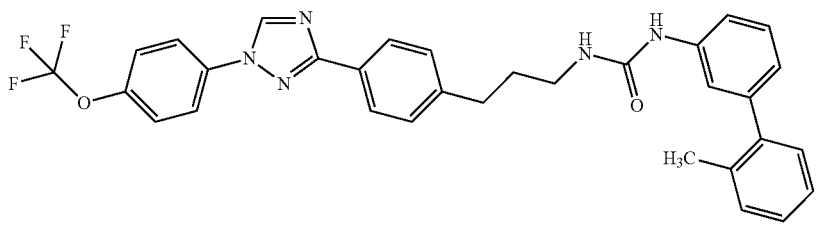 [SMILES: Cc1ccccc1-c1cccc(NC(=O)NCCCc2ccc(-c3ncn(-c4ccc(OC(F)(F)F)cc4)n3)cc2)c1]

Isolated as an off-white solid (0.135 g, 12%).

Example 56

Preparation of 1-(2-isopropylphenyl)-3-(3-(4-(1-(4-(trifluoromethoxy)phenyl)-1H-1,2,4-triazol-3-yl)phenyl)propyl)urea (F76)

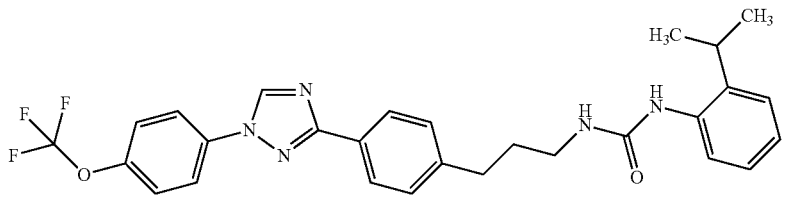 [SMILES: CC(C)c1ccccc1NC(=O)NCCCc1ccc(-c2ncn(-c3ccc(OC(F)(F)F)cc3)n2)cc1]

To 2-isopropylaniline (0.50 g, 3.7 mmol) and sodium bicarbonate (0.93 g, 11 mmol) in dichloromethane and water (36 mL, 2:1) was added triphosgene (0.55 g, 1.9 mmol) at 0° C. The reaction was stirred until complete conversion to the isocyanate, as observed by thin layer chromatography. The reaction was then diluted with dichloromethane (100 mL), and the organic layer was separated from the water layer and concentrated. The residue obtained was dissolved in acetonitrile (15 mL) and 3-(4-(1-(4-(Trifluoromethoxy)phenyl)-1H-1,2,4-triazol-3-yl)phenyl)propan-1-amine (1.2 g, 3.4 mmol) and cesium carbonate (1.1 g, 3.4 mmol) were added. The reaction was stirred at room temperature for 16 hours. The reaction was quenched with water (50 mL) and extracted with dichloromethane (3×100 mL). The organic layers were dried over sodium sulfate, filtered, and concentrated. Purification by flash column chromatography using high pressure liquid chromatography provided the title compound as an off-white solid (0.26 g, 16%).

The following compounds were prepared according to the procedures disclosed in Example 56:

1-(2-Ethyl-6-methylphenyl)-3-(3-(4-(1-(4-(trifluoromethoxy)phenyl)-1H-1,2,4-triazol-3-yl)phenyl)propyl)urea (P5)

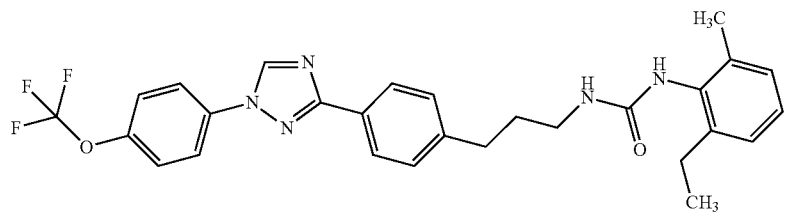 [SMILES: CCc1cccc(C)c1NC(=O)NCCCc1ccc(-c2ncn(-c3ccc(OC(F)(F)F)cc3)n2)cc1]

Isolated as an off-white solid (0.081 g, 5%).

1-(2-Isopropyl-5-methylphenyl)-3-(3-(4-(1-(4-(trifluoromethoxy)phenyl)-1H-1,2,4-triazol-3-yl)phenyl)propyl)urea (P6)

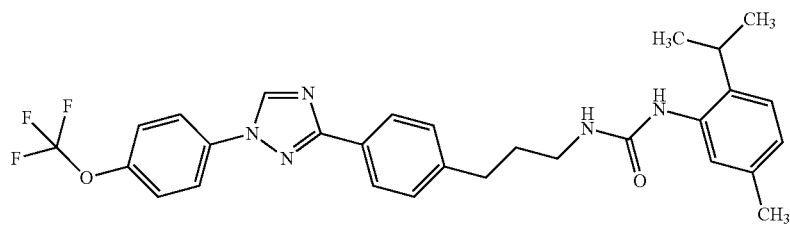 [SMILES: Cc1ccc(C(C)C)c(NC(=O)NCCCc2ccc(-c3ncn(-c4ccc(OC(F)(F)F)cc4)n3)cc2)c1]

Isolated as an off-white solid (0.078 g, 6%).

Example PE1

Prophetic preparation of 1-(3,5-dimethylphenyl)-3-(3-(4-(1-(4-(trifluoromethoxy)phenyl)-1H-1,2,4-triazol-3-yl)phenyl)propyl)urea (P37)

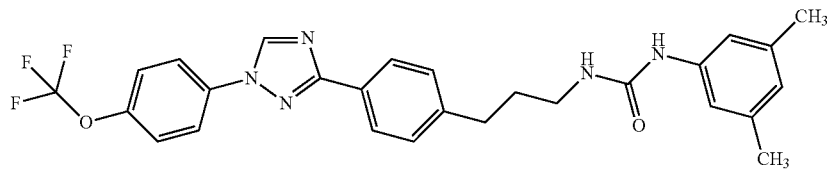 [SMILES: Cc1cc(C)cc(NC(=O)NCCCc2ccc(-c3ncn(-c4ccc(OC(F)(F)F)cc4)n3)cc2)c1]

To 3-(4-(1-(4-(trifluoromethoxy)phenyl)-1H-1,2,4-triazol-3-yl)phenyl)propan-1-amine (1 equiv) and sodium bicarbonate (5 equiv) in an appropriate reaction vessel may be added a solvent such as dichloromethane (at a concentration between about 0.01 M to about 1 M). The reaction may be placed in an ice bath and triphosgene (0.4 equiv) can be added in one portion. The reaction may be monitored by LC/MS to observe formation of the isocyanate, upon which the reaction may be diluted with dichloromethane, filtered through a phase separator, and concentrated. The residue may be suspended in a solvent such as acetonitrile (0.1 M to about 1 M), followed by addition of 3,5-dimethylaniline (1.0-1.5 equiv) and cesium carbonate (1.0-1.5 equiv). Following completion of the reaction, the product may be obtained using standard organic chemistry techniques of workup and purification.

The following compounds in Table 1 may be prepared according to the procedures disclosed in Example PE1:

P1, P2, P3, P4, P5, P6, P7, P8, P9, P10, P11, P12, P13, P14

TABLE 1

Structure and Preparation Method for Prophetic Compounds

| No. | Structure | May be Prepared according to Example: |
|-----|-----------|----------------------------------------|
| P1 | 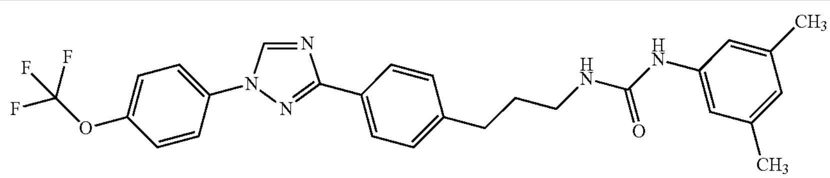 [SMILES: Cc1cc(C)cc(NC(=O)NCCCc2ccc(-c3ncn(-c4ccc(OC(F)(F)F)cc4)n3)cc2)c1] | PE1 |
| P2 | 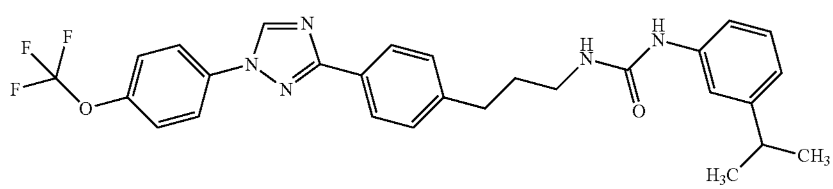 | PE1 |
| P3 | 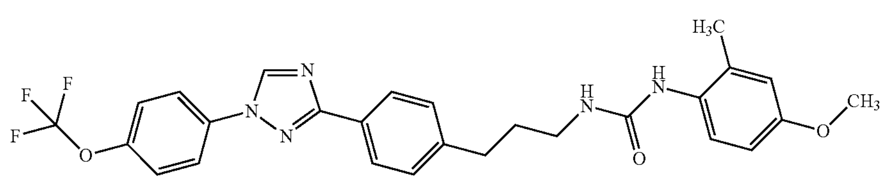 [SMILES: COc1ccc(NC(=O)NCCCc2ccc(-c3ncn(-c4ccc(OC(F)(F)F)cc4)n3)cc2)c(C)c1] | PE1 |
| P4 | 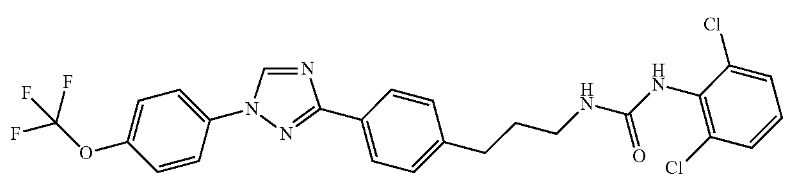 [SMILES: O=C(NCCCc1ccc(-c2ncn(-c3ccc(OC(F)(F)F)cc3)n2)cc1)Nc1c(Cl)cccc1Cl] | PE1 |

TABLE 1-continued
Structure and Preparation Method for Prophetic Compounds
| No. | Structure | May be Prepared according to Example: |
|---|---|---|
| P5 | 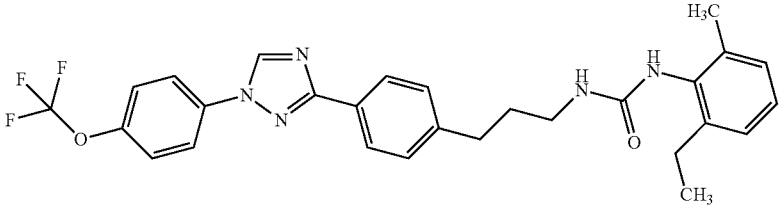 [SMILES: CCc1cccc(C)c1NC(=O)NCCCc1ccc(-c2ncn(-c3ccc(OC(F)(F)F)cc3)n2)cc1] | PE1 |
| P6 | 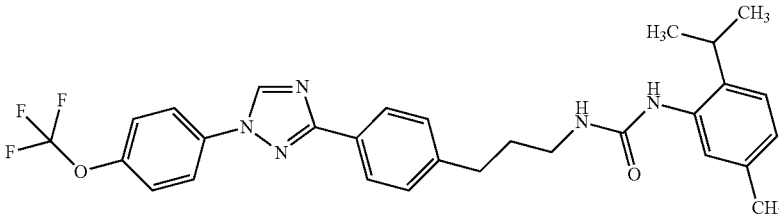 | PE1 |
| P7 | 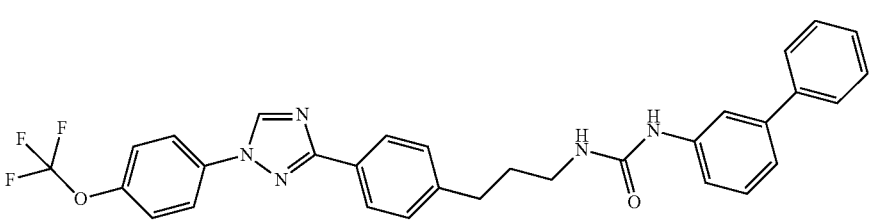 [SMILES: O=C(NCCCc1ccc(-c2ncn(-c3ccc(OC(F)(F)F)cc3)n2)cc1)Nc1cccc(-c2ccccc2)c1] | PE1 |
| P8 | 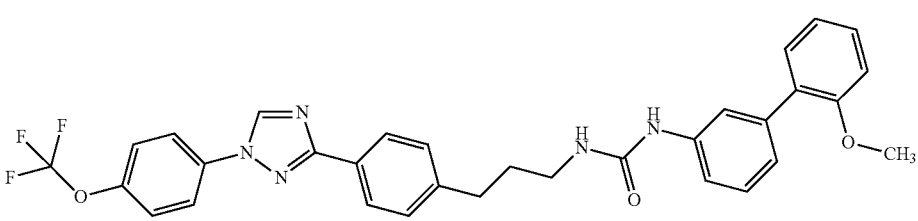 [SMILES: COc1ccccc1-c1cccc(NC(=O)NCCCc2ccc(-c3ncn(-c4ccc(OC(F)(F)F)cc4)n3)cc2)c1] | PE1 |
| P9 | 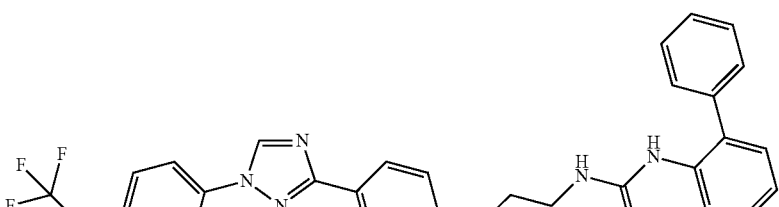 | PE1 |
| P10 | 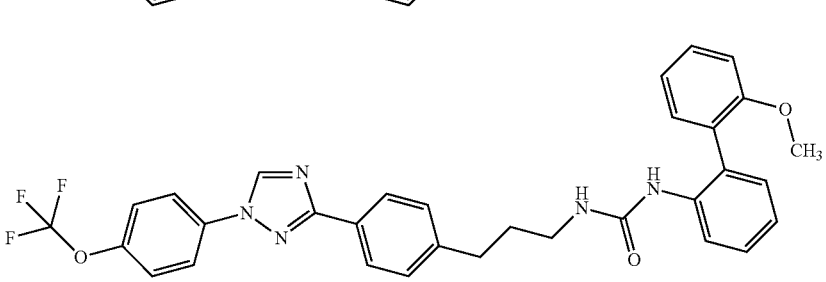 | PE1 |

TABLE 1-continued

Structure and Preparation Method for Prophetic Compounds

| No. | Structure | May be Prepared according to Example: |
|-----|-----------|---------------------------------------|
| P11 | [structure] | PE1 |
| P12 | [structure] | PE1 |
| P13 | [structure] | PE1 |
| P14 | [structure] | PE1 |

Example A

Bioassays on Beet Armyworm (*Spodoptera exigua*, LAPHEG) ("BAW"), Corn Earworm (*Helicoverpa zea*, HELIZE) ("CEW"), and Cabbage Looper (*Trichoplusia ni*, TRIPNI) ("CL")

BAW has few effective parasites, diseases, or predators to lower its population. BAW infests many weeds, trees, grasses, legumes, and field crops. In various places, it is of economic concern upon asparagus, cotton, corn, soybeans, tobacco, alfalfa, sugar beets, peppers, tomatoes, potatoes, onions, peas, sunflowers, and citrus, among other plants. CEW is known to attack corn and tomatoes, but it also attacks artichoke, asparagus, cabbage, cantaloupe, collards, cowpeas, cucumbers, eggplant, lettuce, lima beans, melon, okra, peas, peppers, potatoes, pumpkin, snap beans, spinach, squash, sweet potatoes, and watermelon, among other plants. CEW is also known to be resistant to certain insecticides. Consequently, because of the above factors control of these pests is important. Furthermore, molecules that control these pests are useful in controlling other pests.

CL is a member of the moth family Noctuidae. It is found throughout the world. It is attacks cabbage, cauliflower, broccoli, Brussel sprouts, tomatoes, cucumbers, potatoes, kale, turnips, mustard, peppers, eggplant, watermelons, melons, squash, cantaloupe, peas, beans, collards, lettuce, spinach, celery, parsley, beets, peas, alfalfa, soybeans, and cotton. This species is very destructive to plants due to its voracious consumption of leaves. In the case of cabbage, however, they feed not only on the wrapper leaves, but also may bore into the developing head. The larvae consume three times their weight in plant material daily. The feeding sites are marked by large accumulations of sticky, wet fecal material.

Consequently, because of the above factors control of these pests is important. Furthermore, molecules that control these pests (BAW, CEW, and CL), which are known as chewing pests, are useful in controlling other pests that chew on plants.

Certain molecules disclosed in this document were tested against BAW, CEW, and CL using procedures described in the following examples. In the reporting of the results, the "BAW, CEW, & CL Rating Table" was used (See Table Section).

Bioassays on BAW

Bioassays on BAW were conducted using a 128-well diet tray assay. one to five second instar BAW larvae were placed in each well (3 mL) of the diet tray that had been previously filled with 1 mL of artificial diet to which 50 µg/cm² of the test compound (dissolved in 50 µL of 90:10 acetone-water mixture) had been applied (to each of eight wells) and then allowed to dry. Trays were covered with a clear self-adhesive cover and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Bioassays on CEW

Bioassays on CEW were conducted using a 128-well diet tray assay. one to five second instar CEW larvae were placed in each well (3 mL) of the diet tray that had been previously filled with 1 mL of artificial diet to which 50 μg/cm$^2$ of the test compound (dissolved in 50 μL of 90:10 acetone-water mixture) had been applied (to each of eight wells) and then allowed to dry. Trays were covered with a clear self-adhesive cover, and held at 25° C., 14:10 light-dark for five to seven days. Percent mortality was recorded for the larvae in each well; activity in the eight wells was then averaged. The results are indicated in the table entitled "Table ABC: Biological Results" (See Table Section). Bioassays on CL Bioassays on CL were conducted using a 128-well diet tray assay. one to five second instar CL larvae were placed in each well (3 mL) of the diet tray that had been previously filled with 1 mL of artificial diet to which 50 μg/cm$^2$ of the test compound (dissolved in 50 μL of 90:10 acetone-water mixture) had been applied (to each of eight wells) and then allowed to dry. Trays were covered with a clear self-adhesive cover and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Example B

Bioassays on Green Peach Aphid (*Myzus persicae*, MYZUPE) ("GPA")

GPA is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress, and zucchini, among other plants. GPA also attacks many ornamental crops such as carnation, chrysanthemum, flowering white cabbage, poinsettia, and roses. GPA has developed resistance to many pesticides. Consequently, because of the above factors control of this pest is important. Furthermore, molecules that control this pest (GPA), which is known as a sucking pest, are useful in controlling other pests that suck on plants.

Certain molecules disclosed in this document were tested against GPA using procedures described in the following example. In the reporting of the results, the "GPA Rating Table" was used (See Table Section).

Cabbage seedlings grown in 3-inch pots, with 2-3 small (3-5 cm) true leaves, were used as test substrate. The seedlings were infested with 20-50 GPA (wingless adult and nymph stages) one day prior to chemical application. Four pots with individual seedlings were used for each treatment. Test compounds (2 mg) were dissolved in 2 mL of acetone/methanol (1:1) solvent, forming stock solutions of 1000 ppm test compound. The stock solutions were diluted 5× with 0.025% Tween 20 in water to obtain the solution at 200 ppm test compound. A hand-held aspirator-type sprayer was used for spraying a solution to both sides of cabbage leaves until runoff. Reference plants (solvent check) were sprayed with the diluent only containing 20% by volume of acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol. 18 (1925), pp. 265-267) as follows.

$$\text{Corrected \% Control} = 100*(X-Y)/X$$

where

X=No. of live aphids on solvent check plants and
Y=No. of live aphids on treated plants
The results are indicated in the table entitled "Table ABC: Biological Results" (See Table Section).

Example C

Bioassays on Yellow Fever Mosquito (*Aedes aegypti*, AEDSAE) ("YFM")

YFM prefers to feed on humans during the daytime and is most frequently found in or near human habitations. YFM is a vector for transmitting several diseases. It is a mosquito that can spread the dengue fever and yellow fever viruses. Yellow fever is the second most dangerous mosquito-borne disease after malaria. Yellow fever is an acute viral hemorrhagic disease and up to 50% of severely affected persons without treatment will die from yellow fever. There are an estimated 200,000 cases of yellow fever, causing 30,000 deaths, worldwide each year. Dengue fever is a nasty, viral disease; it is sometimes called "breakbone fever" or "breakheart fever" because of the intense pain it can produce. Dengue fever kills about 20,000 people annually. Consequently, because of the above factors control of this pest is important. Furthermore, molecules that control this pest (YFM), which is known as a sucking pest, are useful in controlling other pests that cause human and animal suffering.

Certain molecules disclosed in this document were tested against YFM using procedures described in the following paragraph. In the reporting of the results, the "YFM Rating Table" was used (See Table Section).

Master plates containing 400 μg of a molecule dissolved in 100 μL of dimethyl sulfoxide (DMSO) (equivalent to a 4000 ppm solution) are used. A master plate of assembled molecules contains 15 μL per well. To this plate, 135 μL of a 90:10 water:acetone mixture is added to each well. A robot (Biomek® NXP Laboratory Automation Workstation) is programmed to dispense 15 μL aspirations from the master plate into an empty 96-well shallow plate ("daughter" plate). There are 6 reps ("daughter" plates) created per master. The created daughter plates are then immediately infested with YFM larvae.

The day before plates are to be treated, mosquito eggs are placed in Millipore water containing liver powder to begin hatching (4 g. into 400 mL). After the daughter plates are created using the robot, they are infested with 220 μL of the liver powder/larval mosquito mixture (about 1 day-old larvae). After plates are infested with mosquito larvae, a non-evaporative lid is used to cover the plate to reduce drying. Plates are held at room temperature for 3 days prior to grading. After 3 days, each well is observed and scored based on mortality.

The results are indicated in the table entitled "Table ABC: Biological Results" (See Table Section).

Agriculturally Acceptable Acid Addition Salts, Salt Derivatives, Solvates, Ester Derivatives, Polymorphs, Isotopes, and Radionuclides Molecules of Formula One may be formulated into agriculturally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxyl-methanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Molecules of Formula One may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous sodium hydroxide, potassium carbonate, ammonia, and sodium bicarbonate. As an example, in many cases, a pesticide, such as 2,4-D, is made more water-soluble by converting it to its dimethylamine salt.

Molecules of Formula One may be formulated into stable complexes with a solvent, such that the complex remains intact after the non-complexed solvent is removed. These complexes are often referred to as "solvates." However, it is particularly desirable to form stable hydrates with water as the solvent.

Molecules of Formula One may be made into ester derivatives. These ester derivatives can then be applied in the same manner as the molecules disclosed in this document is applied.

Molecules of Formula One may be made as various crystal polymorphs. Polymorphism is important in the development of agrochemicals since different crystal polymorphs or structures of the same molecule can have vastly different physical properties and biological performances.

Molecules of Formula One may be made with different isotopes. Of particular importance are molecules having $^2H$ (also known as deuterium) in place of $^1H$.

Molecules of Formula One may be made with different radionuclides. Of particular importance are molecules having $^{14}C$.

Stereoisomers

Molecules of Formula One may exist as one or more stereoisomers. Thus, certain molecules can be produced as racemic mixtures. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. Certain molecules disclosed in this document can exist as two or more isomers. The various isomers include geometric isomers, diastereomers, and enantiomers. Thus, the molecules disclosed in this document include geometric isomers, racemic mixtures, individual stereoisomers, and optically active mixtures. It will be appreciated by those skilled in the art that one isomer may be more active than the others. The structures disclosed in the present disclosure are drawn in only one geometric form for clarity, but are intended to represent all geometric forms of the molecule.

Combinations

In another embodiment, molecules of Formula One may be used in combination (such as, in a compositional mixture, or a simultaneous or sequential application) with one or more compounds each having a mode of action that is the same as, similar to, or different from, the mode of action ("MoA") of the molecules of Formula One. Modes of action include, for example the following: Acetylcholinesterase (AChE) inhibitors; GABA-gated chloride channel antagonists; Sodium channel modulators; Nicotinic acetylcholine (nAChR) agonists; Nicotinic acetylcholine receptor (nAChR) allosteric activators; Chloride channel activators; Juvenile hormone mimics; Miscellaneous non-specific (multi-site) inhibitors; Selective homopteran feeding blockers; Mite growth inhibitors; Microbial disruptors of insect midgut membranes; Inhibitors of mitochondrial ATP synthase; Uncouplers of oxidative phosphorylation via disruption of the proton gradient; Nicotinic acetylcholine receptor (nAChR) channel blockers; Inhibitors of chitin biosynthesis, type 0; Inhibitors of chitin biosynthesis, type 1; Moulting disruptor, Dipteran; Ecdysone receptor agonists; Octopamine receptor agonists; Mitochondrial complex III electron transport inhibitors; Mitochondrial complex I electron transport inhibitors; Voltage-dependent sodium channel blockers; Inhibitors of acetyl CoA carboxylase; Mitochondrial complex IV electron transport inhibitors; Mitochondrial complex II electron transport inhibitors; and Ryanodine receptor modulators.

In another embodiment, molecules of Formula One may be used in combination (such as, in a compositional mixture, or a simultaneous or sequential application) with one or more compounds having acaricidal, algicidal, avicidal, bactericidal, fungicidal, herbicidal, insecticidal, molluscicidal, nematicidal, rodenticidal, and/or virucidal properties.

In another embodiment, the molecules of Formula One may be used in combination (such as, in a compositional mixture, or a simultaneous or sequential application) with one or more compounds that are antifeedants, bird repellents, chemosterilants, herbicide safeners, insect attractants, insect repellents, mammal repellents, mating disrupters, plant activators, plant growth regulators, and/or synergists.

In another embodiment, the molecules of Formula One may be used in combination (such as, in a compositional mixture, or a simultaneous or sequential application) with "another compound", such as one or more of the following compounds—(3-ethoxypropyl)mercury bromide, 1,2-dichloropropane, 1,3-dichloropropene, 1-methylcyclopropene, 1-naphthol, 2-(octylthio)ethanol, 2,3,5-tri-iodobenzoic acid, 2,3,6-TBA, 2,3,6-TBA-dimethylammonium, 2,3,6-TBA-lithium, 2,3,6-TBA-potassium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-

D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl) ammonium, 2,4-D-trolamine, 2iP, 2-methoxyethylmercury chloride, 2-phenylphenol, 3,4-DA, 3,4-DB, 3,4-DP, 4-aminopyridine, 4-CPA, 4-CPA-diolamine, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-S-methyl, acifluorfen, acifluorfen-methyl, acifluorfen-sodium, aclonifen, acrep, acrinathrin, acrolein, acrylonitrile, acypetacs, acypetacs-copper, acypetacs-zinc, afidopyropen, afoxolaner, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amiprophos, amisulbrom, amiton, amiton oxalate, amitraz, amitrole, ammonium sulfamate, ammonium α-naphthaleneacetate, amobam, ampropylfos, anabasine, anabasine sulfate, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinphos-methyl, aziprotryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, benodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzovindiflupyr, benzoximate, benzoylprop, benzoylprop-ethyl, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluron, bitertanol, bithionol, bixafen, blasticidin-S, borax, Bordeaux mixture, boric acid, boscalid, brassinolide, brassinolide-ethyl, brevicomin, brodifacoum, brofenvalerate, broflanilide, brofluthrinate, bromacil, bromacil-lithium, bromacil-sodium, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chloranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlornidine, chlornitrofen, chlorobenzilate, chlorodinitronaphthalenes, chloroform, chloromebuform, chloromethiuron, chloroneb, chlorophacinone, chlorophacinone-sodium, chloropicrin, chloropon, chloroprallethrin, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, cholecalciferol, chromafenozide, cinerin I, cinerin II, cinerins, cinidon-ethyl, cinmethylin, cinosulfuron, ciobutide, cisanilide, cismethrin, clacyfos, clethodim, climbazole, cliodinate, clodinafop, clodinafop-propargyl, cloethocarb, clofencet, clofencet-potassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatetralyl, coumithoate, coumoxystrobin, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclaniliprole, cyclethrin, cycloate, cycloheximide, cycloprate, cycloprothrin, cyclopyrimorate, cyclosulfamuron, cycloxaprid, cycloxydim, cycluron, cyenopyrafen, cyflufenamid, cyflumetofen, cyfluthrin, cyhalodiamide, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarb, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmedipham, desmetryn, d-fanshiluquebingjuzhi, diafenthiuron, dialifos, di-allate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicapthon, dichlobenil, dichlofenthion, dichlofluanid, dichlone, dichloralurea, dichlorbenzuron, dichlorflurenol, dichlorflurenol-methyl, dichlormate, dichlormid, dicloromezotiaz, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-P-potassium, dichlorprop-P-sodium, dichlorprop-sodium, dichlorvos, dichlozoline, diclobutrazol, diclocymet, diclofop, diclofop-methyl, diclomezine, diclomezine-sodium, dicloran, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, dietholate, diethyl pyrocarbonate, diethyltoluamide, difenacoum, difenoconazole, difenopten, difenopten-ethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlone, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenton, dinoprop, dinosam, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipymetitrone, dipyrithione, diquat, diquat dibromide, disparlure, disul, disulfiram, disulfoton, disul-sodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, enoxastrobin, EPN, epocholeone, epofenonane, epoxiconazole, eprinomectin, epronaz, epsilon-metofluthrin, epsilon-momfluorothrin, EPTC, erbon, ergocalciferol, erlujixiancaoan, esdépalléthrine, esfenvalerate, esprocarb, etacelasil, etaconazole, etaphos, etem, ethaboxam, ethachlor, ethalfluralin, ethametsulfuron, ethametsulfuron-methyl, ethaprochlor, ethephon, ethidimuron, ethiofencarb, ethiolate, ethion, ethiozin, ethiprole, ethirimol, ethoate-methyl, ethofumesate, ethohexadiol, ethoprophos, ethoxyfen, ethoxyfen-ethyl, ethoxyquin, ethoxysulfuron, ethychlozate, ethyl formate, ethyl α-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenaminstrobin, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butometyl, fenoprop-butotyl, fenoprop-butyl, fenoprop-isoctyl, fenoprop-methyl, fenoprop-potassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpirithrin, fenpropathrin, fenpropidin, fenpropimorph, fenpyrazamine, fenpyroximate, fenquinotrione, fenridazon, fenridazon-potassium, fenridazon-propyl, fenson, fensulfothion, fenteracol, fenthiaprop, fenthiaprop-ethyl, fenthion, fenthion-ethyl, fentin, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flometoquin, flonicamid, florasulam, fluacrypyrim, fluazaindolizine, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, fl ufenoxystrobin, flufenprox, flufenpyr, flufenpyr-ethyl, flufiprole, fluhexafon, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyradifurone, flupyrsulfuron, flupyrsulfuron-methyl, flupyrsulfuron-methyl-sodium, fluquinconazole, fluralaner, flurazole, flurenol, flurenol-butyl, flurenol-methyl, fluridone, flurochloridone, fluroxypyr, fluroxypyr-butometyl, fluroxypyr-meptyl, flurprimidol, flursulamid, flurtamone, flusilazole, flusulfamide, fluthiacet, fluthiacet-methyl, flutianil, flutolanil, flutriafol, fluvalinate, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminium, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halauxifen, halauxifen-methyl, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptafluthrin, heptenophos, heptopargil, herbimycin, heterophos, hexachloroacetone, hexachlorobenzene, hexachlorobutadiene, hexachlorophene, hexaconazole, hexaflumuron, hexaflurate, hexalure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, iodobonil, iodocarb, iodomethane, iodosulfuron, iodosulfuron-methyl, iodosulfuron-methyl-sodium, iofensulfuron, iofensulfuron-sodium, ioxynil, ioxynil octanoate, ioxynil-lithium, ioxynil-sodium, ipazine, ipconazole, ipfencarbazone, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isofetamid, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, kappa-bifenthrin, kappa-tefluthrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, latilure, lead arsenate, lenacil, lepimectin, leptophos, lindane, lineatin, linuron, lirimfos, litlure, looplure, lufenuron, lvdingjunzhi, lvxiancaolin, lythidathion, MAA, malathion, maleic hydrazide, malonoben, maltodextrin, MAMA, mancopper, mancozeb, mandipropamid, mandestrobin, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotrione, mesulfen, mesulfenfos, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquin-butyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron, metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, momfluorothrin, monalide, monisouron, monochloroacetic acid, monocrotophos, monolinuron, monosulfuron, monosulfuron-ester, monuron, monuron TCA, morfamquat, morfamquat dichloride, moroxydine, moroxydine hydrochloride, morphothion, morzid, moxidectin, MSMA, muscalure, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, napropamide-M, naptalam, naptalam-sodium, natamycin, neburon, niclosamide, niclosamide-olamine, nicosulfuron, nicotine, nifluridide, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nornicotine, noruron, novaluron, noviflumuron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxathiapiprolin, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluron, penoxsulam, pentachlorophenol, pentachlorophenyl laurate, pentanochlor, penthiopyrad, pentmethrin, pentoxazone, perfluidone, permethrin, pethoxamid, phenamacril, phenazine oxide, phenisopham, phenkapton, phenmedipham, phenmedipham-ethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picarbutrazox, picloram, picloram-2-ethylhexyl, picloram-isoctyl, picloram-methyl, picloram-olamine, picloram-potassium, picloram-triethylammonium, picloram-tris(2-hydroxypropyl)ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium α-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, profluralin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiocarb, prothiocarb hydrochloride, prothioconazole, prothiofos, prothoate, protrifenbute, proxan, proxan-sodium, prynachlor, pydanon, pydiflumetofen, pyflubumide, pymetrozine, pyracarbolid, pyraclofos, pyraclonil, pyraclostrobin, pyraflufen, pyraflufen-ethyl, pyrafluprole, pyramat, pyrametostrobin, pyraoxystrobin, pyrasulfotole, pyraziflumid, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyriminostrobin, pyrimisulfan, pyrimitate, pyrinuron, pyriofenone, pyriprole, pyripropanol, pyriproxyfen, pyrisoxazole, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, rescalure, resmethrin, rhodethanil, rhodojaponin-III, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium α-naphthaleneacetate, sophamide, spinetoram, spinosad, spirodiclofen, spiromesifen, spirotetramat, spiroxamine, streptomycin, streptomycin sesquisulfate, strychnine, sulcatol, sulcofuron, sulcofuron-sodium, sulcotrione, sulfallate, sulfentrazone, sulfiram, sulfluramid, sulfometuron, sulfometuron-methyl, sulfosulfuron, sulfotep, sulfoxaflor, sulfoxide, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluron, tetramethrin, tetramethylfluthrin, tetramine, tetranactin, tetraniliprole, tetrasul, thallium sulfate, thenylchlor, theta-cypermethrin, thiabendazole, thiacloprid, thiadifluor, thiamethoxam, thiapronil, thiazafluron, thiazopyr, thicrofos, thicyofen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiafenacil, tiaojiean, tiocarbazil, tioclorim, tioxazafen, tioxymid, tirpate, tolclofos-methyl, tolfenpyrad, tolprocarb, tolpyralate, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichloronat, triclopyr, triclopyr-butotyl, triclopyr-ethyl, triclopyricarb, triclopyr-triethylammonium, tricyclazole, tridemorph, tridiphane, trietazine, trifenmorph, trifenofos, trifloxystrobin, trifloxysulfuron, trifloxysulfuron-sodium, trifludimoxazin, triflumezopyrim, triflumizole, triflumuron, trifluralin, triflusulfuron, triflusulfuron-methyl, trifop, trifop-methyl, trifopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid. For more information consult the "COMPENDIUM OF PESTICIDE COMMON NAMES" located at alanwood.net. Also consult "THE PESTICIDE MANUAL" 15th Edition, edited by C D S Tomlin, copyright 2009 by British Crop Production Council, or its prior, or more recent editions.

In another embodiment, molecules of Formula One may also be used in combination (such as in a compositional mixture, or a simultaneous or sequential application) with the following compound.

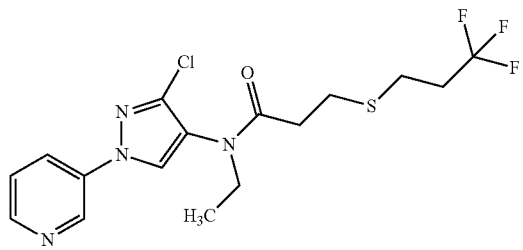 [SMILES: CCN(C(=O)CCSCCC(F)(F)F)c1cn(-c2cccnc2)nc1Cl]

In another embodiment, molecules of Formula One may also be used in combination (such as in a compositional mixture, or a simultaneous or sequential application) with one or more biopesticides. The term "biopesticide" is used for microbial biological pest control agents that are applied in a similar manner to chemical pesticides. Commonly these are bacterial, but there are also examples of fungal control agents, including *Trichoderma* spp. and *Ampelomyces quisqualis* (a control agent for grape powdery mildew). *Bacillus subtilis* are used to control plant pathogens. Weeds and rodents have also been controlled with microbial agents. One well-known insecticide example is *Bacillus thuringiensis*, a bacterial disease of Lepidoptera, Coleoptera, and Diptera. Because it has little effect on other organisms, it is considered more environmentally friendly than synthetic pesticides. Biological insecticides include products based on: entomopathogenic fungi (e.g. *Metarhizium anisopliae*); entomopathogenic nematodes (e.g. *Steinernema feltiae*); and entomopathogenic viruses (e.g. *Cydia pomonella* granulovirus).

Other examples of entomopathogenic organisms include, but are not limited to, baculoviruses, bacteria and other prokaryotic organisms, fungi, protozoa and Microsproridia. Biologically derived insecticides include, but not limited to, rotenone, veratridine, as well as microbial toxins; insect tolerant or resistant plant varieties; and organisms modified by recombinant DNA technology to either produce insecticides or to convey an insect resistant property to the genetically modified organism. In one embodiment, the molecules of Formula One may be used with one or more biopesticides in the area of seed treatments and soil amendments. The Manual of Biocontrol Agents gives a review of the available biological insecticide (and other biology-based control) products. Copping L. G. (ed.) (2004). *The Manual of Biocontrol Agents* (formerly the *Biopesticide Manual*) 3rd Edition. British Crop Production Council (BCPC), Farnham, Surrey UK.

In another embodiment, the above possible combinations may be used in a wide variety of weight ratios. For example, a two component mixture, the weight ratio of a molecule of Formula One to another compound, can be from about 100:1 to about 1:100; in another example the weight ratio can be about 50:1 to about 1:50; in another example the weight ratio can be about 20:1 to about 1 to 20; in another example the weight ratio can be about 10:1 to about 1:10; in another example the weight ratio can be about 5:1 to 1:5; in another example the weight ratio can be about 3:1 to about 1:3; in another example the weight ratio can be about 2:1 to about 1:2; and in a final example the weight ratio can be about 1:1. However, preferably, weight ratios less than about 10:1 to about 1:10 are preferred. It is also preferred sometimes to use a three or four component mixture comprising one or more molecules of Formula One and one or more other compounds from the above possible combinations.

TABLE A

| No. | Range of the Weight Ratio of a molecule of the Formula One to another compound |
|---|---|
| 1 | 100:1 to 1:100 |
| 2 | 50:1 to 1:50 |
| 3 | 20:1 to 1:20 |
| 4 | 10:1 to 1:10 |
| 5 | 5:1 to 1:5 |
| 6 | 3:1 to 1:3 |
| 7 | 2:1 to 1:2 |
| 8 | 1:1 |

Weight ratios of a molecule of the Formula One or any agriculturally acceptable salt thereof to another compound envisioned to be synergistic pesticidal compositions may be depicted as X:Y; wherein X is the parts by weight of a molecule of the Formula One or any agriculturally acceptable salt thereof, and Y is the parts by weight of another compound. The numerical range of the parts by weight for X is $0<X\leq100$ and the parts by weight for Y is $0<Y\leq100$ as shown graphically in TABLE B. By way of non-limiting example, the weight ratio of the pesticide to another compound may be about 20:1.

TABLE B

| Another Compound (Y) Parts by weight | 100 | X, Y | | X, Y | | | X, Y | | | |
|---|---|---|---|---|---|---|---|---|---|---|
| | 50 | X, Y | X, Y | X, Y | | | X, Y | X, Y | | |
| | 20 | X, Y | | X, Y | X, Y | | X, Y | | X, Y | |
| | 15 | X, Y | X, Y | | | | | X, Y | X, Y | X, Y |
| | 10 | X, Y | | X, Y | | | | | | |
| | 5 | X, Y | X, Y | X, Y | | | X, Y | | | |
| | 3 | X, Y | X, Y | | X, Y | X, Y | | X, Y | X, Y | X, Y |
| | 2 | X, Y | | X, Y | X, Y | | X, Y | | X, Y | |
| | 1 | X, Y | X, Y | X, Y | X, Y | X, Y | X, Y | X, Y | X, Y | X, Y |
| | | 1 | 2 | 3 | 5 | 10 | 15 | 20 | 50 | 100 |
| | | Molecule of the Formula One (X) Parts by weight | | | | | | | | |

Ranges of weight ratios of a molecule of the Formula One or any agriculturally acceptable salt thereof to another compound envisioned to be synergistic pesticidal compositions may be depicted as $X_1:Y_1$ to $X_2:Y_2$, wherein X and Y are defined as above. In one particular embodiment, the range of weight ratios may be $X_1:Y_1$ to $X_2:Y_2$, wherein $X_1>Y_1$ and $X_2<Y_2$. By way of non-limiting example, the range of weight ratios of a molecule of the Formula One or any agriculturally acceptable salt thereof to another compound may be between about 3:1 and about 1:3. In some embodiments, the range of weight ratios may be $X_1:Y_1$ to $X_2:Y_2$, wherein $X_1>Y_1$ and $X_2>Y_2$. By way of non-limiting example, the range of a molecule of the Formula One or any agriculturally acceptable salt thereof to another compound may be between about 15:1 and about 3:1. In further embodiments, the range of weight ratios may be $X_1:Y_1$ to $X_2:Y_2$, wherein $X_1<Y_1$ and $X_2<Y_2$. By way of non-limiting example, the range of weight ratios of a molecule of the Formula One or any agriculturally acceptable salt thereof to another compound may be between about 1:3 and about 1:20.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra-low volume solutions. For further information on formulation types see "Catalogue of Pesticide Formulation Types and International Coding System" Technical Monograph n° 2, 5th Edition by CropLife International (2002).

Pesticides are applied most often as aqueous suspensions or emulsions prepared from concentrated formulations of such pesticides. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from the group consisting of the group consisting of among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from the group consisting of the group consisting of conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They can be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use, this embodiment will be referred to as "OIWE".

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mallis, 9th Edition, copyright 2004 by GIE Media Inc.

Other Formulation Components

Generally, when the molecules disclosed in Formula One are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspoemulsions, and ultra-low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

For further information, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Pests

In general, the molecules of Formula One may be used to control pests e.g. ants, aphids, beetles, bristletails, cockroaches, crickets, earwigs, fleas, flies, grasshoppers, leafhoppers, lice, locusts, mites, moths, nematodes, scales, symphylans, termites, thrips, ticks, wasps, and whiteflies.

In another embodiment, the molecules of Formula One may be used to control pests in the Phyla Nematoda and/or Arthropoda.

In another embodiment, the molecules of Formula One may be used to control pests in the Subphyla Chelicerata, Myriapoda, and/or Hexapoda.

In another embodiment, the molecules of Formula One may be used to control pests in the Classes of Arachnida, Symphyla, and/or Insecta.

In another embodiment, the molecules of Formula One may be used to control pests of the Order Anoplura. A non-exhaustive list of particular genera includes, but is not limited to, *Haematopinus* spp., *Hoplopleura* spp., *Linognathus* spp., *Pediculus* spp., and *Polyplax* spp. A non-exhaustive list of particular species includes, but is not limited to, *Haematopinus asini*, *Haematopinus suis*, *Linognathus setosus*, *Linognathus ovillus*, *Pediculus humanus capitis*, *Pediculus humanus humanus*, and *Pthirus pubis*.

In another embodiment, the molecules of Formula One may be used to control pests in the Order Coleoptera. A non-exhaustive list of particular genera includes, but is not limited to, *Acanthoscelides* spp., *Agriotes* spp., *Anthonomus* spp., *Apion* spp., *Apogonia* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Hypera* spp., *Ips* spp., *Lyctus* spp., *Megascelis* spp., *Meligethes* spp., *Otiorhynchus* spp., *Pantomorus* spp., *Phyllophaga* spp., *Phyllotreta* spp., *Rhizotrogus* spp., *Rhynchites* spp., *Rhynchophorus* spp., *Scolytus* spp., *Sphenophorus* spp., *Sitophilus* spp., and *Tribolium* spp. A non-exhaustive list of particular species includes, but is not limited to, *Acanthoscelides obtectus*, *Agrilus planipennis*, *Anoplophora glabripennis*, *Anthonomus grandis*, *Ataenius spretulus*, *Atomaria linearis*, *Bothynoderes punctiventris*, *Bruchus pisorum*, *Callosobruchus maculatus*, *Carpophilus hemipterus*, *Cassida vittata*, *Cerotoma trifurcata*, *Ceutorhynchus assimilis*, *Ceutorhynchus napi*, *Conoderus scalaris*, *Conoderus stigmosus*, *Conotrachelus nenuphar*, *Cotinis nitida*, *Crioceris asparagi*, *Cryptolestes ferrugineus*, *Cryptolestes pusillus*, *Cryptolestes turcicus*, *Cylindrocopturus adspersus*, *Deporaus marginatus*, *Dermestes lardarius*, *Dermestes maculatus*, *Epilachna varivestis*, *Faustinus cubae*, *Hylobius pales*, *Hypera postica*, *Hypothenemus hampei*, *Lasioderma serricome*, *Leptinotarsa decemlineata*, *Liogenys fuscus*, *Liogenys suturalis*, *Lissorhoptrus oryzophilus*, *Maecolaspis joliveti*, *Melanotus communis*, *Meligethes aeneus*, *Melolontha melolontha*, *Oberea brevis*, *Oberea linearis*, *Oryctes rhinoceros*, *Oryzaephilus mercator*, *Oryzaephilus surinamensis*, *Oulema melanopus*, *Oulema oryzae*, *Phyllophaga cuyabana*, *Popillia japonica*, *Prostephanus truncatus*, *Rhyzopertha dominica*, *Sitona lineatus*, *Sitophilus granarius*, *Sitophilus oryzae*, *Sitophilus zeamais*, *Stegobium paniceum*, *Tribolium castaneum*, *Tribolium confusum*, *Trogoderma variabile*, and *Zabrus tenebrioides*.

In another embodiment, the molecules of Formula One may be used to control pests of the Order Dermaptera.

In another embodiment, the molecules of Formula One may be used to control pests of the Order Blattaria. A non-exhaustive list of particular species includes, but is not limited to, *Blattella germanica*, *Blatta orientalis*, *Parcoblatta pennsylvanica*, *Periplaneta americana*, *Periplaneta australasiae*, *Periplaneta brunnea*, *Periplaneta fuliginosa*, *Pycnoscelus surinamensis*, and *Supella longipalpa*.

In another embodiment, the molecules of Formula One may be used to control pests of the Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., *Fannia* spp., *Hylemyia* spp., *Liriomyza* spp., *Musca* spp., *Phorbia* spp., *Tabanus* spp., and *Tipula* spp. A non-exhaustive list of particular species includes, but is not limited to, *Agromyza frontella*, *Anastrepha suspensa*, *Anastrepha ludens*, *Anastrepha obliqa*, *Bactrocera cucurbitae*, *Bactrocera dorsalis*,

*Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestics, Oestrus ovis, Oscinella frit, Pegomya betae, Psila rosae, Rhagoletis cerasi, Rhagoletis pomonella, Rhagoletis mendax, Sitodiplosis mosellana,* and *Stomoxys calcitrans.*

In another embodiment, the molecules of Formula One may be used to control pests of the Order Hemiptera. A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chlysomphalus* spp., *Coccus* spp., *Empoasca* spp., *Lepidosaphes* spp., *Lagynotomus* spp., *Lygus* spp., *Macrosiphum* spp., *Nephotettix* spp., *Nezara* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp. and *Unaspis* spp. A non-exhaustive list of particular species includes, but is not limited to, *Acrosternum hilare, Acyrthosiphon pisum, Aleyrodes proletella, Aleurodicus dispersus, Aleurothrixus floccosus, Amrasca biguttula biguttula, Aonidiella aurantii, Aphis gossypii, Aphis glycines, Aphis pomi, Aulacorthum solani, Bemisia argentifolii, Bemisia tabaci, Blissus leucopterus, Brachycorynella asparagi, Brevennia rehi, Brevicoryne brassicae, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus heros, Euschistus servus, Helopeltis antonii, Helopeltis theivora, Icerya purchasi, Idioscopus nitidulus, Laodelphax striatellus, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Metopolophium dirhodum, Mictis longicornis, Myzus persicae, Nephotettix cinctipes, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris californicus, Phytocoris relativus, Piezodorus guildinii, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis,* and *Zulia entrerriana.*

In another embodiment, the molecules of Formula One may be used to control pests of the Order Hymenoptera. A non-exhaustive list of particular genera includes, but is not limited to, *Acromyrmex* spp., *Atta* spp., *Camponotus* spp., *Diprion* spp., *Formica* spp., *Monomorium* spp., *Neodiprion* spp., *Pogonomyrmex* spp., *Polistes* spp., *Solenopsis* spp., *Vespula* spp., *and Xylocopa* spp. A non-exhaustive list of particular species includes, but is not limited to, *Athalia rosae, Atta texana, Iridomyrmex humilis, Monomorium minimum, Monomorium pharaonis, Solenopsis invicta, Solenopsis geminata, Solenopsis molesta, Solenopsis richtery, Solenopsis xyloni,* and *Tapinoma sessile.*

In another embodiment, the molecules of Formula One may be used to control pests of the Order Isoptera. A non-exhaustive list of particular genera includes, but is not limited to, *Coptotermes* spp., *Comitermes* spp., *Cryptotermes* spp., *Heterotermes* spp., *Kalotermes* spp., *Incisitermes* spp., *Macrotermes* spp., *Marginitermes* spp., *Microcerotermes* spp., *Procomitermes* spp., *Reticulitermes* spp., *Schedorhinotermes* spp., and *Zootermopsis* spp. A non-exhaustive list of particular species includes, but is not limited to, *Coptotermes curvignathus, Coptotermes frenchi, Coptotermes formosanus, Heterotermes aureus, Microtermes obesi, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis,* and *Reticulitermes virginicus.*

In another embodiment, the molecules of Formula One may be used to control pests of the Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Collas* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Peridroma* spp., *Phyllonorycter* spp., *Pseudaletia* spp., *Sesamia* spp., *Spodoptera* spp., *Synanthedon* spp., and *Yponomeuta* spp. A non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Cossus cossus, Cydia caryana, Cydia funebrana, Cydia molesta, Cydia nigricana, Cydia pomonella, Darna diducta, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Eupoecilia ambiguella, Euxoa auxiliaris, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Pieris rapae, Plathypena scabra, Plodia interpunctella, Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tineola bisselliella, Trichoplusia ni, Tuta absoluta, Zeuzera coffeae,* and *Zeuzera pyrina.*

In another embodiment, the molecules of Formula One may be used to control pests of the Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae,* and *Trichodectes canis.*

In another embodiment, the molecules of Formula One may be used to control pests of the Order Orthoptera. A non-exhaustive list of particular genera includes, but is not limited to, *Melanoplus* spp., and *Pterophylla* spp. A non-exhaustive list of particular species includes, but is not limited to, *Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria,* and *Scudderia furcata.*

In another embodiment, the molecules of Formula One may be used to control pests of the Order Siphonaptera. A non-exhaustive list of particular species includes, but is not limited to, *Ceratophyllus gallinae, Ceratophyllus niger, Ctenocephalides canis, Ctenocephalides fells,* and *Pulex irritans.*

In another embodiment, the molecules of Formula One may be used to control pests of the Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular sp. includes, but is not limited to, *Frankliniella fusca, Frankliniella occidentalis, Frankliniella schultzei, Frankliniella williamsi, Heliothrips haemorrhoidalis, Rhipiphorothrips cruentatus, Scirtothrips citri, Scirtothrips dorsalis,* and *Taeniothrips rhopalantennalis, Thrips hawaiiensis, Thrips nigropilosus, Thrips orientalis, Thrips tabaci.*

In another embodiment, the molecules of Formula One may be used to control pests of the Order Thysanura. A non-exhaustive list of particular genera includes, but is not limited to, *Lepisma* spp. and *Thermobia* spp.

In another embodiment, the molecules of Formula One may be used to control pests of the Order Acarina. A non-exhaustive list of particular genera includes, but is not limited to, *Acarus* spp., *Aculops* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Notoedres cati, Oligonychus coffeae, Oligonychus ilicis, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae,* and *Varroa destructor.*

In another embodiment, the molecules of Formula One may be used to control pest of the Order Symphyla. A non-exhaustive list of particular sp. includes, but is not limited to, *Scutigerella immaculata.*

In another embodiment, the molecules of Formula One may be used to control pests of the Phylum Nematoda. A non-exhaustive list of particular genera includes, but is not limited to, *Aphelenchoides* spp., *Belonolaimus* spp., *Criconemella* spp., Ditylenchus spp., *Heterodera* spp., *Hirschmanniella* spp., *Hoplolaimus* spp., *Meloidogyne* spp., *Pratylenchus* spp., and *Radopholus* spp. A non-exhaustive list of particular sp. includes, but is not limited to, *Dirofilaria immitis, Heterodera zeae, Meloidogyne incognita, Meloidogyne javanica, Onchocerca volvulus, Radopholus similis,* and *Rotylenchulus reniformis.*

For additional information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

Applications

Controlling pests of Phyla Nematoda, Arthropoda, and/or Mollusca generally means that pest populations, pest activity, or both, are reduced in an locus. This can come about when:

(a) pest populations are repulsed from a locus;
(b) pests are incapacitated in, or around, a locus; or
(c) pests are exterminated in, or around, a locus.

Of course, a combination of these results can occur. Generally, pest populations, activity, or both are desirably reduced more than fifty percent, preferably more than 90 percent, and most preferably more than 98 percent. Generally, the locus is not in, or on, a human; consequently, the locus is generally a non-human locus.

In another embodiment, the locus to which a molecule of Formula One is applied can be any locus that is inhabited, or that may become inhabited, or that may be traversed, by a pest of Phyla Nematoda, Arthropoda, and/or Mollusca. For example, the locus can be:

(a) where crops, trees, fruits, cereals, fodder species, vines, turf, and/or ornamental plants, are growing;
(b) where domesticated animals are residing;
(c) the interior or exterior surfaces of buildings (such as places where grains are stored);
(d) the materials of construction used in buildings (such as impregnated wood); and
(e) the soil around buildings.

Particular crop areas to use a molecule of Formula One include areas where apples, corn, sunflowers, cotton, soybeans, canola, wheat, rice, sorghum, barley, oats, potatoes, oranges, alfalfa, lettuce, strawberries, tomatoes, peppers, crucifers, pears, tobacco, almonds, sugar beets, beans and other valuable crops are growing or the seeds thereof are going to be planted. It is also advantageous to use ammonium sulfate with a molecule of Formula One when growing various plants.

In another embodiment, molecules of Formula One are generally used in amounts from about 0.0001 grams per hectare to about 5000 grams per hectare to provide control. In another embodiment, it is preferred that molecules of Formula One are used in amounts from about 0.001 grams per hectare to about 500 grams per hectare. In another embodiment, it is more preferred that molecules of Formula One are used in amounts from about 0.01 gram per hectare to about 50 grams per hectare.

The molecules of Formula One may be used in mixtures, applied simultaneously or sequentially, alone or with other compounds to enhance plant vigor (e.g. to grow a better root system, to better withstand stressful growing conditions). Such other compounds are, for example, compounds that modulate plant ethylene receptors, most notably 1-methylcyclopropene (also known as 1-MCP). Furthermore, such molecules may be used during times when pest activity is low, such as before the plants that are growing begin to produce valuable agricultural commodities. Such times include the early planting season when pest pressure is usually low.

The molecules of Formula One can be applied to the foliar and fruiting portions of plants to control pests. The molecules will either come in direct contact with the pest, or the pest will consume the pesticide when eating leaf, fruit mass, or extracting sap, that contains the pesticide. The molecules of Formula One can also be applied to the soil, and when applied in this manner, root and stem feeding pests can be controlled. The roots can absorb a molecule taking it up into the foliar portions of the plant to control above ground chewing and sap feeding pests.

Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait. Baits can comprise a molecule of Formula One.

The molecules of Formula One can be encapsulated inside, or placed on the surface of a capsule. The size of the capsules can range from nanometer size (about 100-900 nanometers in diameter) to micrometer size (about 10-900 microns in diameter).

Because of the unique ability of the eggs of some pests to resist certain pesticides, repeated applications of the molecules of Formula One may be desirable to control newly emerged larvae.

Systemic movement of pesticides in plants may be utilized to control pests on one portion of the plant by applying (for example by spraying an area) the molecules of Formula One to a different portion of the plant. For example, control of foliar-feeding insects can be achieved by drip irrigation or furrow application, by treating the soil with for example pre- or post-planting soil drench, or by treating the seeds of a plant before planting.

Seed treatment can be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement, drought resistance, or any other beneficial traits. Furthermore, such seed treatments with the molecules of Formula One may further enhance the ability of a plant to better withstand stressful growing conditions. This results in a healthier, more vigorous plant, which can lead to higher yields at harvest time. Generally, about 1 gram of the molecules of Formula One to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits.

It should be readily apparent that the molecules of Formula One may be used on, in, or around plants genetically modified to express specialized traits, such as *Bacillus thuringiensis* or other insecticidal toxins, or those expressing herbicide resistance, or those with "stacked" foreign genes expressing insecticidal toxins, herbicide resistance, nutrition-enhancement, or any other beneficial traits.

The molecules of Formula One may be used for controlling endoparasites and ectoparasites in the veterinary medicine sector or in the field of non-human animal keeping. The molecules of Formula One are applied, such as by oral administration in the form of, for example, tablets, capsules, drinks, granules, by dermal application in the form of, for example, dipping, spraying, pouring on, spotting on, and dusting, and by parenteral administration in the form of, for example, an injection.

The molecules of Formula One may also be employed advantageously in livestock keeping, for example, cattle, sheep, pigs, chickens, and geese. They may also be employed advantageously in pets such as, horses, dogs, and cats. Particular pests to control would be fleas and ticks that are bothersome to such animals. Suitable formulations are administered orally to the animals with the drinking water or feed. The dosages and formulations that are suitable depend on the species.

The molecules of Formula One may also be used for controlling parasitic worms, especially of the intestine, in the animals listed above.

The molecules of Formula One may also be employed in therapeutic methods for human health care. Such methods include, but are limited to, oral administration in the form of, for example, tablets, capsules, drinks, granules, and by dermal application.

Pests around the world have been migrating to new environments (for such pest) and thereafter becoming a new invasive species in such new environment. The molecules of Formula One may also be used on such new invasive species to control them in such new environment.

The molecules of Formula One may also be used in an area where plants, such as crops, are growing (e.g. pre-planting, planting, pre-harvesting) and where there are low levels (even no actual presence) of pests that can commercially damage such plants. The use of such molecules in such area is to benefit the plants being grown in the area. Such benefits, may include, but are not limited to, improving the health of a plant, improving the yield of a plant (e.g. increased biomass and/or increased content of valuable ingredients), improving the vigor of a plant (e.g. improved plant growth and/or greener leaves), improving the quality of a plant (e.g. improved content or composition of certain ingredients), and improving the tolerance to abiotic and/or biotic stress of the plant.

Before a pesticide can be used or sold commercially, such pesticide undergoes lengthy evaluation processes by various governmental authorities (local, regional, state, national, and international). Voluminous data requirements are specified by regulatory authorities and must be addressed through data generation and submission by the product registrant or by a third party on the product registrant's behalf, often using a computer with a connection to the World Wide Web. These governmental authorities then review such data and if a determination of safety is concluded, provide the potential user or seller with product registration approval. Thereafter, in that locality where the product registration is granted and supported, such user or seller may use or sell such pesticide.

A molecule according to Formula One can be tested to determine its efficacy against pests. Furthermore, mode of action studies can be conducted to determine if said molecule has a different mode of action than other pesticides. Thereafter, such acquired data can be disseminated, such as by the internet, to third parties.

The headings in this document are for convenience only and must not be used to interpret any portion hereof.

Table Section

TABLE 2

Structure and Preparation Method for F Series Compounds

| No. | Structure | Prep. according to example |
|-----|-----------|-----------------------------|
| F1  | 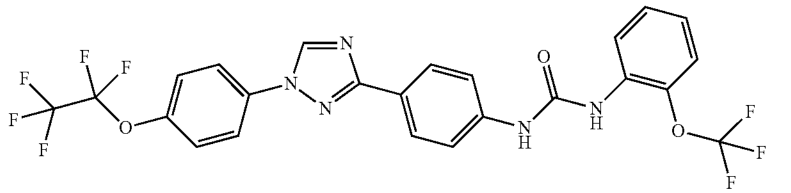 [SMILES: O=C(Nc1ccc(-c2ncn(-c3ccc(OC(F)(F)C(F)(F)F)cc3)n2)cc1)Nc1ccccc1OC(F)(F)F]          | 7                           |
| F2  | 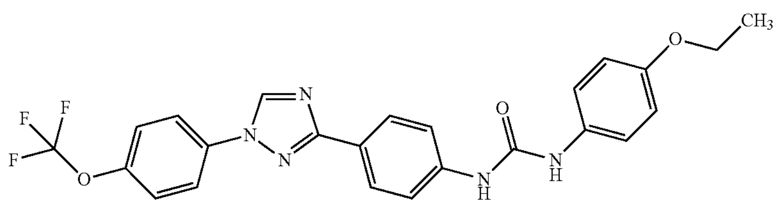 [SMILES: CCOc1ccc(NC(=O)Nc2ccc(-c3ncn(-c4ccc(OC(F)(F)F)cc4)n3)cc2)cc1]          | 26                          |
| F3  | 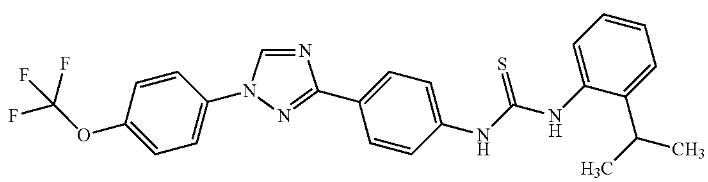          | 21                          |
| F4  | 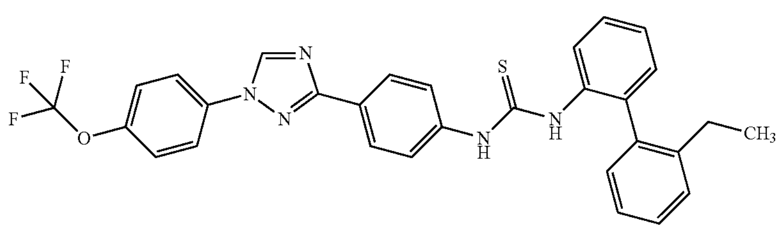          | 24                          |
| F5  | 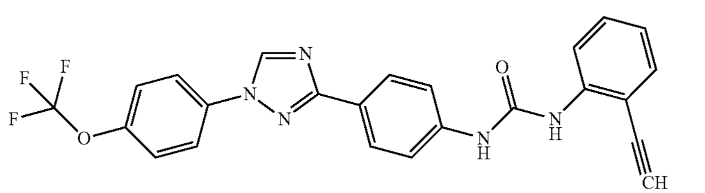 [SMILES: C#Cc1ccccc1NC(=O)Nc1ccc(-c2ncn(-c3ccc(OC(F)(F)F)cc3)n2)cc1]          | 4                           |
| F6  | 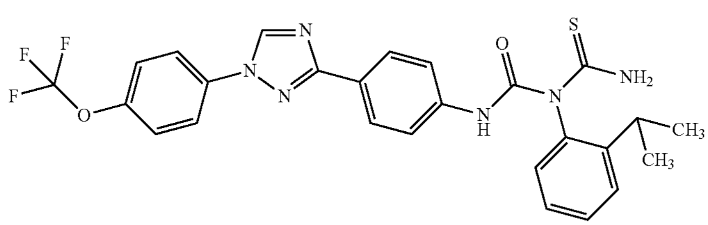 [SMILES: CC(C)c1ccccc1N(C(=O)Nc1ccc(-c2ncn(-c3ccc(OC(F)(F)F)cc3)n2)cc1)C(N)=S]          | 19                          |
| F7  | 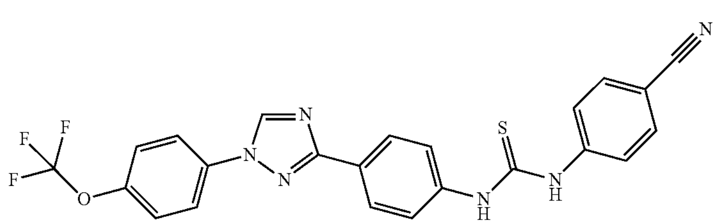 [SMILES: N#Cc1ccc(NC(=S)Nc2ccc(-c3ncn(-c4ccc(OC(F)(F)F)cc4)n3)cc2)cc1]          | 21                          |

TABLE 2-continued

Structure and Preparation Method for F Series Compounds

| No. | Structure | Prep. according to example |
|-----|-----------|----------------------------|
| F8  | 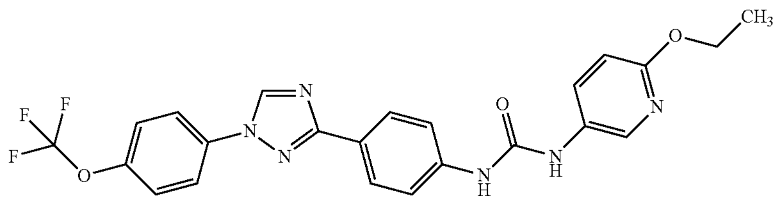          | 26 |
| F9  | 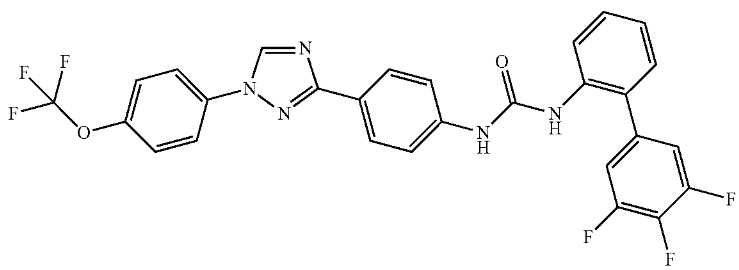 [SMILES: O=C(Nc1ccc(-c2ncn(-c3ccc(OC(F)(F)F)cc3)n2)cc1)Nc1ccccc1-c1cc(F)c(F)c(F)c1]          | 6  |
| F10 | 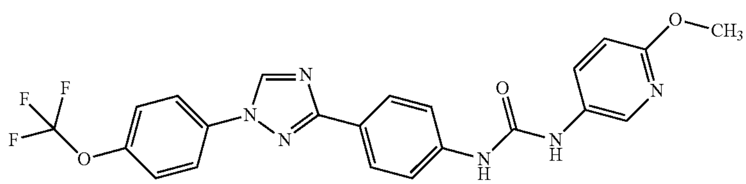 [SMILES: COc1ccc(NC(=O)Nc2ccc(-c3ncn(-c4ccc(OC(F)(F)F)cc4)n3)cc2)cn1]          | 26 |
| F11 | 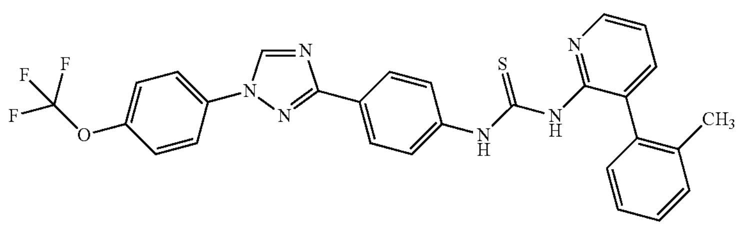          | 24 |
| F12 | 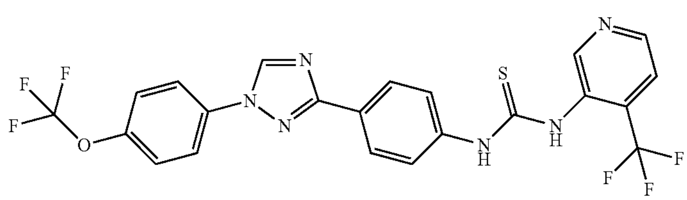 [SMILES: FC(F)(F)Oc1ccc(-n2cnc(-c3ccc(NC(=S)Nc4cnccc4C(F)(F)F)cc3)n2)cc1]          | 20 |
| F13 | 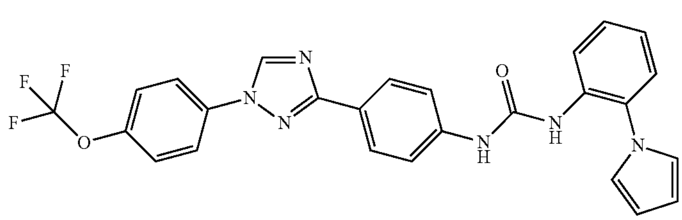          | 20 |
| F14 | 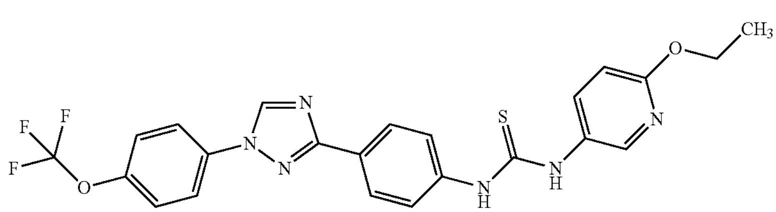 [SMILES: CCOc1ccc(NC(=S)Nc2ccc(-c3ncn(-c4ccc(OC(F)(F)F)cc4)n3)cc2)cn1]          | 39 |

TABLE 2-continued

Structure and Preparation Method for F Series Compounds

| No. | Structure | Prep. according to example |
|---|---|---|
| F15 | 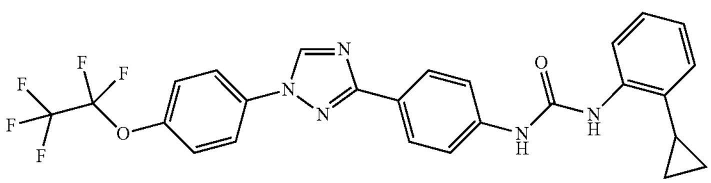 [SMILES: O=C(Nc1ccc(-c2ncn(-c3ccc(OC(F)(F)C(F)(F)F)cc3)n2)cc1)Nc1ccccc1C1CC1] | 7 |
| F16 | 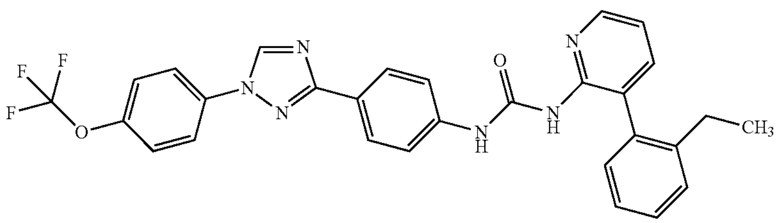 | 25 |
| F17 | 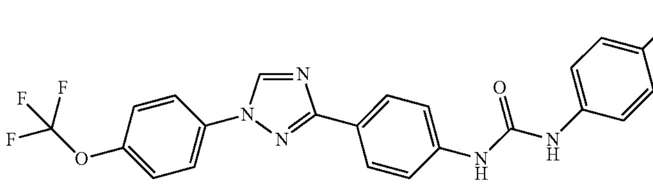 | 27 |
| F18 | 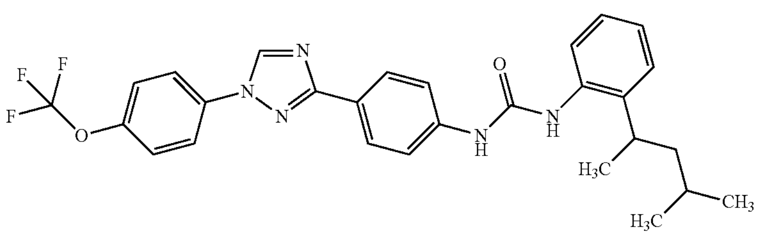 [SMILES: CC(C)CC(C)c1ccccc1NC(=O)Nc1ccc(-c2ncn(-c3ccc(OC(F)(F)F)cc3)n2)cc1] | 5 |
| F19 | 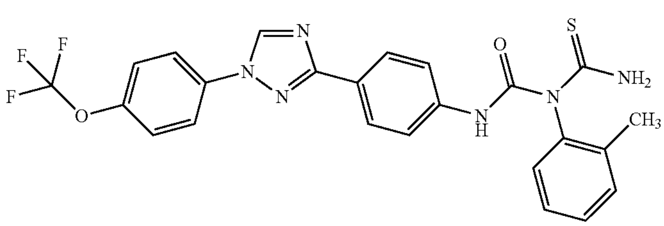 [SMILES: Cc1ccccc1N(C(=O)Nc1ccc(-c2ncn(-c3ccc(OC(F)(F)F)cc3)n2)cc1)C(N)=S] | 19 |
| F20 | 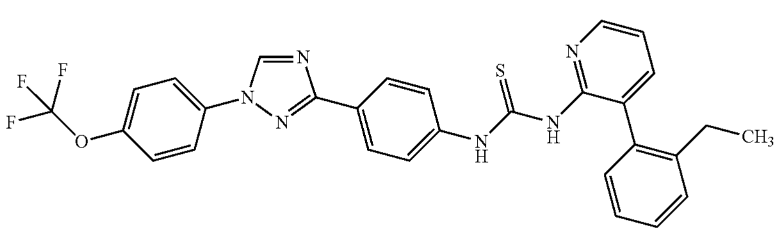 | 24 |

TABLE 2-continued

Structure and Preparation Method for F Series Compounds

| No. | Structure | Prep. according to example |
|---|---|---|
| F21 | 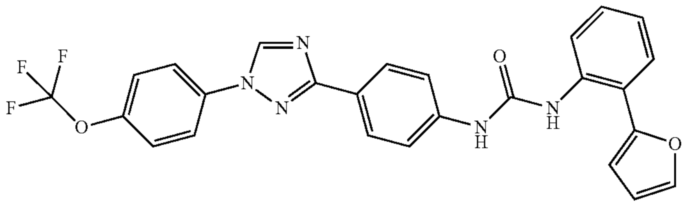 [SMILES: O=C(Nc1ccc(-c2ncn(-c3ccc(OC(F)(F)F)cc3)n2)cc1)Nc1ccccc1-c1ccco1] | 20 |
| F22 | 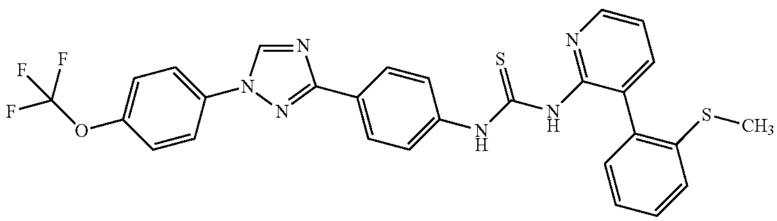 | 24 |
| F23 | 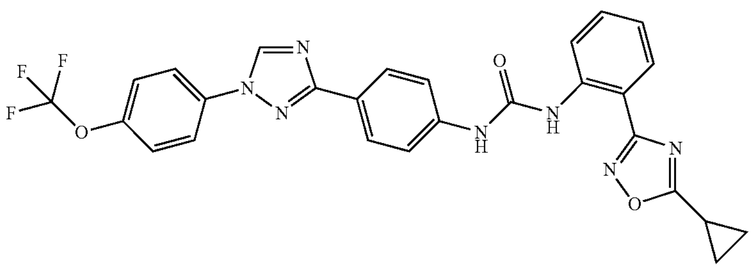 [SMILES: O=C(Nc1ccc(-c2ncn(-c3ccc(OC(F)(F)F)cc3)n2)cc1)Nc1ccccc1-c1noc(C2CC2)n1] | 21 |
| F24 | 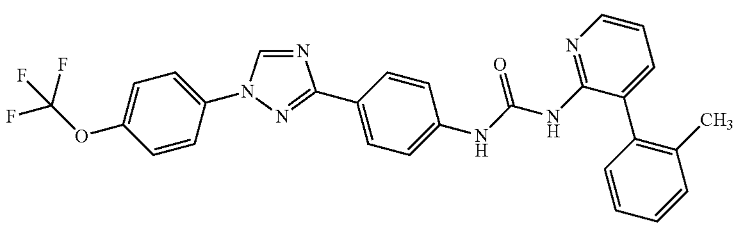 | 25 |
| F25 | 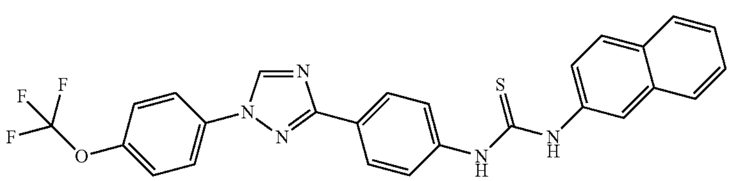 [SMILES: FC(F)(F)Oc1ccc(-n2cnc(-c3ccc(NC(=S)Nc4ccc5ccccc5c4)cc3)n2)cc1] | 21 |
| F26 | 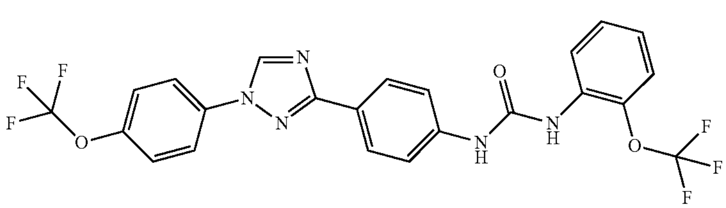 [SMILES: O=C(Nc1ccc(-c2ncn(-c3ccc(OC(F)(F)F)cc3)n2)cc1)Nc1ccccc1OC(F)(F)F] | 6 |
| F27 | 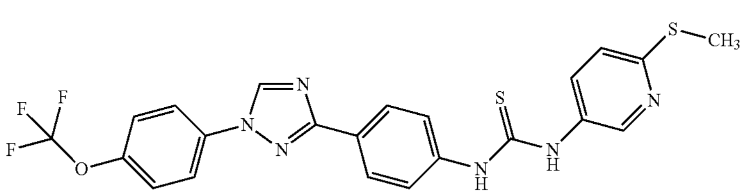 | 39 |

TABLE 2-continued

Structure and Preparation Method for F Series Compounds

| No. | Structure | Prep. according to example |
|---|---|---|
| F28 | 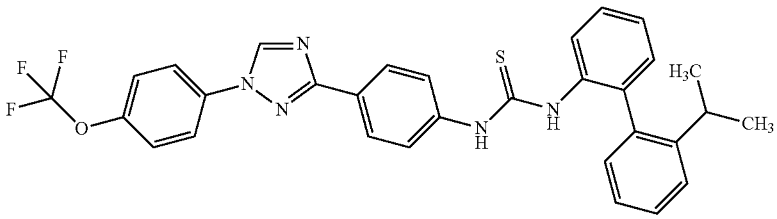 | 24 |
| F29 | 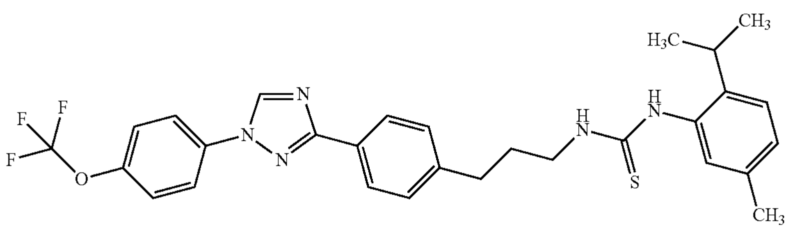 | 16 |
| F30 | 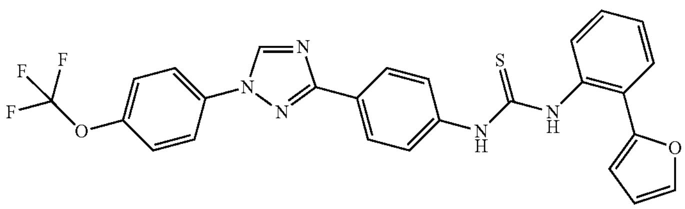 | 21 |
| F31 | 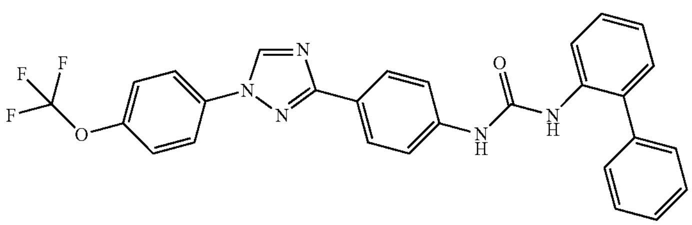 | 25 |
| F32 | 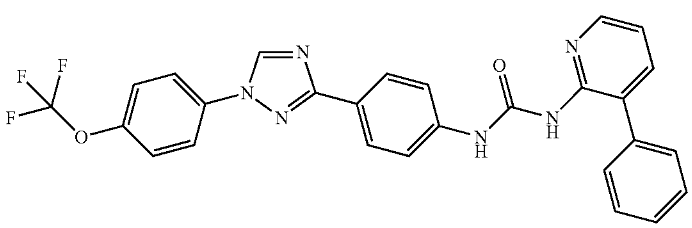 | 25 |
| F33 | 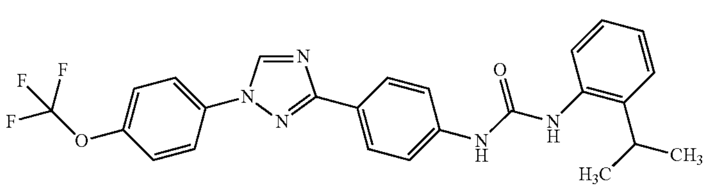 | 7 |

TABLE 2-continued

Structure and Preparation Method for F Series Compounds

| No. | Structure | Prep. according to example |
|-----|-----------|----------------------------|
| F34 | 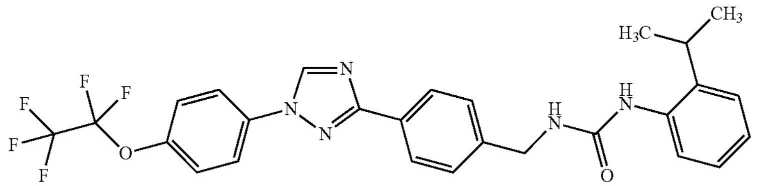 [SMILES: CC(C)c1ccccc1NC(=O)NCc1ccc(-c2ncn(-c3ccc(OC(F)(F)C(F)(F)F)cc3)n2)cc1] | 37 |
| F35 | 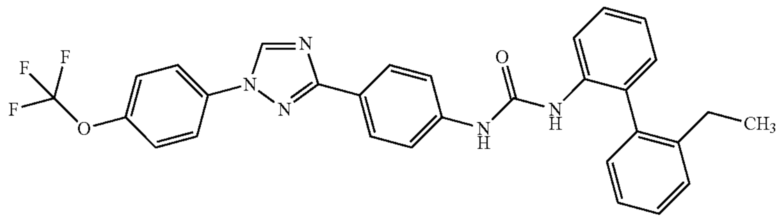 | 25 |
| F36 | 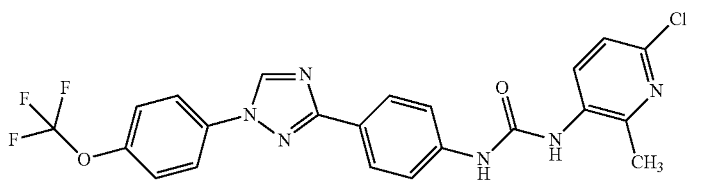 [SMILES: Cc1nc(Cl)ccc1NC(=O)Nc1ccc(-c2ncn(-c3ccc(OC(F)(F)F)cc3)n2)cc1] | 26 |
| F37 | 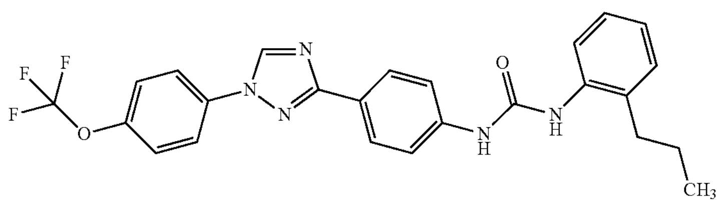 [SMILES: CCCc1ccccc1NC(=O)Nc1ccc(-c2ncn(-c3ccc(OC(F)(F)F)cc3)n2)cc1] | 4 |
| F38 | 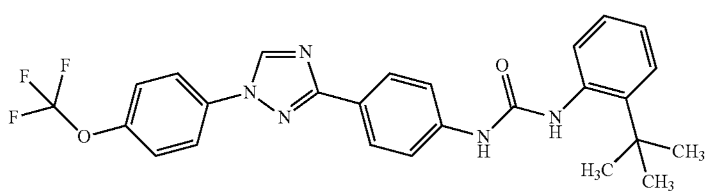 [SMILES: CC(C)(C)c1ccccc1NC(=O)Nc1ccc(-c2ncn(-c3ccc(OC(F)(F)F)cc3)n2)cc1] | 4 |
| F39 | 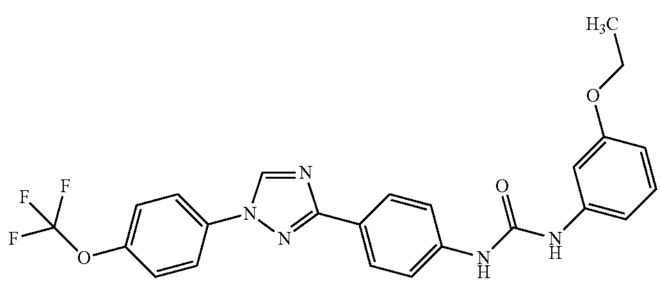 [SMILES: CCOc1cccc(NC(=O)Nc2ccc(-c3ncn(-c4ccc(OC(F)(F)F)cc4)n3)cc2)c1] | 8 |
| F40 | 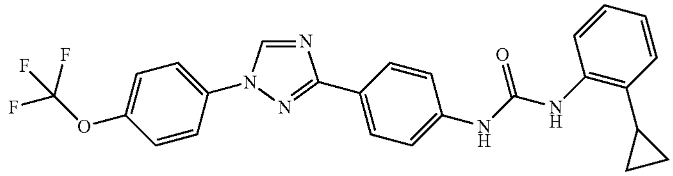 [SMILES: O=C(Nc1ccc(-c2ncn(-c3ccc(OC(F)(F)F)cc3)n2)cc1)Nc1ccccc1C1CC1] | 23 |

TABLE 2-continued

Structure and Preparation Method for F Series Compounds

| No. | Structure | Prep. according to example |
|---|---|---|
| F41 | 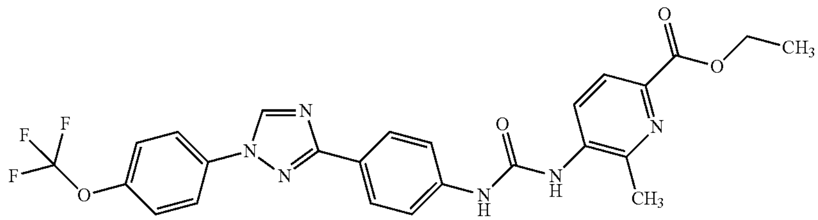 [SMILES: CCOC(=O)c1ccc(NC(=O)Nc2ccc(-c3ncn(-c4ccc(OC(F)(F)F)cc4)n3)cc2)c(C)n1] | 26 |
| F42 | 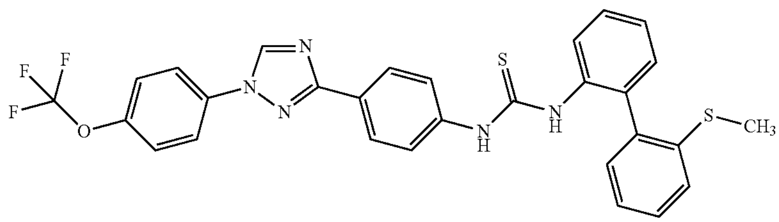 | 24 |
| F43 | 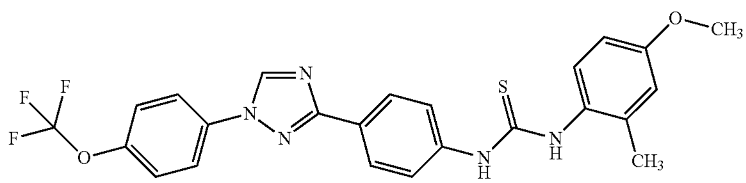 [SMILES: COc1ccc(NC(=S)Nc2ccc(-c3ncn(-c4ccc(OC(F)(F)F)cc4)n3)cc2)c(C)c1] | 39 |
| F44 | 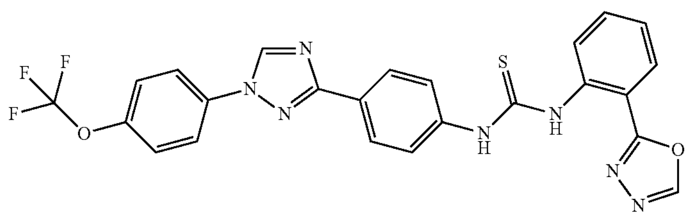 | 21 |
| F45 | 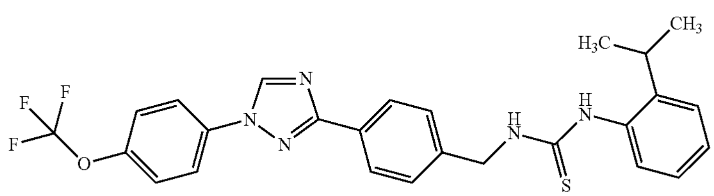 [SMILES: CC(C)c1ccccc1NC(=S)NCc1ccc(-c2ncn(-c3ccc(OC(F)(F)F)cc3)n2)cc1] | 32, 42 |
| F46 | 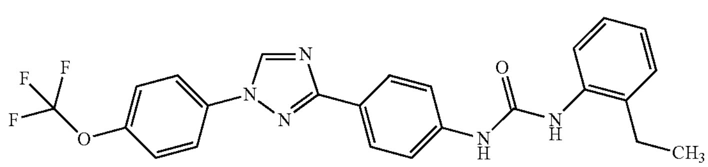 [SMILES: CCc1ccccc1NC(=O)Nc1ccc(-c2ncn(-c3ccc(OC(F)(F)F)cc3)n2)cc1] | 5 |
| F47 | 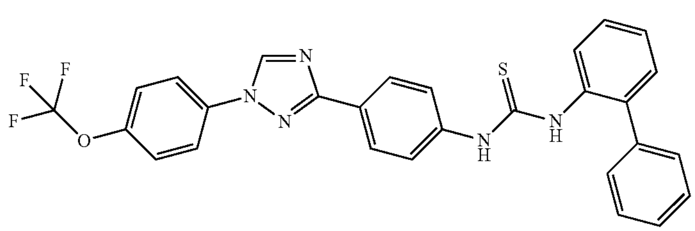 | 24 |

TABLE 2-continued

Structure and Preparation Method for F Series Compounds

| No. | Structure | Prep. according to example |
|---|---|---|
| F48 | 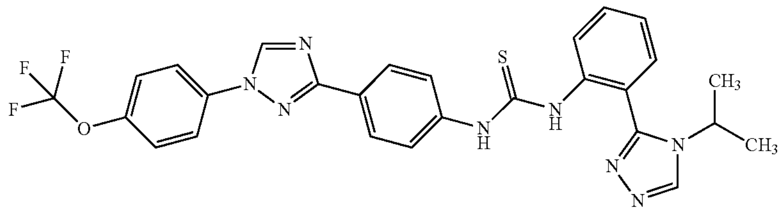 | 21 |
| F49 | 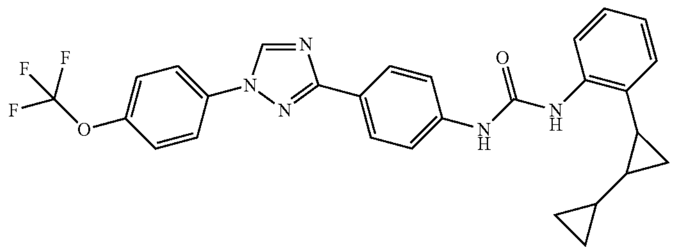 [SMILES: O=C(Nc1ccc(-c2ncn(-c3ccc(OC(F)(F)F)cc3)n2)cc1)Nc1ccccc1C1CC1C1CC1] | 5 |
| F50 | 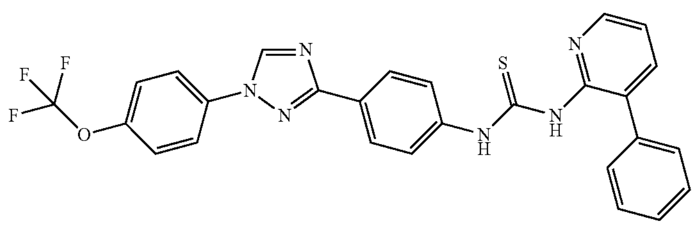 | 24 |
| F51 | 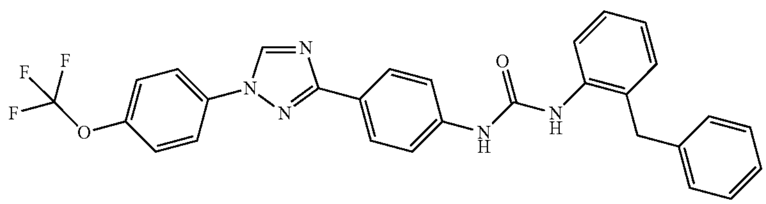 | 20 |
| F52 | 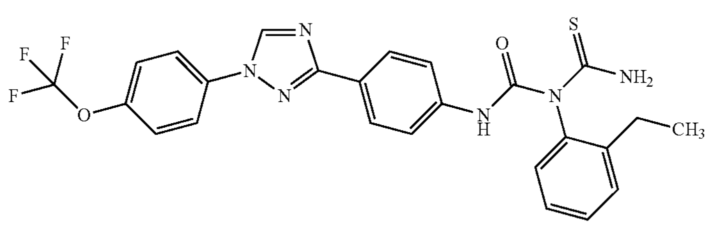 [SMILES: CCc1ccccc1N(C(=O)Nc1ccc(-c2ncn(-c3ccc(OC(F)(F)F)cc3)n2)cc1)C(N)=S] | 19 |
| F53 | 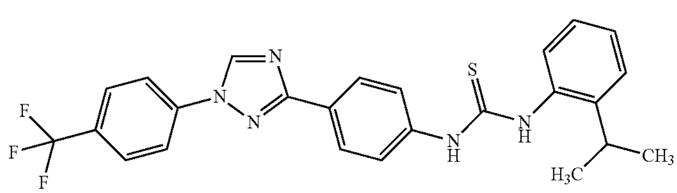 [SMILES: CC(C)c1ccccc1NC(=S)Nc1ccc(-c2ncn(-c3ccc(C(F)(F)F)cc3)n2)cc1] | 3 |
| F54 | 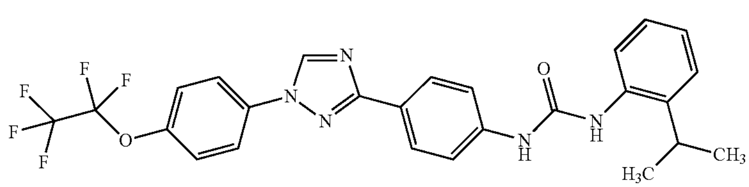 [SMILES: CC(C)c1ccccc1NC(=O)Nc1ccc(-c2ncn(-c3ccc(OC(F)(F)C(F)(F)F)cc3)n2)cc1] | 7 |

TABLE 2-continued

Structure and Preparation Method for F Series Compounds

| No. | Structure | Prep. according to example |
|---|---|---|
| F55 | 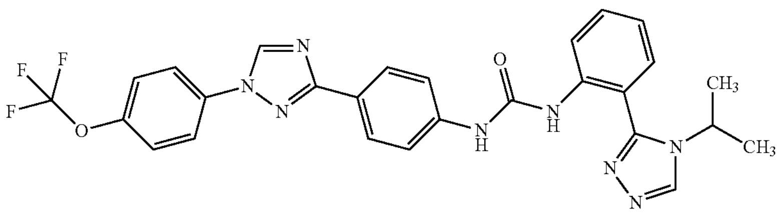 [SMILES: CC(C)n1cnnc1-c1ccccc1NC(=O)Nc1ccc(-c2ncn(-c3ccc(OC(F)(F)F)cc3)n2)cc1] | 20 |
| F56 | 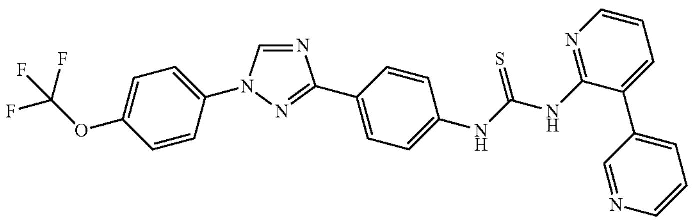 [SMILES: FC(F)(F)Oc1ccc(-n2cnc(-c3ccc(NC(=S)Nc4ncccc4-c4cccnc4)cc3)n2)cc1] | 24 |
| F57 | 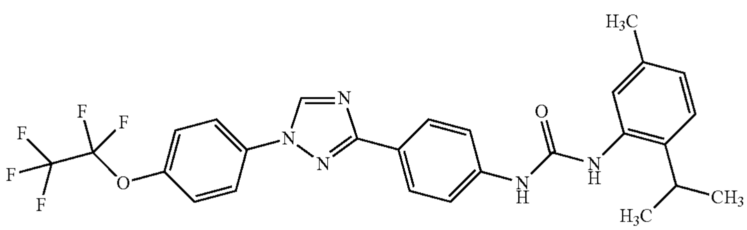 [SMILES: Cc1ccc(C(C)C)c(NC(=O)Nc2ccc(-c3ncn(-c4ccc(OC(F)(F)C(F)(F)F)cc4)n3)cc2)c1] | 7 |
| F58 | 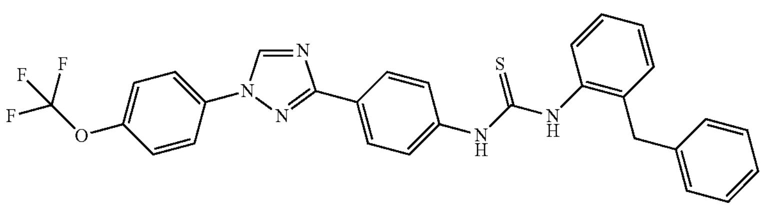 | 21 |
| F59 | 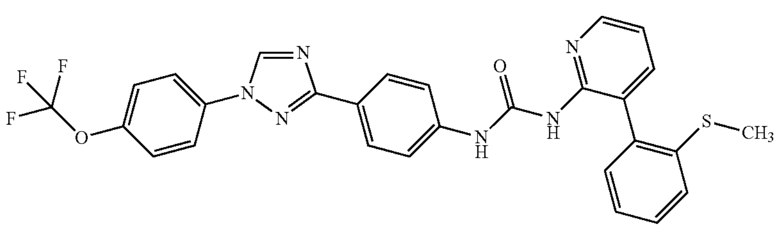 [SMILES: CSc1ccccc1-c1cccnc1NC(=O)Nc1ccc(-c2ncn(-c3ccc(OC(F)(F)F)cc3)n2)cc1] | 25 |
| F60 | 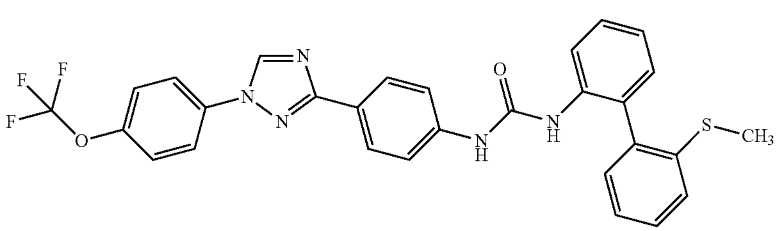 | 25 |

TABLE 2-continued

Structure and Preparation Method for F Series Compounds

| No. | Structure | Prep. according to example |
|-----|-----------|---------------------------|
| F61 | 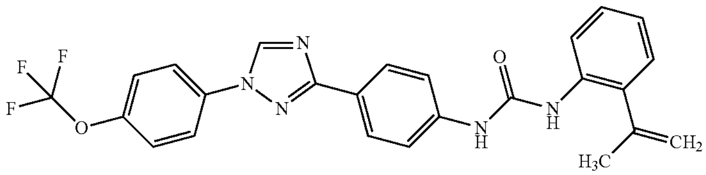 | 6 |
| F62 | 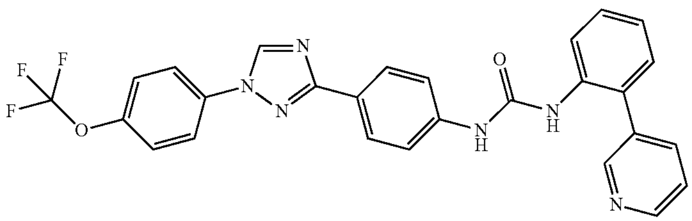 | 25 |
| F63 | 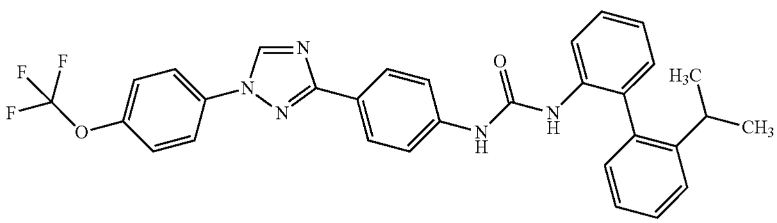 | 25 |
| F64 | 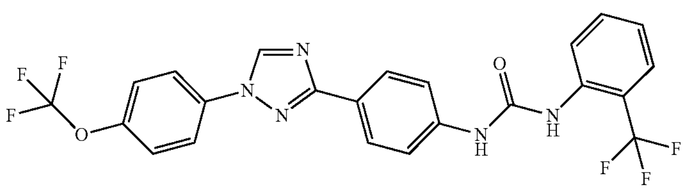 [SMILES: O=C(Nc1ccc(-c2ncn(-c3ccc(OC(F)(F)F)cc3)n2)cc1)Nc1ccccc1C(F)(F)F] | 6 |
| F65 | 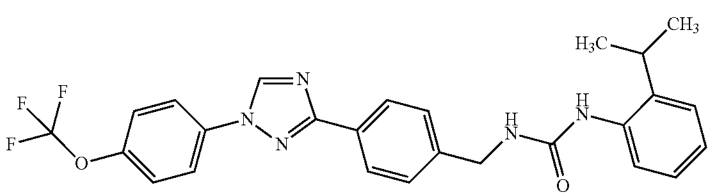 | 36 |
| F66 | 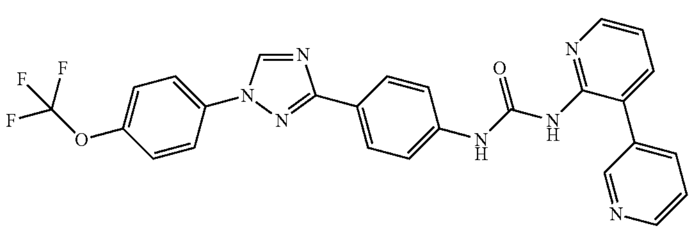 | 25 |
| F67 | 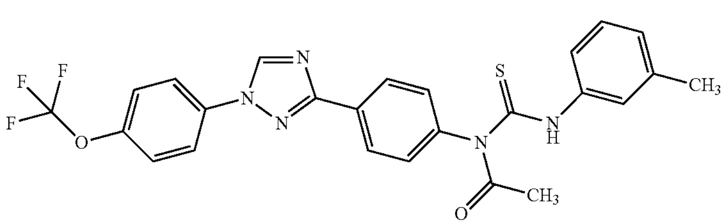 [SMILES: CC(=O)N(C(=S)Nc1cccc(C)c1)c1ccc(-c2ncn(-c3ccc(OC(F)(F)F)cc3)n2)cc1] | 18 |

TABLE 2-continued

Structure and Preparation Method for F Series Compounds

| No. | Structure | Prep. according to example |
|---|---|---|
| F68 | 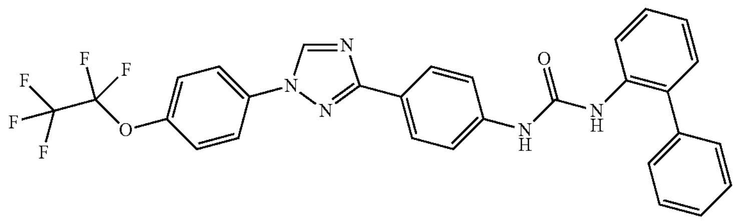 [SMILES: O=C(Nc1ccc(-c2ncn(-c3ccc(OC(F)(F)C(F)(F)F)cc3)n2)cc1)Nc1ccccc1-c1ccccc1] | 7 |
| F69 | 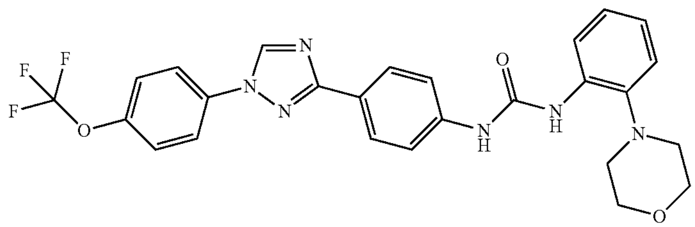 [SMILES: O=C(Nc1ccc(-c2ncn(-c3ccc(OC(F)(F)F)cc3)n2)cc1)Nc1ccccc1N1CCOCC1] | 6 |
| F70 | 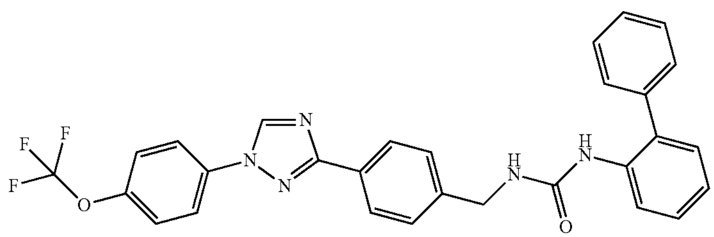 [SMILES: O=C(NCc1ccc(-c2ncn(-c3ccc(OC(F)(F)F)cc3)n2)cc1)Nc1ccccc1-c1ccccc1] | 36 |
| F71 | 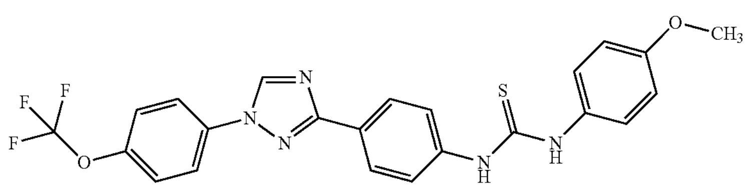 [SMILES: COc1ccc(NC(=S)Nc2ccc(-c3ncn(-c4ccc(OC(F)(F)F)cc4)n3)cc2)cc1] | 39 |
| F72 | 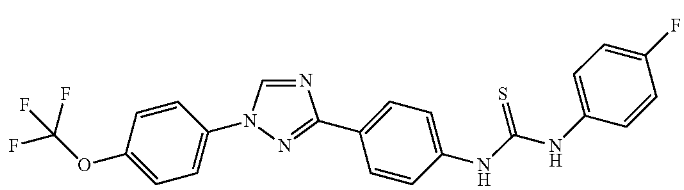 [SMILES: Fc1ccc(NC(=S)Nc2ccc(-c3ncn(-c4ccc(OC(F)(F)F)cc4)n3)cc2)cc1] | 39 |
| F73 | 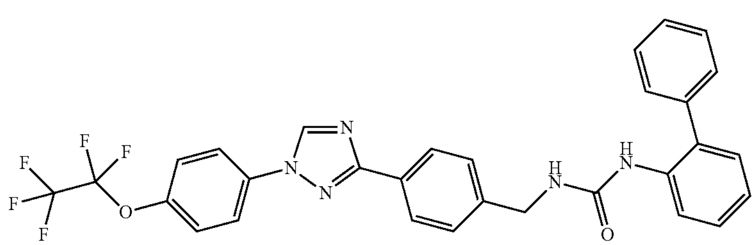 [SMILES: O=C(NCc1ccc(-c2ncn(-c3ccc(OC(F)(F)C(F)(F)F)cc3)n2)cc1)Nc1ccccc1-c1ccccc1] | 37 |

TABLE 2-continued

Structure and Preparation Method for F Series Compounds

| No. | Structure | Prep. according to example |
|---|---|---|
| F74 | 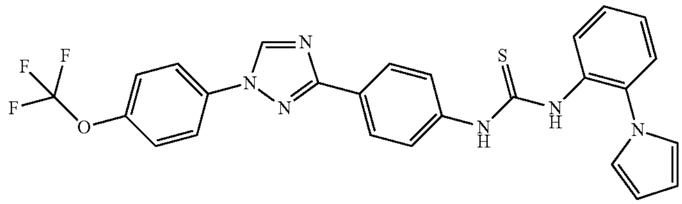 [SMILES: FC(F)(F)Oc1ccc(-n2cnc(-c3ccc(NC(=S)Nc4ccccc4-n4cccc4)cc3)n2)cc1] | 21 |
| F75 | 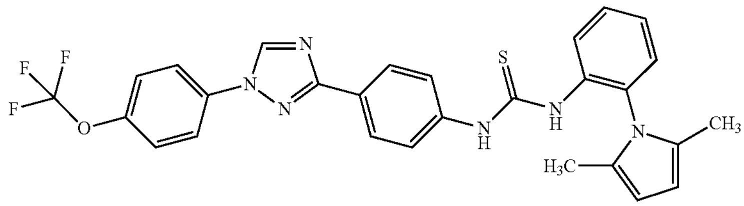 [SMILES: Cc1ccc(C)n1-c1ccccc1NC(=S)Nc1ccc(-c2ncn(-c3ccc(OC(F)(F)F)cc3)n2)cc1] | 21 |
| F76 | 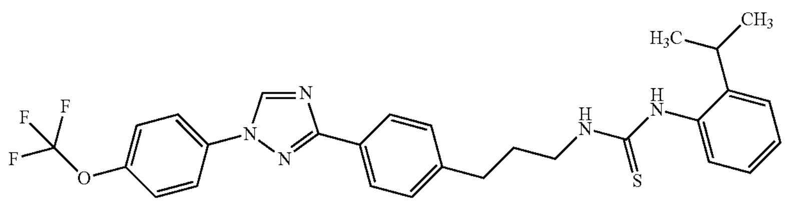 [SMILES: CC(C)c1ccccc1NC(=S)NCCCc1ccc(-c2ncn(-c3ccc(OC(F)(F)F)cc3)n2)cc1] | 40 |
| F77 | 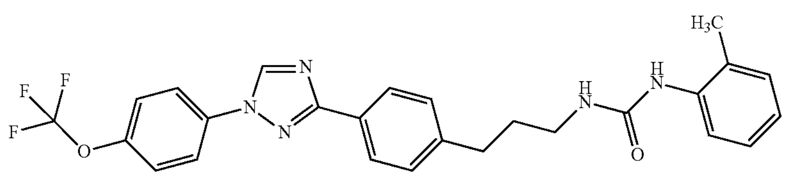 [SMILES: Cc1ccccc1NC(=O)NCCCc1ccc(-c2ncn(-c3ccc(OC(F)(F)F)cc3)n2)cc1] | 41 |
| F78 | 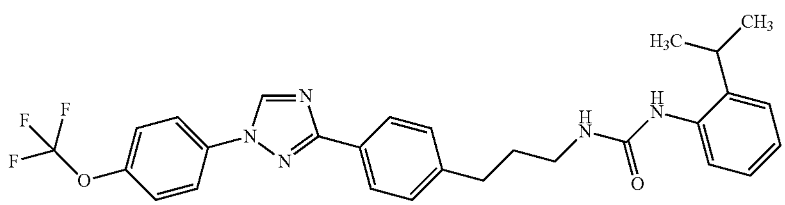 | 41 |
| F79 | 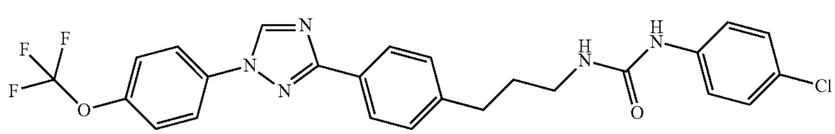 [SMILES: O=C(NCCCc1ccc(-c2ncn(-c3ccc(OC(F)(F)F)cc3)n2)cc1)Nc1ccc(Cl)cc1] | 41 |
| F80 | 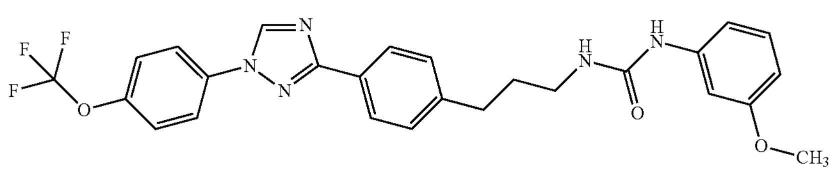 [SMILES: COc1cccc(NC(=O)NCCCc2ccc(-c3ncn(-c4ccc(OC(F)(F)F)cc4)n3)cc2)c1] | 41 |
| F81 | 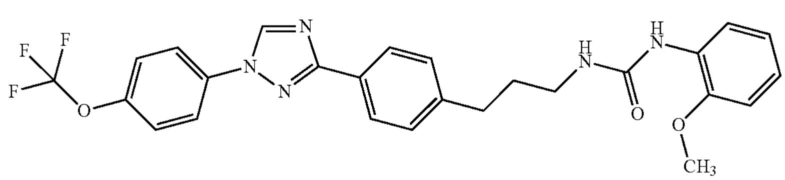 | 41 |

TABLE 2-continued

Structure and Preparation Method for F Series Compounds

| No. | Structure | Prep. according to example |
|-----|-----------|----------------------------|
| F82 | 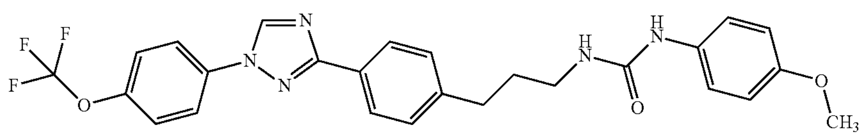 [SMILES: COc1ccc(NC(=O)NCCCc2ccc(-c3ncn(-c4ccc(OC(F)(F)F)cc4)n3)cc2)cc1] | 41 |
| F83 | 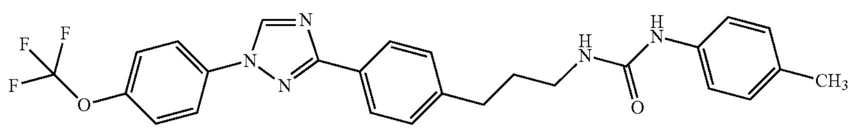 [SMILES: Cc1ccc(NC(=O)NCCCc2ccc(-c3ncn(-c4ccc(OC(F)(F)F)cc4)n3)cc2)cc1] | 41 |
| F84 | 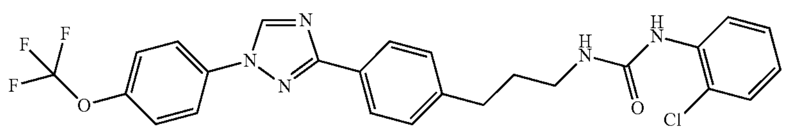 [SMILES: O=C(NCCCc1ccc(-c2ncn(-c3ccc(OC(F)(F)F)cc3)n2)cc1)Nc1ccccc1Cl] | 41 |
| F85 | 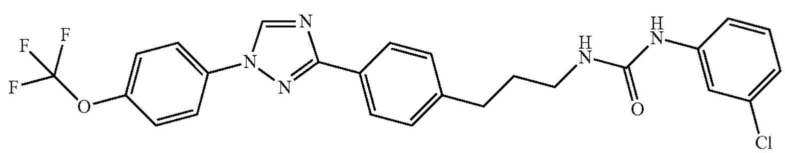 [SMILES: O=C(NCCCc1ccc(-c2ncn(-c3ccc(OC(F)(F)F)cc3)n2)cc1)Nc1cccc(Cl)c1] | 41 |
| F86 | 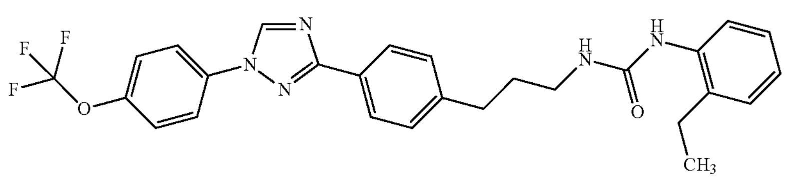 | 41 |
| F87 | 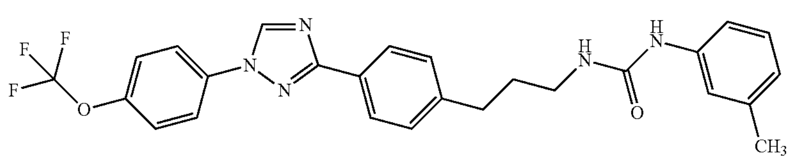 [SMILES: Cc1cccc(NC(=O)NCCCc2ccc(-c3ncn(-c4ccc(OC(F)(F)F)cc4)n3)cc2)c1] | 41 |
| F88 | 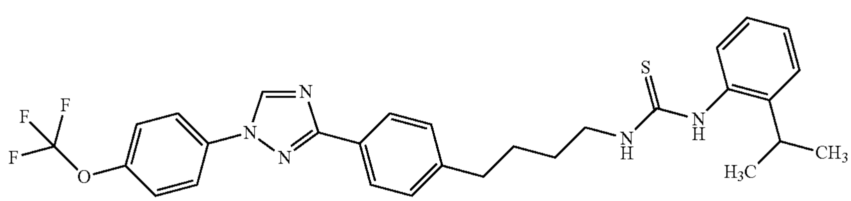 | 40 |
| F89 | 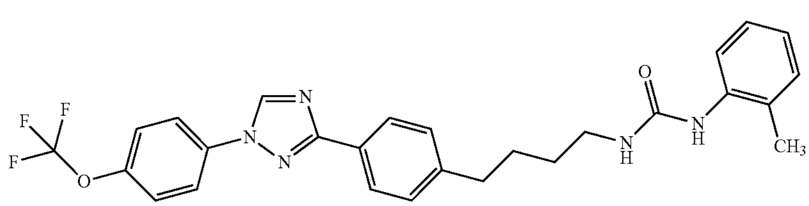 [SMILES: Cc1ccccc1NC(=O)NCCCCc1ccc(-c2ncn(-c3ccc(OC(F)(F)F)cc3)n2)cc1] | 41 |

TABLE 2-continued
Structure and Preparation Method for F Series Compounds
| No. | Structure | Prep. according to example |
|---|---|---|
| F90 | 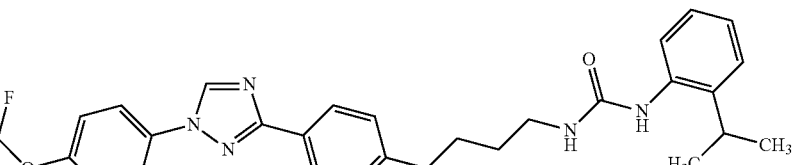 | 41 |
| F91 | 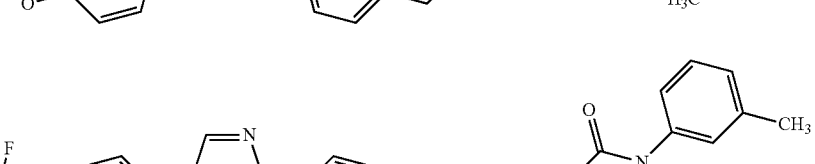 | 41 |
| F92 | 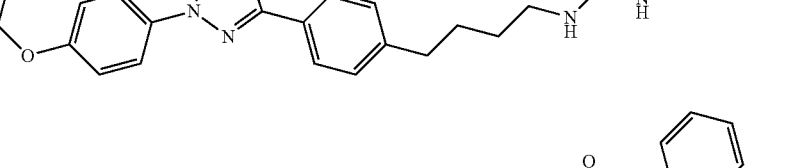 | 41 |
| F93 | 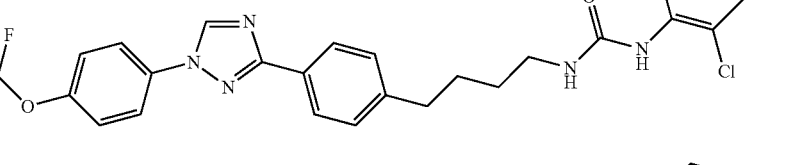 | 41 |
| F94 | 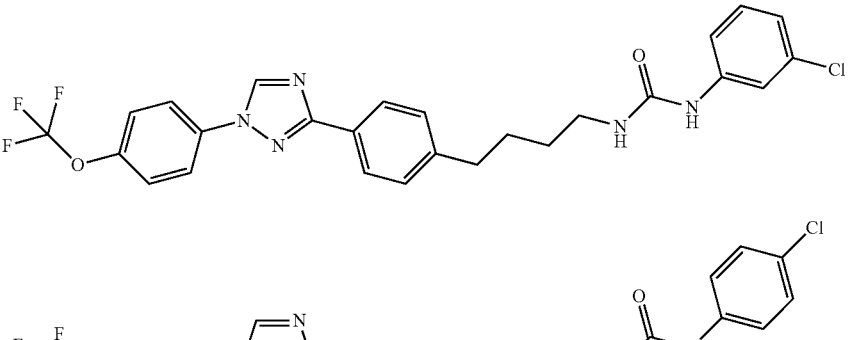 | 41 |
| F95 | 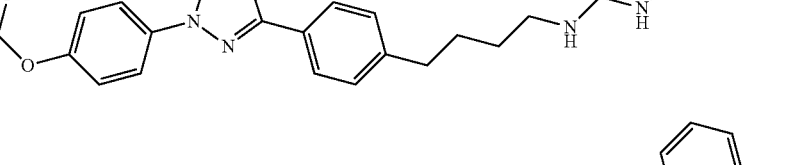 | 41 |
| F96 | 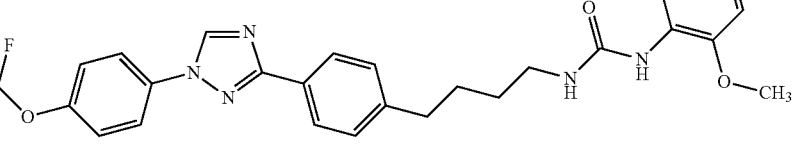 | 41 |

TABLE 2-continued

Structure and Preparation Method for F Series Compounds

| No. | Structure | Prep. according to example |
|-----|-----------|---------------------------|
| F97 | 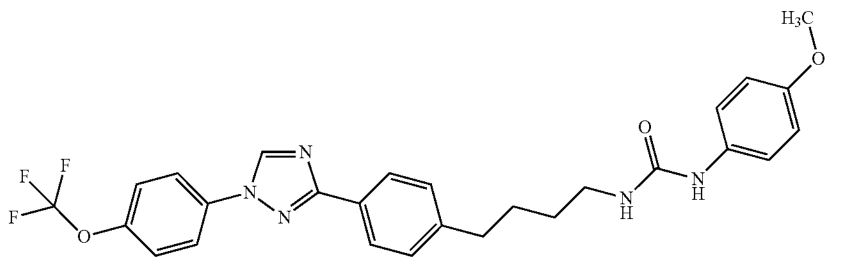 [SMILES: COc1ccc(NC(=O)NCCCCc2ccc(-c3ncn(-c4ccc(OC(F)(F)F)cc4)n3)cc2)cc1] | 41 |
| F98 | 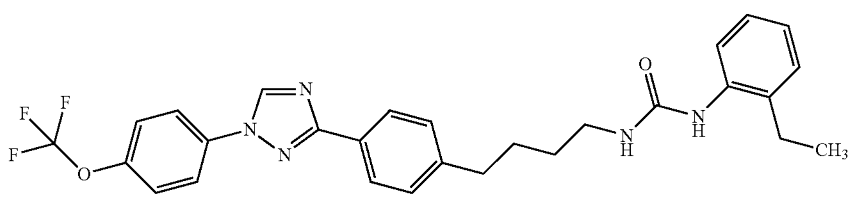 | 41 |
| F99 | 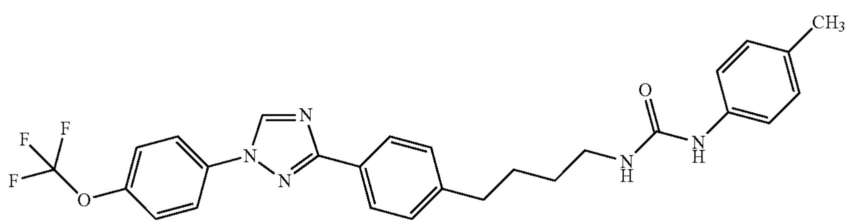 [SMILES: Cc1ccc(NC(=O)NCCCCc2ccc(-c3ncn(-c4ccc(OC(F)(F)F)cc4)n3)cc2)cc1] | 41 |
| F100 | 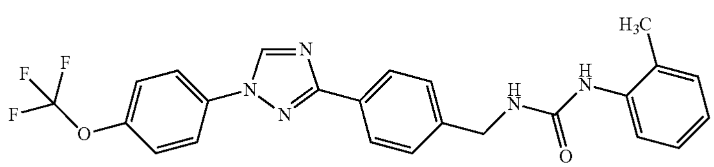 [SMILES: Cc1ccccc1NC(=O)NCc1ccc(-c2ncn(-c3ccc(OC(F)(F)F)cc3)n2)cc1] | 41 |
| F101 | 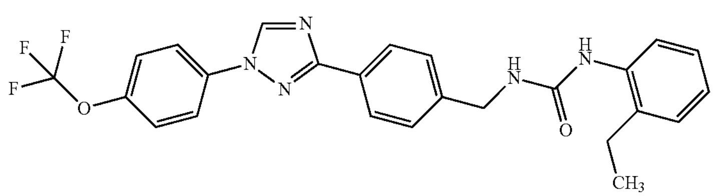 | 41 |
| F102 | 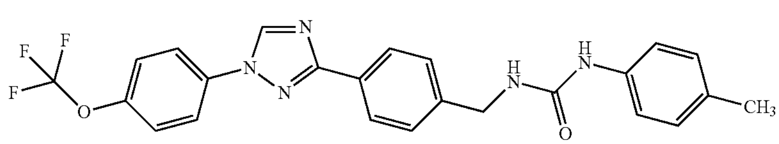 [SMILES: Cc1ccc(NC(=O)NCc2ccc(-c3ncn(-c4ccc(OC(F)(F)F)cc4)n3)cc2)cc1] | 41 |
| F103 | 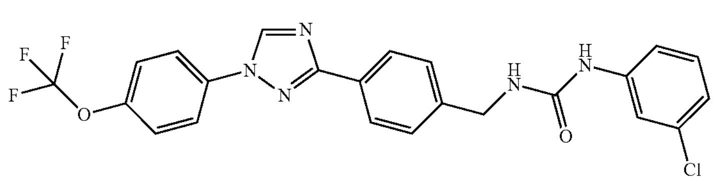 [SMILES: O=C(NCc1ccc(-c2ncn(-c3ccc(OC(F)(F)F)cc3)n2)cc1)Nc1cccc(Cl)c1] | 41 |

TABLE 2-continued

Structure and Preparation Method for F Series Compounds

| No. | Structure | Prep. according to example |
|---|---|---|
| F104 | 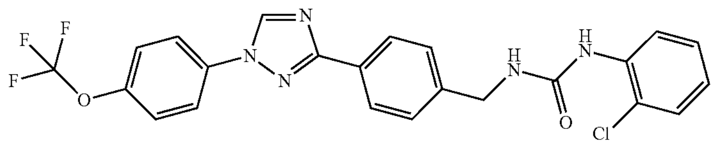 [SMILES: O=C(NCc1ccc(-c2ncn(-c3ccc(OC(F)(F)F)cc3)n2)cc1)Nc1ccccc1Cl] | 41 |
| F105 | 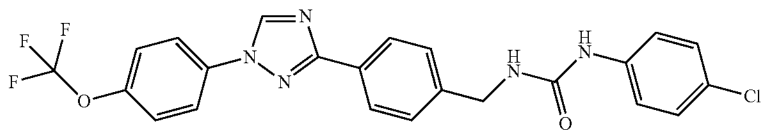 [SMILES: O=C(NCc1ccc(-c2ncn(-c3ccc(OC(F)(F)F)cc3)n2)cc1)Nc1ccc(Cl)cc1] | 41 |
| F106 | 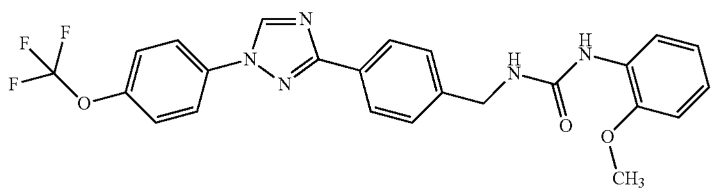 | 41 |
| F107 | 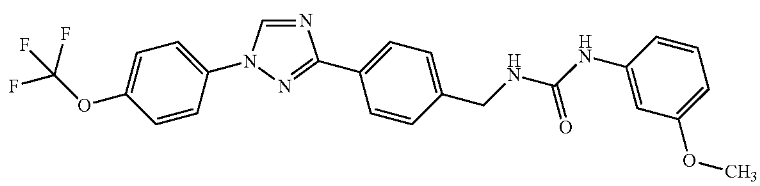 [SMILES: COc1cccc(NC(=O)NCc2ccc(-c3ncn(-c4ccc(OC(F)(F)F)cc4)n3)cc2)c1] | 41 |
| F108 | 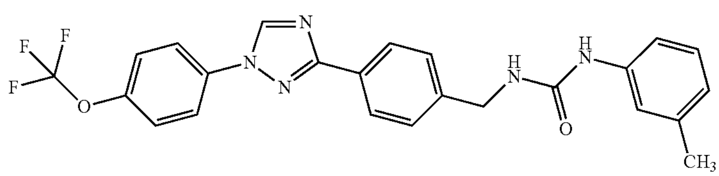 [SMILES: Cc1cccc(NC(=O)NCc2ccc(-c3ncn(-c4ccc(OC(F)(F)F)cc4)n3)cc2)c1] | 41 |
| F109 | 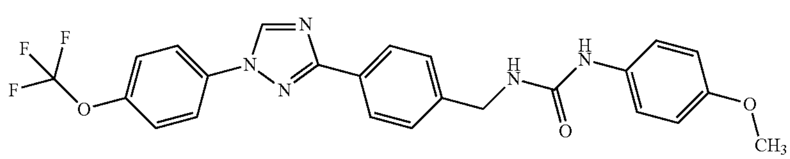 | 41 |
| F110 | 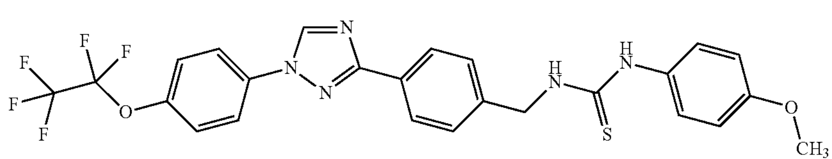 | 50 |
| F111 | 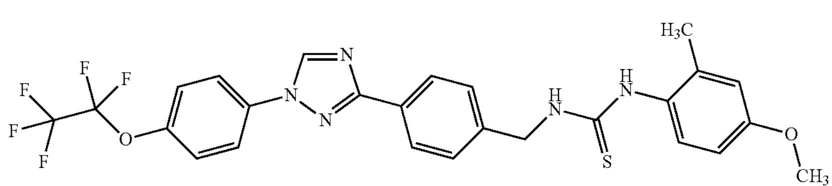 [SMILES: COc1ccc(NC(=S)NCc2ccc(-c3ncn(-c4ccc(OC(F)(F)C(F)(F)F)cc4)n3)cc2)c(C)c1] | 50 |

TABLE 2-continued
Structure and Preparation Method for F Series Compounds
| No. | Structure | Prep. according to example |
|---|---|---|
| F112 | 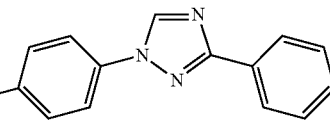 | 50 |
TABLE 3
Structure and Preparation Method for C Series Compounds
| No. | Structure | Prep. according to Example |
|---|---|---|
| C1 | 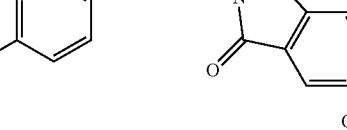 | 1 |
| C2 | 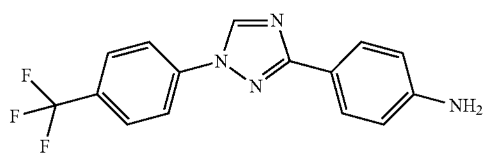 [SMILES: Nc1ccc(-c2ncn(-c3ccc(C(F)(F)F)cc3)n2)cc1] | 2 |
| C3 | 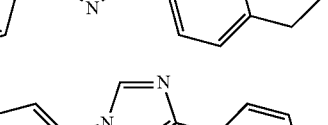 | 9 |
| C4 | 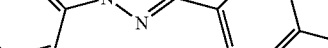 | 10 |
| C5 | 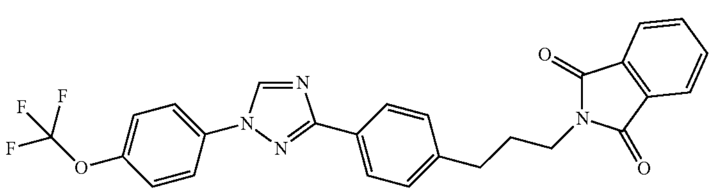 [SMILES: O=C1c2ccccc2C(=O)N1CCCc1ccc(-c2ncn(-c3ccc(OC(F)(F)F)cc3)n2)cc1] | 11, 46 |
| C6 | 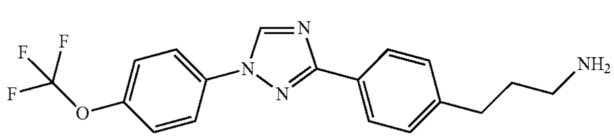 [SMILES: NCCCc1ccc(-c2ncn(-c3ccc(OC(F)(F)F)cc3)n2)cc1] | 12, 47 |

TABLE 3-continued

Structure and Preparation Method for C Series Compounds

| No. | Structure | Prep. according to Example |
|---|---|---|
| C7 | 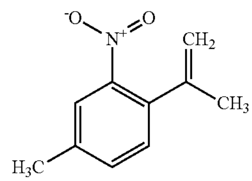 | 13 |
| C8 | 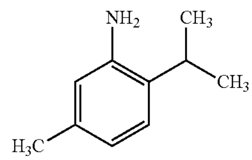 | 14 |
| C9 | 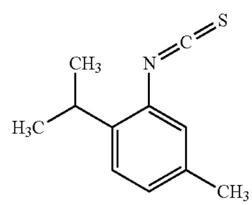 | 15 |
| C10 | 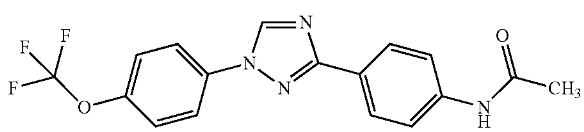 [SMILES: CC(=O)Nc1ccc(-c2ncn(-c3ccc(OC(F)(F)F)cc3)n2)cc1] | 17 |
| C11 | 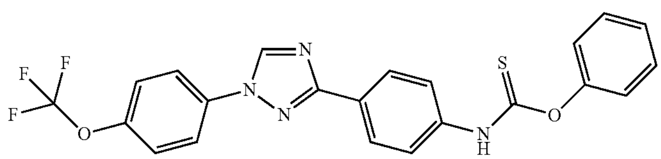 [SMILES: FC(F)(F)Oc1ccc(-n2cnc(-c3ccc(NC(=S)Oc4ccccc4)cc3)n2)cc1] | 22 |
| C12 | 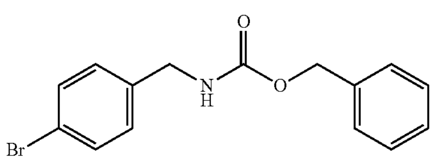 [SMILES: O=C(NCc1ccc(Br)cc1)OCc1ccccc1] | 28 |
| C13 | 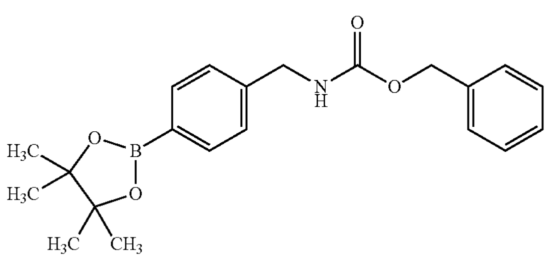 [SMILES: CC1(C)OB(c2ccc(CNC(=O)OCc3ccccc3)cc2)OC1(C)C] | 29 |
| C14 | 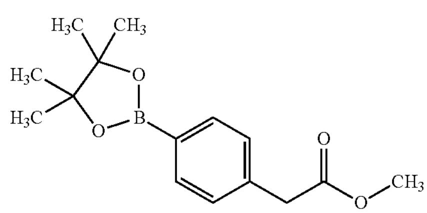 | 29 |

TABLE 3-continued

Structure and Preparation Method for C Series Compounds

| No. | Structure | Prep. according to Example |
|---|---|---|
| C15 | 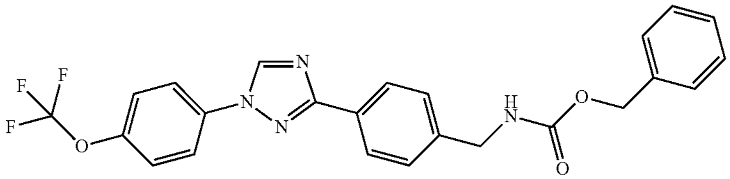 [SMILES: O=C(NCc1ccc(-c2ncn(-c3ccc(OC(F)(F)F)cc3)n2)cc1)OCc1ccccc1] | 30 |
| C16 | 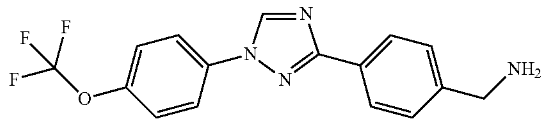 [SMILES: NCc1ccc(-c2ncn(-c3ccc(OC(F)(F)F)cc3)n2)cc1] | 31 |
| C16A | 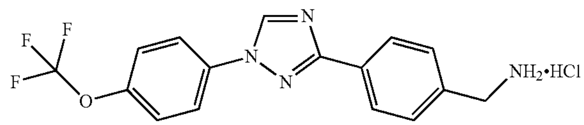 | 49 |
| C17 | 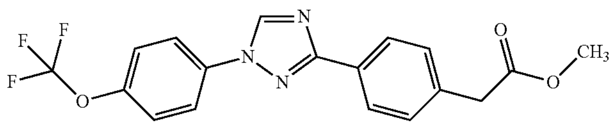 [SMILES: COC(=O)Cc1ccc(-c2ncn(-c3ccc(OC(F)(F)F)cc3)n2)cc1] | 33 |
| C18 | 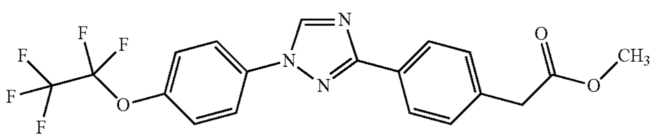 [SMILES: COC(=O)Cc1ccc(-c2ncn(-c3ccc(OC(F)(F)C(F)(F)F)cc3)n2)cc1] | 33 |
| C19 | 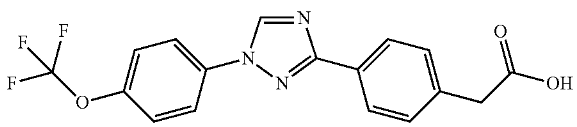 [SMILES: O=C(O)Cc1ccc(-c2ncn(-c3ccc(OC(F)(F)F)cc3)n2)cc1] | 34 |
| C20 | 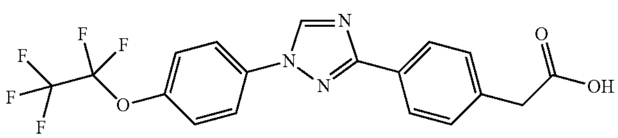 [SMILES: O=C(O)Cc1ccc(-c2ncn(-c3ccc(OC(F)(F)C(F)(F)F)cc3)n2)cc1] | 34 |
| C21 | 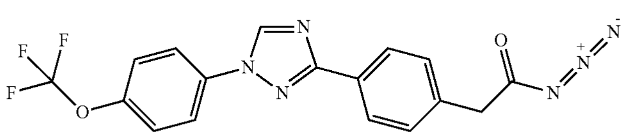 | 35 |
| C22 | 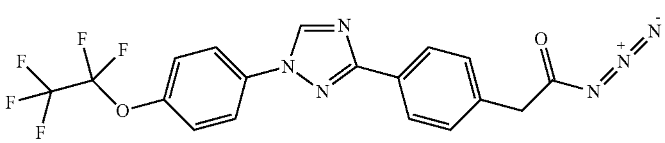 | 35 |
| C23 | 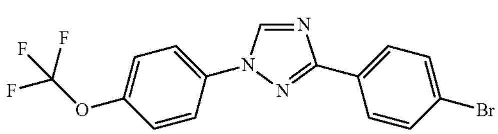 [SMILES: FC(F)(F)Oc1ccc(-n2cnc(-c3ccc(Br)cc3)n2)cc1] | 43 |

TABLE 3-continued

Structure and Preparation Method for C Series Compounds

| No. | Structure | Prep. according to Example |
|---|---|---|
| C24 | 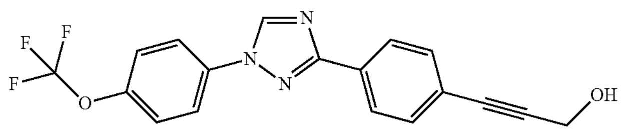 [SMILES: OCC#Cc1ccc(-c2ncn(-c3ccc(OC(F)(F)F)cc3)n2)cc1] | 44 |
| C25 | 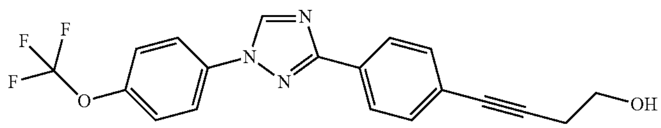 [SMILES: OCCC#Cc1ccc(-c2ncn(-c3ccc(OC(F)(F)F)cc3)n2)cc1] | 44 |
| C26 | 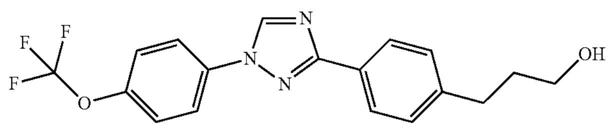 [SMILES: OCCCc1ccc(-c2ncn(-c3ccc(OC(F)(F)F)cc3)n2)cc1] | 45 |
| C27 | 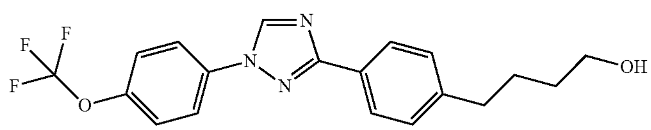 [SMILES: OCCCCc1ccc(-c2ncn(-c3ccc(OC(F)(F)F)cc3)n2)cc1] | 45 |
| C28 | 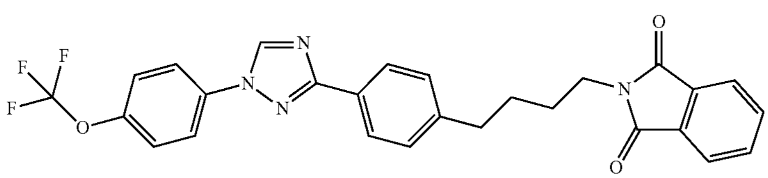 [SMILES: O=C1c2ccccc2C(=O)N1CCCCc1ccc(-c2ncn(-c3ccc(OC(F)(F)F)cc3)n2)cc1] | 46 |
| C29 | 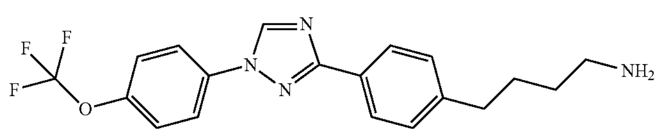 [SMILES: NCCCCc1ccc(-c2ncn(-c3ccc(OC(F)(F)F)cc3)n2)cc1] | 47 |
| C30 | 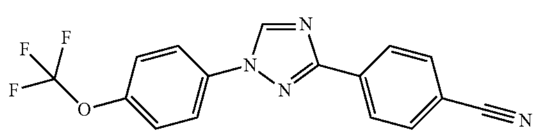 [SMILES: N#Cc1ccc(-c2ncn(-c3ccc(OC(F)(F)F)cc3)n2)cc1] | 48 |
| C31 | 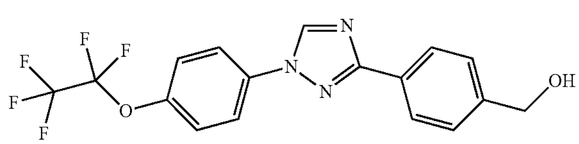 [SMILES: OCc1ccc(-c2ncn(-c3ccc(OC(F)(F)C(F)(F)F)cc3)n2)cc1] | 51 |
| C32 | 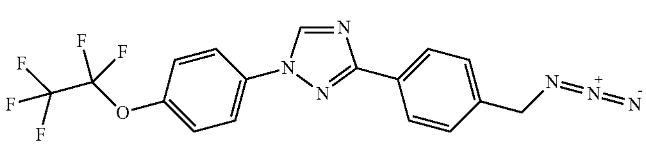 | 52 |
| C33 | 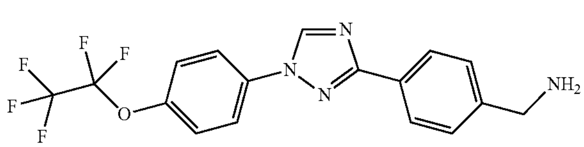 [SMILES: NCc1ccc(-c2ncn(-c3ccc(OC(F)(F)C(F)(F)F)cc3)n2)cc1] | 53 |

TABLE 3-continued

Structure and Preparation Method for C Series Compounds

| No. | Structure | Prep. according to Example |
|---|---|---|
| CA1 | 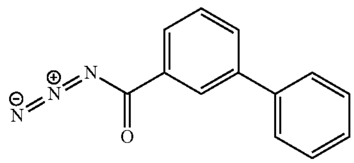 [SMILES: [N-]=[N+]=NC(=O)c1cccc(-c2ccccc2)c1] | 54 |
| CA2 | 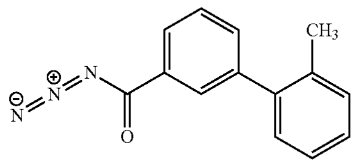 [SMILES: Cc1ccccc1-c1cccc(C(=O)N=[N+]=[N-])c1] | 54 |
| CA3 | 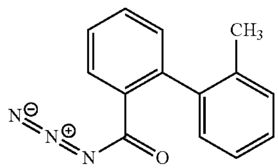 [SMILES: Cc1ccccc1-c1ccccc1C(=O)N=[N+]=[N-]] | 54 |
| CA4 | 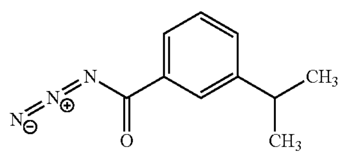 | 54 |
| CA5 | 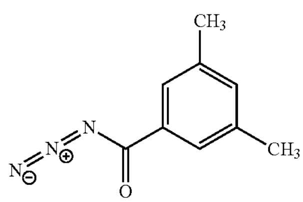 | 54 |

TABLE 4

Analytical Data for Compounds in Table 2

| No. | Mp (° C.) | IR (cm$^{-1}$) | Mass (m/z) | $^1$H NMR | $^{13}$CNMR; $^{19}$F NMR |
|---|---|---|---|---|---|
| F1 | 227-228 | | ESIMS m/z 574 ([M + H]$^+$) | $^1$H NMR (400 MHz, DMSO-d$_6$) δ 9.53 (d, J = 5.0 Hz, 1H), 9.39 (s, 1H), 8.55 (s, 1H), 8.29 (dt, J = 8.3, 2.3 Hz, 1H), 8.13 – 8.02 (m, 4H), 7.62 (dd, J = 8.4, 1.4 Hz, 4H), 7.42 – 7.32 (m, 2H), 7.11 (ddd, J = 8.3, 7.5, 1.6 Hz, 1H). | |
| F2 | 243-245 | | ESIMS m/z 484 ([M + H]$^+$) | $^1$H NMR (300 MHz, DMSO-d$_6$) δ 9.36 (s, 1H), 8.84 (s, 1H), 8.54 (s, 1H), 8.06 (d, J = 9.1 Hz, 2H), 8.01 (d, J = 8.8 Hz, 2H), 7.65 – 7.55 (m, 4H), 7.36 (d, J = 9.0 Hz, 2H), 6.86 (d, J = 9.0 Hz, 2H), 3.98 (q, J = 7.0 Hz, 2H), 1.31 (t, J = 7.0 Hz, 3H). | |
| F3 | 139-143 | | ESIMS m/z 498 ([M + H]$^+$) | δ 8.57 (s, 1H), 8.20 (d, J = 8.6 Hz, 2H), 8.10 (d, J = 8.4 Hz, 2H), 7.80 (d, J = 8.6 Hz, 2H), 7.61 (s, 1H), 7.60 – 7.33 (m, 6H), 7.20 (2, 1H), 3.24 (p, J = 6.9 Hz, 1H), 1.27 (d, J = 6.9 Hz, 6H). | |
| F4 | 150-152 | | ESIMS m/z: 560.2 ([M + H]$^+$) | $^1$H NMR (400 MHz, CDCl$_3$) δ 8.83 (s, 1H), 8.24 (s, 1H), 8.05 (d, J = 7.7 Hz, 2H), 7.85 (d, J = 7.5 Hz, 2H), 7.74 (s, 1H), 7.43 (d, J = 9.4 Hz, 4H), 7.32 (d, J = 24.0 Hz, 3H), 7.22 (d, J = 6.0 Hz, 2H), 7.07 (d, J = 7.3 Hz, 1H), 6.93 (m, 2H), 2.36 (d, J = 13.8 Hz, 2H), 0.98 (m, 3H). | |

TABLE 4-continued

Analytical Data for Compounds in Table 2

| No. | Mp (° C.) | IR (cm$^{-1}$) | Mass (m/z) | $^1$H NMR | $^{13}$CNMR; $^{19}$F NMR |
|---|---|---|---|---|---|
| F5 | 194-196 | | ESIMS m/z 464 ([M + H]$^+$) | $^1$H NMR (400 MHz, DMSO-d$_6$) δ 9.83 (d, J = 3.7 Hz, 1H), 9.37 (d, J = 2.3 Hz, 1H), 8.28 (d, J = 2.3 Hz, 1H), 8.16 (dt, J = 8.4, 1.2 Hz, 1H), 8.11 – 8.02 (m, 4H), 7.67 – 7.59 (m, 4H), 7.46 (dd, J = 7.8, 1.6 Hz, 1H), 7.37 (ddd, J = 8.6, 7.4, 1.7 Hz, 1H), 7.02 (td, J = 7.5, 1.2 Hz, 1H), 4.70 (s, 1H). | |
| F6 | 130 (dec.) | | ESIMS m/z 541 ([M + H]$^+$) | $^1$H NMR (400 MHz, DMSO-d$_6$) δ 10.20 (s, 1H), 9.38 (s, 1H), 8.97 (s, 1H), 8.11 (s, 1H), 8.09 – 8.01 (m, 4H), 7.66 – 7.56 (m, 4H), 7.50 – 7.38 (m, 2H), 7.30 (dd, J = 4.7, 1.2 Hz, 2H), 3.15 – 2.98 (m, 1H), 1.19 (dd, J = 26.3, 6.8 Hz, 6H). | $^{19}$F NMR (376 MHz, DMSO-d$_6$) δ –56.96. |
| F7 | 172-175 | | ESIMS m/z 481 ([M + H]$^+$) | $^1$H NMR (400 MHz, DMSO-d$_6$) δ 10.35 (s, 1H), 10.32 (s, 1H), 9.40 (s, 1H), 8.11 – 8.04 (m, 4H), 7.79 (d, J = 1.1 Hz, 4H), 7.70 – 7.60 (m, 4H). | |
| F8 | >290 (dec.) | | ESIMS m/z 485 ([M + H]$^+$) | $^1$H NMR (300 MHz, DMSO-d$_6$) δ 9.36 (s, 1H), 9.03 (s, 1H), 8.71 (s, 1H), 8.20 (d, J = 2.5 Hz, 1H), 8.06 (d, J = 9.1 Hz, 2H), 8.02 (d, J = 8.7 Hz, 2H), 7.82 (dd, J = 8.9, 2.7 Hz, 1H), 7.61 (d, J = 8.7 Hz, 2H), 7.60 (d, J = 8.6 Hz, 2H), 6.76 (d, J = 8.8 Hz, 1H), 4.25 (q, J = 7.1 Hz, 2H), 1.30 (t, J = 7.1 Hz, 3H). | |
| F9 | >300 (dec.) | | ESIMS m/z 570 ([M + H]$^+$) | $^1$H NMR (400 MHz, DMSO-d$_6$) δ 9.36 (s, 1H), 9.15 (s, 1H), 8.11 – 8.03 (m, 2H), 8.03 – 7.95 (m, 3H), 7.84 (s, 1H), 7.67 – 7.58 (m, 2H), 7.58 – 7.53 (m, 2H), 7.47 – 7.36 (m, 3H), 7.27 (dd, J = 7.8, 1.6 Hz, 1H), 7.17 (td, J = 7.5, 1.2 Hz, 1H). | $^{19}$F NMR (376 MHz, DMSO-d$_6$) δ –56.96, –135.11 (d, JFF = 22.0 Hz), –163.58 (t, jFF = 22.3 Hz). |
| F10 | 234-236 | | ESIMS m/z 471 ([M + H]$^+$) | $^1$H NMR (300 MHz, DMSO-d$_6$) δ 9.36 (s, 1H), 8.97 (s, 1H), 8.66 (s, 1H), 8.23 (d, J = 2.5 Hz, 1H), 8.06 (d, J = 9.1 Hz, 2H), 8.02 (d, J = 8.7 Hz, 2H), 7.84 (dd, J = 8.9, 2.7 Hz, 1H), 7.61 (d, J = 8.9 Hz, 2H), 7.60 (d, J = 8.9 Hz, 2H), 6.80 (d, J = 8.9 Hz, 1H), 3.82 (s, 3H). | |
| F11 | 173-174 | | ESIMS m/z 547.2 ([M + H]$^+$) | $^1$H NMR (400 MHz, DMSO-d$_6$) δ 13.87 (s, 1H), 9.42 (s, 1H), 8.50 (s, 1H), 8.08 – 8.15 (m, 4H), 7.90 – 7.94 (m, 3H), 7.82 (d, J = 5.80 Hz, 1H), 7.48 (d, J = 1.92 Hz, 2H), 7.44 (d, J = 7.56 Hz, 2H), 7.35 (t, J = 3.08 Hz, 1H), 7.34 – 7.34 (m, 2H), 2.15 (s, 3H). | |
| F12 | 150-155 | | ESIMS m/z 525 ([M + H]$^+$) | $^1$H NMR (400 MHz, DMSO-d$_6$) δ 10.40 (s, 1H), 9.60 (s, 1H), 9.40 (s, 1H), 8.81 (s, 1H), 8.72 (d, J = 5.2 Hz, 1H), 8.09 (t, J = 8.8 Hz, 4H), 7.79 (d, J = 5.2 Hz, 1H), 7.75 – 7.70 (m, 2H), 7.66 – 7.60 (m, 2H). | |
| F13 | 116 (dec.) | | ESIMS m/z 505 ([M + H]$^+$) | $^1$H NMR (400 MHz, CDCl$_3$) δ 8.52 (s, 1H), 8.22 (dd, J = 8.3, 1.3 Hz, 1H), 8.12 – 8.04 (m, 2H), 7.85 – 7.73 (m, 2H), 7.45 – 7.33 (m, 5H), 7.24 (d, J = 1.6 Hz, 1H), 7.13 (td, J = 7.6, 1.4 Hz, 1H), 6.86 (s, 1H), 6.78 (t, J = 2.1 Hz, 2H), 6.67 (d, J = 1.9 Hz, 1H), 6.32 (t, J = 2.0 Hz, 2H) | $^{19}$F NMR (376 MHz, CDCl$_3$) δ –58.02. |
| F14 | 164-170 | | ESIMS m/z 501 ([M + H]$^+$) | $^1$H NMR (400 MHz, DMSO-d$_6$) δ 10.04 (s, 1H), 9.73 (s, 1H), 9.39 (s, 1H), 8.14 – 8.00 (m, 5H), 7.77 (dd, J = 8.8, 2.8 Hz, 1H), 7.71 – 7.57 (m, 4H), 6.80 (dd, J = 8.7, 0.7 Hz, 1H), 4.29 (q, J = 7.0 Hz, 2H), 1.32 (t, J = 7.0 Hz, 3H). | |
| F15 | 222-224 | | ESIMS m/z 530 ([M + H]$^+$) | $^1$H NMR (400 MHz, DMSO-d$_6$) δ 9.49 (d, J = 3.1 Hz, 1H), 9.38 (s, 1H), 8.14 (s, 1H), 8.11 – 8.00 (m, 4H), 7.90 (dd, J = 8.2, 1.2 Hz, 1H), 7.63 (ddd, J = 8.9, 4.4, 2.3 Hz, 4H), 7.20 – 7.12 (m, 1H), 7.03 (dd, J = 7.8, 1.7 Hz, 1H), 6.97 (td, J = 7.4, 1.3 Hz, 1H), 1.89 (ddd, J = 13.7, 8.4, 5.2 Hz, 1H), 1.04 – 0.97 (m, 2H), 0.67 – 0.59 (m, 2H). | |
| F16 | 184-187 | | ESIMS m/z 545.2 ([M + H]$^+$) | $^1$H NMR (400 MHz, DMSO-d$_6$) δ 11.87 (s, 1H), 9.38 (s, 1H), 8.48 (s, 1H), 8.06 (m, 4H), 7.73 (s, 3H), 7.61 (s, 2H), 7.48 (s, 2H), 7.37 (d, J = 8.6 Hz, 1H), 7.25 (s, 2H), 7.03 (s, 1H), 2.42 (m, 1H), 2.36 (d, J = 14.3 Hz, 1H), 1.03 (s, 3H). | |
| F17 | >250 (dec.) | | ESIMS m/z 458 ([M + H]$^+$) | $^1$H NMR (400 MHz, DMSO-d$_6$) δ 9.39 (s, 1H), 8.94 (s, 1H), 8.78 (s, 1H), 8.09 – 7.99 (m, 4H), 7.64 – 7.59 (m, 2H), 7.52 – 7.43 (m, 2H), 7.18 – 7.09 (m, 4H). | |

TABLE 4-continued

Analytical Data for Compounds in Table 2

| No. | Mp (° C.) | IR (cm$^{-1}$) | Mass (m/z) | $^1$H NMR | $^{13}$CNMR; $^{19}$F NMR |
|---|---|---|---|---|---|
| F18 | 205-208 | | ESIMS m/z 524 ([M + H]$^+$) | $^1$H NMR (400 MHz, DMSO-d$_6$) δ 9.36 (s, 1H), 9.13 (s, 1H), 8.11 – 7.99 (m, 5H), 7.67 – 7.56 (m, 5H), 7.26 (dd, J = 7.5, 2.0 Hz, 1H), 7.19 – 7.05 (m, 2H), 3.11 (q, J = 7.0 Hz, 1H), 1.64 – 1.49 (m, 1H), 1.44 – 1.32 (m, 2H), 1.16 (d, J = 6.8 Hz, 3H), 0.83 (dd, J = 6.2, 3.4 Hz, 6H). | |
| F19 | 149 (dec.) | | ESIMS m/z 511 ([M + H]$^-$) | $^1$H NMR (400 MHz, DMSO-d$_6$) δ 10.09 (s, 1H), 9.39 (s, 1H), 9.02 (s, 1H), 8.26 (s, 1H), 8.09 – 8.03 (m, 4H), 7.62 (dd, J = 8.7, 1.9 Hz, 4H), 7.37 – 7.29 (m, 4H), 2.25 (s, 3H). | $^{19}$F NMR (376 MHz, DMSO-d$_6$) δ −56.96. |
| F20 | 189-191 | | ESIMS m/z: 561.0 ([M + H]$^+$) | $^1$H NMR (400 MHz, DMSO-d$_6$) δ 13.93 (s, 1H), 9.42 (s, 1H), 8.50 (d, J = 5.16 Hz, 1H), 8.08 – 8.14 (m, 4H), 7.92 – 7.94 (m, 2H), 7.82 – 7.84 (m, 2H), 7.54 (d, J = 4.00 Hz, 2H), 7.43 (d, J = 4.48 Hz, 2H), 7.35 (d, J = 6.64 Hz, 1H), 7.30 – 7.32 (m, 2H), 2.38 (q, J = 21.88 Hz, 2H), 1.08 (t, J = 7.48 Hz, 3H). | |
| F21 | 182 (dec.) | | ESIMS m/z 506 ([M + H]$^+$) | $^1$H NMR (400 MHz, CDCl$_3$) δ 8.56 (s, 1H), 8.20 – 8.13 (m, 2H), 7.98 (dd, J = 8.2, 1.2 Hz, 1H), 7.84 – 7.76 (m, 2H), 7.61 (dd, J = 7.9, 1.6 Hz, 1H), 7.52 (s, 1H), 7.50 – 7.46 (m, 2H), 7.44 – 7.33 (m, 4H), 7.24 – 7.15 (m, 1H), 6.65 (dd, J = 3.4, 0.8 Hz, 1H), 6.62 (s, 1H), 6.47 (dd, J = 3.4, 1.8 Hz, 1H). | $^{19}$F NMR (376 MHz, CDCl$_3$) δ −58.02. |
| F22 | 195-197 | | ESIMS m/z: 579.9 ([M + H]$^+$) | $^1$H NMR (400 MHz, DMSO-d$_6$) δ 13.91 (s, 1H), 9.42 (s, 1H), 8.50 (d, J = 3.36 Hz, 1H), 8.08 – 8.15 (m, 4H), 7.93 (d, J = 8.68 Hz, 2H), 7.80 (d, J = 6.20 Hz, 2H), 7.55 – 7.65 (m, 4H), 7.32 – 7.33 (m, 3H), 2.48 – 2.51 (m, 3H). | |
| F23 | 66-69 | | ESIMS m/z 564 ([M + H]$^+$) | $^1$H NMR (400 MHz, DMSO-d$_6$) δ 10.41 (s, 1H), 9.80 (s, 1H), 9.41 (s, 1H), 8.12 – 8.05 (m, 4H), 7.93 (dd, J = 7.9, 1.6 Hz, 1H), 7.80 (dd, J = 8.2, 1.2 Hz, 1H), 7.75 – 7.68 (m, 2H), 7.63 (d, J = 8.6 Hz, 2H), 7.56 (td, J = 7.7, 1.7 Hz, 1H), 1.24 (dt, J = 8.0, 3.4 Hz, 1H), 1.16 – 1.11 (m, 2H), 0.87 – 0.82 (m, 2H). | |
| F24 | 137-140 | | ESIMS m/z 531.2 ([M + H]$^+$) | $^1$H NMR (400 MHz, CDCl$_3$) δ 12.32 (s, 1H), 8.58 (s, 1H), 8.29 (s, 1H), 8.18 (s, 2H), 7.82 (d, J = 7.9 Hz, 2H), 7.75 (d, J = 4.0 Hz, 2H), 7.37 (d, J = 33.1 Hz, 7H), 7.21 (d, J = 12.3 Hz, 2H), 2.20 (m, 3H). | |
| F25 | 165-169 | | ESIMS m/z 506 ([M + H]$^+$) | $^1$H NMR (400 MHz, DMSO-d$_6$) δ 10.00 (s, 1H), 9.97 (s, 1H), 9.39 (s, 1H), 8.06 (dd, J = 8.7, 6.7 Hz, 4H), 7.99 (t, J = 9.0 Hz, 2H), 7.88 (dd, J = 6.4, 3.0 Hz, 1H), 7.72 (d, J = 8.3 Hz, 2H), 7.67 – 7.50 (m, 6H). | |
| F26 | 271 (dec.) | | ESIMS m/z 524 ([M + H]$^+$) | $^1$H NMR (400 MHz, DMSO-d$_6$) δ 9.53 (d, J = 4.8 Hz, 1H), 9.38 (s, 1H), 8.55 (s, 1H), 8.28 (dd, J = 8.3, 1.6 Hz, 1H), 8.12 – 8.01 (m, 4H), 7.62 (dd, J = 8.9, 1.9 Hz, 4H), 7.42 – 7.32 (m, 2H), 7.11 (ddd, J = 8.2, 7.4, 1.6 Hz, 1H). | |
| F27 | 179-182 | | ESIMS m/z 503 ([M + H]$^+$) | $^1$H NMR (400 MHz, DMSO-d$_6$) δ 10.15 (s, 1H), 9.90 (s, 1H), 9.39 (s, 1H), 8.47 (m, 1H), 8.07 (m, 4H), 7.80 (dd, J = 8.6, 2.6 Hz, 1H), 7.69 – 7.60 (m, 4H), 7.30 (dd, J = 8.6, 0.8 Hz, 1H); 3.34 (s, 3H). | |
| F28 | 175-177 | | ESIMS m/z: 574.2 ([M + H]$^+$) | $^1$H NMR (400 MHz, CDCl$_3$) δ 8.85 (s, 1H), 8.25 (d, J = 8.08 Hz, 1H), 8.05 (d, J = 8.12 Hz, 2H), 7.87 (d, J = 8.64 Hz, 2H), 7.76 (s, 1H), 7.41 – 7.43 (m, 6H), 7.32 – 7.34 (m, 1H), 7.21 – 7.22 (m, 2H), 7.07 (d, J = 7.48 Hz, 1H), 6.91 (d, J = 7.96 Hz, 2H), 2.68 (t, J = 6.96 Hz, 1H), 1.03 – 1.18 (m, 6H). | |
| F29 | 114-118 | | ESIMS m/z 554 ([M + H]$^+$) | $^1$H NMR (400 MHz, CDCl$_3$) δ 8.55 (s, 1H), 8.10 – 8.04 (m, 2H), 7.83 – 7.77 (m, 2H), 7.39 (dt, J = 8.0, 1.0 Hz, 2H), 7.30 – 7.27 (m, 2H), 7.22 (d, J = 8.2 Hz, 2H), 7.20 – 7.14 (m, 1H), 6.98 (d, J = 1.7 Hz, 1H), 5.62 (s, 1H), 3.68 (q, J = 6.9 Hz, 2H), 3.10 (p, J = 6.8 Hz, 1H), 2.67 (t, J = 7.7 Hz, 2H), 2.33 (s, 3H), 2.00 – 1.84 (m, 2H), 1.18 (d, J = 6.9 Hz, 6H). | $^{19}$F NMR (376 MHz, CDCl$_3$) δ −58.03. |
| F30 | 121-126 | | ESIMS m/z 522 ([M + H]$^+$) | $^1$H NMR (400 MHz, DMSO-d$_6$) δ 9.91 (s, 1H), 9.60 (s, 1H), 9.39 (s, 1H), 8.06 (ddd, J = 10.8, 8.8, 2.5 Hz, 4H), 7.86 – 7.75 (m, 2H), 7.65 (dd, J = 17.2, 8.4 Hz, 4H), 7.40 (dtd, J = 19.5, 7.3, 2.0 Hz, 3H), 6.85 (d, J = 3.4 Hz, 1H), 6.66 (dd, J = 3.3, 1.8 Hz, 1H). | |
| F31 | 187-189 | | ESIMS m/z 516.3 ([M + H]$^+$) | $^1$H NMR (400 MHz, CDCl$_3$) δ 6.72 (s, 1H), 6.92 (s, 1H), 7.19 – 7.44 (m, 12H), 7.82 (dd, J = 15.44, Hz, 1H), 8.01 (dd, J = 8.16, Hz, 1H), 8.06 (dd, J = 8.68, Hz, 2H), 8.62 (s, 1H). | |
| F32 | | | ESIMS m/z 517.2 | $^1$H NMR (400 MHz, CDCl$_3$) δ 12.17 (s, 1H), 8.66 (s, 1H), | |

TABLE 4-continued

Analytical Data for Compounds in Table 2

| No. | Mp (° C.) | IR (cm⁻¹) | Mass (m/z) | ¹H NMR | ¹³CNMR; ¹⁹F NMR |
|---|---|---|---|---|---|
| | | | ([M + H]⁺) | 8.25 (s, 1H), 8.15 (s, 1H), 7.83 (s, 1H), 7.75 (s, 1H), 7.57 (s, 2H), 7.44 (d, J = 11.2 Hz, 2H), 7.31 (s, 8H), 7.21 (s, 1H). | |
| F33 | 223-226 | | ESIMS m/z 482 ([M + H]⁺) | ¹H NMR (400 MHz, DMSO-d₆) δ 9.37 (s, 1H), 9.20 (s, 1H), 8.11 – 7.98 (m, 5H), 7.67 (dd, J = 8.0, 1.5 Hz, 1H), 7.65 – 7.58 (m, 4H), 7.30 (dd, J = 7.7, 1.7 Hz, 1H), 7.16 (td, J = 7.7, 1.7 Hz, 1H), 7.09 (td, J = 7.5, 1.5 Hz, 1H), 3.17 (hept, J = 6.8 Hz, 1H), 1.21 (d, J = 6.8 Hz, 6H). | |
| F34 | | | ESIMS m/z 546 ([M + H]⁺) | ¹H NMR (400 MHz, CDCl₃) δ 8.56 (s, 1H), 8.22 – 8.06 (m, 2H), 7.90 – 7.72 (m, 2H), 7.35 (dddd, J = 22.4, 8.0, 6.6, 2.0 Hz, 6H), 7.26 (dd, J = 14.8, 1.5 Hz, 1H), 7.20 (td, J = 7.5, 1.8 Hz, 1H), 6.04 (s, 1H), 4.89 (t, J = 6.0 Hz, 1H), 4.49 (d, J = 5.9 Hz, 2H), 3.23 (hept, J = 7.0 Hz, 1H), 1.19 (d, J = 6.9 Hz, 6H). | ¹⁹F NMR (376 MHz, CDCl₃) δ –85.90, –87.85. |
| F35 | 75-83 | | ESIMS m/z 544.4 ([M + H]⁺) | ¹H NMR (400 MHz, DMSO-d₆) δ 9.33 (d, J = 10.00 Hz, 2H), 8.04 (d, J = 8.92 Hz, 3H), 7.98 (d, J = 8.64 Hz, 2H), 7.60 (d, J = 8.52 Hz, 2H), 7.51 (d, J = 8.72 Hz, 2H), 7.40 (d, J = 4.08 Hz, 2H), 7.29 – 7.35 (m, 3H), 7.08 – 7.15 (m, 3H), 2.32 (q, J = 21.60 Hz, 2H), 0.97 (t, J = 15.04 Hz, 3H). | |
| F36 | 244-247 | | ESIMS m/z 489 ([M + H]⁺) | ¹H NMR (400 MHz, DMSO-d₆) δ 10.0 – 8.50 (br, 2H), 9.36 (s, 1H), 8.29 (d, J = 8.6 Hz, 1H), 8.05 (app t, J = 8.8 Hz, 4H), 7.61 (app t, J = 7.8 Hz, 4H), 7.30 (d, J = 8.6 Hz, 1H), 2.45 (s, 3H). | |
| F37 | 218-220 | | ESIMS m/z 482 ([M + H]⁺) | ¹H NMR (400 MHz, DMSO-d₆) δ 9.36 (s, 1H), 9.26 (s, 1H), 8.11 – 8.00 (m, 4H), 7.96 (s, 1H), 7.82 – 7.71 (m, 1H), 7.66 – 7.57 (m, 4H), 7.21 – 7.12 (m, 2H), 7.05 – 6.99 (m, 1H), 2.63 – 2.54 (m, 2H), 1.66 – 1.53 (m, 2H), 0.96 (t, J = 7.3 Hz, 3H). | |
| F38 | 213-216 | | ESIMS m/z 496 ([M + H]⁺) | ¹H NMR (400 MHz, DMSO-d₆) δ 9.36 (s, 1H), 9.27 (s, 1H), 8.11 – 8.04 (m, 2H), 8.04 – 7.99 (m, 2H), 7.67 – 7.58 (m, 5H), 7.38 (dd, J = 7.9, 1.8 Hz, 1H), 7.31 (dd, J = 7.6, 1.7 Hz, 1H), 7.21 (td, J = 7.5, 1.7 Hz, 1H), 7.16 (td, J = 7.5, 1.8 Hz, 1H), 1.39 (s, 9H). | |
| F39 | 249-251 | | ESIMS m/z 484 ([M + H]⁺) | ¹H NMR (400 MHz, DMSO-d₆) δ 9.36 (s, 1H), 8.83 (s, 1H), 8.54 (s, 1H), 8.11 – 8.04 (m, 2H), 8.04 – 7.99 (m, 2H), 7.65 – 7.56 (m, 4H), 7.40 – 7.32 (m, 2H), 6.90 – 6.83 (m, 2H), 3.98 (q, J = 7.0 Hz, 2H), 1.31 (t, J = 7.0 Hz, 3H). | |
| F40 | 211-213 | | | ¹H NMR (400 MHz, CDCl₃) δ 8.55 (d, J = 4.4 Hz, 1H), 8.17 (m, 2H), 7.77 (m, 2H), 7.51 (m, 2H), 7.38 (ddd, J = 9.2, 2.3, 1.2 Hz, 2H), 7.26 (m, 1H), 7.11 (m, 2H), 6.79 (s, 1H), 6.65 (m, 2H), 1.85 (ddd, J = 13.6, 8.4, 5.2 Hz, 1H), 1.26 (t, J = 7.1 Hz, 1H), 0.94 (dddd, J = 26.7, 8.4, 6.3, 4.4 Hz, 2H), 0.65 (m, 2H). | ¹⁹F NMR (376 MHz, CDCl₃) δ –58.03. |
| F41 | 246-248 | | ESIMS m/z 527 ([M + H]⁺) | ¹H NMR (300 MHz, DMSO-d₆) δ 9.54 (s, 1H), 9.37 (s, 1H), 8.54 (d, J = 8.6 Hz, 1H), 8.42 (s, 1H), 8.12 – 8.00 (m, 4H), 7.91 (d, J = 8.6 Hz, 1H), 7.64 (d, J = 6.8 Hz, 2H), 7.61 (d, J = 6.4 Hz, 2H), 4.31 (q, J = 7.0 Hz, 2H), 2.54 (s, 3H), 1.32 (t, J = 7.1 Hz, 3H). | |
| F24 | 87-96 | | ESIMS m/z: 578.2 ([M + H]⁺) | 1H NMR (400 MHz, CDCl₃) δ 8.82 (d, J = 17.8 Hz, 1H), 8.12 (d, J = 7.7 Hz, 2H), 7.85 (m, 5H), 7.49 (m, 1H), 7.40 (m, 5H), 7.30 (d, J = 7.5 Hz, 1H), 7.16 (dd, J = 30.5, 22.5 Hz, 3H), 7.10 (m, 1H), 2.14 (s, 3H). | |
| F43 | 171-173 | | ESIMS m/z 500 ([M + H]⁺) | ¹H NMR (400 MHz, DMSO-d₆) δ 9.72 (s, 1H), 9.38 (s, 1H), 9.36 (s, 1H), 8.06 (m, 4H), 7.71 – 7.58 (m, 4H), 7.13 (d, J = 8.6 Hz, 1H), 6.88 – 6.81 (m, 1H), 6.81 – 6.73 (m, 1H), 3.75 (s, 3H), 2.23 (s, 3H). | |
| F44 | 177-180 | | ESIMS m/z 524 ([M + H]⁺) | ¹H NMR (400 MHz, DMSO-d₆) δ 10.76 (s, 1H), 9.41 (s, 1H), 8.35 (s, 1H), 8.22 (d, J = 7.9 Hz, 1H), 8.09 (m, 1H), 8.09 (t, J = 9.2 Hz, 4H), 7.91 (t, J = 7.8 Hz, 1H), 7.82 – 7.57 (m, 7H). | |
| F45 | | | ESIMS m/z 512 ([M + H]⁺) | ¹H NMR (400 MHz, DMSO-d₆) δ 9.40 (s, 1H), 9.30 (s, 1H), 8.07 (dd, J = 9.4, 7.3 Hz, 4H), 7.81 (s, 1H), 7.68 – 7.58 (m, 2H), 7.44 (d, J = 8.0 Hz, 2H), 7.36 (d, J = 7.7 Hz, 1H), 7.29 (t, J = 7.5 Hz, 1H), 7.21 (dd, J = 13.2, 6.1 Hz, 2H), 4.78 (s, 2H), 3.11 (s, 1H), 1.15 (d, J = 6.9 Hz, 6H). | ¹⁹F NMR (376 MHz, DMSO-d₆) δ –56.96. |
| F46 | 232-236 | | ESIMS m/z 468 ([M + H]⁺) | ¹H NMR (400 MHz, DMSO-d₆) δ 9.36 (s, 1H), 9.26 (d, J = 3.7 Hz, 1H), 8.10 – 7.96 (m, 5H), 7.84 – 7.77 (m, 1H), 7.62 (dd, J = 8.6, 1.6 Hz, 4H), 7.24 – 7.13 (m, 2H), | |

TABLE 4-continued

Analytical Data for Compounds in Table 2

| No. | Mp (° C.) | IR (cm$^{-1}$) | Mass (m/z) | $^1$H NMR | $^{13}$CNMR; $^{19}$F NMR |
|---|---|---|---|---|---|
| | | | | 7.03 (td, J = 7.5, 1.3 Hz, 1H), 2.63 (q, J = 7.5 Hz, 2H), 1.19 (t, J = 7.5 Hz, 3H). | |
| F47 | 163-167 | | ESIMS m/z: 533.2 ([M + H]$^+$) | $^1$H NMR (400 MHz, DMSO-d$_6$) δ 9.82 (s, 1H), 9.55 (s, 1H), 9.37 (s, 1H), 8.70 (s, 1H), 8.61 (d, J = 4.68 Hz, 1H), 8.05 (d, J = 8.92 Hz, 2H), 7.98 (d, J = 8.52 Hz, 3H), 7.55 – 7.59 (m, 4H), 7.42 – 7.48 (m, 6H). | |
| F48 | 130 (dec.) | | ESIMS m/z 565 ([M + H]$^+$) | $^1$H NMR (400 MHz, DMSO-d$_6$) δ 10.11 (s, 1H), 9.49 (s, 1H), 9.39 (s, 1H), 8.91 (s, 1H), 8.13 – 7.98 (m, 4H), 7.79 (d, J = 8.3 Hz, 1H), 7.68 – 7.54 (m, 5H), 7.52 – 7.32 (m, 2H), 4.24 (p, J = 6.8 Hz, 1H), 1.36 (d, J = 6.7 Hz, 6H). | $^{19}$F NMR (376 MHz, DMSO-d$_6$) δ –56.96. |
| F49 | 294 (dec.) | | ESIMS m/z 520 ([M + H]$^+$) | Mixture of at least 2 diastereoisomers – $^1$H NMR (400 MHz, DMSO-d$_6$) δ 9.59 (s, 1H), 9.37 (d, J = 1.1 Hz, 2H), 8.16 – 8.00 (m, 7H), 7.75 (d, J = 8.0 Hz, 1H), 7.63 (dt, J = 9.2, 4.7 Hz, 5H), 7.26 – 7.06 (m, 2H), 7.01 – 6.91 (m, 2H), 1.92 (d, J = 6.6 Hz, 1H), 1.71 (dt, J = 9.1, 5.3 Hz, 1H), 1.17 (dt, J = 6.9, 3.5 Hz, 1H), 1.12 – 0.94 (m, 2H), 0.83 (dt, J = 9.5, 5.0 Hz, 1H), 0.63 (dt, J = 9.2, 4.9 Hz, 1H), 0.51 – 0.33 (m, 2H), 0.27 – 0.11 (m, 2H). | |
| F50 | 174-177 | | ESIMS m/z: 533.2 ([M + H]$^+$) | $^1$H NMR (400 MHz, CDCl$_3$) δ 14.06 (s, 1H), 8.62 (s, 1H), 8.45 (s, 1H), 8.31 (s, 1H), 8.25 (t, J = 4.8 Hz, 2H), 7.90 (d, J = 7.7 Hz, 2H), 7.83 (d, J = 8.8 Hz, 2H), 7.68 (d, J = 8.7 Hz, 1H), 7.59 (m, 2H), 7.53 (d, J = 7.4 Hz, 1H), 7.47 (d, J = 7.1 Hz, 2H), 7.41 (d, J = 8.8 Hz, 2H), 7.15 (d, J = 7.2 Hz, 1H). | |
| F51 | 276-280 | | ESIMS m/z 530 ([M + H]$^+$) | $^1$H NMR (400 MHz, CDCl$_3$) δ 8.55 (s, 1H), 8.14 – 8.03 (m, 2H), 7.83 – 7.76 (m, 1H), 7.58 – 7.45 (m, 5H), 7.30 – 7.21 (m, 4H), 7.17 (t, J = 7.3 Hz, 1H), 7.13 – 7.04 (m, 2H), 6.30 (s, 1H), 6.06 (s, 1H), 4.02 (s, 2H). | $^{19}$F NMR (376 MHz, CDCl$_3$) δ –58.03. |
| F52 | 149 (dec.) | | ESIMS m/z 527 ([M + H]$^+$) | $^1$H NMR (400 MHz, CDCl$_3$) δ 9.71 (s, 1H), 8.54 (s, 1H), 8.18 – 8.08 (m, 2H), 7.82 – 7.74 (m, 2H), 7.51 (tt, J = 7.9, 6.3 Hz, 2H), 7.39 (qdd, J = 7.6, 6.8, 1.6 Hz, 6H), 7.13 (s, 1H), 2.79 – 2.55 (m, 2H), 1.30 (t, J = 7.6 Hz, 3H). | $^{13}$C NMR (101 MHz, CDCl$_3$) δ 185.15, 162.79, 153.24, 148.42, 142.45, 141.55, 137.73, 137.56, 135.49, 130.50, 130.07, 129.62, 127.90, 127.50, 127.39, 127.05, 122.40, 121.24, 120.57, 23.52, 13.52; $^{19}$F NMR (376 MHz, CDCl$_3$) δ –58.03. |
| F53 | 152-155 | | ESIMS m/z 483 ([M + H]$^+$) | $^1$H NMR (400 MHz, CDCl$_3$) δ 8.65 (s, 1H), 8.25 – 8.17 (m, 2H), 7.90 (d, J = 8.4 Hz, 2H), 7.80 (d, J = 8.6 Hz, 2H), 7.60 – 7.53 (m, 3H), 7.48 – 7.39 (m, 2H), 3.24 (p, J = 6.9 Hz, 1H), 1.27 (d, J = 6.9 Hz, 6H). | |
| F54 | 228-230 | | ESIMS m/z 532 ([M + H]$^+$) | $^1$H NMR (400 MHz, DMSO-d$_6$) δ 9.38 (s, 1H), 9.20 (s, 1H), 8.11 – 8.06 (m, 2H), 8.06 – 7.99 (m, 3H), 7.67 (dd, J = 8.0, 1.5 Hz, 1H), 7.65 – 7.58 (m, 4H), 7.30 (dd, J = 7.7, 1.7 Hz, 1H), 7.16 (td, J = 7.6, 1.7 Hz, 1H), 7.09 (td, J = 7.4, 1.5 Hz, 1H), 3.17 (hept, J = 6.8 Hz, 1H), 1.21 (d, J = 6.8 Hz, 6H). | |
| F55 | 205-209 | | ESIMS m/z 549 ([M + H]$^+$) | $^1$H NMR (400 MHz, DMSO-d$_6$) δ 9.47 (s, 1H), 9.36 (s, 1H), 8.96 (s, 1H), 8.20 (s, 1H), 8.12 (dd, J = 8.4, 1.1 Hz, 1H), 8.09 – 7.97 (m, 4H), 7.61 (dq, J = 8.1, 1.0 Hz, 2H), 7.58 – 7.49 (m, 3H), 7.37 (dd, J = 7.7, 1.6 Hz, 1H), 7.22 (td, J = 7.5, 1.2 Hz, 1H), 4.11 (p, J = 6.7 Hz, 1H), 1.36 (d, J = 6.7 Hz, 6H). | $^{19}$F NMR (376 MHz, DMSO-d$_6$) δ –56.96. |
| F56 | 147-148 | | ESIMS m/z: 534.1 ([M + H]$^+$) | $^1$H NMR (400 MHz, DMSO-d$_6$) 13.00 (s, 1H), 9.41 (s, 1H), 9.13 (s, 1H), 8.69 – 8.70 (m, 2H), 8.52 (d, J = 3.44 Hz, 1H), 8.08 – 8.12 (m, 4H), 7.84 – 8.01 (m, 4H), 7.58 – 7.65 (m, 3H), 7.37 – 7.39 (m, 1H). | |
| F57 | 207-211 | | ESIMS m/z 546 ([M + H]$^+$) | $^1$H NMR (400 MHz, DMSO-d$_6$) δ 9.38 (s, 1H), 9.21 – 9.14 (m, 1H), 8.11 – 8.05 (m, 2H), 7.96 (s, 1H), 8.05 – 7.99 (m, 2H), 7.66 – 7.57 (m, 4H), 7.51 (dd, J = 1.9, 0.8 Hz, 1H), 7.16 (d, J = 7.9 Hz, 1H), 6.94 – 6.87 (m, | $^{19}$F NMR (376 MHz, DMSO-d$_6$) δ –85.18, –86.90. |

TABLE 4-continued

Analytical Data for Compounds in Table 2

| No. | Mp (° C.) | IR (cm$^{-1}$) | Mass (m/z) | $^1$H NMR | $^{13}$CNMR; $^{19}$F NMR |
|---|---|---|---|---|---|
| F58 | 160-162 | | ESIMS m/z 546 ([M + H]$^+$) | $^1$H NMR (400 MHz, DMSO-d$_6$) δ 9.86 (s, 1H), 9.45 (s, 1H), 9.38 (s, 1H), 8.11 – 7.96 (m, 4H), 7.68 – 7.54 (m, 4H), 7.34 – 7.16 (m, 8H), 7.13 (dd, J = 7.4, 1.9 Hz, 1H), 4.00 (s, 2H). 1H), 3.11 (p, J = 6.8 Hz, 1H), 2.26 (s, 3H), 1.18 (d, J = 6.8 Hz, 6H). | |
| F59 | 118-122 | | ESIMS m/z 563.2 ([M + H]$^+$) | $^1$H NMR (400 MHz, CDCl$_3$) δ 12.31 (s, 1H), 8.58 (s, 1H), 8.17 (s, 3H), 7.83 (s, 3H), 7.75 (d, J = 11.1 Hz, 3H), 7.56 (s, 1H), 7.38 (d, J = 18.7 Hz, 4H), 7.19 (d, J = 27.4 Hz, 2H), 1.28 (s, 3H). | |
| F60 | 117-127 | | ESIMS m/z 562.2 ([M + H]$^+$) | $^1$H NMR (400 MHz, CDCl$_3$) δ 8.60 (s, 1H), 8.04 (d, J = 8.64 Hz, 2H), 8.00 (d, J = 8.12 Hz, 1H), 7.82 (dd, J = 9.00, Hz, 2H), 7.46 – 0.00 (m, 1H), 7.41 (d, J = 8.40 Hz, 2H), 7.33 – 7.35 m, 1H), 7.28 – 7.30 (m, 2H), 7.23 – 7.24 (m, 2H), 7.17 – 7.19 (m, 3H), 6.86 (s, 1H), 6.53 (s, 1H), 2.29 (s, 3H). | |
| F61 | 199-201 | | ESIMS m/z 480 ([M + H]$^+$) | $^1$H NMR (400 MHz, DMSO-d$_6$) δ 9.47 (d, J = 4.0 Hz, 1H), 9.36 (s, 1H), 8.10 – 7.99 (m, 4H), 7.95 (dd, J = 8.2, 1.2 Hz, 1H), 7.86 (s, 1H), 7.61 (ddt, J = 7.5, 4.5, 1.8 Hz, 4H), 7.29 – 7.20 (m, 1H), 7.15 (dd, J = 7.6, 1.7 Hz, 1H), 7.03 (td, J = 7.4, 1.2 Hz, 1H), 5.37 (q, J = 1.7 Hz, 1H), 5.02 (dd, J = 2.1, 1.1 Hz, 1H), 2.06 (t, J = 1.2 Hz, 3H). | |
| F62 | 72-81 | | ESIMS m/z 517 ([M + H]$^+$) | $^1$H NMR (400 MHz, DMSO-d$_6$) δ 9.35 (s, 1H), 9.11 (s, 1H), 8.76 (s, 1H), 8.72 (d, J = 4.76 Hz, 1H), 8.00 – 8.10 (m, 6H), 7.89 (d, J = 7.88 Hz, 1H), 7.72 (dd, J = 5.16, 7.68 Hz, 1H), 7.61 (d, J = 8.68 Hz, 2H), 7.52 (d, J = 8.72 Hz, 2H), 7.46 (m, 1H), 7.33 (dd, J = 1.52, 7.64 Hz, 1H), 7.26 (m, 1H). | |
| F63 | 83-86 | | ESIMS m/z 558.4 ([M + H]$^+$) | $^1$H NMR (400 MHz, DMSO-d$_6$) δ 9.33 (d, J = 5.92 Hz, 2H), 7.97 – 8.06 (m, 5H), 7.60 (d, J = 8.48 Hz, 2H), 7.06 – 7.52 (m, 10H), 2.62 – 2.68 (m, 1H), 1.12 (d, J = 6.84 Hz, 3H), 0.98 (d, J = 6.84 Hz, 3H). | |
| F64 | 224-225 | | ESIMS m/z 508 ([M + H]$^+$) | $^1$H NMR (400 MHz, DMSO-d$_6$) δ 9.62 (d, J = 7.0 Hz, 1H), 9.37 (s, 1H), 8.17 (s, 1H), 8.10 – 8.02 (m, 4H), 7.96 (d, J = 8.1 Hz, 1H), 7.73 – 7.57 (m, 6H), 7.31 (t, J = 7.7 Hz, 1H). | |
| F65 | | | ESIMS m/z 496 ([M + H]$^+$) | $^1$H NMR (400 MHz, DMSO-d$_6$) δ 9.40 (s, 1H), 8.16 – 8.05 (m, 4H), 7.80 (s, 1H), 7.71 – 7.59 (m, 3H), 7.53 – 7.41 (m, 2H), 7.24 (dd, J = 7.7, 1.6 Hz, 1H), 7.11 (td, J = 7.8, 1.7 Hz, 1H), 7.07 – 6.95 (m, 2H), 4.38 (d, J = 5.8 Hz, 2H), 3.14 (hept, J = 7.0 Hz, 1H), 1.18 (d, J = 6.8 Hz, 6H). | $^{19}$F NMR (376 MHz, DMSO-d$_6$) δ – 56.96. |
| F66 | 152-155 | | ESIMS m/z 518 ([M + H]$^+$) | $^1$H NMR (400 MHz, DMSO-d$_6$) δ 10.96 (s, 1H), 9.36 (s, 1H), 8.93 (s, 2H), 8.80 (s, 1H), 8.52 (s, 1H), 8.34 (s, 1H), 8.03 (d, J = 9.1 Hz, 4H), 7.89 (d, J = 21.2 Hz, 2H), 7.62 (s, 4H), 7.36 (s, 1H). | |
| F67 | 98-101 | | ESIMS m/z 512 ([M + H]$^+$) | $^1$H NMR (400 MHz, CDCl$_3$) δ 10.99 (s, 1H), 8.05 (d, J = 8.6 Hz, 2H), 7.72 – 7.45 (m, 7H), 7.33 – 7.25 (m, 3H), 7.10 (d, J = 7.6 Hz, 1H), 2.37 (s, 3H), 2.15 (s, 3H). | |
| F68 | 181-184 | | ESIMS m/z 566 ([M + H]$^+$) | $^1$H NMR (400 MHz, DMSO-d$_6$) δ 9.37 (s, 1H), 9.26 (d, J = 4.1 Hz, 1H), 8.11 – 8.03 (m, 8.03 – 7.98 (m, 2H), 7.94 (dd, J = 8.3, 1.2 Hz, 1H), 7.74 (s, 1H), 7.65 – 7.59 (m, 4H), 7.58 – 7.49 (m, 4H), 7.47 – 7.40 (m, 3H), 7.39 – 7.31 (m, 1H), 7.23 (dd, J = 7.7, 1.7 Hz, 1H), 7.16 (td, J = 7.4, 1.2 Hz, 1H). | |
| F69 | >300 (dec.) | | ESIMS m/z 525 ([M + H]$^+$) | $^1$H NMR (400 MHz, DMSO-d$_6$) δ 9.77 (s, 1H), 9.37 (s, 1H), 8.21 (s, 1H), 8.11 – 8.01 (m, 5H), 7.71 – 7.58 (m, 4H), 7.20 (dd, J = 7.9, 1.5 Hz, 1H), 7.09 (td, J = 7.8, 1.5 Hz, 1H), 7.00 (td, J = 7.6, 1.6 Hz, 1H), 3.86 (dd, J = 5.8, 3.3 Hz, 4H), 2.86 – 2.78 (m, 4H). | |
| F70 | | | ESIMS m/z 530 ([M + H]$^+$) | $^1$H NMR (400 MHz, DMSO-d$_6$) δ 9.40 (s, 1H), 8.12 – 8.04 (m, 4H), 7.90 (dd, J = 8.2, 1.2 Hz, 1H), 7.63 (dq, J = 9.0, 0.9 Hz, 2H), 7.55 – 7.46 (m, 3H), 7.45 – 7.36 (m, 5H), 7.33 – 7.26 (m, 1H), 7.18 (dd, J = 7.6, 1.7 Hz, 1H), 7.14 – 7.06 (m, 2H), 4.32 (d, J = 5.8 Hz, 2H). | $^{19}$F NMR (376 MHz, DMSO-d$_6$) δ – 56.96. |
| F71 | 167-172 | | ESIMS m/z 486 ([M + H]$^+$) | $^1$H NMR (400 MHz, DMSO-d$_6$) δ 9.83 (s, 1H), 9.75 (s, 1H), 9.38 (s, 1H), 8.1 – 7.95 (m, 4H), 7.69 –7.57 (m, 4H), 7.35 (d, J = 8.9 Hz, 2H), 6.92 (d, J = 8.9 Hz, 2H), 3.75 (s, 3H). | |
| F72 | 168-170 | | ESIMS m/z 474 ([M + H]$^+$) | $^1$H NMR (400 MHz, DMSO-d$_6$) δ 10.01 (s, 1H), 9.90 (s, 1H), | |

TABLE 4-continued

Analytical Data for Compounds in Table 2

| No. | Mp (° C.) | IR (cm⁻¹) | Mass (m/z) | ¹H NMR | ¹³CNMR; ¹⁹F NMR |
|---|---|---|---|---|---|
| F73 | | | ESIMS m/z 508 ([M + H]⁺) | ¹H NMR (400 MHz, CDCl₃) δ 9.39 (s, 1H), 8.11 – 8.03 (m, 4H), 7.68 – 7.60 (m, 4H), 7.53 – 7.45 (m, 2H), 7.19 (t, J = 8.8 Hz, 2H). 8.53 (s, 1H), 8.14 – 8.07 (m, 2H), 7.89 (dd, J = 8.0, 1.2 Hz, 1H), 7.84 – 7.76 (m, 2H), 7.48 – 7.28 (m, 11H), 7.24 (d, J = 1.7 Hz, 1H), 7.16 (td, J = 7.5, 1.3 Hz, 1H), 6.23 (s, 1H), 4.41 (d, J = 5.9 Hz, 2H). | ¹⁹F NMR (376 MHz, CDCl₃) δ – 85.89, –87.85. |
| F74 | 203-207 | | ESIMS m/z 521 ([M + H]⁺) | ¹H NMR (400 MHz, DMSO-d₆) δ 9.96 (s, 1H), 9.38 (d, J = 2.0 Hz, 2H), 8.10 – 8.00 (m, 4H), 7.63 (d, J = 8.6 Hz, 2H), 7.58 – 7.52 (m, 2H), 7.52 – 7.46 (m, 1H), 7.40 (q, J = 3.0 Hz, 3H), 7.05 (t, J = 2.1 Hz, 2H), 6.26 (t, J = 2.2 Hz, 2H). | |
| F75 | 153-158 | | ESIMS m/z 549 ([M + H]⁺) | ¹H NMR (400 MHz, DMSO-d₆) δ 10.17 (s, 1H), 9.40 (s, 1H), 8.78 (s, 1H), 8.12 – 8.00 (m, 4H), 7.90 (d, J = 8.0 Hz, 1H), 7.63 (d, J = 8.6 Hz, 2H), 7.48 (t, J = 7.1 Hz, 3H), 7.36 (t, J = 7.6 Hz, 1H), 7.26 – 7.16 (m, 1H), 5.86 (s, 2H), 1.94 (s, 6H). | |
| F76 | 72-75 | | APCI-MS m/z 540 ([M + H]⁺) | ¹H NMR (300 MHz, DMSO-d₆) δ 9.38 (s, 1H), 9.05 (s, 1H), 8.14 – 7.81 (m, 4H), 7.75 – 7.47 (m, 2H), 7.47 – 7.00 (m, 7H), 3.63 – 3.41 (m, 2H), 3.16 – 2.97 (m, 1H), 2.65 (t, J = 7.7 Hz, 2H), 2.00 – 1.69 (m, 2H), 1.15 (d, J = 6.8 Hz, 6H). | |
| F77 | 191-195 | | APCI-MS m/z 496 ([M + H]⁺) | ¹H NMR (300 MHz, DMSO-d₆) δ 9.38 (s, 1H), 8.05 (dd, J = 10.5, 8.5 Hz, 4H), 7.89 – 7.76 (m, 1H), 7.62 (d, J = 9.3 Hz, 3H), 7.38 (d, J = 7.9 Hz, 2H), 7.16 – 7.02 (m, 2H), 6.92 – 6.80 (m, 1H), 6.61 (t, J = 5.5 Hz, 1H), 3.13 (q, J = 6.5 Hz, 2H), 2.70 (t, J = 7.7 Hz, 2H), 2.19 (s, 3H), 1.89 – 1.67 (m, 2H). | |
| F78 | 186-189 | | APCI-MS m/z 524 ([M + H]⁺) | ¹H NMR (300 MHz, DMSO-d₆) δ 9.38 (s, 1H), 8.15 – 7.96 (m, 4H), 7.62 (td, J = 4.8, 4.4, 2.4 Hz, 4H), 7.38 (d, J = 8.0 Hz, 2H), 7.22 (dd, J = 7.7, 1.7 Hz, 1H), 7.08 (td, J = 7.6, 1.7 Hz, 1H), 7.03 – 6.94 (m, 1H), 6.52 (t, J = 5.5 Hz, 1H), 3.11 (p, J = 6.9 Hz, 3H), 2.69 (t, J = 7.6 Hz, 2H), 1.79 (p, J = 7.1 Hz, 2H), 1.17 (d, J = 6.8 Hz, 6H). | |
| F79 | 245-249 | | ESIMS m/z 516 ([M + H]⁺) | ¹H NMR (300 MHz, DMSO-d₆) δ 9.38 (s, 1H), 8.57 (s, 1H), 8.13 – 7.96 (m, 4H), 7.62 (d, J = 8.6 Hz, 2H), 7.48 – 7.32 (m, 4H), 7.25 (d, J = 8.9 Hz, 2H), 6.26 (t, J = 5.7 Hz, 1H), 3.12 (q, J = 6.6 Hz, 2H), 2.68 (t, J = 7.7 Hz, 2H), 1.88 – 1.69 (m, 2H). | |
| F80 | 175-178 | | ESIMS m/z 512 ([M + H]⁺) | ¹H NMR (300 MHz, DMSO-d₆) δ 9.38 (s, 1H), 8.43 (s, 1H), 8.12 – 7.97 (m, 4H), 7.62 (d, J = 8.9 Hz, 2H), 7.37 (d, J = 8.0 Hz, 2H), 7.18 – 7.12 (m, 1H), 7.09 (d, J = 8.1 Hz, 1H), 6.91 – 6.81 (m, 1H), 6.46 (dd, J = 8.3, 2.5 Hz, 1H), 6.20 (t, J = 5.6 Hz, 1H), 3.70 (s, 3H), 3.12 (q, J = 6.6 Hz, 2H), 2.68 (t, J = 7.7 Hz, 2H), 1.78 (p, J = 7.4 Hz, 2H). | |
| F81 | 175-179 | | APCI-MS m/z 512 ([M + H]⁺) | ¹H NMR (300 MHz, DMSO-d₆) δ 9.38 (s, 1H), 8.15 – 7.97 (m, 5H), 7.88 (s, 1H), 7.65 – 7.58 (m, 2H), 7.38 (d, J = 8.1 Hz, 2H), 7.00 – 6.90 (m, 2H), 6.84 (ddd, J = 6.8, 4.1, 2.1 Hz, 2H), 3.84 (s, 3H), 3.11 (q, J = 6.5 Hz, 2H), 2.69 (t, J = 7.7 Hz, 2H), 1.77 (p, J = 7.3 Hz, 2H). | |
| F82 | 178-181 | | APCI-MS m/z 512 ([M + H]⁺) | ¹H NMR (300 MHz, DMSO-d₆) δ 9.38 (s, 1H), 8.20 (s, 1H), 8.15 – 7.97 (m, 4H), 7.62 (d, J = 8.6 Hz, 2H), 7.37 (d, J = 8.0 Hz, 2H), 7.28 (d, J = 9.0 Hz, 2H), 6.80 (d, J = 9.0 Hz, 2H), 6.10 (t, J = 5.6 Hz, 1H), 3.69 (s, 3H), 3.11 (q, J = 6.5 Hz, 2H), 2.67 (t, J = 7.7 Hz, 2H), 1.78 (q, J = 7.3 Hz, 2H). | |
| F83 | 215-219 | | APCI-MS m/z 496 ([M + H]⁺) | ¹H NMR (300 MHz, DMSO-d₆) δ 9.38 (s, 1H), 8.28 (s, 1H), 8.16 – 7.93 (m, 4H), 7.62 (d, J = 8.6 Hz, 2H), 7.37 (d, J = 7.9 Hz, 2H), 7.27 (d, J = 8.1 Hz, 2H), 7.01 (d, J = 8.1 Hz, 2H), 6.15 (t, J = 5.6 Hz, 1H), 3.11 (q, J = 6.8, 6.4 Hz, 2H), 2.68 (t, J = 7.8 Hz, 2H), 2.21 (s, 3H), 1.85 – 1.70 (m, 2H). | |
| F84 | 189-192 | | ESIMS m/z 516 ([M + H]⁺) | ¹H NMR (300 MHz, DMSO-d₆) δ 9.38 (s, 1H), 8.15 (dd, J = 8.3, 1.6 Hz, 1H), 8.10 – 8.03 (m, 3H), 8.01 (d, J = 9.9 Hz, 2H), 7.65 – 7.57 (m, 2H), 7.41 – 7.35 (m, 3H), 7.23 (td, J = 8.3, 7.9, 1.5 Hz, 1H), 7.09 (t, J = 5.5 Hz, 1H), 6.94 (td, J = 7.5, 1.6 Hz, 1H), 3.14 (q, J = 6.5 Hz, 2H), 2.70 (t, J = 7.6 Hz, 2H), 1.88 – 1.68 (m, 2H). | |
| F85 | 175-178 | | ESIMS m/z 516 ([M + H]⁺) | ¹H NMR (300 MHz, DMSO-d₆) δ 9.38 (s, 1H), 8.66 (s, 1H), 8.14 – 7.95 (m, 4H), 7.71 – 7.56 (m, 3H), 7.37 (d, J = 8.1 Hz, 2H), 7.29 – 7.12 (m, 2H), 6.92 (dt, J = 7.5, 1.8 Hz, 1H), 6.32 (t, J = 5.7 Hz, 1H), 3.13 (q, J = 6.7 Hz, 2H), 2.68 (dd, J = 8.5, 6.8 Hz, 2H), 1.79 | |

TABLE 4-continued

Analytical Data for Compounds in Table 2

| No. | Mp (° C.) | IR (cm⁻¹) | Mass (m/z) | ¹H NMR | ¹³CNMR; ¹⁹F NMR |
|---|---|---|---|---|---|
| F86 | 208-212 | | APCI-MS m/z 510 ([M + H]⁺) | (p, J = 7.3 Hz, 2H). ¹H NMR (400 MHz, DMSO-d₆) δ 9.38 (s, 1H), 8.11 – 8.00 (m, 4H), 7.81 – 7.72 (m, 1H), 7.67 – 7.56 (m, 3H), 7.45 – 7.32 (m, 2H), 7.16 – 7.02 (m, 2H), 6.92 (td, J = 7.5, 1.3 Hz, 1H), 6.61 (t, J = 5.5 Hz, 1H), 3.13 (q, J = 6.5 Hz, 2H), 2.70 (t, J = 7.7 Hz, 2H), 2.56 (q, J = 7.6 Hz, 2H), 1.79 (p, J = 7.2 Hz, 2H), 1.14 (t, J = 7.5 Hz, 3H). | |
| F87 | 205-209 | | APCI-MS m/z 496 ([M + H]⁺) | ¹H NMR (400 MHz, DMSO-d₆) δ 9.38 (s, 1H), 8.33 (s, 1H), 8.13 – 7.97 (m, 4H), 7.66 – 7.58 (m, 2H), 7.41 – 7.31 (m, 2H), 7.23 (t, J = 1.9 Hz, 1H), 7.16 (dd, J = 8.3, 1.8 Hz, 1H), 7.08 (t, J = 7.7 Hz, 1H), 6.70 (d, J = 7.4 Hz, 1H), 6.20 (t, J = 5.7 Hz, 1H), 3.12 (q, J = 6.6 Hz, 2H), 2.68 (dd, J = 8.6, 6.8 Hz, 2H), 2.24 (s, 3H), 1.78 (p, J = 7.3 Hz, 2H). | |
| F88 | 117-120 | | API-MS m/z 554 ([M + H]⁺) | ¹H NMR (300 MHz, DMSO-d₆) δ 9.38 (d, J = 0.9 Hz, 1H), 9.01 (s, 1H), 8.12 – 7.97 (m, 4H), 7.70 – 7.54 (m, 2H), 7.40 – 7.30 (m, 4H), 7.26 (t, J = 7.4 Hz, 1H), 7.22 – 7.14 (m, 1H), 7.10 (d, J = 7.8 Hz, 1H), 3.48 (s, 2H), 3.05 (p, J = 6.9 Hz, 1H), 2.66 (t, J = 7.1 Hz, 2H), 1.57 (s, 5H), 1.13 (d, J = 6.8 Hz, 6H). | |
| F89 | 200-203 | | API-MS m/z 510 ([M + H]⁺) | ¹H NMR (300 MHz, DMSO-d₆) δ 9.38 (s, 1H), 8.14 – 7.93 (m, 4H), 7.89 – 7.74 (m, 1H), 7.62 (d, J = 8.6 Hz, 2H), 7.55 (s, 1H), 7.37 (d, J = 8.0 Hz, 2H), 7.15 – 7.00 (m, 2H), 6.90 – 6.79 (m, 1H), 6.53 (t, J = 5.5 Hz, 1H), 3.13 (q, J = 6.5 Hz, 2H), 2.68 (t, J = 7.6 Hz, 2H), 2.16 (s, 3H), 1.80 – 1.57 (m, 2H), 1.56 – 1.40 (m, 2H). | |
| F90 | 169-172 | | API-MS m/z 538 ([M + H]⁺) | ¹H NMR (300 MHz, DMSO-d₆) δ 9.38 (s, 1H), 8.14 – 7.95 (m, 4H), 7.67 – 7.53 (m, 4H), 7.36 (d, J = 8.1 Hz, 2H), 7.21 (dd, J = 7.7, 1.7 Hz, 1H), 7.07 (td, J = 7.7, 1.8 Hz, 1H), 6.98 (td, J = 7.5, 1.5 Hz, 1H), 6.44 (t, J = 5.6 Hz, 1H), 3.23 – 2.99 (m, 3H), 2.68 (t, J = 7.5 Hz, 2H), 1.64 (q, J = 7.7 Hz, 2H), 1.49 (q, J = 7.2 Hz, 2H), 1.15 (d, J = 6.8 Hz, 6H). | |
| F91 | 197-200 | | API-MS m/z 510 ([M + H]⁺) | ¹H NMR (300 MHz, DMSO-d₆) δ 9.37 (s, 1H), 8.27 (s, 1H), 8.12 – 7.96 (m, 4H), 7.66 – 7.58 (m, 2H), 7.36 (d, J = 8.0 Hz, 2H), 7.21 (s, 1H), 7.15 (d, J = 8.3 Hz, 1H), 7.07 (t, J = 7.7 Hz, 1H), 6.69 (d, J = 7.3 Hz) 1H), 6.11 (t, J = 5.7 Hz, 1H), 3.11 (q, J = 6.5 Hz, 2H), 2.67 (t, J = 7.5 Hz, 2H), 2.23 (s, 3H), 1.63 (q, J = 7.6 Hz, 2H), 1.48 (q, J = 7.2 Hz, 2H). | |
| F92 | 190-193 | | API-MS m/z 530 ([M + H]⁺) | ¹H NMR (400 MHz, DMSO-d₆) δ 9.38 (s, 1H), 8.15 (dd, J = 8.4, 1.5 Hz, 1H), 8.10 – 7.98 (m, 4H), 7.95 (s, 1H), 7.66 – 7.57 (m, 2H), 7.44 – 7.32 (m, 3H), 7.22 (ddd, J = 8.6, 7.4, 1.5 Hz, 1H), 7.01 (t, J = 5.6 Hz, 1H), 6.98 – 6.89 (m, 1H), 3.14 (q, J = 6.5 Hz, 2H), 2.68 (t, J = 7.5 Hz, 2H), 1.66 (p, J = 7.6 Hz, 2H), 1.49 (p, J = 7.0 Hz, 2H). | |
| F93 | 167-170 | | API-MS m/z 530 ([M + H]⁺) | ¹H NMR (400 MHz, DMSO-d₆) δ 9.37 (s, 1H), 8.60 (s, 1H), 8.14 – 7.95 (m, 4H), 7.70 – 7.57 (m, 3H), 7.36 (d, J = 8.1 Hz, 2H), 7.26 – 7.13 (m, 2H), 6.91 (dt, J = 7.7, 1.6 Hz, 1H), 6.24 (t, J = 5.7 Hz, 1H), 3.12 (q, J = 6.6 Hz, 2H), 2.67 (t, J = 7.6 Hz, 2H), 1.63 (p, J = 7.9, 7.5 Hz, 2H), 1.49 (q, J = 7.3 Hz, 2H). | |
| F94 | 220-224 | | API-MS m/z 530 ([M + H]⁺) | ¹H NMR (400 MHz, DMSO-d₆) δ 9.38 (s, 1H), 8.52 (s, 1H), 8.13 – 7.97 (m, 4H), 7.62 (dd, J = 8.4, 1.3 Hz, 2H), 7.46 – 7.31 (m, 4H), 7.30 – 7.18 (m, 2H), 6.18 (t, J = 5.7 Hz, 1H), 3.12 (q, J = 6.5 Hz, 2H), 2.67 (t, J = 7.6 Hz, 2H), 1.63 (p, J = 7.6 Hz, 2H), 1.47 (p, J = 7.1 Hz, 2H). | |
| F95 | 171-175 | | ESIMS m/z 526 ([M + H]⁺) | ¹H NMR (300 MHz, DMSO-d₆) δ 9.37 (s, 1H), 8.15 – 7.97 (m, 5H), 7.84 (s, 1H), 7.62 (d, J = 8.6 Hz, 2H), 7.36 (d, J = 7.9 Hz, 2H), 6.94 (dd, J = 7.5, 2.2 Hz, 1H), 6.83 (tt, J = 7.5, 5.3 Hz, 3H), 3.82 (s, 3H), 3.12 (q, J = 6.3 Hz, 2H), 2.68 (t, J = 7.6 Hz, 2H), 1.64 (q, J = 7.5 Hz, 2H), 1.48 (q, J = 7.1 Hz, 2H). | |
| F96 | 178-182 | | ESIMS m/z 526 ([M + H]⁺) | ¹H NMR (300 MHz, DMSO-d₆) δ 9.37 (s, 1H), 8.37 (s, 1H), 8.12 – 7.95 (m, 4H), 7.68 – 7.56 (m, 2H), 7.36 (d, J = 7.9 Hz, 2H), 7.13 (t, J = 2.5 Hz, 1H), 7.08 (d, J = 8.1 Hz, 1H), 6.84 (dd, J = 8.1, 1.9 Hz, 1H), 6.51 – 6.41 (m, 1H), 6.12 (t, J = 5.7 Hz, 1H), 3.69 (s, 3H), 3.11 (q, J = 6.4 Hz, 2H), 2.67 (t, J = 7.6 Hz, 2H), 1.62 (q, J = 7.7 Hz, 2H), 1.47 (p, J = 7.1 Hz, 2H). | |

TABLE 4-continued

Analytical Data for Compounds in Table 2

| No. | Mp (° C.) | IR (cm$^{-1}$) | Mass (m/z) | $^1$H NMR | $^{13}$CNMR; $^{19}$F NMR |
|---|---|---|---|---|---|
| F97 | 200-203 | | ESIMS m/z 526 ([M + H]$^+$) | $^1$H NMR (300 MHz, DMSO-d$_6$) δ 9.37 (s, 1H), 8.15 (s, 1H), 8.12 – 7.97 (m, 4H), 7.67 – 7.56 (m, 2H), 7.36 (d, J = 8.0 Hz, 2H), 7.31 – 7.20 (m, 2H), 6.87 – 6.74 (m, 2H), 6.02 (t, J = 5.7 Hz, 1H), 3.68 (s, 3H), 3.10 (q, J = 6.4 Hz, 2H), 2.67 (t, J = 7.5 Hz, 2H), 1.63 (p, J = 7.3 Hz, 2H), 1.46 (p, J = 6.8 Hz, 2H). | |
| F98 | 197-200 | | ESIMS m/z 524 ([M + H]$^+$) | $^1$H NMR (400 MHz, DMSO-d$_6$) δ 9.38 (s, 1H), 8.13 – 7.97 (m, 4H), 7.76 (dd, J = 8.1, 1.3 Hz, 1H), 7.62 (d, J = 8.5 Hz, 2H), 7.54 (s, 1H), 7.36 (d, J = 7.8 Hz, 2H), 7.17 – 7.00 (m, 2H), 6.91 (td, J = 7.5, 1.4 Hz, 1H), 6.52 (t, J = 5.5 Hz, 1H), 3.13 (q, J = 6.5 Hz, 2H), 2.68 (t, J = 7.6 Hz, 2H), 2.60 – 2.51 (m, 2H), 1.66 (p, J = 7.7 Hz, 2H), 1.48 (p, J = 7.0 Hz, 2H), 1.12 (t, J = 7.5 Hz, 3H). | |
| F99 | 193-196 | | ESIMS m/z 510 ([M + H]$^+$) | $^1$H NMR (300 MHz, DMSO-d$_6$) δ 9.37 (s, 1H), 8.23 (s, 1H), 8.16 – 7.92 (m, 4H), 7.62 (d, J = 8.6 Hz, 2H), 7.36 (d, J = 8.0 Hz, 2H), 7.30 – 7.18 (m, 2H), 7.00 (d, J = 8.2 Hz, 2H), 6.07 (t, J = 5.8 Hz, 1H), 3.11 (q, J = 6.5 Hz, 2H), 2.67 (t, J = 7.5 Hz, 2H), 2.20 (s, 3H), 1.63 (p, J = 7.3 Hz, 2H), 1.48 (q, J = 7.1 Hz, 2H). | |
| F100 | 221-224 | | API-MS m/z 468 ([M + H]$^+$) | $^1$H NMR (300 MHz, DMSO-d$_6$) δ 9.39 (s, 1H), 8.13 – 8.02 (m, 4H), 7.84 (d, J = 8.1 Hz, 1H), 7.77 (s, 1H), 7.62 (d, J = 8.6 Hz, 2H), 7.47 (d, J = 8.0 Hz, 2H), 7.17 – 7.00 (m, 3H), 6.88 (dd, J = 8.0, 6.6 Hz, 1H), 4.38 (d, J = 5.8 Hz, 2H), 2.20 (s, 3H). | |
| F101 | 216-220 | | API-MS m/z 482 ([M + H]$^+$) | $^1$H NMR (300 MHz, DMSO-d$_6$) δ 9.39 (s, 1H), 8.14 – 8.02 (m, 4H), 7.79 (dd, J = 8.0, 1.4 Hz, 1H), 7.75 (s, 1H), 7.62 (d, J = 8.4 Hz, 2H), 7.46 (d, J = 8.1 Hz, 2H), 7.19 – 7.09 (m, 2H), 7.09 – 7.02 (m, 1H), 6.94 (td, J = 7.3, 1.3 Hz, 1H), 4.38 (d, J = 5.8 Hz, 2H), 2.57 (q, J = 7.7 Hz, 2H), 1.15 (t, J = 7.5 Hz, 3H). | |
| F102 | 251-254 | | API-MS m/z 468 ([M + H]$^+$) | $^1$H NMR (300 MHz, DMSO-d$_6$) δ 9.39 (s, 1H), 8.47 (s, 1H), 8.16 – 8.01 (m, 4H), 7.70 – 7.55 (m, 2H), 7.44 (d, J = 8.0 Hz, 2H), 7.30 (d, J = 8.4 Hz, 2H), 7.03 (d, J = 8.1 Hz, 2H), 6.70 – 6.57 (m, 1H), 4.36 (d, J = 5.9 Hz, 2H), 2.22 (s, 3H). | |
| F103 | 219-223 | | API-MS m/z 486 ([M + H]$^-$) | $^1$H NMR (300 MHz, DMSO-d$_6$) δ 9.39 (s, 1H), 8.85 (s, 1H), 8.13 – 8.04 (m, 4H), 7.70 (t, J = 1.9 Hz, 1H), 7.62 (d, J = 8.4 Hz, 2H), 7.45 (d, J = 8.1 Hz, 2H), 7.31 – 7.18 (m, 2H), 6.94 (dt, J = 7.0, 2.1 Hz, 1H), 6.80 (t, J = 6.0 Hz, 1H), 4.37 (d, J = 5.9 Hz, 2H). | |
| F104 | 232-235 | | API-MS m/z 488 ([M + H]$^+$) | $^1$H NMR (300 MHz, DMSO-d$_6$) δ 9.39 (s, 1H), 8.23 – 8.13 (m, 2H), 8.12 – 8.03 (m, 4H), 7.62 (d, J = 8.6 Hz, 2H), 7.54 (t, J = 5.7 Hz, 1H), 7.47 (d, J = 8.1 Hz, 2H), 7.41 (dd, J = 8.1, 1.5 Hz, 1H), 7.31 – 7.19 (m, 1H), 6.96 (td, J = 7.7, 1.6 Hz, 1H), 4.40 (d, J = 5.7 Hz, 2H). | |
| F105 | 267-270 | | ESIMS m/z 488 ([M + H]$^+$) | $^1$H NMR (400 MHz, DMSO-d$_6$) δ 9.39 (s, 1H), 8.77 (s, 1H), 8.12 – 8.00 (m, 4H), 7.66 – 7.57 (m, 2H), 7.45 (dd, J = 8.7, 2.8 Hz, 4H), 7.30 – 7.22 (m, 2H), 6.74 (t, J = 6.0 Hz, 1H), 4.37 (d, J = 5.9 Hz, 2H). | |
| F106 | 212-215 | | ESIMS m/z 484 ([M + H]$^+$) | $^1$H NMR (400 MHz, DMSO-d$_6$) δ 9.39 (s, 1H), 8.16 – 8.00 (m, 6H), 7.68 – 7.58 (m, 2H), 7.45 (d, J = 8.2 Hz, 2H), 7.39 (t, J = 5.9 Hz, 1H), 6.97 (dd, J = 7.9, 1.8 Hz, 1H), 6.86 (dtd, J = 16.5, 7.5, 1.8 Hz, 2H), 4.37 (d, J = 5.7 Hz, 2H), 3.84 (s, 3H). | |
| F107 | 203-206 | | ESIMS m/z 484 ([M + H]$^+$) | $^1$H NMR (400 MHz, DMSO-d$_6$) δ 9.39 (s, 1H), 8.62 (s, 1H), 8.15 – 7.99 (m, 4H), 7.67 – 7.57 (m, 2H), 7.44 (d, J = 8.0 Hz, 2H), 7.17 (t, J = 2.2 Hz, 1H), 7.12 (t, J = 8.1 Hz, 1H), 6.95 – 6.84 (m, 1H), 6.67 (t, J = 6.1 Hz, 1H), 6.54 – 6.43 (m, 1H), 4.37 (d, J = 5.9 Hz, 2H), 3.70 (s, 3H). | |
| F108 | 222-225 | | ESIMS m/z 468 ([M + H]$^+$) | $^1$H NMR (300 MHz, DMSO-d$_6$) δ 9.39 (s, 1H), 8.51 (s, 1H), 8.13 – 8.03 (m, 4H), 7.68 – 7.56 (m, 2H), 7.44 (d, J = 8.1 Hz, 2H), 7.26 (s, 1H), 7.19 (d, J = 8.4 Hz, 1H), 7.10 (t, J = 7.7 Hz, 1H), 6.72 (d, J = 7.4 Hz, 1H), 6.66 (t, J = 5.9 Hz, 1H), 4.36 (d, J = 5.8 Hz, 2H), 2.25 (s, 3H). | |
| F109 | 204-206 | | ESIMS m/z 484 ([M + H]$^+$) | $^1$H NMR (300 MHz, DMSO-d$_6$) δ 9.39 (s, 1H), 8.39 (s, 1H), 8.12 – 8.01 (m, 4H), 7.62 (d, J = 8.5 Hz, 2H), 7.44 (d, J = 8.0 Hz, 2H), 7.36 – 7.27 (m, 2H), 6.87 – 6.72 (m, 2H), 6.58 (t, J = 5.9 Hz, 1H), 4.35 (d, J = 5.9 Hz, 2H), 3.69 (s, 3H). | |

TABLE 4-continued

Analytical Data for Compounds in Table 2

| No. | Mp (° C.) | IR (cm⁻¹) | Mass (m/z) | ¹H NMR | ¹³CNMR; ¹⁹F NMR |
|---|---|---|---|---|---|
| F110 | 174-175 | | ESIMS m/z 550 ([M + H]⁺), 548 ([M − H]⁻) | ¹H NMR (300 MHz, DMSO-d₆) δ 9.48 (bs, 1H), 9.38 (s, 1H), 8.04 − 8.08 (m, 5H), 7.60 (d, J = 9.0 Hz, 2H), 7.43 (d, J = 8.4 Hz, 2H), 7.25 (d, J = 9.0 Hz, 2H), 6.90, (m, 2H), 4.77 (d, J = 5.4 Hz, 2H), 3.73 (s, 3H). | |
| F111 | 137-138 | | ESIMS m/z 564 ([M + H]⁺), 562 ([M − H]⁻) | ¹H NMR (300 MHz, DMSO-d₆) δ 9.38 (s, 1H), 9.14 (m, 1H), 8.06 (m, 5H), 8.60 (d, J = 9.0 Hz, 2H), 7.40 (d, J = 8.7 Hz, 2H), 7.06 (d, J = 8.4 Hz, 1H), 6.80 (m, 1H), 6.75 (dd, J = 8.7, 3.0 Hz, 1H), 4.74 (d, J = 5.4 Hz, 2H), 3.72 (s, 3H), 2.13 (s, 3H). | |
| F112 | 173-174 | | ESIMS m/z 563 ([M + H]⁺), 561 ([M − H]⁻) | ¹H NMR (300 MHz, DMSO-d₆) δ 9.39 (s, 1H), 9.36 (s, 1H), 8.04 − 8.08 (m, 5H), 7.60 (d, J = 8.7 Hz, 2H), 7.42 (d, J = 9.0 Hz, 2H), 7.10 (d, J = 8.7 Hz, 2H), 6.90 (d, J = 8.7 Hz, 2H), 4.77 (d, J = 6.0 Hz, 2H), 2.86 (s, 6H). | |

TABLE 5

Structure and Preparation Method for P Series Compounds

| No. | Structure | Prep. according to example |
|---|---|---|
| P1 | 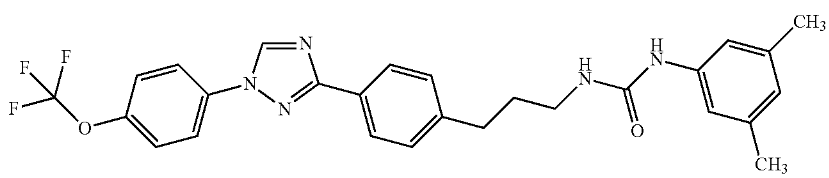 [SMILES: Cc1cc(C)cc(NC(=O)NCCCc2ccc(-c3ncn(-c4ccc(OC(F)(F)F)cc4)n3)cc2)c1] | 55 |
| P2 | 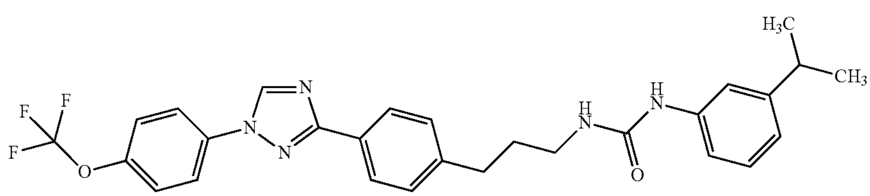 [SMILES: CC(C)c1cccc(NC(=O)NCCCc2ccc(-c3ncn(-c4ccc(OC(F)(F)F)cc4)n3)cc2)c1] | 55 |
| P3 | 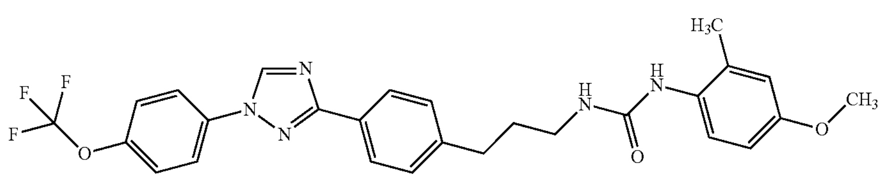 [SMILES: COc1ccc(NC(=O)NCCCc2ccc(-c3ncn(-c4ccc(OC(F)(F)F)cc4)n3)cc2)c(C)c1] | 42 |
| P5 | 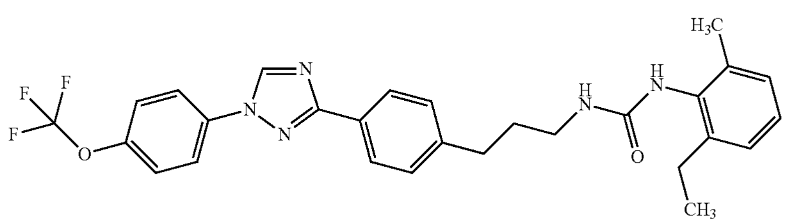 [SMILES: CCc1cccc(C)c1NC(=O)NCCCc1ccc(-c2ncn(-c3ccc(OC(F)(F)F)cc3)n2)cc1] | 56 |

TABLE 5-continued

Structure and Preparation Method for P Series Compounds

| No. | Structure | Prep. according to example |
|---|---|---|
| P6 | 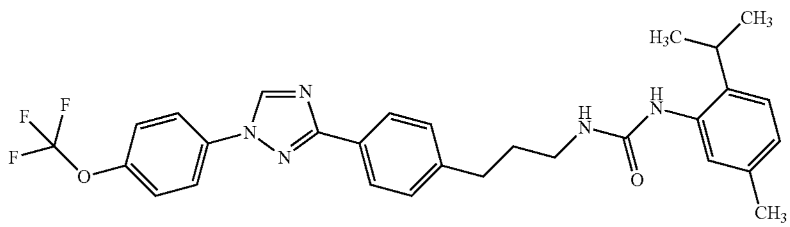 [SMILES: Cc1ccc(C(C)C)c(NC(=O)NCCCc2ccc(-c3ncn(-c4ccc(OC(F)(F)F)cc4)n3)cc2)c1] | 56 |
| P7 | 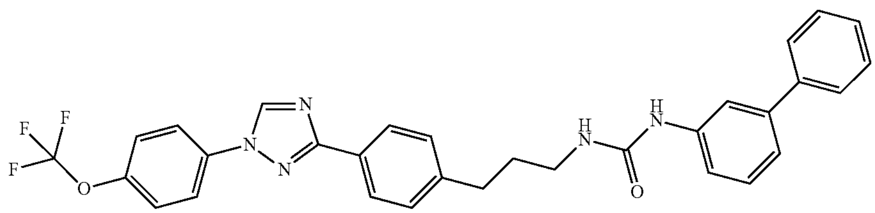 [SMILES: O=C(NCCCc1ccc(-c2ncn(-c3ccc(OC(F)(F)F)cc3)n2)cc1)Nc1cccc(-c2ccccc2)c1] | 55 |
| P9 | 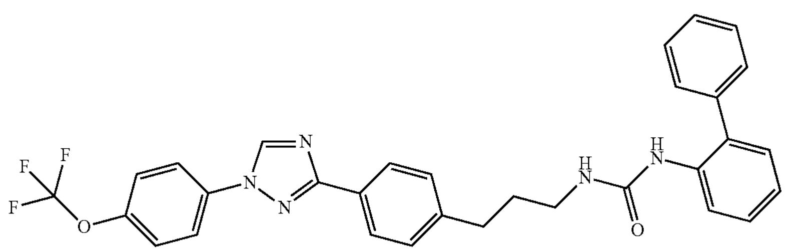 [SMILES: O=C(NCCCc1ccc(-c2ncn(-c3ccc(OC(F)(F)F)cc3)n2)cc1)Nc1ccccc1-c1ccccc1] | 42 |

TABLE 6

Analytical Data for Compounds in Table 5

| No. | Mp (° C.) | IR (cm⁻¹) | Mass (m/z) | ¹H NMR | ¹³CNMR; ¹⁹F NMR |
|---|---|---|---|---|---|
| P1 | 237-240 | | ESIMS 510 ([M + H]⁺) | ¹H NMR (300 MHz, DMSO-d₆) δ 9.38 (s, 1H), 8.25 (s, 1H), 8.06 (dd, J = 10.9, 8.5 Hz, 4H), 7.62 (d, J = 8.4 Hz, 2H), 7.37 (d, J = 7.9 Hz, 2H), 7.01 (s, 2H), 6.53 (s, 1H), 6.18 (t, J = 5.7 Hz, 1H), 3.12 (q, J = 6.6 Hz, 2H), 2.68 (t, J = 7.5 Hz, 2H), 2.19 (s, 6H), 1.79 (q, J = 7.4 Hz, 2H) | ¹³C NMR (75 MHz, DMSO-d₆) δ 162.13, 155.20, 147.05, 143.69, 143.54, 140.38, 137.43, 135.71, 128.78, 127.84, 126.14, 122.55, 121.07, 115.39, 32.35, 31.36, 21.11 |
| P2 | 128-130 | | ESIMS 524 ([M + H]⁺) | ¹H NMR (400 MHz, DMSO-d₆) δ 9.38 (s, 1H), 8.36 (s, 1H), 8.10 - 8.02 (m, 4H), 7.62 (d, J = 8.4 Hz, 2H), 7.37 (d, J = 9.2 Hz, 2H), 7.27 (s, 1H), 7.20 (d, J = 8.0 Hz, 1H), 7.15 (t, J = 7.6 Hz, 1H), 6.77 (d, J = 8.0 Hz, 1H), 6.18 (t, J = 6.0 Hz, 1H), 3.12 (q, J = 6.4 Hz, 2H), 2.80 (p, J = 6.8 Hz, 1H), 2.68 (t, J = 8.0 Hz, 2H), 1.18 (p, J = 7.2 Hz, 2H), 1.17 (d, J = 8.0 Hz, 6H) | ¹³C NMR (75 MHz, DMSO-d₆) δ 162.13, 155.24, 148.79, 147.06, 143.69, 143.54, 140.52, 135.71, 128.78, 128.45, 127.84, 126.15, 122.55, 121.72, 121.07, 118.98, 118.32, 115.57, 115.23, 33.47, 32.36, 31.38, 23.85 |

TABLE 6-continued

Analytical Data for Compounds in Table 5

| No. | Mp (° C.) | IR (cm$^{-1}$) | Mass (m/z) | $^1$H NMR | $^{13}$CNMR; $^{19}$F NMR |
|---|---|---|---|---|---|
| P3 | 206-208 | | ESIMS 526 ([M + H]$^+$) | $^1$H NMR (300 MHz, DMSO-d$_6$) δ 9.38 (s, 1H), 8.09 - 8.01 (m, 4H), 7.64 - 7.59 (m, 2H), 7.51 - 7.45 (m, 2H), 7.40 - 7.34 (m, 2H), 6.73 (d, J = 2.7 Hz, 1H), 6.68 (dd, J = 8.7, 3.0 Hz, 1H), 6.37 (t, J = 5.4 Hz, 1H), 3.69 (s, 3H), 3.11 (q, J = 6.6 Hz, 2H), 2.68 (t, J = 7.5 Hz, 2H), 2.16 (s, 3H), 1.78 (t, J = 7.5 Hz, 2H) | $^{13}$C NMR (75 MHz, DMSO-d$_6$) δ 162.13, 155.89, 154.89, 147.05, 143.70, 143.60, 135.71, 131.08, 130.44, 128.79, 127.83, 126.14, 123.72, 122.56, 121.08, 115.32, 111.07, 55.03, 32.37, 31.44, 18.05 |
| P5 | 220-222 | | ESIMS 524 ([M + H]$^+$) | $^1$H NMR (300 MHz, DMSO-d$_6$) δ 9.38 (s, 1H), 8.05 (q, J = 8.1 Hz, 4H), 7.61 (d, J = 8.4 Hz, 2H), 7.42 (s, 1H), 7.61 (d, J = 7.8 Hz, 2H), 7.05 (s, 3H), 6.12 (s, 1H), 3.10 (d, J = 6.0 Hz, 2H), 2.67 (t, J = 7.5 Hz, 2H), 2.59 - 2.51 (m, 2H), 2.17 (s, 3H), 1.77 (t, J = 6.9 Hz, 2H), 1.11 (t, J = 7.2 Hz, 3H) | $^{13}$C NMR (75 MHz, DMSO-d$_6$) δ 162.13, 156.37, 147.05, 143.70, 141.47, 136.26, 135.71, 135.45, 128.76, 127.81, 127.62, 126.14, 125.92, 122.55, 121.07, 32.32, 31.70, 24.46, 18.24, 14.65 |
| P6 | 191-193 | | ESIMS 536 ([M − H]$^-$) | $^1$H NMR (300 MHz, DMSO-d$_6$) δ 9.38 (s, 1H), 8.09 - 8.02 (m, 4H), 7.64 - 7.56 (m, 3H), 7.45 (d, J = 1.8 Hz, 1H), 7.38 (d, J = 8.1 Hz, 2H), 7.09 (d, J = 7.8 Hz, 1H), 6.81 (dd, J = 8.1, 1.8 Hz, 1H), 6.49 (t, J = 5.4 Hz, 1H), 3.10 (dq, J = 14.4, 6.6 Hz, 3H), 2.69 (t, J = 7.8 Hz, 2H), 2.21 Hz, 2H), 1.14 (d, J = 6.6 Hz, 6H) | $^{13}$C NMR (75 MHz, DMSO-d$_6$) δ 162.13, 155.89, 147.06, 143.69, 143.57, 136.18, 135.71, 134.41, 128.78, 127.84, 126.14, 124.82, 123.76, 123.62, 122.55, 121.73, 121.07, 26.35, 23.12, 20.72 |
| P7 | 177-179 | | ESIMS 558 ([M + H]$^+$) | $^1$H NMR (400 MHz, DMSO-d$_6$) δ 9.38 (s, 1H), 8.57 (s, 1H), 8.09 - 8.02 (m, 4H), 7.75 (t, J = 2.0 Hz, 1H), 7.63 - 7.58 (m, 4H), 7.46 (dd, J = 8.4, 6.8 Hz, 2H), 7.40 - 7.28 (m, 5H), 7.17 (dt, J = 7.2, 1.6 Hz, 1H), 6.31 (t, J = 5.6 Hz, 1H), 3.14 (q, J = 6.4 Hz, 2H), 2.69 (t, J = 7.6 Hz, 2H), 1.80 (p, J = 7.2 Hz, 2H) | $^{13}$C NMR (75 MHz, DMSO-d$_6$) δ 162.13, 155.29, 47.03, 147.06, 143.69, 143.54, 141.15, 140.67, 140.49, 135.70, 129.17, 128.85, 128.79, 127.84, 127.34, 126.56, 126.15, 122.55, 121.07, 119.39, 116.73, 115.93, 38.66, 32.37, 31.35 |
| P9 | 184-187 | | ESIMS 558 ([M + H]$^+$) | $^1$H NMR (300 MHz, DMSO-d$_6$) δ 9.38 (s, 1H), 8.11 - 8.00 (m, 4H), 7.92 - 7.87 (m, 1H), 7.62 (dd, J = 8.4, 1.5 Hz, 2H), 7.48 (dd, J = 7.8, 6.3 Hz, 2H), 7.43 - 7.31 (m, 6H), 7.27 (ddd, J = 8.4, 7.5, 1.8 Hz, 1H), 7.16 (dd, J = 7.5, 1.8 Hz, 1H), 7.06 (td, J = 7.5, 1.2 Hz, 1H), 6.66 (t, J = 5.4 Hz, 1H), 3.08 (q, J = 6.3 Hz, 2H), 2.64 (t, J = 7.5 Hz, 2H), 1.73 (p, J = 7.2 Hz, 2H) | $^{13}$C NMR (75 MHz, DMSO-d$_6$) δ 162.13, 155.46, 147.05, 143.69, 143.53, 138.75, 136.56, 135.71, 132.11, 130.14, 129.09, 128.76, 128.72, 127.83, 127.62, 127.30, 126.12, 122.55, 122.49, 122.36, 121.08, 32.29, 31.20 |

TABLE 7

Structure and Preparation Method for FA Series Compounds

| No. | Structure | Prep. according to example |
|---|---|---|
| FA1 | (structure: 4-(trifluoromethoxy)phenyl-triazole-phenyl-propyl-urea-2-methylbiphenyl) | 55 |
| FA2 | (structure: 4-(trifluoromethoxy)phenyl-triazole-phenyl-propyl-urea-3-(2-methylphenyl)phenyl) | 55 |

TABLE 8

Analytical Data for Compounds in Table 7

| No. | Mp (° C.) | IR (cm$^{-1}$) | Mass (m/z) | $^1$H NMR | $^{13}$CNMR; $^{19}$F NMR |
|---|---|---|---|---|---|
| FA1 | 165-167 | | ESIMS 572 ([M + H]$^+$) | $^1$H NMR (300 MHz, DMSO-d$_6$) δ 9.38 (s, 1H), 8.09 - 7.98 (m, 5H), 7.64 - 7.60 (d, J = 8.4 Hz, 2H), 7.34 - 7.24 (m, 6H), 7.14 - 7.10 (d, J = 6.3 Hz, 1H), 7.02 - 6.99 (m, 2H), 6.91 (s, 1H), 6.76 (t, J = 5.4 Hz, 1H), 3.04 (q, J = 6.6 Hz, 2H), 2.62 (t, J = 7.5 Hz, 2H), 2.03 (s, 3H), 1.70 (p, J = 7.2 Hz, 2H) | $^{13}$C NMR (75 MHz, DMSO-d$_6$) δ 162.11, 155.24, 147.04, 143.68, 143.48, 137.94, 137.22, 136.12, 135.71, 130.79, 130.14, 130.03, 129.83, 128.73, 127.78, 127.51, 126.12, 122.55, 121.61, 121.06, 120.70, 32.31, 31.15, 19.33 |
| FA2 | 140-143 | | ESIMS 572 ([M + H]$^+$) | $^1$H NMR (300 MHz, DMSO-d$_6$) δ 9.38 (s, 1H), 8.52 (s, 1H), 8.05 (dd, J = 10.8, 8.4 Hz, 4H), 7.64 - 7.59 (d, J = 8.4 Hz, 2H), 7.45 - 7.15 (m, 9H), 6.85 (dt, J =7.2, 1.5 Hz, 1H), 6.26 (t, J = 5.4 Hz, 1H), 3.14 (q, J = 6.6 Hz, 2H), 2.69 (t, J = 7.5 Hz, 2H), 2.23 (s, 3H), 1.79 (p, J = 7.2 Hz, 2H) | $^{13}$C NMR (75 MHz, DMSO-d$_6$) δ 162.13, 155.26, 147.06, 143.69, 143.53, 141.65, 141.52, 140.42, 135.71, 134.55, 130.23, 129.26, 128.78, 128.43, 127.84, 127.15, 126.14, 125.82, 122.55, 121.58, 121.07, 118.19, 116.14, 32.36, 20.13 |

BAW, CEW, & CL Rating Table

| % Control (or Mortality) | Rating |
|---|---|
| 50-100 | A |
| More than 0 - Less than 50 | B |
| Not Tested | C |
| No activity noticed in this bioassay | D |

TABLE 8-continued

Analytical Data for Compounds in Table 7

GPA & YFM Rating Table

| % Control (or Mortality) | Rating |
|---|---|
| 80-100 | A |
| More than 0 - Less than 80 | B |
| Not Tested | C |
| No activity noticed in this bioassay | D |

Table ABC

Biological Results

| No. | BAW | CL | CEW | GPA | YFM |
|---|---|---|---|---|---|
| F1 | D | A | C | C | D |
| F2 | D | C | D | D | C |
| F3 | A | C | A | C | C |
| F4 | A | A | C | D | A |
| F5 | A | A | C | D | D |
| F6 | A | A | C | B | A |
| F7 | D | C | D | C | C |
| F8 | D | C | D | D | C |
| F9 | A | A | C | C | D |
| F10 | A | C | A | B | C |
| F11 | A | C | C | B | D |
| F12 | D | C | D | C | C |
| F13 | A | A | C | C | C |
| F14 | D | C | D | C | C |
| F15 | A | A | C | C | B |
| F16 | A | A | C | B | D |
| F17 | D | C | D | C | D |
| F18 | A | A | C | D | D |
| F19 | A | A | C | C | C |
| F20 | B | A | C | B | D |
| F21 | A | A | A | C | D |
| F22 | B | A | C | B | D |
| F23 | A | A | A | C | A |
| F24 | A | A | C | C | C |
| F25 | A | C | A | C | C |
| F26 | A | A | C | C | D |
| F27 | D | C | D | C | C |
| F28 | B | A | C | B | D |
| F29 | A | A | A | C | A |
| F30 | A | A | A | C | A |
| F31 | A | A | C | B | A |
| F32 | C | C | C | C | B |
| F33 | A | A | C | C | B |
| F34 | D | A | A | C | C |
| F35 | A | A | C | D | A |
| F36 | A | C | A | B | C |
| F37 | B | A | C | B | B |
| F38 | B | A | C | D | D |
| F39 | D | A | C | C | D |
| F40 | A | A | A | C | C |
| F41 | D | C | D | D | C |
| F42 | A | A | C | C | B |
| F43 | A | C | A | C | C |
| F44 | D | D | C | C | D |
| F45 | B | A | C | C | A |
| F46 | A | A | C | B | B |
| F47 | D | A | C | C | D |
| F48 | A | A | B | C | A |
| F49 | B | A | C | C | D |
| F50 | D | D | C | C | D |
| F51 | B | B | C | C | D |
| F52 | A | A | C | C | C |
| F53 | A | C | A | B | A |
| F54 | A | A | C | C | D |
| F55 | A | A | D | C | A |
| F56 | B | A | C | C | D |
| F57 | A | A | A | C | D |
| F58 | A | A | A | C | D |
| F59 | A | A | C | C | D |
| F60 | A | A | C | B | A |
| F61 | A | A | C | C | D |
| F62 | A | A | C | C | B |
| F63 | A | A | C | B | D |
| F64 | A | A | C | C | B |
| F65 | D | A | B | C | D |
| F66 | A | A | C | B | D |
| F67 | B | C | D | D | D |
| F68 | A | A | C | B | A |
| F69 | A | A | C | D | A |
| F70 | A | A | C | C | C |
| F71 | A | C | A | C | C |
| F72 | A | C | C | D | B |
| F73 | A | A | A | C | C |
| F74 | A | A | A | C | C |
| F75 | A | A | A | D | D |
| F76 | A | A | C | C | A |
| F77 | A | A | C | C | A |
| F78 | A | A | C | C | A |
| F79 | C | A | C | C | D |
| F80 | A | A | C | C | A |
| F81 | A | A | C | C | B |
| F82 | C | D | C | C | D |
| F83 | C | D | C | C | D |
| F84 | A | A | C | C | B |
| F85 | A | A | C | C | A |
| F86 | A | A | C | C | A |
| F87 | C | D | C | C | D |
| F88 | A | A | C | C | A |
| F89 | D | C | C | C | D |
| F90 | D | D | C | C | D |
| F91 | C | D | C | C | D |
| F92 | C | D | C | C | D |
| F93 | D | A | C | C | D |
| F94 | D | A | C | C | D |
| F95 | D | A | C | C | D |
| F96 | D | C | C | C | D |
| F97 | B | D | C | C | D |
| F98 | B | D | C | C | D |
| F99 | B | D | C | C | D |
| F100 | D | D | C | C | D |
| F101 | D | C | C | C | D |
| F102 | D | D | C | C | D |
| F103 | B | A | C | C | A |
| F104 | A | B | C | C | B |
| F105 | A | A | C | C | B |
| F106 | D | D | C | C | D |
| F107 | D | D | C | C | B |
| F108 | D | D | C | C | D |
| F109 | D | D | C | C | D |
| F110 | A | C | D | D | D |
| F111 | A | C | A | D | A |
| F112 | B | C | D | D | D |
| P1 | D | D | C | D | D |
| P2 | B | D | C | D | D |
| P3 | D | D | C | D | D |
| P5 | D | D | C | D | D |

Table ABC-continued

Biological Results

| No. | Insect species | | | | |
|---|---|---|---|---|---|
| | BAW | CL | CEW | GPA | YFM |
| P6 | A | A | C | D | A |
| P7 | D | D | C | D | D |
| P9 | D | A | C | D | B |
| FA1 | D | A | C | D | A |
| FA2 | D | D | C | D | D |

We claim:

1. A molecule having the following formula

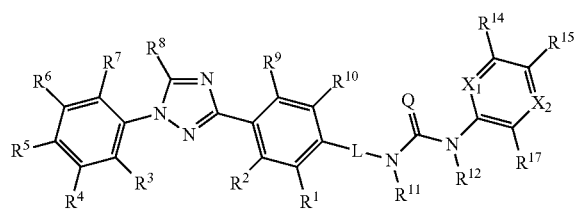

wherein:
(A) $R^1$, $R^2$, $R^3$, $R^4$, $R^5$, $R^6$, $R^7$, $R^9$, and $R^{10}$ are each independently selected from the group consisting of the group consisting of H, F, Cl, Br, I, CN, $NO_2$, OH, $(C_1-C_4)$alkyl, $(C_2-C_4)$alkenyl, $(C_1-C_4)$haloalkyl, $(C_1-C_4)$alkoxy, $(C_1-C_4)$haloalkoxy, and $(C_3-C_6)$cycloalkyl,
wherein each alkyl, alkenyl, haloalkyl, alkoxy, haloalkoxy, cycloalkyl, are optionally substituted with one or more substituents independently selected from the group consisting of the group consisting of H, F, Cl, Br, I, CN, $NO_2$, OH, $(C_1-C_4)$alkyl, $(C_2-C_4)$alkenyl, $(C_1-C_4)$haloalkyl, $(C_1-C_4)$alkoxy, $(C_1-C_4)$haloalkoxy, and $(C_3-C_6)$cycloalkyl;
(B) $R^8$ is H;
(C) L is selected from the group consisting of the group consisting of
(1) a bond connecting nitrogen to carbon in the ring, and
(2) a $(C_1)$alkyl or a $(C_3-C_4)$alkyl wherein said alkyl is optionally substituted with one or more substituents independently selected from the group consisting of the group consisting of F, Cl, CN, OH, and oxo;
(D) $R^{11}$ and $R^{12}$ are each independently selected from the group consisting of the group consisting of H, $(C_1-C_4)$alkyl, $(C_2-C_4)$alkenyl, $(C_2-C_4)$alkenyloxy, $(C_2-C_4)$alkynyl, $(C_2-C_4)$alkynyloxy, $(C_1-C_4)$haloalkyl, $(C_1-C_4)$alkoxy, $(C_1-C_4)$haloalkoxy, $(C_3-C_6)$cycloalkyl, $(C_3-C_6)$cycloalkoxy, $(C_3-C_6)$cycloalkenyl, $(C_3-C_6)$cycloalkenyloxy, $((C_1-C_4)$alkyl$)((C_3-C_6)$cycloalkyl$)$, $C(O)((C_1-C_4)$alkyl$)$, $((C_1-C_4)$alkyl$)C(O)((C_1-C_4)$alkyl$)$, $((C_1-C_4)$alkyl$)C(O)O((C_1-C_4)$alkyl$)$, and $C(S)NH_2$,
wherein each alkyl, alkenyl, alkenyloxy, alkynyl, alkynyloxy, haloalkyl, alkoxy, haloalkoxy, cycloalkyl, cycloalkoxy, cycloalkenyl, and cycloalkenyloxy, are optionally substituted with one or more substituents independently selected from the group consisting of the group consisting of H, F, Cl, Br, I, CN, $NO_2$, OH, and oxo;
(E) $X_1$ is selected from the group consisting of the group consisting of N and $CR^{13}$, wherein $R^{13}$ is selected from the group consisting of the group consisting of H, F, Cl, Br, I, CN, $NO_2$, OH, $(C_1-C_4)$alkyl, $(C_2-C_4)$alkenyl, $(C_2-C_4)$alkenyloxy, $(C_2-C_4)$alkynyl, $(C_2-C_4)$alkynyloxy, $(C_1-C_4)$haloalkyl, $(C_1-C_4)$alkoxy, $(C_1-C_4)$haloalkoxy, $(C_3-C_6)$cycloalkyl, $(C_3-C_6)$cycloalkoxy, $(C_3-C_6)$cycloalkenyl, and $(C_3-C_6)$cycloalkenyloxy,
wherein each alkyl, alkenyl, alkenyloxy, alkynyl, alkynyloxy, haloalkyl, alkoxy, haloalkoxy, cycloalkyl, cycloalkoxy, cycloalkenyl, or cycloalkenyloxy, are optionally substituted with one or more substituents independently selected from the group consisting of the group consisting of H, F, Cl, Br, I, CN, $NO_2$, OH, and oxo;
(F) $X_2$ is selected from the group consisting of the group consisting of N and $CR^{16}$, wherein $R^{16}$ is selected from the group consisting of the group consisting of (H), H, F, Cl, Br, I, CN, $NO_2$, OH, $(C_1-C_4)$alkyl, $(C_2-C_4)$alkenyl, $(C_2-C_4)$alkenyloxy, $(C_2-C_4)$alkynyl, $(C_2-C_4)$alkynyloxy, $(C_1-C_4)$haloalkyl, $(C_1-C_4)$alkoxy, $(C_1-C_4)$haloalkoxy, $(C_3-C_6)$cycloalkyl, $(C_3-C_6)$cycloalkoxy, $(C_3-C_6)$cycloalkenyl, phenyl, and $(C_3-C_6)$cycloalkenyloxy,
wherein each alkyl, alkenyl, alkenyloxy, alkynyl, alkynyloxy, haloalkyl, alkoxy, haloalkoxy, cycloalkyl, cycloalkoxy, cycloalkenyl, phenyl, and cycloalkenyloxy, are optionally substituted with one or more substituents independently selected from the group consisting of the group consisting of H, F, Cl, Br, I, CN, $NO_2$, OH, and oxo;
(G) $R^{14}$ and $R^{15}$ are each independently selected from the group consisting of the group consisting of (H), H, F, Cl, Br, I, CN, $NO_2$, OH, $(C_1-C_4)$alkyl, $(C_1-C_4)$haloalkyl, $(C_1-C_4)$alkoxy, $(C_1-C_4)$haloalkoxy, $C(O)O((C_1-C_4)$alkyl$)$, $S((C_1-C_4)$alkyl$)$, $N((C_1-C_4)$alkyl$)_2$, and phenyl,
wherein each alkyl, alkenyl, haloalkyl, alkoxy, haloalkoxy, and phenyl, are optionally substituted with one or more substituents independently selected from the group consisting of the group consisting of H, F, Cl, Br, I, CN, $NO_2$, OH, and oxo;
(H) $R^{15}$ and $R^{16}$ may together be a 4-membered saturated or unsaturated, hydrocarbyl link,
wherein said hydrocarbyl link may optionally be substituted with one or more substituents independently selected from the group consisting of the group consisting of H, F, Cl, Br, I, CN $NO_2$, OH, $(C_1-C_4)$alkyl, $(C_1-C_4)$haloalkyl, and $(C_1-C_4)$alkoxy;
(I) $R^{17}$ is selected from the group consisting of the group consisting of H, F, Cl, Br, I, CN, $NO_2$, OH, $(C_1-C_8)$alkyl, $(C_2-C_8)$alkenyl, $(C_2-C_4)$alkynyl, $(C_3-C_6)$cycloalkyl, $(C_1-C_4)$alkoxy, $(C_1-C_4)$haloalkyl, $(C_1-C_4)$haloalkoxy, $(C_1-C_8)$alkylphenyl, phenyl, and heterocyclyl,
wherein each alkyl, alkenyl, alkynyl, cycloalkyl, alkoxy, haloalkyl, haloalkoxy, phenyl, and heterocyclyl, are optionally substituted with one or more substituents independently selected from the group consisting of the group consisting of H, F, Cl, Br, I, CN, $NO_2$, OH, $(C_1-C_8)$alkyl, $(C_3-C_6)$cycloalkyl, and $S((C_1-C_4)$alkyl$)$; and
(J) Q is selected from the group consisting of the group consisting of O and S.

2. A molecule according to claim 1 wherein $R^1$, $R^2$, $R^3$, $R^4$, $R^6$, $R^7$, $R^8$, $R^9$, and $R^{10}$ are H.

3. A molecule according to claim 1 wherein $R^5$ is $CF_3$, $OCF_3$, or $OCF_2CF_3$.

4. A molecule according to claim 1 wherein L is a bond.

5. A molecule according to claim 1 wherein L is —$CH_2$—, —$CH_2CH_2CH_2$—, or —$CH_2CH_2CH_2CH_2$—.

6. A molecule according to claim 1 wherein $R^{11}$ is H or $C(O)CH_3$.

7. A molecule according to claim 1 wherein $R^{12}$ is H or $C(S)NH_2$.

8. A molecule according to claim 1 wherein $X_1$ is N.

9. A molecule according to claim 1 wherein $X_1$ is $CR^{13}$, wherein $R^{13}$ is H, Cl, $CH_3$, $CH(CH_3)_2$, $OCH_3$, or $CF_3$.

10. A molecule according to claim 1 wherein $R^{14}$ is H, Cl, $CH_3$, $OCH_2CH_3$, or phenyl.

11. A molecule according to claim 1 wherein $R^{15}$ is H, F, Cl, CN, $CH_3$, $OCH_3$, $OCH_2CH_3$, $SCH_3$, $N(CH_3)_2$, or $C(O)OCH_2CH_3$.

12. A molecule according to claim 1 wherein $R^{16}$ is H, Cl, $CH_3$, $CH(CH_3)_2$, or $OCH_3$.

13. A molecule according to claim 1 wherein $R^{16}$ is phenyl that is substituted with $CH_3$.

14. A molecule according to claim 1 wherein $R^{15}$ and $R^{16}$ together are —CH=CH—CH=CH—.

15. A molecule according to claim 1 wherein $R^{17}$ is H, Cl, $CH_3$, $CH_2CH_3$, $CH_2CH_2CH_3$, $CH(CH_3)_2$, $C(CH_3)_3$, $CH(CH_3)CH_2CH(CH_3)_2$, $CF_3$, —C≡CH, —C($CH_3$)=$CH_2$, $OCH_3$, $OCH_2CH_3$, $OCF_3$, or $CH_2$phenyl.

16. A molecule according to claim 1 wherein $R^{17}$ is cyclopropyl that is substituted with cyclopropyl.

17. A molecule according to claim 1 wherein $R^{17}$ is phenyl that is substituted with one or more substituents selected from the group consisting of the group consisting of F, $CH_3$, $CH_2CH_3$, $CH(CH_3)_2$, cyclopropyl, and $SCH_3$.

18. A molecule according to claim 1 wherein $R^{17}$ is 1-pyrazolyl, 2-furyl, 3-pyridyl, 1-morpholinyl, 2-(1,3,4-oxadiazolyl), 3-(1,2,4-oxadiazolyl), or 2-(1,3,4-triazolyl) that is substituted with one or more substituents selected from the group consisting of the group consisting of $CH(CH_3)_2$ and cyclopropyl.

19. A molecule according to claim 1 wherein Q is O.

20. A molecule according to claim 1 wherein Q is S.

21. A molecule according to claim 1 wherein:

(A) $R^1$, $R^2$, $R^3$, $R^4$, $R^5$, $R^6$, $R^7$, $R^9$, and $R^{10}$ are each independently selected from the group consisting of the group consisting of H, ($C_1$-$C_4$)haloalkyl, and ($C_1$-$C_4$)haloalkoxy;

(B) $R^8$ is H;

(C) L is a bond, ($C_1$)alkyl, or ($C_3$-$C_4$)alkyl;

(D) $R^{11}$ and $R^{12}$ are each independently selected from the group consisting of the group consisting of H, C(O)(($C_1$-$C_4$)alkyl), and $C(S)NH_2$;

(E) $X_1$ is selected from the group consisting of the group consisting of N and $CR^{13}$, wherein $R^{13}$ is selected from the group consisting of the group consisting of H, F, Cl, Br, I, ($C_1$-$C_4$)alkyl, ($C_1$-$C_4$)haloalkyl, ($C_1$-$C_4$)alkoxy, and phenyl;

(F) $X_2$ is selected from the group consisting of the group consisting of N and $CR^{16}$, wherein $R^{16}$ is selected from the group consisting of the group consisting of (H), H, F, Cl, Br, I, ($C_1$-$C_4$)alkyl, and ($C_1$-$C_4$)alkoxy;

(G) $R^{14}$ and $R^{15}$ are each independently selected from the group consisting of the group consisting of (H), H, F, Cl, Br, I, CN, ($C_1$-$C_4$)alkyl, ($C_1$-$C_4$)alkoxy, C(O)O(($C_1$-$C_4$)alkyl), S(($C_1$-$C_4$)alkyl), and N(($C_1$-$C_4$)alkyl)$_2$;

(H) $R^{15}$ and $R^{16}$ may together be a 4-membered saturated or unsaturated, hydrocarbyl link;

(I) $R^{17}$ is selected from the group consisting of the group consisting of H, F, Cl, Br, I, ($C_1$-$C_8$)alkyl, ($C_2$-$C_8$)alkenyl, ($C_2$-$C_4$)alkynyl, ($C_3$-$C_6$)cycloalkyl, ($C_1$-$C_4$)alkoxy, ($C_1$-$C_4$)haloalkyl, ($C_1$-$C_4$)haloalkoxy, ($C_1$-$C_8$)alkylphenyl, phenyl, and heterocyclyl, wherein each alkyl, alkenyl, alkynyl, cycloalkyl, alkoxy, haloalkyl, haloalkoxy, phenyl and heterocyclyl, are optionally substituted with one or more substituents independently selected from the group consisting of the group consisting of H, F, Cl, Br, I, ($C_1$-$C_8$)alkyl, ($C_3$-$C_6$)cycloalkyl, and S(($C_1$-$C_4$)alkyl); and (J) Q is selected from the group consisting of the group consisting of O and S.

22. A molecule according to claim 1 wherein:

(A) $R^1$, $R^2$, $R^3$, $R^4$, $R^5$, $R^6$, $R^7$, $R^9$, and $R^{10}$ are each independently selected from the group consisting of the group consisting of H, ($C_1$-$C_4$)haloalkyl, and ($C_1$-$C_4$)haloalkoxy;

(B) $R^8$ is H;

(C) L is a bond, ($C_1$)alkyl, or ($C_3$-$C_4$)alkyl;

(D) $R^{11}$ and $R^{12}$ are each independently selected from the group consisting of the group consisting of H, C(O)(($C_1$-$C_4$)alkyl), and $C(S)NH_2$;

(E) $X_1$ is selected from the group consisting of the group consisting of N and $CR^{13}$, wherein $R^{13}$ is selected from the group consisting of the group consisting of H and ($C_1$-$C_4$)alkyl;

(F) $X_2$ is selected from the group consisting of the group consisting of N and $CR^{16}$, wherein $R^{16}$ is selected from the group consisting of the group consisting of (H), H, F, Cl, Br, I, ($C_1$-$C_4$)alkyl, and ($C_1$-$C_4$)alkoxy;

(G) $R^{14}$ and $R^{15}$ are each independently selected from the group consisting of the group consisting of (H), H, F, Cl, Br, I, ($C_1$-$C_4$)alkyl, ($C_1$-$C_4$)alkoxy, and N(($C_1$-$C_4$)alkyl)$_2$;

(H) $R^{15}$ and $R^{16}$ may together be a 4-membered saturated or unsaturated, hydrocarbyl link;

(I) $R^{17}$ is selected from the group consisting of the group consisting of H, F, Cl, Br, I, ($C_1$-$C_8$)alkyl, ($C_2$-$C_8$)alkenyl, ($C_2$-$C_4$)alkynyl, ($C_3$-$C_6$)cycloalkyl, ($C_1$-$C_4$)alkoxy, ($C_1$-$C_4$)haloalkyl, ($C_1$-$C_4$)haloalkoxy, ($C_1$-$C_8$)alkylphenyl, phenyl, and heterocyclyl, wherein each alkyl, alkenyl, alkynyl, cycloalkyl, alkoxy, haloalkyl, haloalkoxy, phenyl and heterocyclyl, are optionally substituted with one or more substituents independently selected from the group consisting of the group consisting of H, F, Cl, Br, I, ($C_1$-$C_8$)alkyl, ($C_3$-$C_6$)cycloalkyl, and S(($C_1$-$C_4$)alkyl); and (J) Q is selected from the group consisting of the group consisting of O and S.

23. A molecule according to claim 1 wherein:

(A) $R^1$, $R^2$, $R^3$, $R^4$, $R^5$, $R^6$, $R^7$, $R^9$, and $R^{10}$ are each independently selected from the group consisting of the group consisting of H, ($C_1$-$C_4$)haloalkyl, or ($C_1$-$C_4$)haloalkoxy;

(B) $R^8$ is H;

(C) L is a bond, ($C_1$)alkyl, or ($C_3$-$C_4$)alkyl;

(D) $R^{11}$ and $R^{12}$ are each independently selected from the group consisting of H and $C(S)NH_2$;

(E) $X_1$ is selected from the group consisting of N and $CR^{13}$, wherein $R^{13}$ is selected from the group consisting of H and ($C_1$-$C_4$)alkyl;

(F) $X_2$ is selected from the group consisting of N and $CR^{16}$, wherein R¹⁶ is selected from the group consisting of (H), H, F, Cl, Br, I, and $(C_1-C_4)$alkoxy;

(G) $R^{14}$ and $R^{15}$ are each independently selected from the group consisting of (H), H, F, Cl, Br, I, $(C_1-C_4)$alkyl, and $(C_1-C_4)$alkoxy;

(H) $R^{15}$ and $R^{16}$ may together be a 4-membered saturated or unsaturated, hydrocarbyl link;

(I) $R^{17}$ is selected from the group consisting of H, F, Cl, Br, I, $(C_1-C_8)$alkyl, $(C_2-C_8)$alkenyl, $(C_2-C_4)$alkynyl, $(C_3-C_6)$cycloalkyl, $(C_1-C_4)$alkoxy, $(C_1-C_4)$haloalkyl, $(C_1-C_4)$haloalkoxy, $(C_1-C_8)$alkylphenyl, phenyl, and heterocyclyl, wherein each alkyl, alkenyl, alkynyl, cycloalkyl, alkoxy, haloalkyl, haloalkoxy, phenyl and heterocyclyl, are optionally substituted with one or more substituents independently selected from the group consisting of H, F, Cl, Br, I, $(C_1-C_8)$alkyl, $(C_3-C_6)$cycloalkyl, and $S((C_1-C_4)$alkyl); and (J) Q is selected from the group consisting of O and S.

24. A molecule according to claim 1 wherein:

(A) $R^1$, $R^2$, $R^3$, $R^4$, $R^5$, $R^6$, $R^7$, $R^9$, and $R^{10}$ are each independently selected from the group consisting of H and $(C_1-C_4)$haloalkoxy;

(B) $R^8$ is H;

(C) L is a bond, $(C_1)$alkyl, or $(C_3-C_4)$alkyl;

(D) $R^{11}$ and $R^{12}$ are each independently selected from the group consisting of H and $C(S)NH_2$;

(E) $X_1$ is selected from the group consisting of N and $CR^{13}$, wherein $R^{13}$ is H;

(F) $X_2$ is $CR^{16}$, wherein $R^{16}$ is selected from the group consisting of (H), H, F, Cl, Br, I, and $(C_1-C_4)$ alkoxy;

(G) $R^{14}$ and $R^{15}$ are each independently selected from the group consisting of (H), H, F, Cl, Br, I, $(C_1-C_4)$alkyl, and $(C_1-C_4)$alkoxy;

(H) $R^{15}$ and $R^{16}$ may together be a 4-membered saturated or unsaturated, hydrocarbyl link;

(I) $R^{17}$ is selected from the group consisting of H, $(C_1-C_8)$ alkyl, $(C_3-C_6)$cycloalkyl, phenyl, and heterocyclyl;

wherein each alkyl, alkenyl, alkynyl, cycloalkyl, alkoxy, haloalkyl, haloalkoxy, phenyl and heterocyclyl, are optionally substituted with one or more substituents independently selected from the group consisting of H, $(C_1-C_8)$ alkyl, and $(C_3-C_6)$cycloalkyl; and (J) Q is selected from the group consisting of O and S.

25. A molecule according to claim 1 wherein said molecule is selected from the group consisting of one of the following molecules

| No. | Structure |
|---|---|
| F1 | 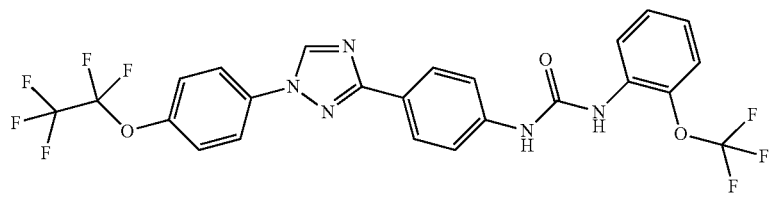 [SMILES: O=C(Nc1ccc(-c2ncn(-c3ccc(OC(F)(F)C(F)(F)F)cc3)n2)cc1)Nc1ccccc1OC(F)(F)F] |
| F2 | 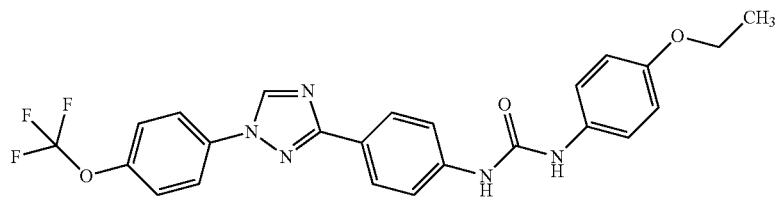 [SMILES: CCOc1ccc(NC(=O)Nc2ccc(-c3ncn(-c4ccc(OC(F)(F)F)cc4)n3)cc2)cc1] |
| F3 | 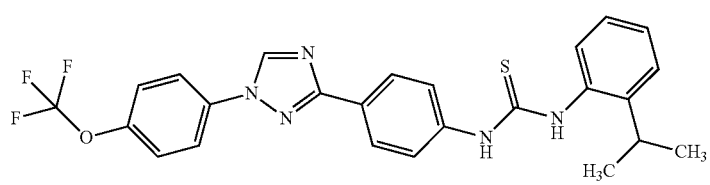 [SMILES: CC(C)c1ccccc1NC(=S)Nc1ccc(-c2ncn(-c3ccc(OC(F)(F)F)cc3)n2)cc1] |
| F4 | 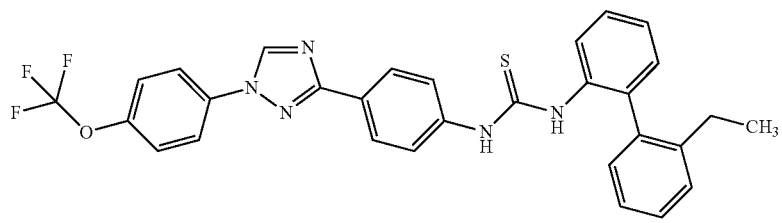 |

-continued
| No. | Structure |
|---|---|
| F5 | 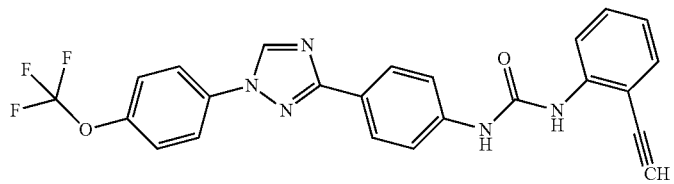 [SMILES: C#Cc1ccccc1NC(=O)Nc1ccc(-c2ncn(-c3ccc(OC(F)(F)F)cc3)n2)cc1] |
| F6 | 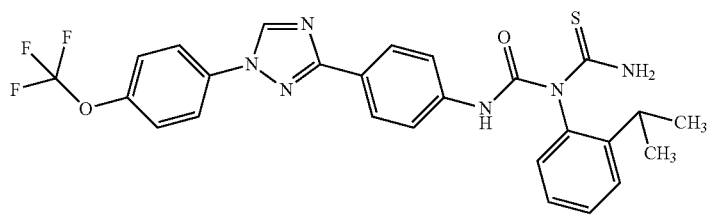 [SMILES: CC(C)c1ccccc1N(C(=O)Nc1ccc(-c2ncn(-c3ccc(OC(F)(F)F)cc3)n2)cc1)C(N)=S] |
| F7 | 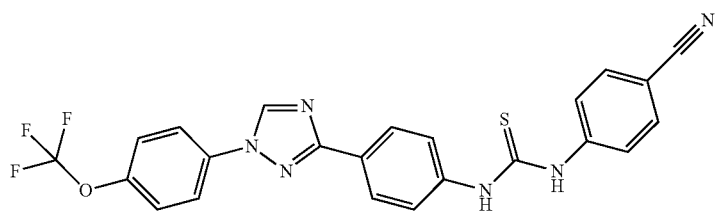 [SMILES: N#Cc1ccc(NC(=S)Nc2ccc(-c3ncn(-c4ccc(OC(F)(F)F)cc4)n3)cc2)cc1] |
| F8 | 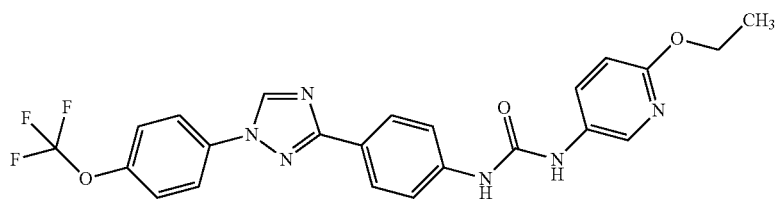 |
| F9 | 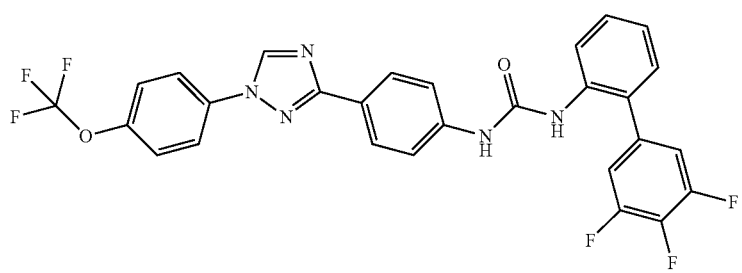 [SMILES: O=C(Nc1ccc(-c2ncn(-c3ccc(OC(F)(F)F)cc3)n2)cc1)Nc1ccccc1-c1cc(F)c(F)c(F)c1] |
| F10 | 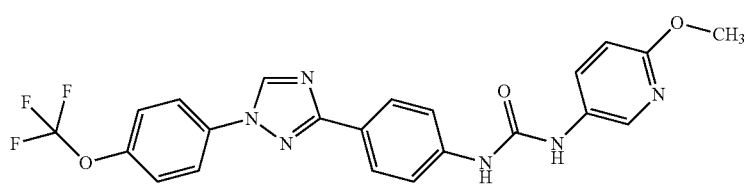 [SMILES: COc1ccc(NC(=O)Nc2ccc(-c3ncn(-c4ccc(OC(F)(F)F)cc4)n3)cc2)cn1] |
| F11 | 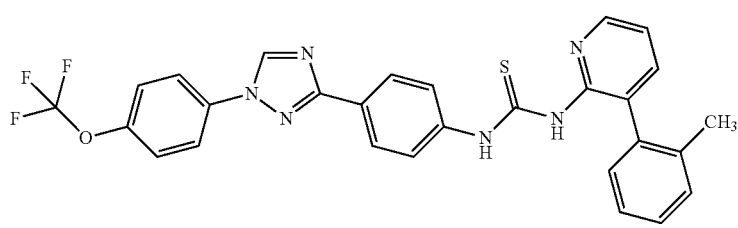 [SMILES: Cc1ccccc1-c1cccnc1NC(=S)Nc1ccc(-c2ncn(-c3ccc(OC(F)(F)F)cc3)n2)cc1] |

| No. | Structure |
|---|---|
| F12 | 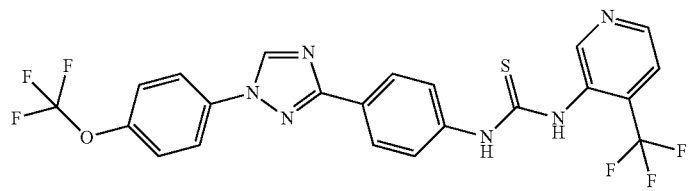 [SMILES: FC(F)(F)Oc1ccc(-n2cnc(-c3ccc(NC(=S)Nc4cnccc4C(F)(F)F)cc3)n2)cc1] |
| F13 | 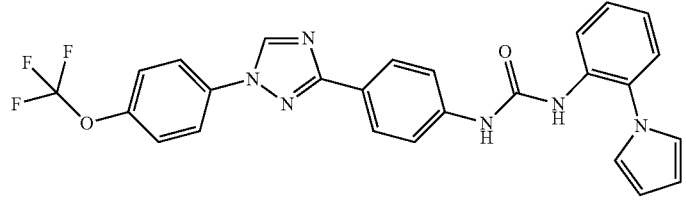 |
| F14 | 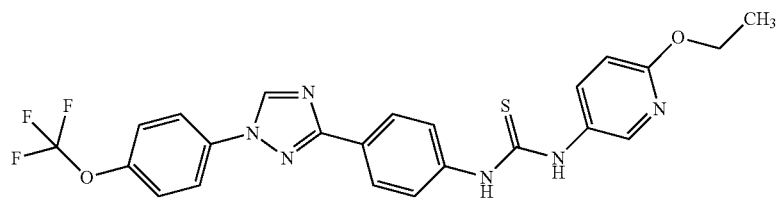 [SMILES: CCOc1ccc(NC(=S)Nc2ccc(-c3ncn(-c4ccc(OC(F)(F)F)cc4)n3)cc2)cn1] |
| F15 | 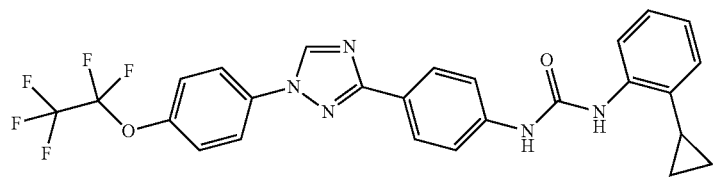 [SMILES: O=C(Nc1ccc(-c2ncn(-c3ccc(OC(F)(F)C(F)(F)F)cc3)n2)cc1)Nc1ccccc1C1CC1] |
| F16 | 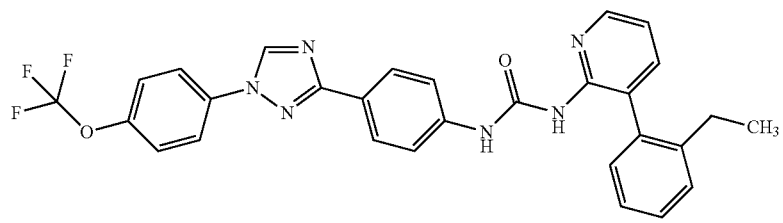 |
| F17 | 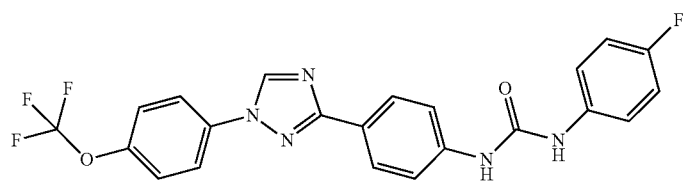 [SMILES: O=C(Nc1ccc(F)cc1)Nc1ccc(-c2ncn(-c3ccc(OC(F)(F)F)cc3)n2)cc1] |
| F18 | 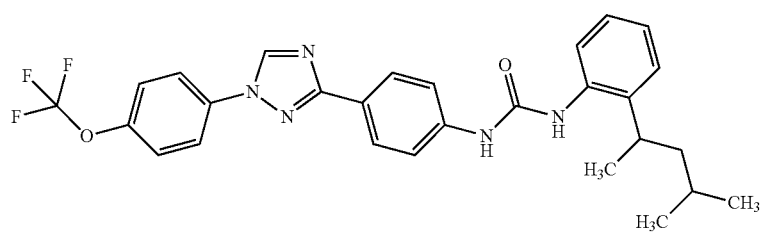 |

-continued
| No. | Structure |
|---|---|
| F19 | 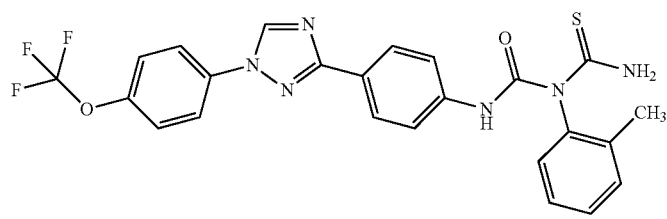 [SMILES: Cc1ccccc1N(C(=O)Nc1ccc(-c2ncn(-c3ccc(OC(F)(F)F)cc3)n2)cc1)C(N)=S] |
| F20 | 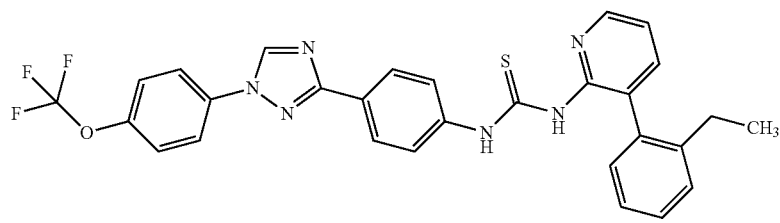 |
| F21 | 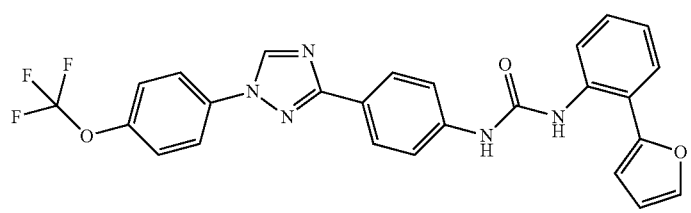 [SMILES: O=C(Nc1ccc(-c2ncn(-c3ccc(OC(F)(F)F)cc3)n2)cc1)Nc1ccccc1-c1ccco1] |
| F22 | 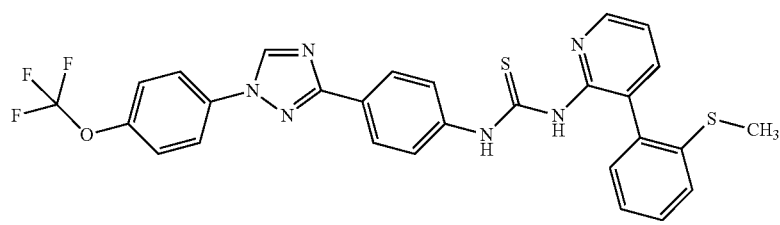 |
| F23 | 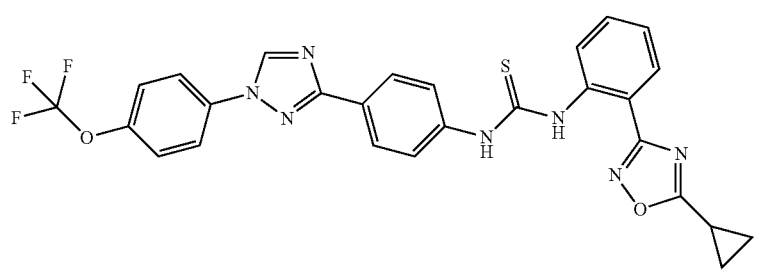 |
| F24 | 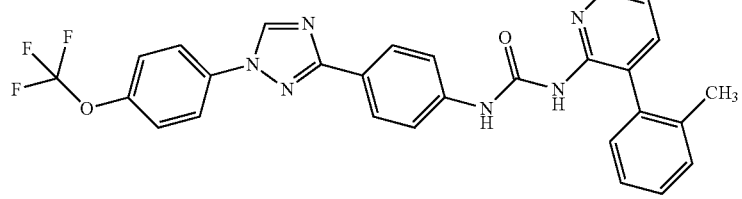 |
| F25 | 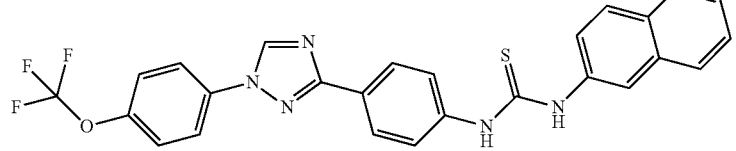 |

| No. | Structure |
|---|---|
| F26 | 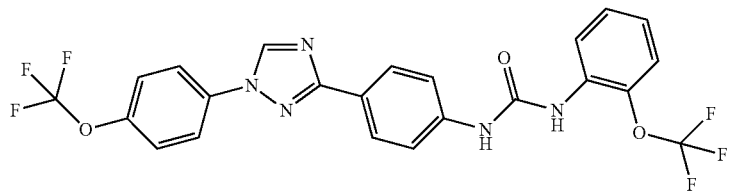 [SMILES: O=C(Nc1ccc(-c2ncn(-c3ccc(OC(F)(F)F)cc3)n2)cc1)Nc1ccccc1OC(F)(F)F] |
| F27 | 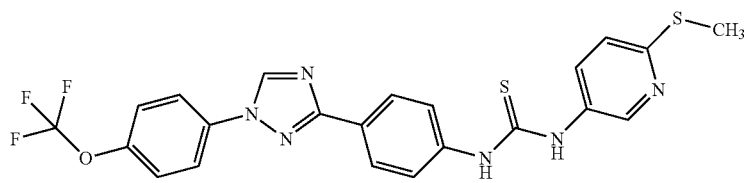 [SMILES: CSc1ccc(NC(=S)Nc2ccc(-c3ncn(-c4ccc(OC(F)(F)F)cc4)n3)cc2)cn1] |
| F28 | 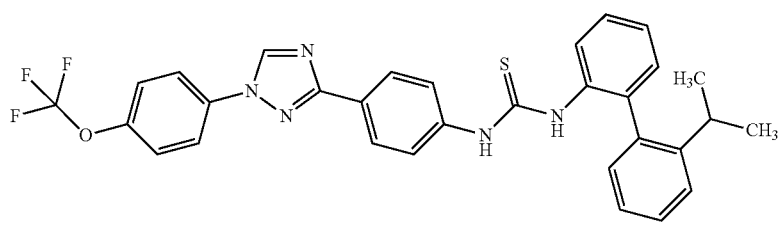 |
| F29 | 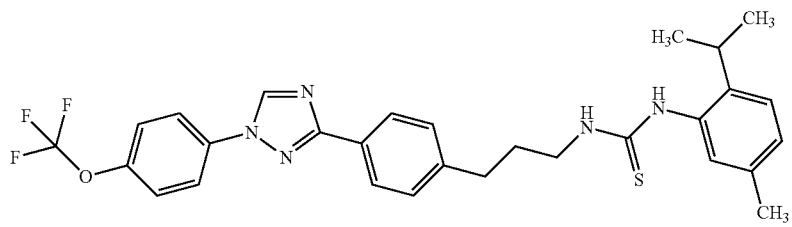 [SMILES: Cc1ccc(C(C)C)c(NC(=S)NCCCc2ccc(-c3ncn(-c4ccc(OC(F)(F)F)cc4)n3)cc2)c1] |
| F30 | 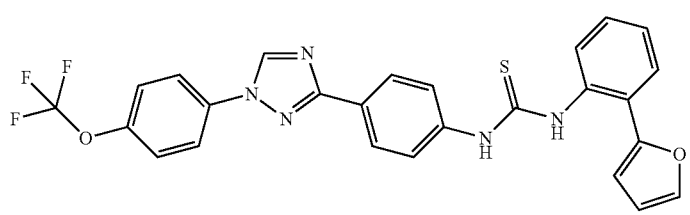 |
| F31 | 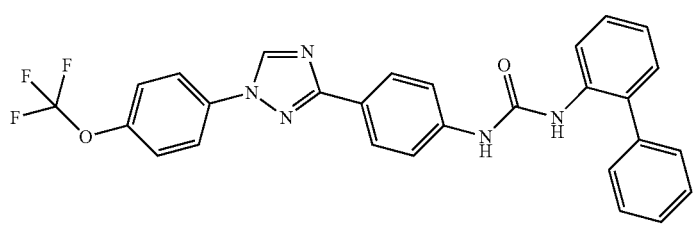 |
| F32 | 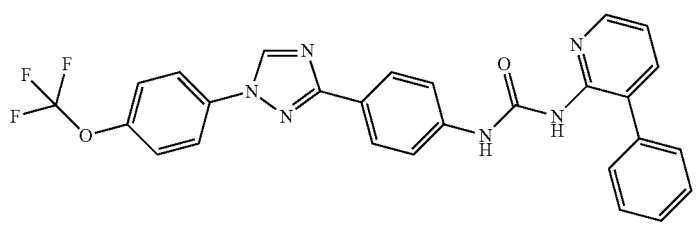 |

| No. | Structure |
|---|---|
| F33 | 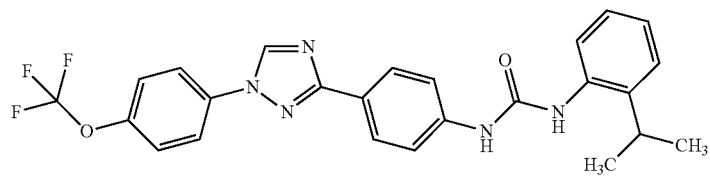 [SMILES: CC(C)c1ccccc1NC(=O)Nc1ccc(-c2ncn(-c3ccc(OC(F)(F)F)cc3)n2)cc1] |
| F34 | 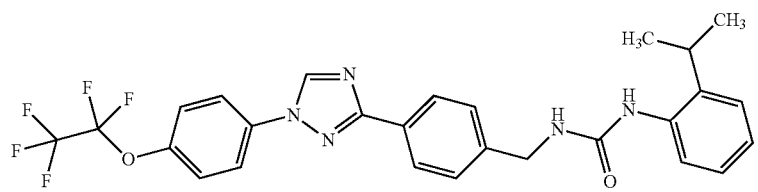 [SMILES: CC(C)c1ccccc1NC(=O)NCc1ccc(-c2ncn(-c3ccc(OC(F)(F)C(F)(F)F)cc3)n2)cc1] |
| F35 | 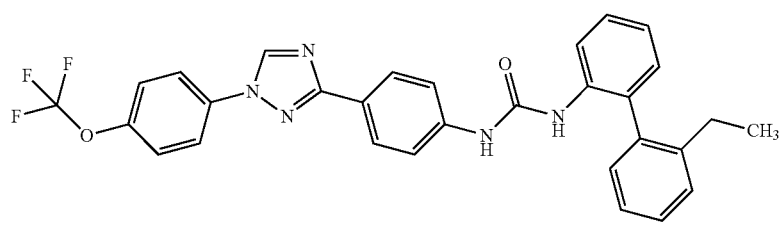 [SMILES: CCc1ccccc1-c1ccccc1NC(=O)Nc1ccc(-c2ncn(-c3ccc(OC(F)(F)F)cc3)n2)cc1] |
| F36 | 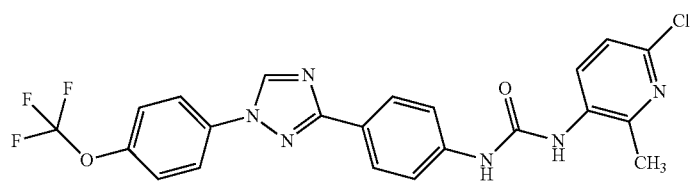 [SMILES: Cc1nc(Cl)ccc1NC(=O)Nc1ccc(-c2ncn(-c3ccc(OC(F)(F)F)cc3)n2)cc1] |
| F37 | 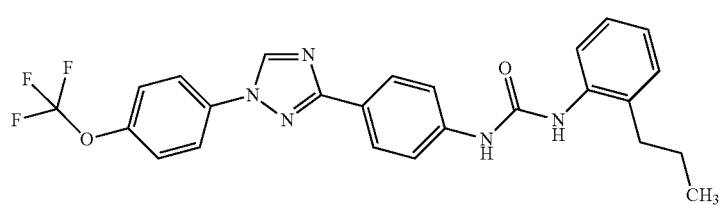 [SMILES: CCCc1ccccc1NC(=O)Nc1ccc(-c2ncn(-c3ccc(OC(F)(F)F)cc3)n2)cc1] |
| F38 | 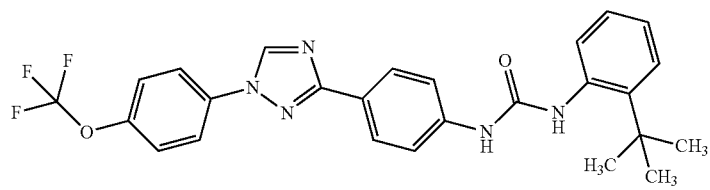 [SMILES: CC(C)(C)c1ccccc1NC(=O)Nc1ccc(-c2ncn(-c3ccc(OC(F)(F)F)cc3)n2)cc1] |
| F39 | 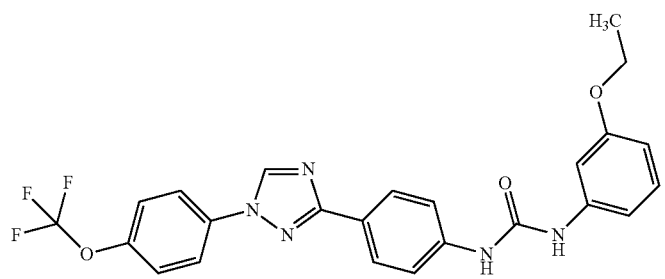 [SMILES: CCOc1cccc(NC(=O)Nc2ccc(-c3ncn(-c4ccc(OC(F)(F)F)cc4)n3)cc2)c1] |

-continued
| No. | Structure |
|---|---|
| F40 | 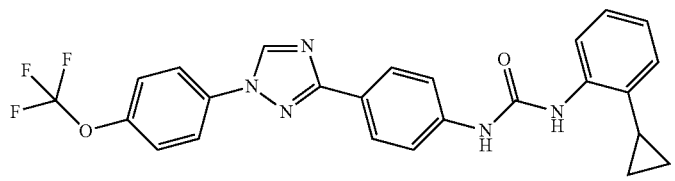 [SMILES: O=C(Nc1ccc(-c2ncn(-c3ccc(OC(F)(F)F)cc3)n2)cc1)Nc1ccccc1C1CC1] |
| F41 | 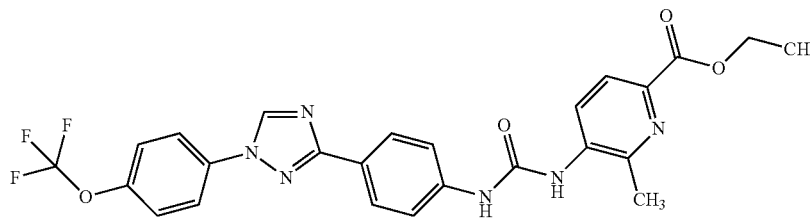 [SMILES: CCOC(=O)c1ccc(NC(=O)Nc2ccc(-c3ncn(-c4ccc(OC(F)(F)F)cc4)n3)cc2)c(C)n1] |
| F42 | 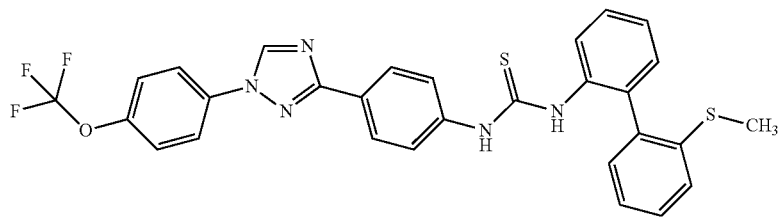 [SMILES: CSc1ccccc1-c1ccccc1NC(=S)Nc1ccc(-c2ncn(-c3ccc(OC(F)(F)F)cc3)n2)cc1] |
| F43 | 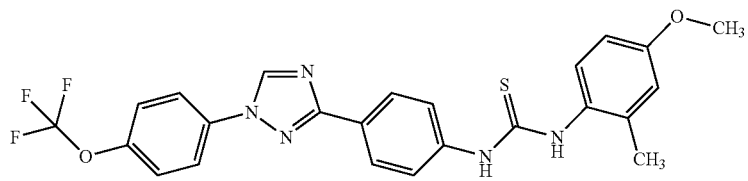 [SMILES: COc1ccc(NC(=S)Nc2ccc(-c3ncn(-c4ccc(OC(F)(F)F)cc4)n3)cc2)c(C)c1] |
| F44 | 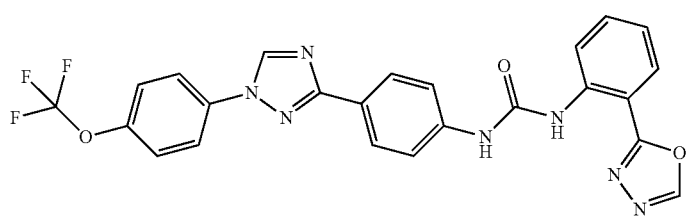 [SMILES: O=C(Nc1ccc(-c2ncn(-c3ccc(OC(F)(F)F)cc3)n2)cc1)Nc1ccccc1-c1nnco1] |
| F45 | 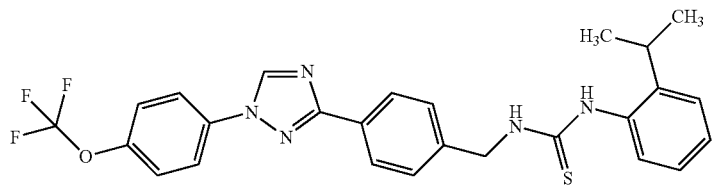 |
| F46 | 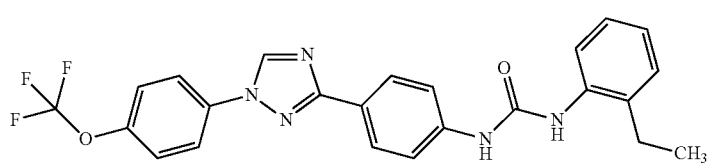 [SMILES: CCc1ccccc1NC(=O)Nc1ccc(-c2ncn(-c3ccc(OC(F)(F)F)cc3)n2)cc1] |

-continued
| No. | Structure |
|---|---|
| F47 | 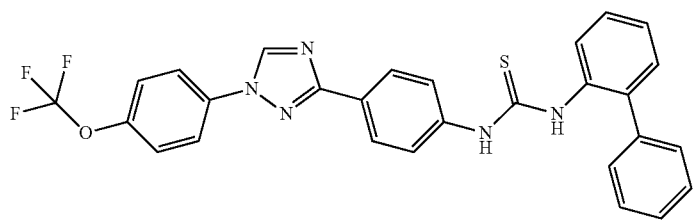 |
| F48 | 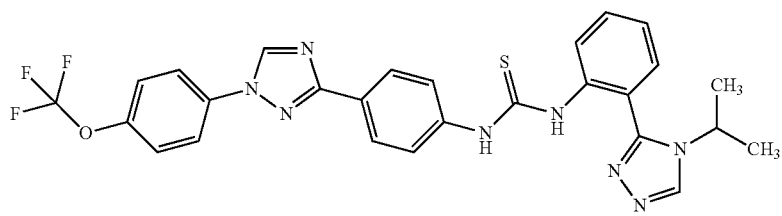 [SMILES: CC(C)n1cnnc1-c1ccccc1NC(=S)Nc1ccc(-c2ncn(-c3ccc(OC(F)(F)F)cc3)n2)cc1] |
| F49 | 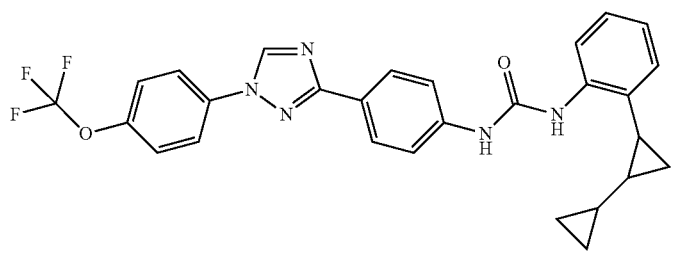 [SMILES: O=C(Nc1ccc(-c2ncn(-c3ccc(OC(F)(F)F)cc3)n2)cc1)Nc1ccccc1C1CC1C1CC1] |
| F50 | 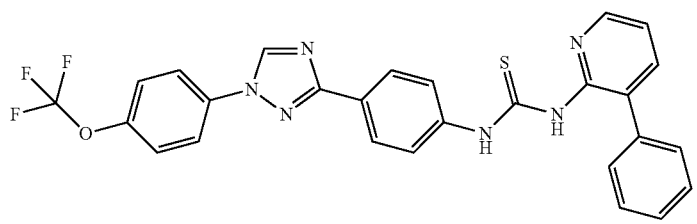 |
| F51 | 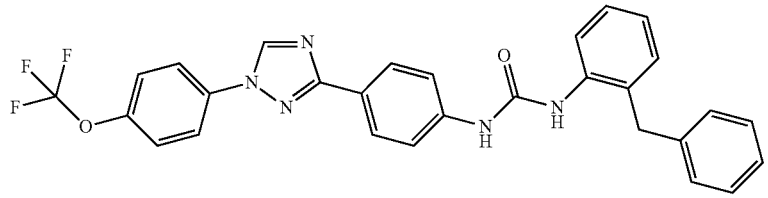 |
| F52 | 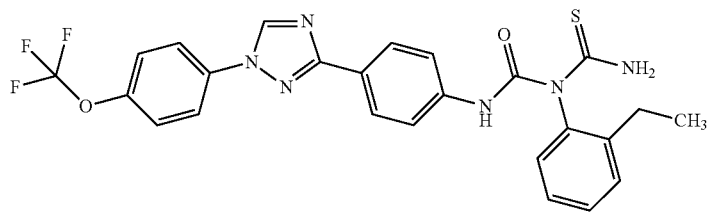 [SMILES: CCc1ccccc1N(C(=O)Nc1ccc(-c2ncn(-c3ccc(OC(F)(F)F)cc3)n2)cc1)C(N)=S] |
| F53 | 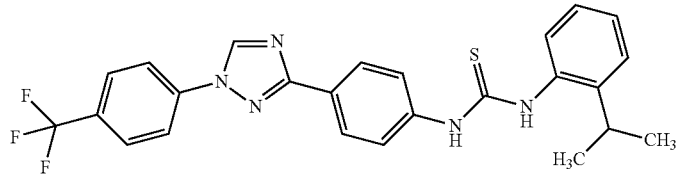 |

| No. | Structure |
|---|---|
| F54 | 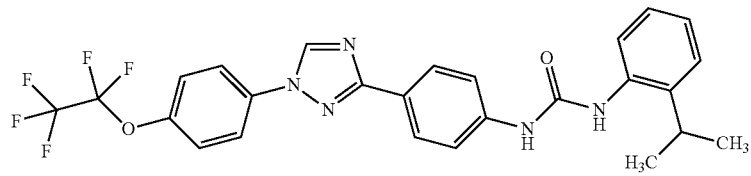 [SMILES: CC(C)c1ccccc1NC(=O)Nc1ccc(-c2ncn(-c3ccc(OC(F)(F)C(F)(F)F)cc3)n2)cc1] |
| F55 | 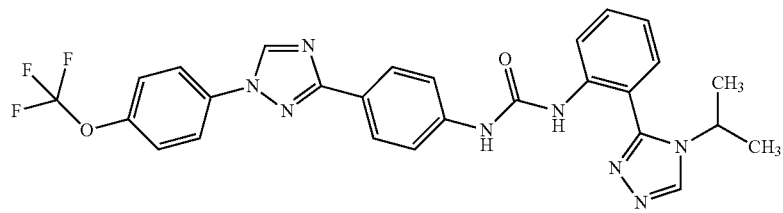 |
| F56 | 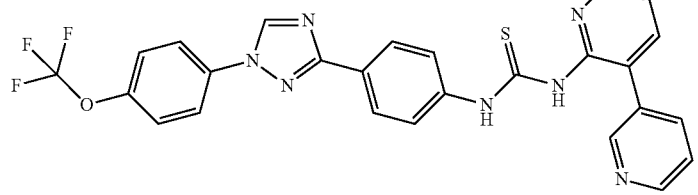 |
| F57 | 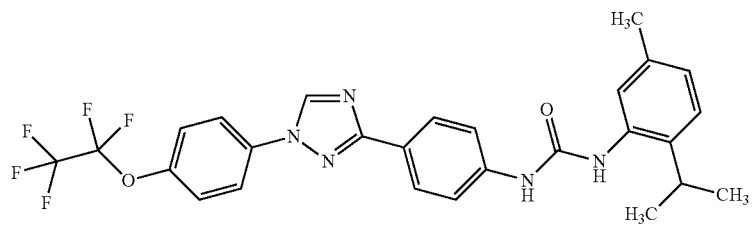 [SMILES: Cc1ccc(C(C)C)c(NC(=O)Nc2ccc(-c3ncn(-c4ccc(OC(F)(F)C(F)(F)F)cc4)n3)cc2)c1] |
| F58 | 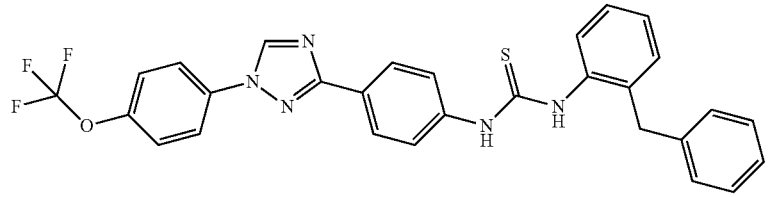 |
| F59 | 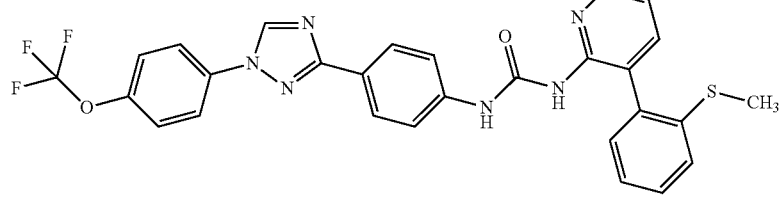 |
| F60 | 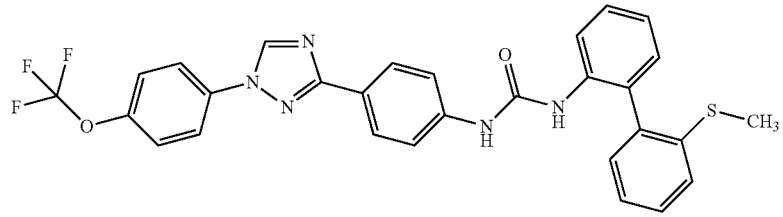 [SMILES: CSc1ccccc1-c1ccccc1NC(=O)Nc1ccc(-c2ncn(-c3ccc(OC(F)(F)F)cc3)n2)cc1] |

-continued
| No. | Structure |
|---|---|
| F61 | 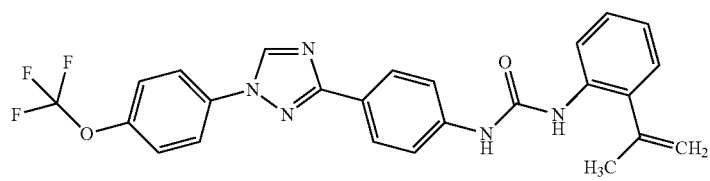 |
| F62 | 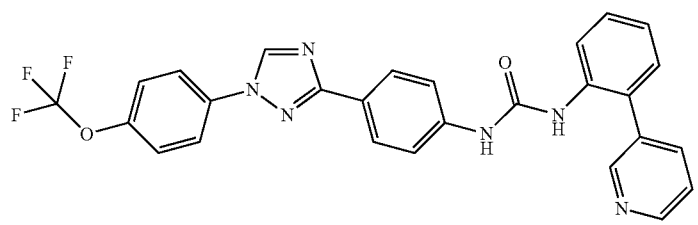 |
| F63 | 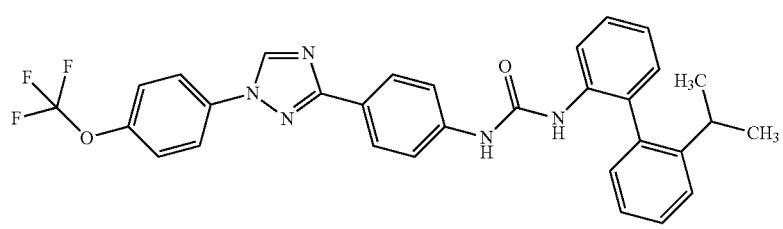 |
| F64 | 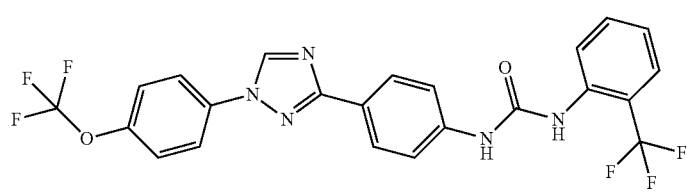 [SMILES: O=C(Nc1ccc(-c2ncn(-c3ccc(OC(F)(F)F)cc3)n2)cc1)Nc1ccccc1C(F)(F)F] |
| F65 | 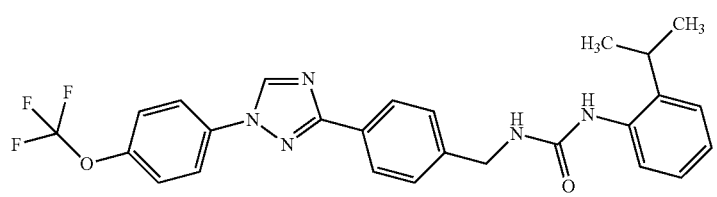 |
| F66 | 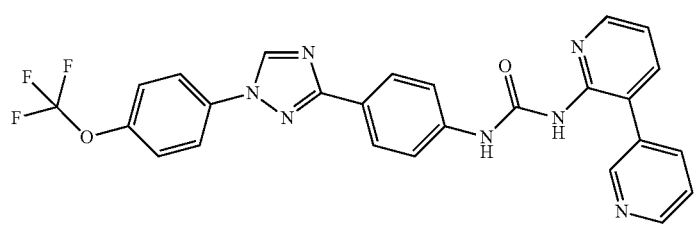 |
| F67 | 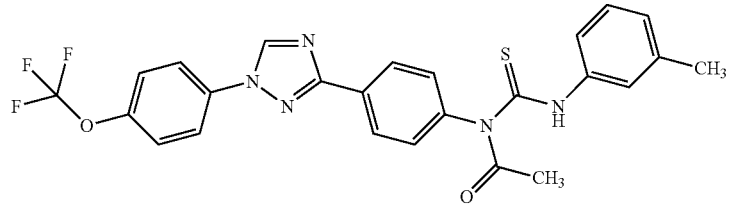 [SMILES: CC(=O)N(C(=S)Nc1cccc(C)c1)c1ccc(-c2ncn(-c3ccc(OC(F)(F)F)cc3)n2)cc1] |

| No. | Structure |
|---|---|
| F68 | 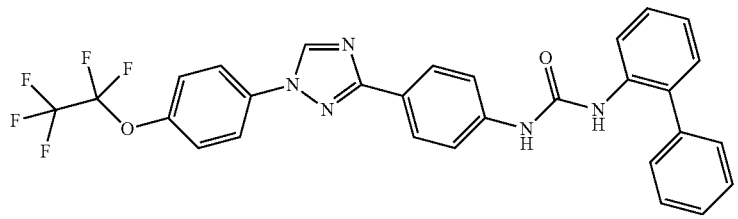 [SMILES: O=C(Nc1ccc(-c2ncn(-c3ccc(OC(F)(F)C(F)(F)F)cc3)n2)cc1)Nc1ccccc1-c1ccccc1] |
| F69 | 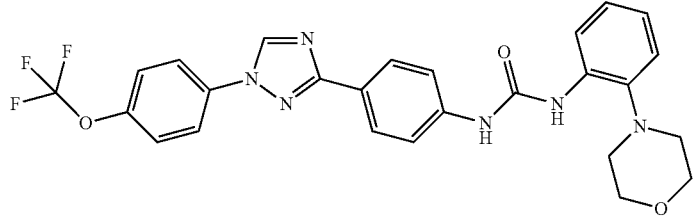 [SMILES: O=C(Nc1ccc(-c2ncn(-c3ccc(OC(F)(F)F)cc3)n2)cc1)Nc1ccccc1N1CCOCC1] |
| F70 | 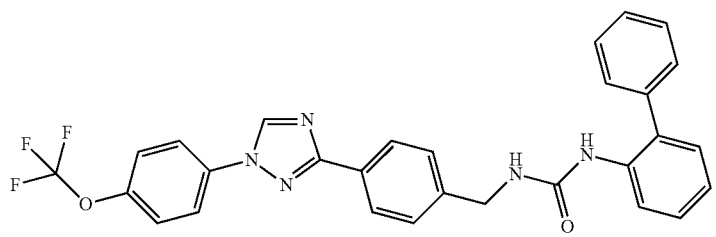 |
| F71 | 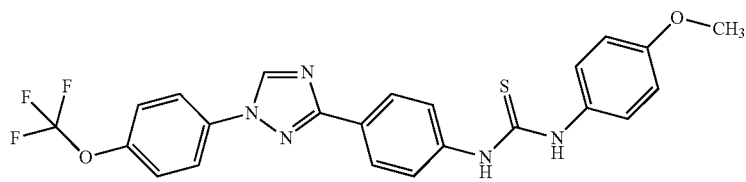 [SMILES: COc1ccc(NC(=S)Nc2ccc(-c3ncn(-c4ccc(OC(F)(F)F)cc4)n3)cc2)cc1] |
| F72 | 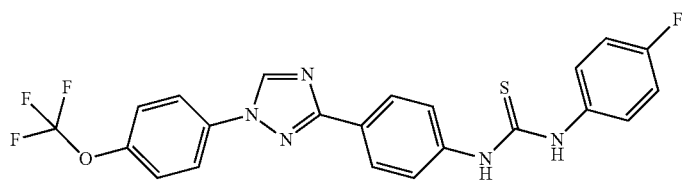 [SMILES: Fc1ccc(NC(=S)Nc2ccc(-c3ncn(-c4ccc(OC(F)(F)F)cc4)n3)cc2)cc1] |
| F73 | 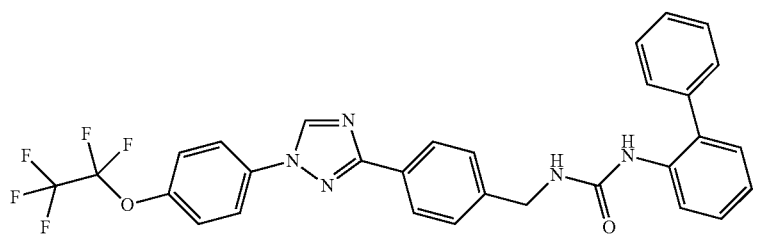 [SMILES: O=C(NCc1ccc(-c2ncn(-c3ccc(OC(F)(F)C(F)(F)F)cc3)n2)cc1)Nc1ccccc1-c1ccccc1] |
| F74 | 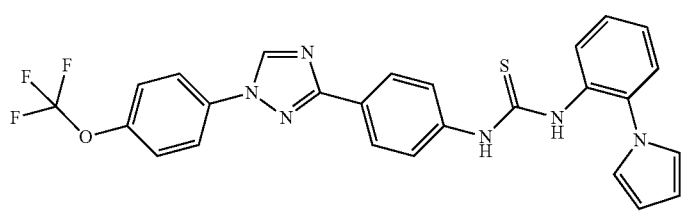 [SMILES: FC(F)(F)Oc1ccc(-n2cnc(-c3ccc(NC(=S)Nc4ccccc4-n4cccc4)cc3)n2)cc1] |

-continued
| No. | Structure |
|---|---|
| F75 | 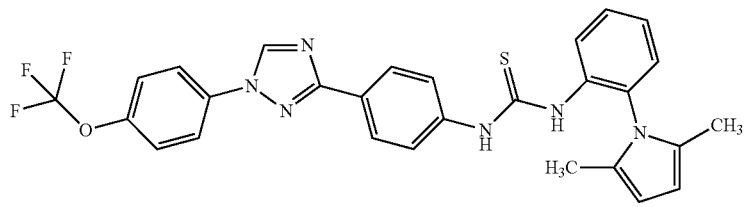 [SMILES: Cc1ccc(C)n1-c1ccccc1NC(=S)Nc1ccc(-c2ncn(-c3ccc(OC(F)(F)F)cc3)n2)cc1] |
| F76 | 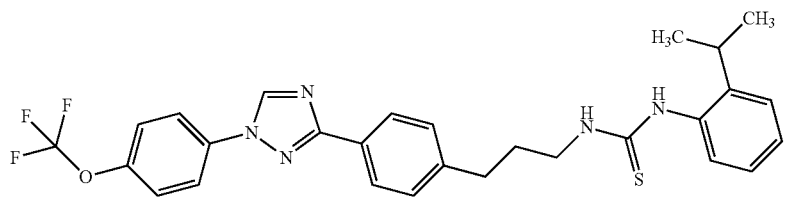 [SMILES: CC(C)c1ccccc1NC(=S)NCCCc1ccc(-c2ncn(-c3ccc(OC(F)(F)F)cc3)n2)cc1] |
| F77 | 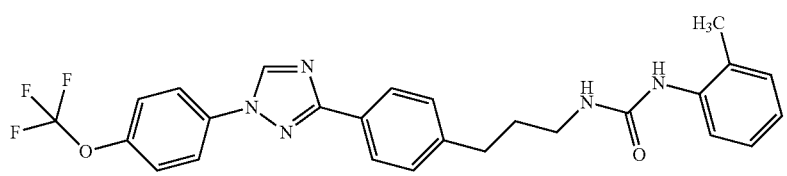 [SMILES: Cc1ccccc1NC(=O)NCCCc1ccc(-c2ncn(-c3ccc(OC(F)(F)F)cc3)n2)cc1] |
| F78 | 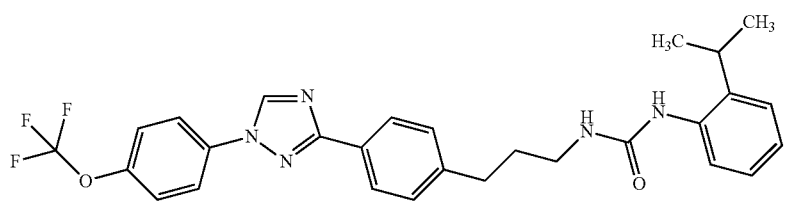 [SMILES: CC(C)c1ccccc1NC(=O)NCCCc1ccc(-c2ncn(-c3ccc(OC(F)(F)F)cc3)n2)cc1] |
| F79 | 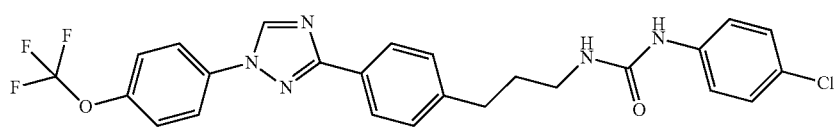 [SMILES: O=C(NCCCc1ccc(-c2ncn(-c3ccc(OC(F)(F)F)cc3)n2)cc1)Nc1ccc(Cl)cc1] |
| F80 | 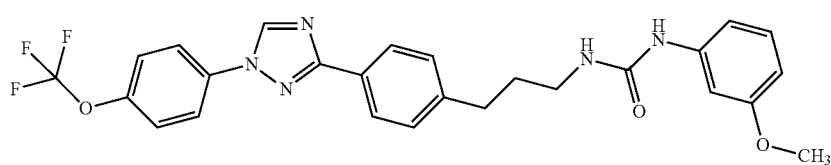 [SMILES: COc1cccc(NC(=O)NCCCc2ccc(-c3ncn(-c4ccc(OC(F)(F)F)cc4)n3)cc2)c1] |
| F81 | 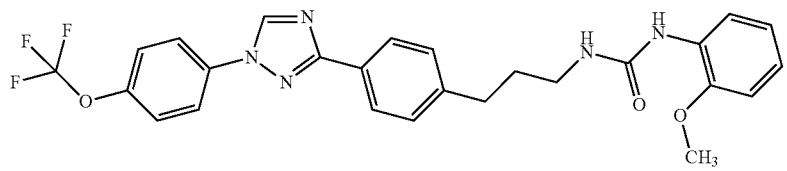 [SMILES: COc1ccccc1NC(=O)NCCCc1ccc(-c2ncn(-c3ccc(OC(F)(F)F)cc3)n2)cc1] |
| F82 | 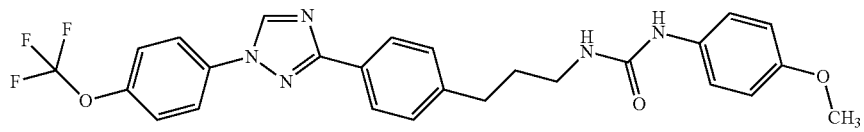 [SMILES: COc1ccc(NC(=O)NCCCc2ccc(-c3ncn(-c4ccc(OC(F)(F)F)cc4)n3)cc2)cc1] |
| F83 | 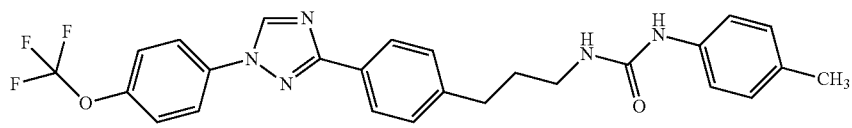 [SMILES: Cc1ccc(NC(=O)NCCCc2ccc(-c3ncn(-c4ccc(OC(F)(F)F)cc4)n3)cc2)cc1] |

-continued
| No. | Structure |
|---|---|
| F84 | 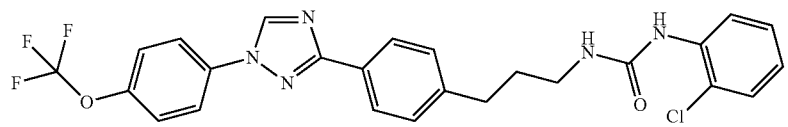 [SMILES: O=C(NCCCc1ccc(-c2ncn(-c3ccc(OC(F)(F)F)cc3)n2)cc1)Nc1ccccc1Cl] |
| F85 | 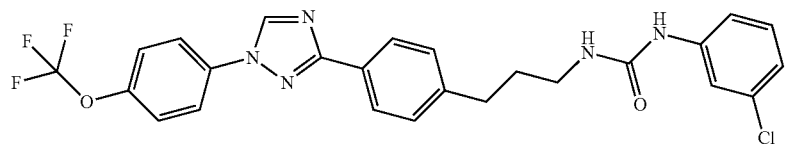 [SMILES: O=C(NCCCc1ccc(-c2ncn(-c3ccc(OC(F)(F)F)cc3)n2)cc1)Nc1cccc(Cl)c1] |
| F86 | 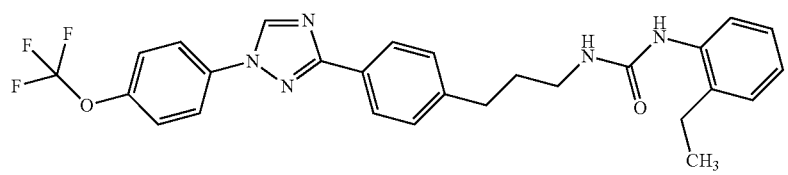 [SMILES: CCc1ccccc1NC(=O)NCCCc1ccc(-c2ncn(-c3ccc(OC(F)(F)F)cc3)n2)cc1] |
| F87 | 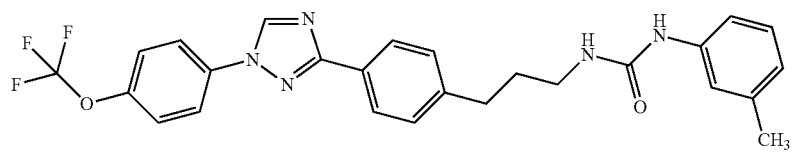 [SMILES: Cc1cccc(NC(=O)NCCCc2ccc(-c3ncn(-c4ccc(OC(F)(F)F)cc4)n3)cc2)c1] |
| F88 | 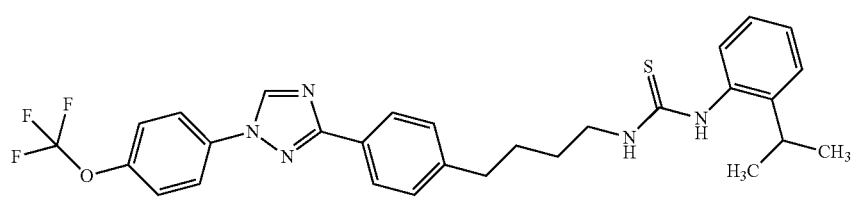 |
| F89 | 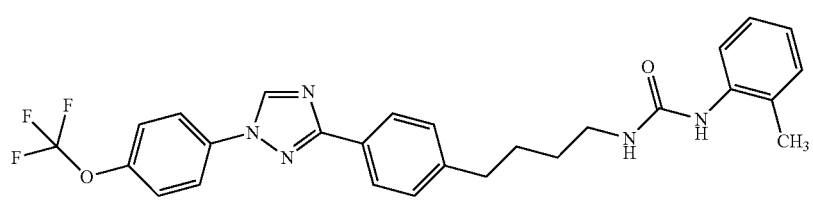 [SMILES: Cc1ccccc1NC(=O)NCCCCc1ccc(-c2ncn(-c3ccc(OC(F)(F)F)cc3)n2)cc1] |
| F90 | 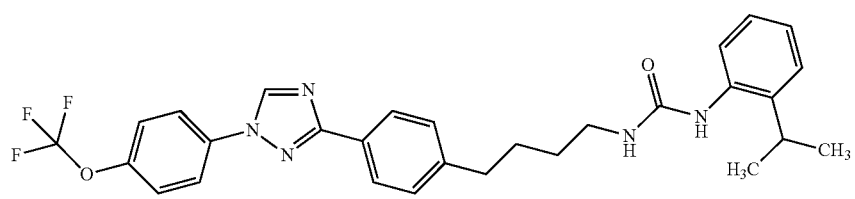 [SMILES: CC(C)c1ccccc1NC(=O)NCCCCc1ccc(-c2ncn(-c3ccc(OC(F)(F)F)cc3)n2)cc1] |
| F91 | 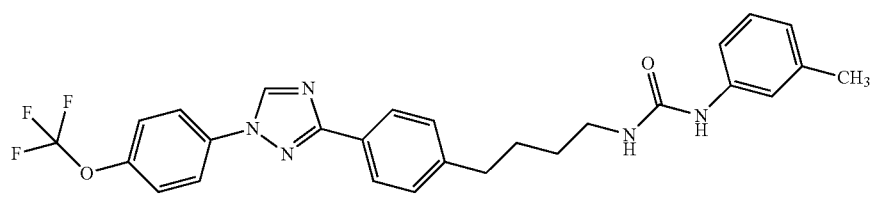 [SMILES: Cc1cccc(NC(=O)NCCCCc2ccc(-c3ncn(-c4ccc(OC(F)(F)F)cc4)n3)cc2)c1] |

| No. | Structure |
|---|---|
| F92 | 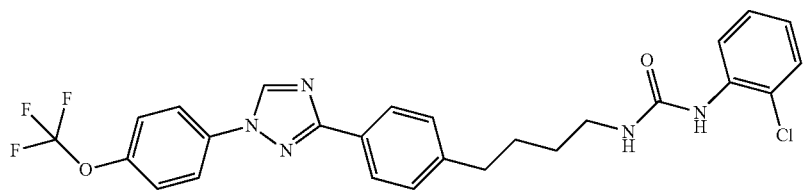 [SMILES: O=C(NCCCCc1ccc(-c2ncn(-c3ccc(OC(F)(F)F)cc3)n2)cc1)Nc1ccccc1Cl] |
| F93 | 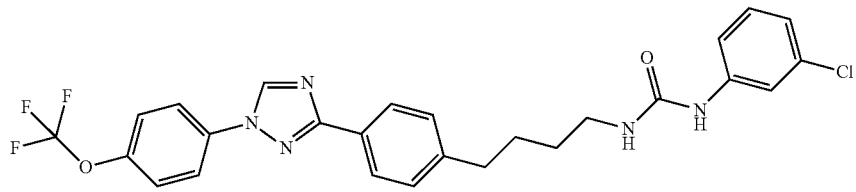 [SMILES: O=C(NCCCCc1ccc(-c2ncn(-c3ccc(OC(F)(F)F)cc3)n2)cc1)Nc1cccc(Cl)c1] |
| F94 | 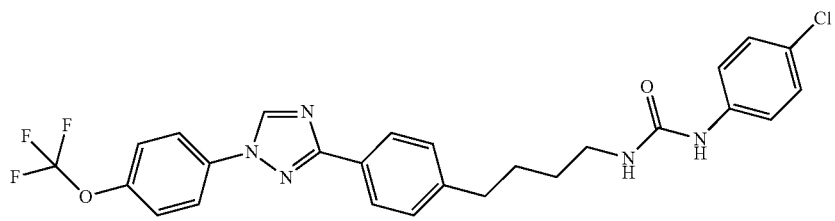 [SMILES: O=C(NCCCCc1ccc(-c2ncn(-c3ccc(OC(F)(F)F)cc3)n2)cc1)Nc1ccc(Cl)cc1] |
| F95 | 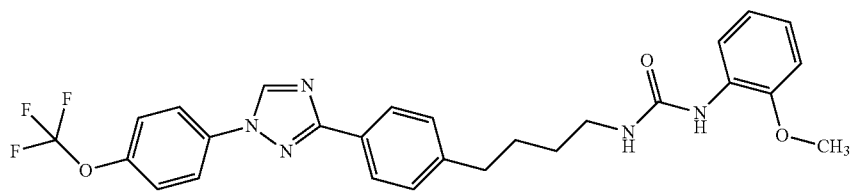 |
| F96 | 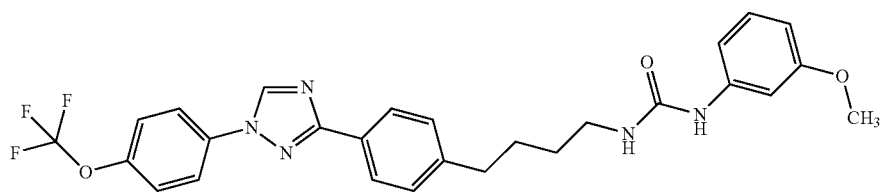 [SMILES: COc1cccc(NC(=O)NCCCCc2ccc(-c3ncn(-c4ccc(OC(F)(F)F)cc4)n3)cc2)c1] |
| F97 | 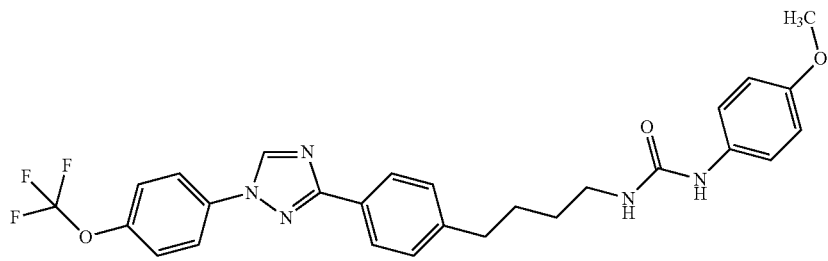 [SMILES: COc1ccc(NC(=O)NCCCCc2ccc(-c3ncn(-c4ccc(OC(F)(F)F)cc4)n3)cc2)cc1] |
| F98 | 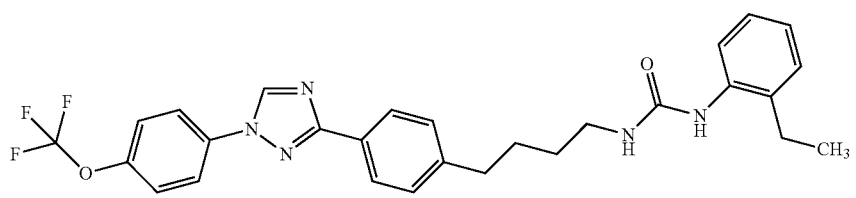 |

-continued
| No. | Structure |
|---|---|
| F99 | 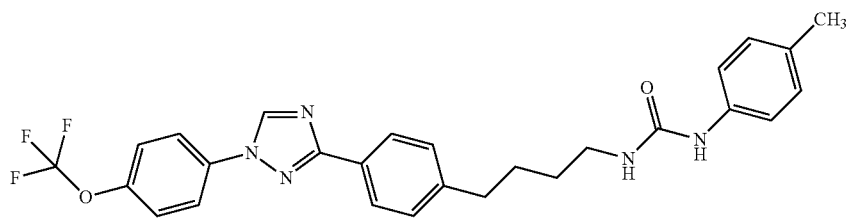 [SMILES: Cc1ccc(NC(=O)NCCCCc2ccc(-c3ncn(-c4ccc(OC(F)(F)F)cc4)n3)cc2)cc1] |
| F100 | 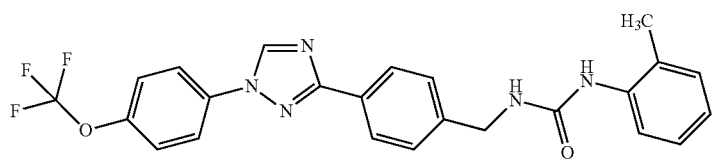 [SMILES: Cc1ccccc1NC(=O)NCc1ccc(-c2ncn(-c3ccc(OC(F)(F)F)cc3)n2)cc1] |
| F101 | 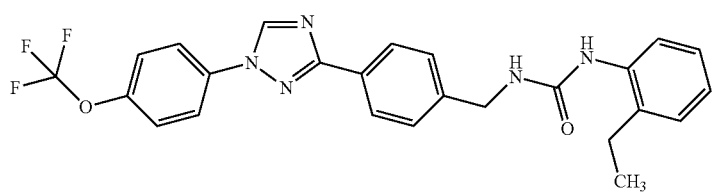 |
| F102 | 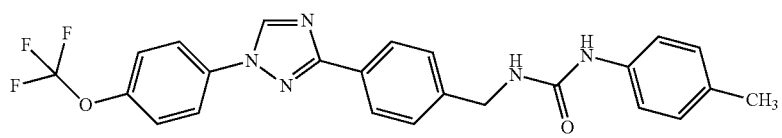 [SMILES: Cc1ccc(NC(=O)NCc2ccc(-c3ncn(-c4ccc(OC(F)(F)F)cc4)n3)cc2)cc1] |
| F103 | 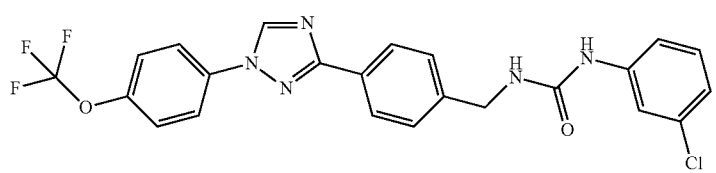 [SMILES: O=C(NCc1ccc(-c2ncn(-c3ccc(OC(F)(F)F)cc3)n2)cc1)Nc1cccc(Cl)c1] |
| F104 | 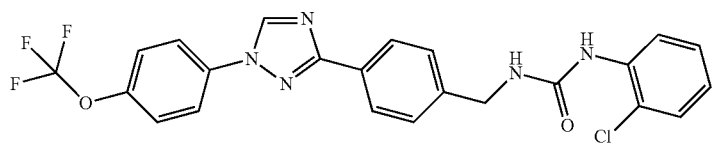 [SMILES: O=C(NCc1ccc(-c2ncn(-c3ccc(OC(F)(F)F)cc3)n2)cc1)Nc1ccccc1Cl] |
| F105 | 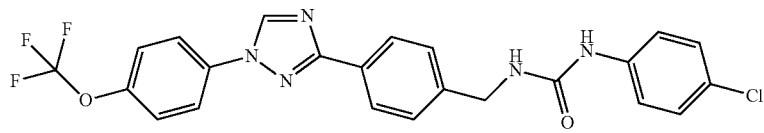 [SMILES: O=C(NCc1ccc(-c2ncn(-c3ccc(OC(F)(F)F)cc3)n2)cc1)Nc1ccc(Cl)cc1] |
| F106 | 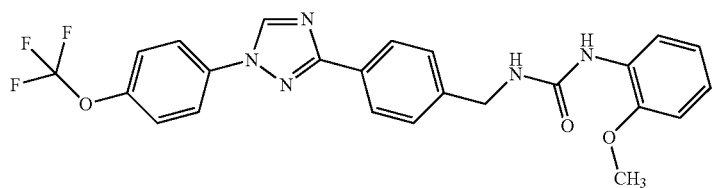 |
| F107 | 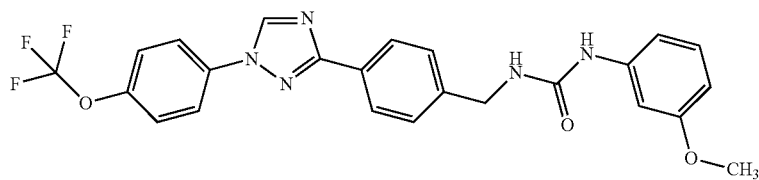 |

| No. | Structure |
|---|---|
| F108 | 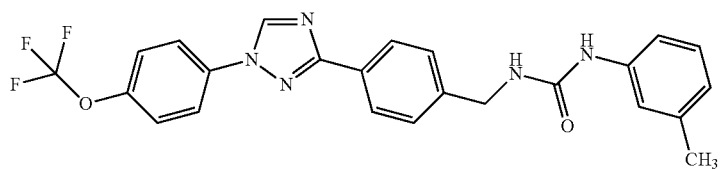 |
| F109 | 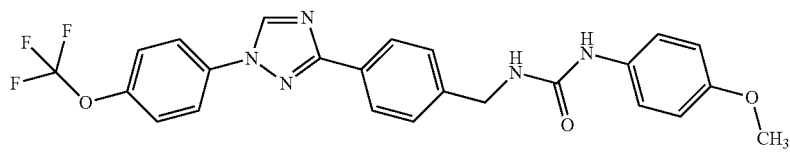 [SMILES: COc1ccc(NC(=O)NCc2ccc(-c3ncn(-c4ccc(OC(F)(F)F)cc4)n3)cc2)cc1] |
| F110 | 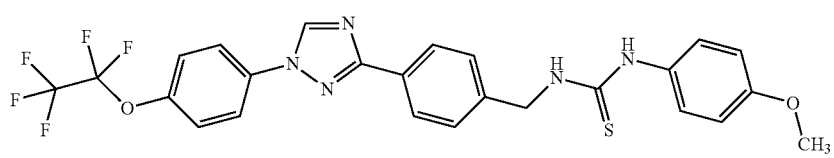 [SMILES: COc1ccc(NC(=S)NCc2ccc(-c3ncn(-c4ccc(OC(F)(F)C(F)(F)F)cc4)n3)cc2)cc1] |
| F111 | 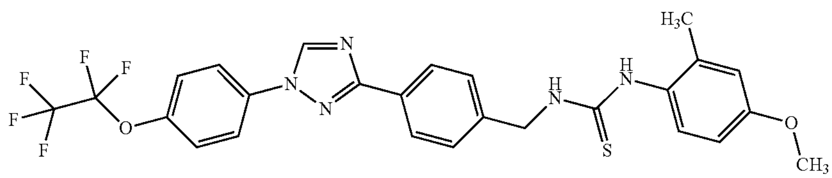 [SMILES: COc1ccc(NC(=S)NCc2ccc(-c3ncn(-c4ccc(OC(F)(F)C(F)(F)F)cc4)n3)cc2)c(C)c1] |
| F112 | 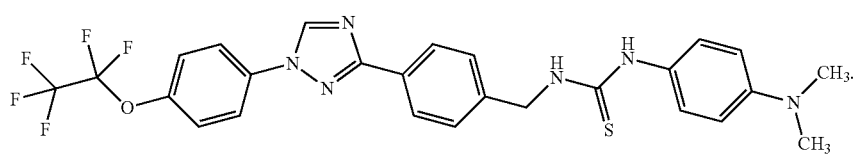 [SMILES: CN(C)c1ccc(NC(=S)NCc2ccc(-c3ncn(-c4ccc(OC(F)(F)C(F)(F)F)cc4)n3)cc2)cc1] |
26. A molecule according to claim 1 wherein said molecule is selected from the group consisting of one of the following molecules
| No. | Structure |
|---|---|
| P1 | 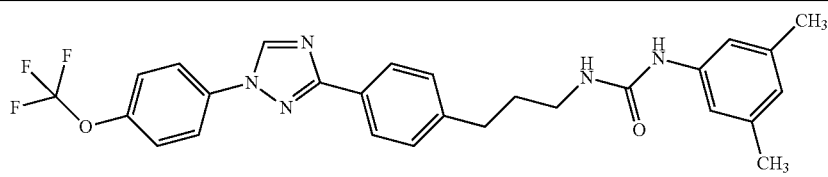 |
| P2 | 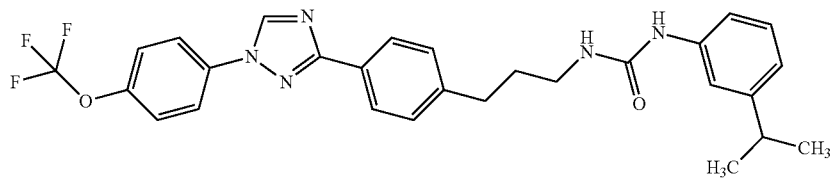 [SMILES: CC(C)c1cccc(NC(=O)NCCCc2ccc(-c3ncn(-c4ccc(OC(F)(F)F)cc4)n3)cc2)c1] |
| P3 | 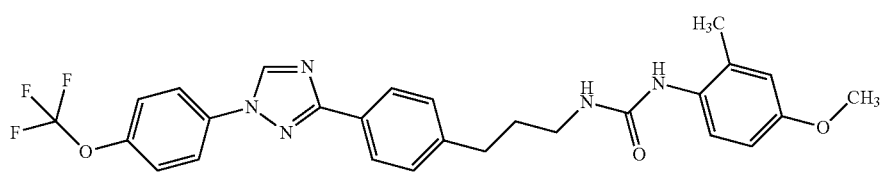 [SMILES: COc1ccc(NC(=O)NCCCc2ccc(-c3ncn(-c4ccc(OC(F)(F)F)cc4)n3)cc2)c(C)c1] |

-continued
| No. | Structure |
|---|---|
| P4 | 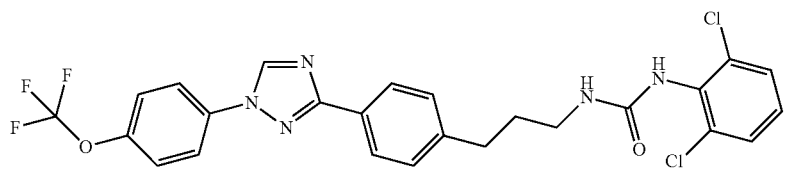 [SMILES: O=C(NCCCc1ccc(-c2ncn(-c3ccc(OC(F)(F)F)cc3)n2)cc1)Nc1c(Cl)cccc1Cl] |
| P5 | 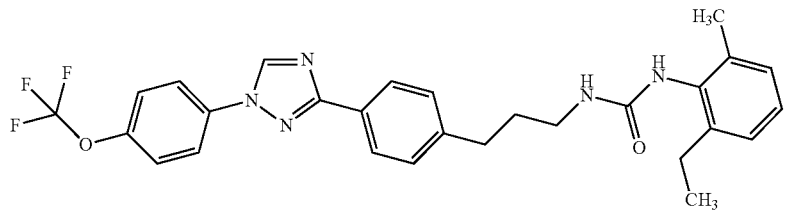 [SMILES: CCc1cccc(C)c1NC(=O)NCCCc1ccc(-c2ncn(-c3ccc(OC(F)(F)F)cc3)n2)cc1] |
| P6 | 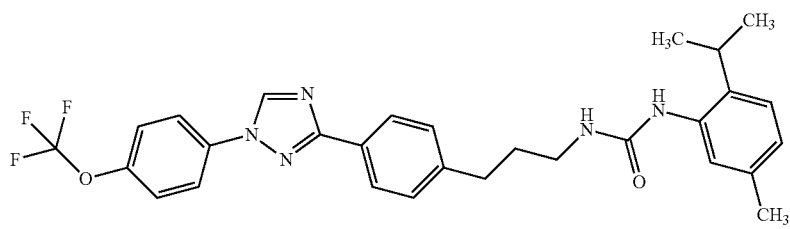 |
| P7 | 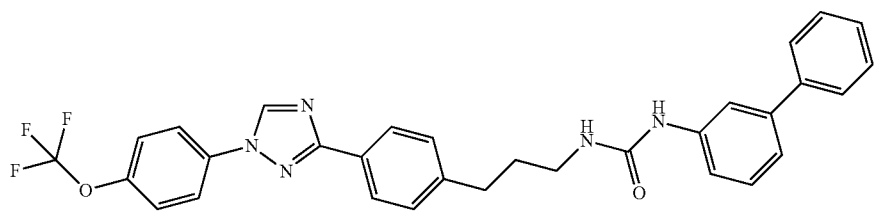 [SMILES: O=C(NCCCc1ccc(-c2ncn(-c3ccc(OC(F)(F)F)cc3)n2)cc1)Nc1cccc(-c2ccccc2)c1] |
| P8 | 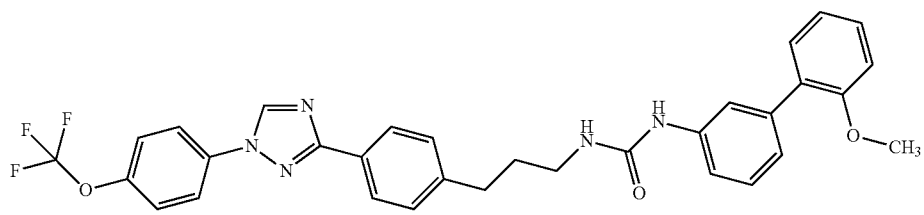 [SMILES: COc1ccccc1-c1cccc(NC(=O)NCCCc2ccc(-c3ncn(-c4ccc(OC(F)(F)F)cc4)n3)cc2)c1] |
| P9 | 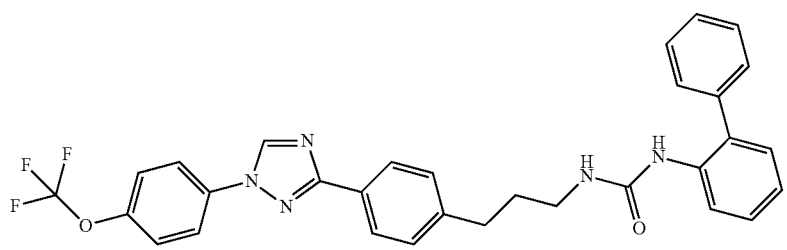 [SMILES: O=C(NCCCc1ccc(-c2ncn(-c3ccc(OC(F)(F)F)cc3)n2)cc1)Nc1ccccc1-c1ccccc1] |
| P10 | 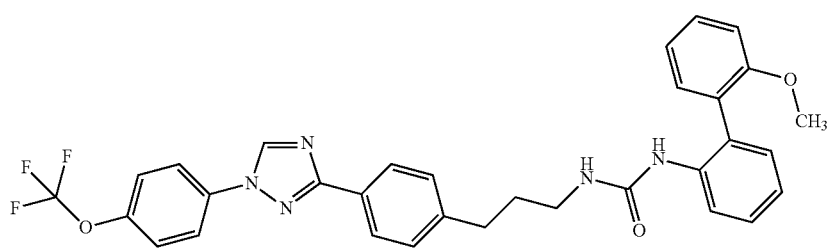 [SMILES: COc1ccccc1-c1ccccc1NC(=O)NCCCc1ccc(-c2ncn(-c3ccc(OC(F)(F)F)cc3)n2)cc1] |

| No. | Structure |
|---|---|
| P11 | 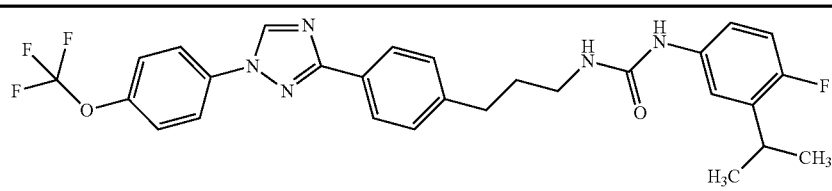 |
| P12 | 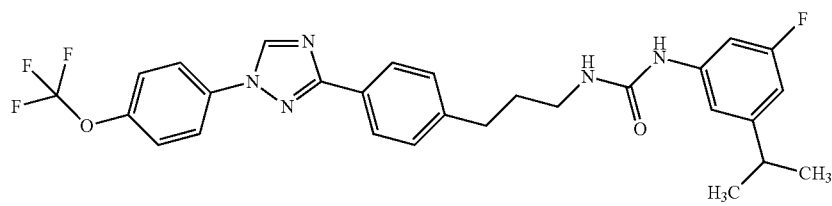 [SMILES: CC(C)c1cc(F)cc(NC(=O)NCCCc2ccc(-c3ncn(-c4ccc(OC(F)(F)F)cc4)n3)cc2)c1] |
| P13 | 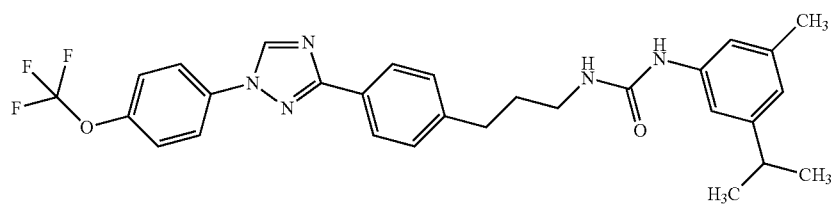 |
| P14 | 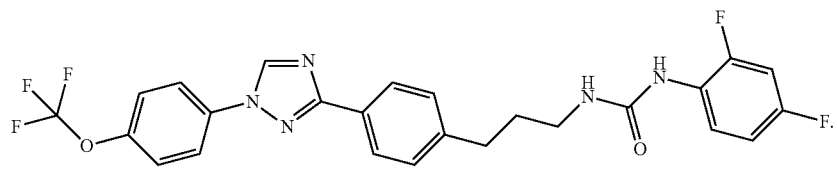 [SMILES: O=C(NCCCc1ccc(-c2ncn(-c3ccc(OC(F)(F)F)cc3)n2)cc1)Nc1ccc(F)cc1F] |
27. A molecule according to claim 1 wherein said molecule is selected from the group consisting of one of the following molecules
| No. | Structure |
|---|---|
| FA1 | 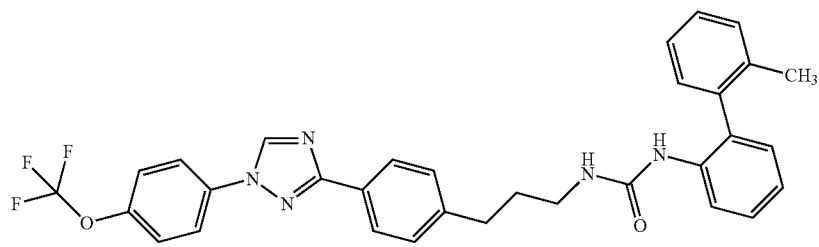 [SMILES: Cc1ccccc1-c1ccccc1NC(=O)NCCCc1ccc(-c2ncn(-c3ccc(OC(F)(F)F)cc3)n2)cc1] |
| FA2 | 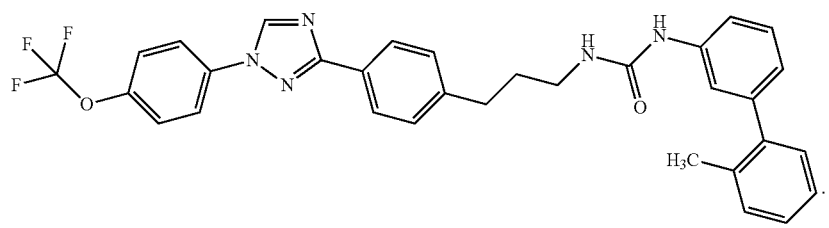 [SMILES: Cc1ccccc1-c1cccc(NC(=O)NCCCc2ccc(-c3ncn(-c4ccc(OC(F)(F)F)cc4)n3)cc2)c1] |

28. A pesticidal composition comprising a molecule according to claim 1 and a carrier.

29. A pesticidal composition according to claim 28 further comprising one or more compounds having a mode of action selected from the group consisting of: Acetylcholinesterase (AChE) inhibitors; GABA-gated chloride channel antagonists; Sodium channel modulators; Nicotinic acetylcholine (nAChR) agonists; Nicotinic acetylcholine receptor (nAChR) allosteric activators; Chloride channel activators; Juvenile hormone mimics; Miscellaneous non-specific (multi-site) inhibitors; Selective homopteran feeding blockers; Mite growth inhibitors; Microbial disruptors of insect midgut membranes; Inhibitors of mitochondrial ATP synthase; Uncouplers of oxidative phosphorylation via disruption of the proton gradient; Nicotinic acetylcholine receptor (nAChR) channel blockers; Inhibitors of chitin biosynthesis, type 0; Inhibitors of chitin biosynthesis, type 1; Moulting disruptor, Dipteran; Ecdysone receptor agonists; Octopamine receptor agonists; Mitochondrial complex III electron transport inhibitors; Mitochondrial complex I electron transport inhibitors; Voltage-dependent sodium channel blockers; Inhibitors of acetyl CoA carboxylase; Mitochondrial complex IV electron transport inhibitors; Mitochondrial complex II electron transport inhibitors; and Ryanodine receptor modulators.

30. A pesticidal composition according to claim 28 further comprising one or more compounds having acaricidal, algicidal, avicidal, bactericidal, fungicidal, herbicidal, insecticidal, molluscicidal, nematicidal, rodenticidal, and/or virucidal properties.

31. A pesticidal composition according to claim 28 further comprising one or more compounds that are antifeedants, bird repellents, chemosterilants, herbicide safeners, insect attractants, insect repellents, mammal repellents, mating disrupters, plant activators, plant growth regulators, and/or synergists.

32. A pesticidal composition according to claim 28 further comprising one or more of the following compounds—(3-ethoxypropyl)mercury bromide, 1,2-dichloropropane, 1,3-dichloropropene, 1-methylcyclopropene, 1-naphthol, 2-(octylthio)ethanol, 2,3,5-tri-iodobenzoic acid, 2,3,6-TBA, 2,3,6-TBA-dimethylammonium, 2,3,6-TBA-lithium, 2,3,6-TBA-potassium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 2iP, 2-methoxyethylmercury chloride, 2-phenylphenol, 3,4-DA, 3,4-DB, 3,4-DP, 4-aminopyridine, 4-CPA, 4-CPA-diolamine, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-S-methyl, acifluorfen, acifluorfen-methyl, acifluorfen-sodium, aclonifen, acrep, acrinathrin, acrolein, acrylonitrile, acypetacs, acypetacs-copper, acypetacs-zinc, afidopyropen, afoxolaner, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, aminocyclopyrachlor-potassium, aminopyralid, aminopyralid-potassium, aminopyralid-tris (2-hydroxypropyl)ammonium, amiprofos-methyl, amiprophos, amisulbrom, amiton, amiton oxalate, amitraz, amitrole, ammonium sulfamate, ammonium α-naphthaleneacetate, amobam, ampropylfos, anabasine, anabasine sulfate, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinphos-methyl, aziprotryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, benodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzovindiflupyr, benzoximate, benzoylprop, benzoylprop-ethyl, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluron, bitertanol, bithionol, bixafen, blasticidin-S, borax, Bordeaux mixture, boric acid, boscalid, brassinolide, brassinolide-ethyl, brevicomin, brodifacoum, brofenvalerate, broflanilide, brofluthrinate, bromacil, bromacil-lithium, bromacil-sodium, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chloranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlornidine, chlornitrofen, chlorobenzilate, chlorodinitronaphthalenes, chloroform, chloromebuform, chloromethiuron, chloroneb, chlorophacinone, chlorophacinone-sodium, chloropicrin, chloropon, chloroprallethrin, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, cholecalciferol, chromafenozide, cinerin I, cinerin II, cinerins, cinidon-ethyl, cinmethylin, cinosulfuron, ciobutide, cisanilide, cismethrin, clacyfos, clethodim, climbazole, cliodinate, clodinafop, clodinafop-propargyl, cloethocarb, clofencet, clofencet-potassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatetralyl, coumithoate, coumoxystrobin, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclaniliprole, cyclethrin, cycloate, cycloheximide, cycloprate, cycloprothrin, cyclopyrimorate, cyclosulfamuron, cycloxaprid, cycloxydim, cycluron, cyenopyrafen, cyflufenamid, cyflumetofen, cyfluthrin, cyhalodiamide, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarb, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmedipham, desmetryn, d-fanshiluquebingjuzhi, diafenthiuron, dialifos, diallate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicapthon, dichlobenil, dichlofenthion, dichlofluanid, dichlone, dichloralurea, dichlorbenzuron, dichlorflurenol, dichlorflurenol-methyl, dichlormate, dichlormid, dicloromezotiaz, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-P-potassium, dichlorprop-P-sodium, dichlorprop-sodium, dichlorvos, dichlozoline, diclobutrazol, diclocymet, diclofop, diclofop-methyl, diclomezine, diclomezine-sodium, dicloran, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, dietholate, diethyl pyrocarbonate, diethyltoluamide, difenacoum, difenoconazole, difenopenten, difenopentenethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlone, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenton, dinoprop, dinosam, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipymetitrone, dipyrithione, diquat, diquat dibromide, disparlure, disul, disulfiram, disulfoton, disul-sodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, enoxastrobin, EPN, epocholeone, epofenonane, epoxiconazole, eprinomectin, epronaz, epsilon-metofluthrin, epsilon-momfluorothrin, EPTC, erbon, ergocalciferol, erlujixiancaoan, esdepallethrine, esfenvalerate, esprocarb, etacelasil, etaconazole, etaphos, etem, ethaboxam, ethachlor, ethalfluralin, ethametsulfuron, ethametsulfuron-methyl, ethaprochlor, ethephon, ethidimuron, ethiofencarb, ethiolate, ethion, ethiozin, ethiprole, ethirimol, ethoate-methyl, ethofumesate, ethohexadiol, ethoprophos, ethoxyfen, ethoxyfen-ethyl, ethoxyquin, ethoxysulfuron, ethychlozate, ethyl formate, ethyl α-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenaminstrobin, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butometyl, fenoprop-butotyl, fenoprop-butyl, fenoprop-isoctyl, fenoprop-methyl, fenoprop-potassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpirithrin, fenpropathrin, fenpropidin, fenpropimorph, fenpyrazamine, fenpyroximate, fenquinotrione, fenridazon, fenridazon-potassium, fenridazon-propyl, fenson, fensulfothion, fenteracol, fenthiaprop, fenthiaprop-ethyl, fenthion, fenthion-ethyl, fentin, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flometoquin, flonicamid, florasulam, fluacrypyrim, fluazaindolizine, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, fl ufenoxystrobin, flufenprox, flufenpyr, flufenpyr-ethyl, flufiprole, fluhexafon, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyradifurone, flupyrsulfuron, flupyrsulfuron-methyl, flupyrsulfuron-methyl-sodium, fluquinconazole, fluralaner, flurazole, flurenol, flurenol-butyl, flurenol-methyl, fluridone, flurochloridone, fluroxypyr, fluroxypyr-butometyl, fluroxypyr-meptyl, flurprimidol, flursulamid, flurtamone, flusilazole, flusulfamide, fluthiacet, fluthiacet-methyl, flutianil, flutolanil, flutriafol, fluvalinate, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminium, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halauxifen, halauxifen-methyl, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptafluthrin, heptenophos, heptopargil, herbimycin, heterophos, hexachloroacetone, hexachlorobenzene, hexachlorobutadiene, hexachlorophene, hexaconazole, hexaflumuron, hexaflurate, hexalure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, iodobonil, iodocarb, iodomethane, iodosulfuron, iodosulfuron-methyl, iodosulfuron-methyl-sodium, iofensulfuron, iofensulfuron-sodium, ioxynil, ioxynil octanoate, ioxynil-lithium, ioxynil-sodium, ipazine, ipconazole, ipfencarbazone, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isofetamid, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, kappa-bifenthrin, kappa-tefluthrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, latilure, lead arsenate, lenacil, lepimectin, leptophos, lindane, lineatin, linuron, lirimfos, litlure, looplure, lufenuron, lvdingjunzhi, lvxiancaolin, lythidathion, MAA, malathion, maleic hydrazide, malonoben, maltodextrin, MAMA, mancopper, mancozeb, mandipropamid, mandestrobin, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotrione, mesulfen, mesulfenfos, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquin-butyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron, metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, momfluorothrin, monalide, monisouron, monochloroacetic acid, monocrotophos, monolinuron, monosulfuron, monosulfuron-ester, monuron, monuron TCA, morfamquat, morfamquat dichloride, moroxydine, moroxydine hydrochloride, morphothion, morzid, moxidectin, MSMA, muscalure, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, napropamide-M, naptalam, naptalam-sodium, natamycin, neburon, niclosamide, niclosamide-olamine, nicosulfuron, nicotine, nifluridide, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nornicotine, noruron, novaluron, noviflumuron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxathiapiprolin, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluron, penoxsulam, pentachlorophenol, pentachlorophenyl laurate, pentanochlor, penthiopyrad, pentmethrin, pentoxazone, perfluidone, permethrin, pethoxamid, phenamacril, phenazine oxide, phenisopham, phenkapton, phenmedipham, phenmedipham-ethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picarbutrazox, picloram, picloram-2-ethylhexyl, picloram-isoctyl, picloram-methyl, picloram-olamine, picloram-potassium, picloram-triethylammonium, picloram-tris(2-hydroxypropyl)ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium α-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, profluralin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiocarb, prothiocarb hydrochloride, prothioconazole, prothiofos, prothoate, protrifenbute, proxan, proxan-sodium, prynachlor, pydanon, pydiflumetofen, pyflubumide, pymetrozine, pyracarbolid, pyraclofos, pyraclonil, pyraclostrobin, pyraflufen, pyraflufen-ethyl, pyrafluprole, pyramat, pyrametostrobin, pyraoxystrobin, pyrasulfotole, pyraziflumid, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenzisopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyriminostrobin, pyrimisulfan, pyrimitate, pyrinuron, pyriofenone, pyriprole, pyripropanol, pyriproxyfen, pyrisoxazole, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, rescalure, resmethrin, rhodethanil, rhodojaponin-III, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium α-naphthaleneacetate, sophamide, spinetoram, spinosad, spirodiclofen, spiromesifen, spirotetramat, spiroxamine, streptomycin, streptomycin sesquisulfate, strychnine, sulcatol, sulcofuron, sulcofuron-sodium, sulcotrione, sulfallate, sulfentrazone, sulfiram, sulfluramid, sulfometuron, sulfometuron-methyl, sulfosulfuron, sulfotep, sulfoxaflor, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluron, tetramethrin, tetramethylfluthrin, tetramine, tetranactin, tetraniliprole, tetrasul, thallium sulfate, thenylchlor, theta-cypermethrin, thiabendazole, thiacloprid, thiadifluor, thiamethoxam, thiapronil, thiazafluron, thiazopyr, thicrofos, thicyofen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiafenacil, tiaojiean, tiocarbazil, tioclorim, tioxazafen, tioxymid, tirpate, tolclofos-methyl, tolfenpyrad, tolprocarb, tolpyralate, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichloronat, triclopyr, triclopyr-butotyl, triclopyr-ethyl, triclopyricarb, triclopyr-triethylammonium, tricyclazole, tridemorph, tridiphane, trietazine, trifenmorph, trifenofos, trifloxystrobin, trifloxysulfuron, trifloxysulfuron-sodium, trifludimoxazin, triflumezopyrim, triflumizole, triflumuron, trifluralin, triflusulfuron, triflusulfuron-methyl, trifop, trifop-methyl, trifopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid.

33. A pesticidal composition according to claim 28 further comprising one or more biopesticides.

34. A pesticidal composition according to claim 28 further comprising a seed.

35. A process comprising applying a pesticidal composition according to claim 28 to a locus to control a pest, in a sufficient amount to control said pest.

36. A process according to claim 35 wherein said pest is selected from the group consisting of ants, aphids, beetles, bristletails, cockroaches, crickets, earwigs, fleas, flies, grasshoppers, leafhoppers, lice, locusts, mites, moths, nematodes, scales, symphylans, termites, thrips, ticks, wasps, and whiteflies.

37. A process according to claim 35, wherein said pest is LAPHEG, TRIPNI, HELIZE, MYZUPE, or AEDSAE.

38. A process according to claim 35 wherein said locus is
(a) where crops, trees, fruits, cereals, fodder species, vines, turf, and/or ornamental plants, are growing;
(b) where domesticated animals are residing;
(c) the interior or exterior surfaces of buildings;
(d) the materials of construction used in buildings; and/or
(e) the soil around buildings.

39. A process according to claim 35 wherein said locus has one or more of the following growing apples, corn, sunflowers, cotton, soybeans, canola, wheat, rice, sorghum, barley, oats, potatoes, oranges, alfalfa, lettuce, strawberries, tomatoes, peppers, crucifers, pears, tobacco, almonds, sugar beets, and beans.

* * * * *